US012491239B2

(12) United States Patent
Shone et al.

(10) Patent No.: US 12,491,239 B2
(45) Date of Patent: Dec. 9, 2025

(54) ***CLOSTRIDIUM DIFFICILE* ANTIGENS**

(71) Applicants: Secretary of State for Health and Social Care, London (GB); MicroPharm Limited, Newcastle Emlyn (GB)

(72) Inventors: Clifford Shone, Salisbury (GB); April Roberts, Salisbury (GB); Helen Ahern, Salisbury (GB); Michael Maynard-Smith, Salisbury (GB); John Landon, Newcastle Emlyn (GB)

(73) Assignees: Secretary of State for Health and Social Care, London (GB); MicroPharm Limited, Carmarthenshire (GB)

( * ) Notice: Subject to any disclaimer, the term of this patent is extended or adjusted under 35 U.S.C. 154(b) by 0 days.

(21) Appl. No.: 17/821,730

(22) Filed: Aug. 23, 2022

(65) Prior Publication Data

US 2023/0165949 A1 Jun. 1, 2023

Related U.S. Application Data

(60) Continuation of application No. 17/224,404, filed on Apr. 7, 2021, which is a division of application No. 16/511,503, filed on Jul. 15, 2019, now abandoned, which is a division of application No. 13/878,150, filed as application No. PCT/GB2011/051910 on Oct. 5, 2011, now Pat. No. 10,369,206.

(30) Foreign Application Priority Data

Oct. 5, 2010 (GB) ..................................... 1016742

(51) Int. Cl.

| | |
|---|---|
| ***A61K 39/08*** | (2006.01) |
| ***A61K 38/16*** | (2006.01) |
| ***A61K 39/00*** | (2006.01) |
| ***A61K 39/40*** | (2006.01) |
| ***C07K 14/33*** | (2006.01) |
| ***C07K 16/12*** | (2006.01) |

(52) U.S. Cl.

CPC ............ *A61K 39/08* (2013.01); *A61K 38/164* (2013.01); *A61K 39/40* (2013.01); *C07K 14/33* (2013.01); *C07K 16/1282* (2013.01); *A61K 2039/505* (2013.01); *C07K 2317/76* (2013.01); *C07K 2319/00* (2013.01)

(58) Field of Classification Search

CPC ...... A61K 39/08; A61K 38/164; A61K 39/40; A61K 2039/505; C07K 14/33; C07K 16/1282; C07K 2317/76; C07K 2319/00

See application file for complete search history.

(56) References Cited

U.S. PATENT DOCUMENTS

| | | | | |
|---|---|---|---|---|
| 5,919,463 | A | 7/1999 | Thomas, Jr. et al. | |
| 8,481,692 | B2 * | 7/2013 | Sidhu | A61P 31/04 530/409 |
| 9,745,354 | B2 * | 8/2017 | Ruppen | A61P 37/02 |
| 2005/0287150 | A1 | 12/2005 | Ambrosino et al. | |
| 2007/0065466 | A1 | 3/2007 | Windle et al. | |

FOREIGN PATENT DOCUMENTS

| | | | |
|---|---|---|---|
| WO | 96/12802 | A1 | 5/1996 |
| WO | 98/59053 | A1 | 12/1998 |
| WO | 00/61762 | A1 | 10/2000 |
| WO | 2007/146139 | A2 | 12/2007 |
| WO | 2010/017383 | A1 | 2/2010 |
| WO | 2011/067616 | A1 | 6/2011 |
| WO | 2012/046061 | A3 | 4/2012 |

OTHER PUBLICATIONS

Alpar et al. (Expert Opinion Drug Delivery vol. 2 No. 5, pp. 829-842).*

Belyi, I.F., and N.A. Varfolomeeva, "Construction of a Fusion Protein Carrying Antigenic Determinants of Enteric Clostridial Toxins," FEMS Microbiology Letters 225(2):325-329, Aug. 2003.

Boslego, J.W., and C.D. Deal, "Gonorrhea Vaccines: Etiologic Agent and Pathogenesis," Vaccines and Immunotherapy, Chapter 17, 1 page, 1991.

Castagliuolo, I., et al., "Clostridium difficile Toxin A Carboxyl-Terminus Peptide Lacking ADP-Ribosyltransferase Activity Acts as a Mucosal Adjuvant," Infections and Immunity 72(5):2827-2836, May 2004.

Colman, P.M., "Effects of Amino Acid Sequence Changes on Antibody-Antigen Interactions," Research in Immunology 145(1):33-36, 1994.

(Continued)

*Primary Examiner* — Robert A Zeman

(74) *Attorney, Agent, or Firm* — Christensen O'Connor Johnson Kindness PLLC

(57) ABSTRACT

The present application relates to recombinant *Clostridium difficile* antigens based on a fusion protein that consists of or comprises a first amino acid sequence and a second amino acid sequence, wherein: a) the first amino acid sequence is provided by an amino acid sequence that has at least 80% sequence identity with an amino acid sequence consisting of residues 1500-1850 of a *C. difficile* Toxin A sequence or residues 1500-1851 of a *C. difficile* Toxin B sequence; and b) the second amino acid sequence is provided by an amino acid sequence that has at least 80% sequence identity with an amino acid sequence consisting of a long repeat unit located within amino acid residues 1851-2710 of a *C. difficile* Toxin A sequence or within amino acid residues 1852-2366 of a *C. difficile* Toxin B sequence; though with the proviso that the fusion protein is not a polypeptide comprising amino acid residues 543-2710 of a *C. difficile* Toxin A and with the proviso that the fusion protein is not a polypeptide comprising amino acid residues 543-2366 of a *C. difficile* Toxin B. Also provided is the use of said antigens for the prevention/treatment/suppression of *Clostridium difficile* infection (CDI), together with methods for generating said antigens, methods for generating antibodies that bind to said antigens, and the use of said antibodies for the prevention/treatment/suppression of CDI.

1 Claim, 5 Drawing Sheets

Specification includes a Sequence Listing.

(56) References Cited

OTHER PUBLICATIONS

Ellis, R.W., "New Technologies for Making Vaccines," in Stanley J. Cryz, Jr. (ed.), Vaccines, W.B. Saunders Company, Philadelphia, 1988, Chapter 29, pp. 568-574.
Greenspan, N.S., and E.Di Cera, "Defining Epitopes: It's Not as Easy as It Seems," Nature Biotechnology 17(10):936-937, Oct. 1999.
Harlow, E., and D. Lane, "Antibodies a Laboratory Manual," Cold Spring Harbor Press Inc., Cold Spring Harbor, New York, 1988, pp. 23-35.
Ho, J.G.S., et al., "Crystal Structure of Receptor-Binding C-Terminal Repeats From Clostridium difficile Toxin A," Proceedings of the National Academy of Sciences of the USA (PNAS) 102(51):18373-18378, Dec. 2005.
Houghten, R.A., et al., "Relative Importance of Position and Individual Amino Acid Residues in Peptide Antigen-Antibody Interactions: Implications in the Mechanism of Antigenic Drift and Antigenic Shift," in Cold Spring Harbor Laboratory, "Vaccines 86 New Approaches to Immunization: Developing Vaccines Against Parasitic, Bacterial, and Viral Diseases," Cold Spring Harbor, New York, 1986, pp. 21-26.
Pruitt, R.N., et al., "Structural Determinants of Clostridium difficile Toxin A Glucosyltransferase Activity," Journal of Biological Chemistry 287(11):8013-8020, Mar. 2012.
Pruitt, R.N., et al., "Structural Organization of the Functional Domains of Clostridium difficile Toxins A and B," Proceedings of the National Academy of Sciences of the USA (PNAS) 107(30):13467-13472, Jul. 2010.
Reinert, D.J., et al., "Structural Basis for the Function of Clostridium difficile Toxin B," Journal of Molecular Biology 351(5):973-981, Sep. 2005.
Skolnick, J., and J.S. Fetrow, "From Genes to Protein Structure and Function: Novel Applications of Computational Approaches in the Genomic Era," Trends in Biotechnology 18(1):34-39, Jan. 2000.
Von Eichel-Streiber, C., et al., "Comparative Sequence Analysis of the Clostridium difficile Toxins A and B," Molecular and General Genetics 233(1-2):260-268, May 1992.
United Kingdom Intellectual Property Office, Patents Act 1977: Search Report Under Section 17, mailed Feb. 4, 2011, issued in corresponding Great Britain Application No. GB 101672.7, filed Oct. 5, 2010, 5 pages.
European Patent Office Written Opinion mailed Feb. 15, 2013, issued in corresponding International Patent Application No. PCT/GB2011/051910, 7 pages.
Written Opinion of the International Searching Authority mailed Apr. 5, 2013, issued in corresponding International Patent Application No. PCT/GB2011/051910, 6 pages.
Response to the Written Opinion of the International Searching Authority issued in corresponding International Patent Application No. PCT/GB2011/051910, mailed Apr. 15, 2013, 9 pages.
International Preliminary Report on Patentabilily mailed May 14, 2013, issued in corresponding International Patent Application No. PCT/GB2011/051910, 8 pages.
Redwan, EL.-R.M., et al., "Production and Purification of Ovine Anti-Tetanus Antibody," Comparative Immunology, Microbiology and Infectious Diseases 28(3):167-176, May 2005.

* cited by examiner

SEQUENCE LISTING

```
Sequence total quantity: 81
SEQ ID NO: 1           moltype = AA  length = 2710
FEATURE                Location/Qualifiers
source                 1..2710
                       mol_type = protein
                       organism = Clostridium difficile
SEQUENCE: 1
MSLISKEELI KLAYSIRPRE NEYKTILTNL DEYNKLTTNN NENKYLQLKK LNESIDVFMN  60
KYKTSSRNRA LSNLKKDILK EVILIKNSNT SPVEKNLHFV WIGGEVSDIA LEYIKQWADI  120
NAEYNIKLWY DSEAFLVNTL KKAIVESSTT EALQLLEEEI QNPQFDNMKF YKKRMEFIYD  180
RQKRFINYYK SQINKPTVPT IDDIIKSHLV SEYNRDETVL ESYRTNSLRK INSNHGIDIR  240
ANSLFTEQEL LNIYSQELLN RGNLAAASDI VRLLALKNFG GVYLDVDMLP GIHSDLFKTI  300
SRPSSIGLDR WEMIKLEAIM KYKKYINNYT SENFDKLDQQ LKDNFKLIIE SKSEKSEIFS  360
KLENLNVSDL EIKIAFALGS VINQALISKQ GSYLTNLVIE QVKNRYQFLN QHLNPAIESD  420
NNFTDTTKIF HDSLFNSATA ENSMFLTKIA PYLQVGFMPE ARSTISLSGP GAYASAYYDF  480
INLQENTIEK TLKASDLIEF KFPENNLSQL TEQEINSLWS FDQASAKYQF EKYVRDYTGG  540
SLSEDNGVDF NKNTALDKNY LLNNKIPSNN VEEAGSKNYV HYIIQLQGDD ISYEATCNLF  600
SKNPKNSIII QRNMNESAKS YFLSDDGESI LELNKYRIPE RLKNKEKVKV TFIGHGKDEF  660
NTSEFARLSV DSLSNEISSF LDTIKLDISP KNVEVNLLGC NMFSYDFNVE ETYPGKLLLS  720
IMDKITSTLP DVNKNSITIG ANQYEVRINS EGRKELLAHS GKWINKEEAI MSDLSSKEYI  780
FFDSIDNKLK AKSKNIPGLA SISEDIKTLL LDASVSPDTK FILNNLKLNI ESSIGDYIYY  840
EKLEPVKNII HNSIDDLIDE FNLLENVSDE LYELKKLNNL DEKYLISFED ISKNNSTYSV  900
RFINKSNGES VYVETEKEIF SKYSEHITKE ISTIKNSIIT DVNGNLLDNI QLDHTSQVNT  960
LNAAFFIQSL IDYSSNKDVL NDLSTSVKVQ LYAQLFSTGL NTIYDSIQLV NLISNAVNDT  1020
INVLPTITEG IPIVSTILDG INLGAAIKEL LDEHDPLLKK ELEAKVGVLA INMSLSIAAT  1080
VASIVGIGAE VTIFLLPIAG ISAGIPSLVN NELILHDKAT SVVNYFNHLS ESKKYGPLKT  1140
EDDKILVPID DLVISEIDFN NNSIKLGTCN ILAMEGGSGH TVTGNIDHFF SSPSISSHIP  1200
SLSIYSAIGI ETENLDFSKK IMMLPNAPSR VFWWETGAVP GLRSLENDGT RLLDSIRDLY  1260
PGKFYWRFYA FFDYAITTLK PVYEDTNIKI KLDKDTRNFI MPTITTNEIR NKLSYSFDGA  1320
GGTYSLLLSS YPISTNINLS KDDLWIFNID NEVREISIEN GTIKKGKLIK DVLSKIDINK  1380
NKLIIGNQTI DFSGDIDNKD RYIFLTCELD DKISLIIEIN LVAKSYSLLL SGDKNYLISN  1440
LSNTIEKINT LGLDSKNIAY NYTDESNNKY FGAISKTSQK SIIHYKKDSK NILEFYNDST  1500
LEFNSKDFIA EDINVFMKDD INTITGKYYV DNNTDKSIDF SISLVSKNQV KVNGLYLNES  1560
VYSSYLDFVK NSDGHHNTSN FMNLFLDNIS FWKLFGFENI NFVIDKYFTL VGKTNLGYVE  1620
FICDNNKNID IYFGEWKTSS SKSTIFSGNG RNVVVEPIYN PDTGEDISTS LDFSYEPLYG  1680
IDRYINKVLI APDLYTSLIN INTNYYSNEY YPEIIVLNPN TFHKKVNINL DSSSFEYKWS  1740
TEGSDFILVR YLEESNKKIL QKIRIKGILS NTQSFNKMSI DFKDIKKLSL GYIMSNFKSF  1800
NSENELDRDH LGFKIIDNKT YYYDEDSKLV KGLININNSL FYFDPIEFNL VTGWQTINGK  1860
KYYFDINTGA ALTSYKIING KHFYFNNDGV MQLGVFKGPD GFEYFAPANT QNNNIEGQAI  1920
VYQSKFLTLN GKKYYFDNNS KAVTGWRIIN NEKYYFNPNN AIAAVGLQVI DNNKYYFNPD  1980
TAIISKGWQT VNGSRYYFDT DTAIAFNGYK TIDGKHFYFD SDCVVKIGVF STSNGFEYFA  2040
PANTYNNNIE GQAIVYQSKF LTLNGKKYYF DNNSKAVTGL QTIDSKKYYF NTNTAEAATG  2100
WQTIDGKKYY FNTNTAEAAT GWQTIDGKKY YFNTNTAIAS TGYTIINGKH FYFNTDGIMQ  2160
IGVFKGPNGF EYFAPANTDA NNIEGQAILY QNEFLTLNGK KYYFGSDSKA VTGWRIINNK  2220
KYYFNPNNAI AAIHLCTINN DKYYFSYDGI LQNGYITIER NNFYFDANNE SKMVTGVFKG  2280
PNGFEYFAPA NTHNNNIEGQ AIVYQNKFLT LNGKKYYFDN DSKAVTGWQT IDGKKYYFNL  2340
NTAEAATGWQ TIDGKKYYFN LNTAEAATGW QTIDGKKYYF NTNTFIASTG YTSINGKHFY  2400
FNTDGIMQIG VFKGPNGFEY FAPANTDANN IEGQAILYQN KFLTLNGKKY YFGSDSKAVT  2460
```

GLRTIDGKKY YFNTNTAVAV TGWQTINGKK YYFNTNTSIA STGYTIISGK HFYFNTDGIM 2520
QIGVFKGPDG FEYFAPANTD ANNIEGQAIR YQNRFLYLHD NIYYFGNNSK AATGWVTIDG 2580
NRYYFEPNTA MGANGYKTID NKNFYFRNGL PQIGVFKGSN GFEYFAPANT DANNIEGQAI 2640
RYQNRFLHLL GKIYYFGNNS KAVTGWQTIN GKVYYFMPDT AMAAAGGLFE IDGVIYFFGV 2700
DGVKAPGIYG 2710

SEQ ID NO: 2 moltype = AA length = 2366
FEATURE Location/Qualifiers
source 1..2366
mol_type = protein
organism = Clostridium difficile
SEQUENCE: 2
MSLVNRKQLE KMANVRFRTQ EDEYVAILDA LEEYHNMSEN TVVEKYLKLK DINSLTDIYI 60
DTYKKSGRNK ALKKFKEYLV TEVLELKNNN LTPVEKNLHF VWIGGQINDT AINYINQWKD 120
VNSDYNVNVF YDSNAFLINT LKKTVVESAI NDTLESFREN LNDPRFDYNK FFRKRMEIIY 180
DKQKNFINYY KAQREENPEL IIDDIVKTYL SNEYSKEIDE LNTYIEESLN KITQNSGNDV 240
RNFEEFKNGE SFNLYEQELV ERWNLAAASD ILRISALKEI GGMYLDVDML PGIQPDLFES 300
IEKPSSVTVD FWEMTKLEAI MKYKEYIPEY TSEHFDMLDE EVQSSFESVL ASKSDKSEIF 360
SSLGDMEASP LEVKIAFNSK GIINQGLISV KDSYCSNLIV KQIENRYKIL NNSLNPAISE 420
DNDFNTTTNT FIDSIMAEAN ADNGRFMMEL GKYLRVGFFP DVKTTINLSG PEAYAAAYQD 480
LLMFKEGSMN IHLIEADLRN FEISKTNISQ STEQEMASLW SFDDARAKAQ FEEYKRNYFE 540
GSLGEDDNLD FSQNIVVDKE YLLEKISSLA RSSERGYIHY IVQLQGDKIS YEAACNLFAK 600
TPYDSVLFQK NIEDSEIAYY YNPGDGEIQE IDKYKIPSII SDRPKIKLTF IGHGKDEFNT 660
DIFAGFDVDS LSTEIEAAID LAKEDISPKS IEINLLGCNM FSYSINVEET YPGKLLLKVK 720
DKISELMPSI SQDSIIVSAN QYEVRINSEG RRELLDHSGE WINKEESIIK DISSKEYISF 780
NPKENKITVK SKNLPELSTL LQEIRNNSNS SDIELEEKVM LTECEINVIS NIDTQIVEER 840
IEEAKNLTSD SINYIKDEFK LIESISDALC DLKQQNELED SHFISFEDIS ETDEGFSIRF 900
INKETGESIF VETEKTIFSE YANHITEEIS KIKGTIFDTV NGKLVKKVNL DTTHEVNTLN 960
AAFFIQSLIE YNSSKESLSN LSVAMKVQVY AQLFSTGLNT ITDAAKVVEL VSTALDETID 1020
LLPTLSEGLP IIATIIDGVS LGAAIKELSE TSDPLLRQEI EAKIGIMAVN LTTATTAIIT 1080
SSLGIASGFS ILLVPLAGIS AGIPSLVNNE LVLRDKATKV VDYFKHVSLV ETEGVFTLLD 1140
DKIMMPQDDL VISEIDFNNN SIVLGKCEIW RMEGGSGHTV TDDIDHFFSA PSITYREPHL 1200
SIYDVLEVQK EELDLSKDLM VLPNAPNRVF AWETGWTPGL RSLENDGTKL LDRIRDNYEG 1260
EFYWRYFAFI ADALITTLKP RYEDTNIRIN LDSNTRSFIV PIITTEYIRE KLSYSFYGSG 1320
GTYALSLSQY NMGINIELSE SDVWIIDVDN VVRDVTIESD KIKKGDLIEG ILSTLSIEEN 1380
KIILNSHEIN FSGEVNGSNG FVSLTFSILE GINAIIEVDL LSKSYKLLIS GELKILMLNS 1440
NHIQQKIDYI GFNSELQKNI PYSFVDSEGK ENGFINGSTK EGLFVSELPD VVLISKVYMD 1500
DSKPSFGYYS NNLKDVKVIT KDNVNILTGY YLKDDIKISL SLTLQDEKTI KLNSVHLDES 1560
GVAEILKFMN RKGNTNTSDS LMSFLESMNI KSIFVNFLQS NIKFILDANF IISGTTSIGQ 1620
FEFICDENDN IQPYFIKFNT LETNYTLYVG NRQNMIVEPN YDLDDSGDIS STVINFSQKY 1680
LYGIDSCVNK VVISPNIYTD EINITPVYET NNTYPEVIVL DANYINEKIN VNINDLSIRY 1740
VWSNDGNDFI LMSTSEENKV SQVKIRFVNV FKDKTLANKL SFNFSDKQDV PVSEIILSFT 1800
PSYYEDGLIG YDLGLVSLYN EKFYINNFGM MVSGLIYIND SLYYFKPPVN NLITGFVTVG 1860
DDKYYFNPIN GGAASIGETI IDDKNYYFNQ SGVLQTGVFS TEDGFKYFAP ANTLDENLEG 1920
EAIDFTGKLI IDENIYYFDD NYRGAVEWKE LDGEMHYFSP ETGKAFKGLN QIGDYKYYFN 1980
SDGVMQKGFV SINDNKHYFD DSGVMKVGYT EIDGKHFYFA ENGEMQIGVF NTEDGFKYFA 2040
HHNEDLGNEE GEEISYSGIL NFNNKIYYFD DSFTAVVGWK DLEDGSKYYF DEDTAEAYIG 2100
LSLINDGQYY FNDDGIMQVG FVTINDKVFY FSDSGIIESG VQNIDDNYFY IDDNGIVQIG 2160
VFDTSDGYKY FAPANTVNDN IYGQAVEYSG LVRVGEDVYY FGETYTIETG WIYDMENESD 2220
KYYFNPETKK ACKGINLIDD IKYYFDEKGI MRTGLISFEN NNYYFNENGE MQFGYINIED 2280
KMFYFGEDGV MQIGVFNTPD GFKYFAHQNT LDENFEGESI NYTGWLDLDE KRYYFTDEYI 2340
AATGSVIIDG EEYYFDPDTA QLVISE 2366

SEQ ID NO: 3 moltype = AA length = 2710
FEATURE Location/Qualifiers
source 1..2710
mol_type = protein
organism = Clostridium difficile
SEQUENCE: 3
MSLISKEELI KLAYSIRPRE NEYKTILTNL DEYNKLTTNN NENKYLQLKK LNESIDVFMN 60
KYKNSSRNRA LSNLKKDILK EVILIKNSNT SPVEKNLHFV WIGGEVSDIA LEYIKQWADI 120
NAEYNIKLWY DSEAFLVNTL KKAIVESSTT EALQLLEEEI QNPQFDNMKF YKKRMEFIYD 180
RQKRFINYYK SQINKPTVPT IDDIIKSHLV SEYNRDETLL ESYRTNSLRK INSNHGIDIR 240
ANSLFTEQEL LNIYSQELLN RGNLAAASDI VRLLALKNFG GVYLDVDMLP GIHSDLFKTI 300
PRPSSIGLDR WEMIKLEAIM KYKKYINNYT SENFDKLDQQ LKDNFKLIIE SKSEKSEIFS 360
KLENLNVSDL EIKIAFALGS VINQALISKQ GSYLTNLVIE QVKNRYQFLN QHLNPAIESD 420
NNFTDTTKIF HDSLFNSATA ENSMFLTKIA PYLQVGFMPE ARSTISLSGP GAYASAYYDF 480
INLQENTIEK TLKASDLIEF KFPENNLSQL TEQEINSLWS FDQASAKYQF EKYVRDYTGG 540
SLSEDNGVDF NKNTALDKNY LLNNKIPSNN VEEAGSKNYV HYIIQLQGDD ISYEATCNLF 600
SKNPKNSIII QRNMNESAKS YFLSDDGESI LELNKYRIPE RLKNKEKVKV TFIGHGKDEF 660
NTSEFARLSV DSLSNEISSF LDTIKLDISP KNVEVNLLGC NMFSYDFNVE ETYPGKLLLS 720
IMDKITSTLP DVNKDSITIG ANQYEVRINS EGRKELLAHS GKWINKEEAI MSDLSSKEYI 780
FFDSIDNKLK AKSKNIPGLA SISEDIKTLL LDASVSPDTK FILNNLKLNI ESSIGDYIYY 840
EKLEPVKNII HNSIDDLIDE FNLLENVSDE LYELKKLNNL DEKYLISFED ISKNNSTYSV 900
RFINKSNGES VYVETEKEIF SKYSEHITKE ISTIKNSIIT DVNGNLLDNI QLDHTSQVNT 960
LNAAFFIQSL IDYSSNKDVL NDLSTSVKVQ LYAQLFSTGL NTIYDSIQLV NLISNAVNDT 1020
INVLPTITEG IPIVSTILDG INLGAAIKEL LDEHDPLLKK ELEAKVGVLA INMSLSIAAT 1080
VASIVGIGAE VTIFLLPIAG ISAGIPSLVN NELILHDKAT SVVNYFNHLS ESKEYGPLKT 1140
EDDKILVPID DLVISEIDFN NNSIKLGTCN ILAMEGGSGH TVTGNIDHFF SSPYISSHIP 1200

-continued

```
SLSVYSAIGI KTENLDFSKK IMMLPNAPSR VFWWETGAVP GLRSLENNGT KLLDSIRDLY  1260
PGKFYWRFYA FFDYAITTLK PVYEDTNTKI KLDKDTRNFI MPTITTDEIR NKLSYSFDGA  1320
GGTYSLLLSS YPISMNINLS KDDLWIFNID NEVREISIEN GTIKKGNLIE DVLSKIDINK  1380
NKLIIGNQTI DFSGDIDNKD RYIFLTCELD DKISLIIEIN LVAKSYSLLL SGDKNYLISN  1440
LSNTIEKINT LGLDSKNIAY NYTDESNNKY FGAISKTSQK SIIHYKKDSK NILEFYNGST  1500
LEFNSKDFIA EDINVFMKDD INTITGKYYV DNNTDKSIDF SISLVSKNQV KVNGLYLNES  1560
VYSSYLDFVK NSDGHHNTSN FMNLFLNNIS FWKLFGFENI NFVIDKYFTL VGKTNLGYVE  1620
FICDNNKNID IYFGEWKTSS SKSTIFSGNG RNVVVEPIYN PDTGEDISTS LDFSYEPLYG  1680
IDRYINKVLI APDLYTSLIN INTNYYSNEY YPEIIVLNPN TFHKKVNINL DSSSFEYKWS  1740
TEGSDFILVR YLEESNKKIL QKIRIKGILS NTQSFNKMSI DFKDIKKLSL GYIMSNFKSF  1800
NSENELDRDH LGFKIIDNKT YYYDEDSKLV KGLININNSL FYFDPIESNL VTGWQTINGK  1860
KYYFDINTGA ASTSYKIING KHFYFNNNGV MQLGVFKGPD GFEYFAPANT QNNNIEGQAI  1920
VYQSKFLTLN GKKYYFDNDS KAVTGWRIIN NEKYYFNPNN AIAAVGLQVI DNNKYYFNPD  1980
TAIISKGWQT VNGSRYYFDT DTAIAFNGYK TIDGKHFYFD SDCVVKIGVF SGSNGFEYFA  2040
PANTYNNNIE GQAIVYQSKF LTLNGKKYYF DNNSKAVTGW QTIDSKKYYF NTNTAEAATG  2100
WQTIDGKKYY FNTNTAEAAT GWQTIDGKKY YFNTNTSIAS TGYTIINGKY FYFNTDGIMQ  2160
IGVFKVPNGF EYFAPANTHN NNIEGQAILY QNKFLTLNGK KYYFGSDSKA ITGWQTIDGK  2220
KYYFNPNNAI AATHLCTINN DKYYFSYDGI LQNGYITIER NNFYFDANNE SKMVTGVFKG  2280
PNGFEYFAPA NTHNNNIEGQ AIVYQNKFLT LNGKKYYFDN DSKAVTGWQT IDSKKYYFNL  2340
NTAVAVTGWQ TIDGEKYYFN LNTAEAATGW QTIDGKRYYF NTNTYIASTG YTIINGKHFY  2400
FNTDGIMQIG VFKGPDGFEY FAPANTHNNN IEGQAILYQN KFLTLNGKKY YFGSDSKAVT  2460
GLRTIDGKKY YFNTNTAVAV TGWQTINGKK YYFNTNTYIA STGYTIISGK HFYFNTDGIM  2520
QIGVFKGPDG FEYFAPANTD ANNIEGQAIR YQNRFLYLHD NIYYFGNDSK AATGWATIDG  2580
NRYYFEPNTA MGANGYKTID NKNFYFRNGL PQIGVFKGPN GFEYFAPANT DANNIDGQAI  2640
RYQNRFLHLL GKIYYFGNNS KAVTGWQTIN SKVYYFMPDT AMAAAGGLFE IDGVIYFFGV  2700
DGVKAPGIYG                                                        2710

SEQ ID NO: 4           moltype = AA  length = 2366
FEATURE                Location/Qualifiers
source                 1..2366
                       mol_type = protein
                       organism = Clostridium difficile
SEQUENCE: 4
MSLVNRKQLE KMANVRFRVQ EDEYVAILDA LEEYHNMSEN TVVEKYLKLK DINSLTDIYI  60
DTYKKSGRNK ALKKFKEYLV TEVLELKNNN LTPVEKNLHF VWIGGQINDT AINYINQWKD  120
VNSDYNVNVF YDSNAFLINT LKKTIVESAT NDTLESFREN LNDPRFDYNK FYRKRMEIIY  180
DKQKNFINYY KTQREENPDL IIDDIVKIYL SNEYSKDIDE LNSYIEESLN KVTENSGNDV  240
RNFEEFKGGE SFKLYEQELV ERWNLAAASD ILRISALKEV GGVYLDVDML PGIQPDLFES  300
IEKPSSVTVD FWEMVKLEAI MKYKEYIPGY TSEHFDMLDE EVQSSFESVL ASKSDKSEIF  360
SSLGDMEASP LEVKIAFNSK GIINQGLISV KDSYCSNLIV KQIENRYKIL NNSLNPAISE  420
DNDFNTTTNA FIDSIMAEAN ADNGRFMMEL GKYLRVGFFP DVKTTINLSG PEAYAAAYQD  480
LLMFKEGSMN IHLIEADLRN FEISKTNISQ STEQEMASLW SFDDARAKAQ FEEYKKNYFE  540
GSLGEDDNLD FSQNTVVDKE YLLEKISSLA RSSERGYIHY IVQLQGDKIS YEAACNLFAK  600
TPYDSVLFQK NIEDSEIAYY YNPGDGEIQE IDKYKIPSII SDRPKIKLTF IGHGKDEFNT  660
DIFAGLDVDS LSTEIETAID LAKEDISPKS IEINLLGCNM FSYSVNVEET YPGKLLLRVK  720
DKVSELMPSI SQDSIIVSAN QYEVRINSEG RRELLDHSGE WINKEESIIK DISSKEYISF  780
NPKENKIIVK SKNLPELSTL LQEIRNNSNS SDIELEEKVM LAECEINVIS NIDTQVVEGR  840
IEEAKSLTSD SINYIKNEFK LIESISDALY DLKQQNELEE SHFISFEDIL ETDEGFSIRF  900
IDKETGESIF VETEKAIFSE YANHITEEIS KIKGTIFDTV NGKLVKKVNL DATHEVNTLN  960
AAFFIQSLIE YNSSKESLSN LSVAMKVQVY AQLFSTGLNT ITDAAKVVEL VSTALDETID  1020
LLPTLSEGLP VIATIIDGVS LGAAIKELSE TSDPLLRQEI EAKIGIMAVN LTAATTAIIT  1080
SSLGIASGFS ILLVPLAGIS AGIPSLVNNE LILRDKATKV VDYFSHISLA ESEGAFTSLD  1140
DKIMMPQDDL VISEIDFNNN SITLGKCEIW RMEGGSGHTV TDDIDHFFSA PSITYREPHL  1200
SIYDVLEVQK EELDLSKDLM VLPNAPNRVF AWETGWTPGL RSLENDGTKL LDRIRDNYEG  1260
EFYWRYFAFI ADALITTLKP RYEDTNIRIN LDSNTRSFIV PVITTEYIRE KLSYSFYGSG  1320
GTYALSLSQY NMNINIELNE NDTWVIDVDN VVRDVTIESD KIKKGDLIEN ILSKLSIEDN  1380
KIILDNHEIN FSGTLNGGNG FVSLTFSILE GINAVIEVDL LSKSYKVLIS GELKTLMANS  1440
NSVQQKIDYI GLNSELQKNI PYSFMDDKGK ENGFINCSTK EGLFVSELSD VVLISKVYMD  1500
NSKPLFGYCS NDLKDVKVIT KDDVIILTGY YLKDDIKISL SFTIQDENTI KLNGVYLDEN  1560
GVAEILKFMN KKGSTNTSDS LMSFLESMNI KSIFINSLQS NTKLILDTNF IISGTTSIGQ  1620
FEFICDKDNN IQPYFIKFNT LETKYTLYVG NRQNMIVEPN YDLDDSGDIS STVINFSQKY  1680
LYGIDSCVNK VIISPNIYTD EINITPIYEA NNTYPEVIVL DTNYISEKIN ININDLSIRY  1740
VWSNDGSDFI LMSTDEENKV SQVKIRFTNV FKGNTISDKI SFNFSDKQDV SINKVISTFT  1800
PSYYVEGLLN YDLGLISLYN EKFYINNFGM MVSGLVYIND SLYYFKPPIK NLITGFTTIG  1860
DDKYYFNPDN GGAASVGETI IDGKNYYFSQ NGVLQTGVFS TEDGFKYFAP ADTLDENLEG  1920
EAIDFTGKLT IDENVYYFGD NYRAAIEWQT LDDEVYYFST DTGRAFKGLN QIGDDKFYFN  1980
SDGIMQKGFV NINDKTFYFD DSGVMKSGYT EIDGKYFYFA ENGEMQIGVF NTADGFKYFA  2040
HHDEDLGNEE GEALSYSGIL NFNNKIYYFD DSFTAVVGWK DLEDGSKYYF DEDTAEAYIG  2100
ISIINDGKYY FNDSGIMQIG FVTINNEVFY FSDSGIVESG MQNIDDNYFY IDENGLVQIG  2160
VFDTSDGYKY FAPANTVNDN IYGQAVEYSG LVRVGEDVYY FGETYTIETG WIYDMENESD  2220
KYYFDPETKK AYKGINVIDD IKYYFDENGI MRTGLITFED NHYYFNEDGI MQYGYLNIED  2280
KTFYFSEDGI MQIGVFNTPD GFKYFAHQNT LDENFEGESI NYTGWLDLDE KRYYFTDEYI  2340
AATGSVIIDG EEYYFDPDTA QLVISE                                      2366

SEQ ID NO: 5           moltype = AA  length = 1580
FEATURE                Location/Qualifiers
source                 1..1580
                       mol_type = protein
                       organism = Clostridium difficile
```

```
SEQUENCE: 5
ESKKYGPLKT EDDKILVPID DLVISEIDFN NNSIKLGTCN ILAMEGGSGH TVTGNIDHFF  60
SSPSISSHIP SLSIYSAIGI ETENLDFSKK IMMLPNAPSR VFWWETGAVP GLRSLENDGT  120
RLLDSIRDLY PGKFYWRFYA FFDYAITTLK PVYEDTNIKI KLDKDTRNFI MPTITTNEIR  180
NKLSYSFDGA GGTYSLLLSS YPISTNINLS KDDLWIFNID NEVREISIEN GTIKKGKLIK  240
DVLSKIDINK NKLIIGNQTI DFSGDIDNKD RYIFLTCELD DKISLIIEIN LVAKSYSLLL  300
SGDKNYLISN LSNIIEKINT LGLDSKNIAY NYTDESNNKY FGAISKTSQK SIIHYKKDSK  360
NILEFYNDST LEFNSKDFIA EDINVFMKDD INTITGKYYV DNNTDKSIDF SISLVSKNQV  420
KVNGLYLNES VYSSYLDFVK NSDGHHNTSN FMNLFLDNIS FWKLFGFENI NFVIDKYFTL  480
VGKTNLGYVE FICDNNKNID IYFGEWKTSS SKSTIFSGNG RNVVVEPIYN PDTGEDISTS  540
LDFSYEPLYG IDRYINKVLI APDLYTSLIN INTNYYSNEY YPEIIVLNPN TFHKKVNINL  600
DSSSFEYKWS TEGSDFILVR YLEESNKKIL QKIRIKGILS NTQSFNKMSI DFKDIKKLSL  660
GYIMSNFKSF NSENELDRDH LGFKIIDNKT YYYDEDSKLV KGLININNSL FYFDPIEFNL  720
VTGWQTINGK KYYFDINTGA ALISYKIING KHFYFNNDGV MQLGVFKGPD GFEYFAPANT  780
QNNNIEGQAI VYQSKFLTLN GKKYYFDNDS KAVTGWRIIN NEKYYFNPNN AIAAVGLQVI  840
DNNKYYFNPD TAIISKGWQT VNGSRYYFDT DTAIAFNGYK TIDGKHFYFD SDCVVKIGVF  900
STSNGFEYFA PANTYNNNIE GQAIVYQSKF LTLNGKKYYF DNNSKAVTGW QTIDSKKYYF  960
NTNTAEAATG WQTIDGKKYY FNTNTAEAAT GWQTIDGKKY YFNTNTAIAS TGYTIINGKH  1020
FYFNTDGIMQ IGVFKGPNGF EYFAPANTDA NNIEGQAILY QNEFLTLNGK KYYFGSDSKA  1080
VTGWRIINNK KYYFNPNNAI AAIHLCTINN DKYYFSYDGI LQNGYITIER NNFYFDANNE  1140
SKMVTGVFKG PNGFEYFAPA NTHNNNIEGQ AIVYQNKFLT LNGKKYYFDN DSKAVTGWQT  1200
IDGKKYYFNL NTAEAATGWQ TIDGKKYYFN LNTAEAATGW QTIDGKKYYF NTNTFIASTG  1260
YTSINGKHFY FNTDGIMQIG VFKGPNGFEY FAPANTHNNN IEGQAILYQN KFLTLNGKKY  1320
YFGSDSKAVT GLRTIDGKKY YFNTNTAVAV TGWQTINGKK YYFNTNTSIA STGYTIISGK  1380
HFYFNTDGIM QIGVFKGPDG FEYFAPANTD ANNIEGQAIR YQNRFLYLHD NIYYFGNNSK  1440
AATGWVTIDG NRYYFEPNTA MGANGYKTID NKNFYFRNGL PQIGVFKGSN GFEYFAPANT  1500
DANNIEGQAI RYQNRFLHLL GKIYYFGNNS KAVTGWQTIN GKVYYFMPDT AMAAAGGLFE  1560
IDGVIYFFGV DGVKAPGIYG                                              1580

SEQ ID NO: 6            moltype = AA  length = 1580
FEATURE                 Location/Qualifiers
source                  1..1580
                        mol_type = protein
                        organism = Clostridium difficile
SEQUENCE: 6
ESKKYGPLKT EDDKILVPID DLVISEIDFN NNSIKLGTCN ILAMEGGSGH TVTGNIDHFF  60
SSPSISSHIP SLSIYSAIGI ETENLDFSKK IMMLPNAPSR VFWWETGAVP GLRSLENDGT  120
RLLDSIRDLY PGKFYWRFYA FFDYAITTLK PVYEDTNIKI KLDKDTRNFI MPTITTNEIR  180
NKLSYSFDGA GGTYSLLLSS YPISTNINLS KDDLWIFNID NEVREISIEN GTIKKGKLIK  240
DVLSKIDINK NKLIIGNQTI DFSGDIDNKD RYIFLTCELD DKISLIIEIN LVAKSYSLLL  300
SGDKNYLISN LSNTIEKINT LGLDSKNIAY NYTDESNNKY FGAISKTSQK SIIHYKKDSK  360
NILEFYNDST LEFNSKDFIA EDINVFMKDD INTITGKYYV DNNTDKSIDF SISLVSKNQV  420
KVNGLYLNES VYSSYLDFVK NSDGHHNTSN FMNLFLDNIS FWKLFGFENI NFVIDKYFTL  480
VGKTNLGYVE FICDNNKNID IYFGEWKTSS SKSTIFSGNG RNVVVEPIYN PDTGEDISTS  540
LDFSYEPLYG IDRYINKVLI APDLYTSLIN INTNYYSNEY YPEIIVLNPN TFHKKVNINL  600
DSSSFEYKWS TEGSDFILVR YLEESNKKIL QKIRIKGILS NTQSFNKMSI DFKDIKKLSL  660
GYIMSNFKSF NSENELDRDH LGFKIIDNKT YYYDEDSKLV KGLININNSL FYFDPIEFNL  720
VTGWQTINGK KYYFDINTGA ALTSYKIING KHFYFNNDGV MQLGVFKGPD GFEYFAPANT  780
QNNNIEGQAI VYQSKFLTLN GKKYYFDNNS KAVTGWRIIN NEKYYFNPNN AIAAVGLQVI  840
DNNKYYFNPD TAIISKGWQT VNGSRYYFDT DTAIAFNGYK TIDGKHFYFD SDCVVKIGVF  900
STSNGFEYFA PANTYNNNIE GQAIVYQSKF LTLNGKKYYF DNNSKAVTGL QTIDSKKYYF  960
NTNTAEAATG WQTIDGKKYY FNTNTAEAAT GWQTIDGKKY YFNTNTAIAS TGYTIINGKH  1020
FYFNTDGIMQ IGVFKGPNGF EYFAPANTDA NNIEGQAILY QNEFLTLNGK KYYFGSDSKA  1080
VTGWRIINNK KYYFNPNNAI AAIHLCTINN DKYYFSYDGI LQNGYITIER NNFYFDANNE  1140
SKMVTGVFKG PNGFEYFAPA NTHNNNIEGQ AIVYQNKFLT LNGKKYYFDN DSKAVTGWQT  1200
IDGKKYYFNL NTAEAATGWQ TIDGKKYYFN LNTAEAATGW QTIDGKKYYF NTNTFIASTG  1260
YTSINGKHFY FNTDGIMQIG VFKGPNGFEY FAPANTDANN IEGQAILYQN KFLTLNGKKY  1320
YFGSDSKAVT GLRTIDGKKY YFNTNTAVAV TGWQTINGKK YYFNTNTSIA STGYTIISGK  1380
HFYFNTDGIM QIGVFKGPDG FEYFAPANTD ANNIEGQAIR YQNRFLYLHD NIYYFGNNSK  1440
AATGWVTIDG NRYYFEPNTA MGANGYKTID NKNFYFRNGL PQIGVFKGSN GFEYFAPANT  1500
DANNIEGQAI RYQNRFLHLL GKIYYFGNNS KAVTGWQTIN GKVYYFMPDT AMAAAGGLFE  1560
IDGVIYFFGV DGVKAPGIYG                                              1580

SEQ ID NO: 7            moltype = AA  length = 1941
FEATURE                 Location/Qualifiers
source                  1..1941
                        mol_type = protein
                        organism = Clostridium difficile
SEQUENCE: 7
IMSDLSSKEY IFFDSIDNKL KAKSKNIPGL ASISEDIKTL LLDASVSPDT KFILNNLKLN  60
IESSIGDYIY YEKLEPVKNI IHNSIDDLID EFNLLENVSD ELYELKKLNN LDEKYLISFE  120
DISKNNSTYS VRFINKSNGE SVYVETEKEI FSKYSEHITK EISTIKNSII TDVNGNLLDN  180
IQLDHTSQVN TLNAAFFIQS LIDYSSNKDV LNDLSTSVKV QLYAQLFSTG LNTIYDSIQL  240
VNLISNAVND TINVLPTITE GIPIVSTILD GINLGAAIKE LLDEHDPLLK KELEAKVGVL  300
AINMSLSIAA TVASIVGIGA EVTIFLLPIA GISAGIPSLV NNELILHDKA TSVVNYFNHL  360
SESKKYGPLK TEDDKILVPI DDLVISEIDF NNNSIKLGTC NILAMEGGSG HTVTGNIDHF  420
FSSPSISSHI PSLSIYSAIG IETENLDFSK KIMMLPNAPS RVFWWETGAV PGLRSLENDG  480
TRLLDSIRDL YPGKFYWRFY AFFDYAITTL KPVYEDTNIK IKLDKDTRNF IMPTITTNEI  540
RNKLSYSFDG AGGTYSLLLS SYPISTNINL SKDDLWIFNI DNEVREISIE NGTIKKGKLI  600
```

-continued

```
KDVLSKIDIN KNKLIIGNQT IDFSGDIDNK DRYIFLTCEL DDKISLIIEI NLVAKSYSLL  660
LSGDKNYLIS NLSNIIEKIN TLGLDSKNIA YNYTDESNNK YFGAISKTSQ KSIIHYKKDS  720
KNILEFYNDS TLEFNSKDFI AEDINVFMKD DINTITGKYY VDNNTDKSID FSISLVSKNQ  780
VKVNGLYLNE SVYSSYLDFV KNSDGHHNTS NFMNLFLDNI SFWKLFGFEN INFVIDKYFT  840
LVGKTNLGYV EFICDNNKNI DIYFGEWKTS SSKSTIFSGN GRNVVVEPIY NPDTGEDIST  900
SLDFSYEPLY GIDRYINKVL IAPDLYTSLI NINTNYYSNE YYPEIIVLNP NTFHKKVNIN  960
LDSSSFEYKW STEGSDFILV RYLEESNKKI LQKIRIKGIL SNTQSFNKMS IDFKDIKKLS  1020
LGYIMSNFKS FNSENELDRD HLGFKIIDNK TYYYDEDSKL VKGLININNS LFYFDPIEFN  1080
LVTGWQTING KKYYFDINTG AALISYKIIN GKHFYFNNDG VMQLGVFKGP DGFEYFAPAN  1140
TQNNNIEGQA IVYQSKFLTL NGKKYYFDND SKAVTGWRII NNEKYYFNPN NAIAAVGLQV  1200
IDNNKYYFNP DTAIISKGWQ TVNGSRYYFD TDTAIAFNGY KTIDGKHFYF DSDCVVKIGV  1260
FSTSNGFEYF APANTYNNNI EGQAIVYQSK FLTLNGKKYY FDNNSKAVTG WQTIDSKKYY  1320
FNTNTAEAAT GWQTIDGKKY YFNTNTAEAA TGWQTIDGKK YYFNTNTAIA STGYTIINGK  1380
HFYFNTDGIM QIGVFKGPNG FEYFAPANTD ANNIEGQAIL YQNEFLTLNG KKYYFGSDSK  1440
AVTGWRIINN KKYYFNPNNA IAAIHLCTIN NDKYYFSYDG ILQNGYITIE RNNFYFDANN  1500
ESKMVTGVFK GPNGFEYFAP ANTHNNNIEG QAIVYQNKFL TLNGKKYYFD NDSKAVTGWQ  1560
TIDGKKYYFN LNTAEAATGW QTIDGKKYYF NLNTAEAATG WQTIDGKKYY FNTNTFIAST  1620
GYTSINGKHF YFNTDGIMQI GVFKGPNGFE YFAPANTHNN NIEGQAILYQ NKFLTLNGKK  1680
YYFGSDSKAV TGLRTIDGKK YYFNTNTAVA VTGWQTINGK KYYFNTNTSI ASTGYTIISG  1740
KHFYFNTDGI MQIGVFKGPD GFEYFAPANT DANNIEGQAI RYQNRFLYLH DNIYYFGNNS  1800
KAATGWVTID GNRYYFEPNT AMGANGYKTI DNKNFYFRNG LPQIGVFKGS NGFEYFAPAN  1860
TDANNIEGQA IRYQNRFLHL LGKIYYFGNN SKAVTGWQTI NGKVYYFMPD TAMAAAGGLF  1920
EIDGVIYFFG VDGVKAPGIY G                                           1941
```

```
SEQ ID NO: 8            moltype = AA  length = 1941
FEATURE                 Location/Qualifiers
source                  1..1941
                        mol_type = protein
                        organism = Clostridium difficile
SEQUENCE: 8
IMSDLSSKEY IFFDSIDNKL KAKSKNIPGL ASISEDIKTL LLDASVSPDT KFILNNLKLN  60
IESSIGDYIY YEKLEPVKNI IHNSIDDLID EFNLLENVSD ELYELKKLNN LDEKYLISFE  120
DISKNNSTYS VRFINKSNGE SVYVETEKEI FSKYSEHITK EISTIKNSII TDVNGNLLDN  180
IQLDHTSQVN TLNAAFFIQS LIDYSSNKDV LNDLSTSVKV QLYAQLFSTG LNTIYDSIQL  240
VNLISNAVND TINVLPTITE GIPIVSTILD GINLGAAIKE LLDEHDPLLK KELEAKVGVL  300
AINMSLSIAA TVASIVGIGA EVTIFLLPIA GISAGIPSLV NNELILHDKA TSVVNYFNHL  360
SESKEYGPLK TEDDKILVPI DDLVISEIDF NNNSIKLGTC NILAMEGGSG HTVTGNIDHF  420
FSSPYISSHI PSLSVYSAIG IKTENLDFSK KIMMLPNAPS RVFWWETGAV PGLRSLENNG  480
TKLLDSIRDL YPGKFYWRFY AFFDYAITTL KPVYEDTNTK IKLDKDTRNF IMPTITTDEI  540
RNKLSYSFDG AGGTYSLLLS SYPISMNINL SKDDLWIFNI DNEVREISIE NGTIKKGNLI  600
EDVLSKIDIN KNKLIIGNQT IDFSGDIDNK DRYIFLTCEL DDKISLIIEI NLVAKSYSLL  660
LSGDKNYLIS NLSNTIEKIN TLGLDSKNIA YNYTDESNNK YFGAISKTSQ KSIIHYKKDS  720
KNILEFYNGS TLEFNSKDFI AEDINVFMKD DINTITGKYY VDNNTDKSID FSISLVSKNQ  780
VKVNGLYLNE SVYSSYLDFV KNSDGHHNTS NFMNLFLNNI SFWKLFGFEN INFVIDKYFT  840
LVGKTNLGYV EFICDNNKNI DIYFGEWKTS SSKSTIFSGN GRNVVVEPIY NPDTGEDIST  900
SLDFSYEPLY GIDRYINKVL IAPDLYTSLI NINTNYYSNE YYPEIIVLNP NTFHKKVNIN  960
LDSSSFEYKW STEGSDFILV RYLEESNKKI LQKIRIKGIL SNTQSFNKMS IDFKDIKKLS  1020
LGYIMSNFKS FNSENELDRD HLGFKIIDNK TYYYDEDSKL VKGLININNS LFYFDPIESN  1080
LVTGWQTING KKYYFDINTG AASTSYKIIN GKHFYFNNNG VMQLGVFKGP DGFEYFAPAN  1140
TQNNNIEGQA IVYQSKFLTL NGKKYYFDND SKAVTGWRII NNEKYYFNPN NAIAAVGLQV  1200
IDNNKYYFNP DTAIISKGWQ TVNGSRYYFD TDTAIAFNGY KTIDGKHFYF DSDCVVKIGV  1260
FSGSNGFEYF APANTYNNNI EGQAIVYQSK FLTLNGKKYY FDNNSKAVTG WQTIDSKKYY  1320
FNTNTAEAAT GWQTIDGKKY YFNTNTAEAA TGWQTIDGKK YYFNTNTSIA STGYTIINGK  1380
YFYFNTDGIM QIGVFKVPNG FEYFAPANTH NNNIEGQAIL YQNKFLTLNG KKYYFGSDSK  1440
AITGWQTIDG KKYYFNPNNA IAATHLCTIN NDKYYFSYDG ILQNGYITIE RNNFYFDANN  1500
ESKMVTGVFK GPNGFEYFAP ANTHNNNIEG QAIVYQNKFL TLNGKKYYFD NDSKAVTGWQ  1560
TIDSKKYYFN LNTAVAVTGW QTIDGEKYYF NLNTAEAATG WQTIDGKRYY FNTNTYIAST  1620
GYTIINGKHF YFNTDGIMQI GVFKGPDGFE YFAPANTHNN NIEGQAILYQ NKFLTLNGKK  1680
YYFGSDSKAV TGLRTIDGKK YYFNTNTAVA VTGWQTINGK KYYFNTNTYI ASTGYTIISG  1740
KHFYFNTDGI MQIGVFKGPD GFEYFAPANT DANNIEGQAI RYQNRFLYLH DNIYYFGNDS  1800
KAATGWATID GNRYYFEPNT AMGANGYKTI DNKNFYFRNG LPQIGVFKGP NGFEYFAPAN  1860
TDANNIDGQA IRYQNRFLHL LGKIYYFGNN SKAVTGWQTI NSKVYYFMPD TAMAAAGGLF  1920
EIDGVIYFFG VDGVKAPGIY G                                           1941
```

```
SEQ ID NO: 9            moltype = AA  length = 1222
FEATURE                 Location/Qualifiers
source                  1..1222
                        mol_type = protein
                        organism = Clostridium difficile
SEQUENCE: 9
MPQDDLVISE IDFNNNSIVL GKCEIWRMEG GSGHTVTDDI DHFFSAPSIT YREPHLSIYD  60
VLEVQKEELD LSKDLMVLPN APNRVFAWET GWTPGLRSLE NDGTKLLDRI RDNYEGEFYW  120
RYFAFIADAL ITTLKPRYED TNIRINLDSN TRSFIVPIIT TEYIREKLSY SFYGSGGTYA  180
LSLSQYNMGI NIELSESDVW IIDVDNVVRD VTIESDKIKK GDLIEGILST LSIEENKIIL  240
NSHEINFSGE VNGSNGFVSL TFSILEGINA IIEVDLLSKS YKLLISGELK ILMLNSNHIQ  300
QKIDYIGFNS ELQKNIPYSF VDSEGKENGF INGSTKEGLF VSELPDVVLI SKVYMDDSKP  360
SFGYYSNNLK DVKVITKDNV NILTGYYLKD DIKISLSLTL QDEKTIKLNS VHLDESGVAE  420
ILKFMNRKGN TNTSDSLMSF LESMNIKSIF VNFLQSNIKF ILDANFIISG TTSIGQFEFI  480
CDENDNIQPY FIKFNTLETN YTLYVGNRQN MIVEPNYDLD DSGDISSTVI NFSQKYLYGI  540
```

-continued

```
DSCVNKVVIS PNIYTDEINI TPVYETNNTY PEVIVLDANY INEKINVNIN DLSIRYVWSN  600
DGNDFILMST SEENKVSQVK IRFVNVFKDK TLANKLSFNF SDKQDVPVSE IILSFTPSYY  660
EDGLIGYDLG LVSLYNEKFY INNFGMMVSG LIYINDSLYY FKPPVNNLIT GFVTVGDDKY  720
YFNPINGGAA SIGETIIDDK NYYFNQSGVL QTGVFSTEDG FKYFAPANTL DENLEGEAID  780
FTGKLIIDEN IYYFDDNYRG AVEWKELDGE MHYFSPETGK AFKGLNQIGD YKYYFNSDGV  840
MQKGFVSIND NKHYFDDSGV MKVGYTEIDG KHFYFAENGE MQIGVFNTED GFKYFAHHNE  900
DLGNEEGEEI SYSGILNFNN KIYYFDDSFT AVVGWKDLED GSKYYFDEDT AEAYIGLSLI  960
NDGQYYFNDD GIMQVGFVTI NDKVFYFSDS GIIESGVQNI DDNYFYIDDN GIVQIGVFDT  1020
SDGYKYFAPA NTVNDNIYGQ AVEYSGLVRV GEDVYYFGET YTIETGWIYD MENESDKYYF  1080
NPETKKACKG INLIDDIKYY FDEKGIMRTG LISFENNNYY FNENGEMQFG YINIEDKMFY  1140
FGEDGVMQIG VFNTPDGFKY FAHQNTLDEN FEGESINYTG WLDLDEKRYY FTDEYIAATG  1200
SVIIDGEEYY FDPDTAQLVI SE                                         1222

SEQ ID NO: 10          moltype = AA  length = 1222
FEATURE                Location/Qualifiers
source                 1..1222
                       mol_type = protein
                       organism = Clostridium difficile
SEQUENCE: 10
MPQDDLVISE IDFNNNSITL GKCEIWRMEG GSGHTVTDDI DHFFSAPSIT YREPHLSIYD  60
VLEVQKEELD LSKDLMVLPN APNRVFAWET GWTPGLRSLE NDGTKLLDRI RDNYEGEFYW  120
RYFAFIADAL ITTLKPRYED TNIRINLDSN TRSFIVPVIT TEYIREKLSY SFYGSGGTYA  180
LSLSQYNMNI NIELNENDTW VIDVDNVVRD VTIESDKIKK GDLIENILSK LSIEDNKIIL  240
DNHEINFSGT LNGGNGFVSL TFSILEGINA VIEVDLLSKS YKVLISGELK TLMANSNSVQ  300
QKIDYIGLNS ELQKNIPYSF MDDKGKENGF INCSTKEGLF VSELSDVVLI SKVYMDNSKP  360
LFGYCSNDLK DVKVITKDDV IILTGYYLKD DIKISLSFTI QDENTIKLNG VYLDENGVAE  420
ILKFMNKKGS TNTSDSLMSF LESMNIKSIF INSLQSNTKL ILDTNFIISG TTSIGQFEFI  480
CDKDNNIQPY FIKFNTLETK YTLYVGNRQN MIVEPNYDLD DSGDISSTVI NFSQKYLYGI  540
DSCVNKVIIS PNIYTDEINI TPIYEANNTY PEVIVLDTNY ISEKINININ DLSIRYVWSN  600
DGSDFILMST DEENKVSQVK IRFTNVFKGN TISDKISFNF SDKQDVSINK VISTFTPSYY  660
VEGLLNYDLG LISLYNEKFY INNFGMMVSG LVYINDSLYY FKPPIKNLIT GFTTIGDDKY  720
YFNPDNGGAA SVGETIIDGK NYYFSQNGVL QTGVFSTEDG FKYFAPADTL DENLEGEAID  780
FTGKLTIDEN VYYFGDNYRA AIEWQTLDDE VYYFSTDTGR AFKGLNQIGD DKFYFNSDGI  840
MQKGFVNIND KTFYFDDSGV MKSGYTEIDG KYFYFAENGE MQIGVFNTAD GFKYFAHHDE  900
DLGNEEGEAL SYSGILNFNN KIYYFDDSFT AVVGWKDLED GSKYYFDEDT AEAYIGISII  960
NDGKYYFNDS GIMQIGFVTI NNEVFYFSDS GIVESGMQNI DDNYFYIDEN GLVQIGVFDT  1020
SDGYKYFAPA NTVNDNIYGQ AVEYSGLVRV GEDVYYFGET YTIETGWIYD MENESDKYYF  1080
DPETKKAYKG INVIDDIKYY FDENGIMRTG LITFEDNHYY FNEDGIMQYG YLNIEDKTFY  1140
FSEDGIMQIG VFNTPDGFKY FAHQNTLDEN FEGESINYTG WLDLDEKRYY FTDEYIAATG  1200
SVIIDGEEYY FDPDTAQLVI SE                                         1222

SEQ ID NO: 11          moltype = AA  length = 1410
FEATURE                Location/Qualifiers
source                 1..1410
                       mol_type = protein
                       organism = Clostridium difficile
SEQUENCE: 11
NTLNAAFFIQ SLIEYNSSKE SLSNLSVAMK VQVYAQLFST GLNTITDAAK VVELVSTALD  60
ETIDLLPTLS EGLPIIATII DGVSLGAAIK ELSETSDPLL RQEIEAKIGI MAVNLTTATT  120
AIITSSLGIA SGFSILLVPL AGISAGIPSL VNNELVLRDK ATKVVDYFKH VSLVETEGVF  180
TLLDDKIMMP QDDLVISEID FNNNSIVLGK CEIWRMEGGS GHTVTDDIDH FFSAPSITYR  240
EPHLSIYDVL EVQKEELDLS KDLMVLPNAP NRVFAWETGW TPGLRSLEND GTKLLDRIRD  300
NYEGEFYWRY FAFIADALIT TLKPRYEDTN IRINLDSNTR SFIVPIITTE YIREKLSYSF  360
YGSGGTYALS LSQYNMGINI ELSESDVWII DVDNVVRDVT IESDKIKKGD LIEGILSTLS  420
IEENKIILNS HEINFSGEVN GSNGFVSLTF SILEGINAII EVDLLSKSYK LLISGELKIL  480
MLNSNHIQQK IDYIGFNSEL QKNIPYSFVD SEGKENGFIN GSTKEGLFVS ELPDVVLISK  540
VYMDDSKPSF GYYSNNLKDV KVITKDNVNI LTGYYLKDDI KISLSLTLQD EKTIKLNSVH  600
LDESGVAEIL KFMNRKGNTN TSDSLMSFLE SMNIKSIFVN FLQSNIKFIL DANFIISGTT  660
SIGQFEFICD ENDNIQPYFI KFNTLETNYT LYVGNRQNMI VEPNYDLDDS GDISSTVINF  720
SQKYLYGIDS CVNKVVISPN IYTDEINITP VYETNNTYPE VIVLDANYIN EKINVNINDL  780
SIRYVWSNDG NDFILMSTSE ENKVSQVKIR FVNVFKDKTL ANKLSFNFSD KQDVPVSEII  840
LSFTPSYYED GLIGYDLGLV SLYNEKFYIN NFGMMVSGLI YINDSLYYFK PPVNNLITGF  900
VTVGDDKYYF NPINGGAASI GETIIDDKNY YFNQSGVLQT GVFSTEDGFK YFAPANTLDE  960
NLEGEAIDFT GKLIIDENIY YFDDNYRGAV EWKELDGEMH YFSPETGKAF KGLNQIGDYK  1020
YYFNSDGVMQ KGFVSINDNK HYFDDSGVMK VGYTEIDGKH FYFAENGEMQ IGVFNTEDGF  1080
KYFAHHNEDL GNEEGEEISY SGILNFNNKI YYFDDSFTAV VGWKDLEDGS KYYFDEDTAE  1140
AYIGLSLIND GQYYFNDDGI MQVGFVTIND KVFYFSDSGI IESGVQNIDD NYFYIDDNGI  1200
VQIGVFDTSD GYKYFAPANT VNDNIYGQAV EYSGLVRVGE DVYYFGETYT IETGWIYDME  1260
NESDKYYFNP ETKKACKGIN LIDDIKYYFD EKGIMRTGLI SFENNNYYFN ENGEMQFGYI  1320
NIEDKMFYFG EDGVMQIGVF NTPDGFKYFA HQNTLDENFE GESINYTGWL DLDEKRYYFT  1380
DEYIAATGSV IIDGEEYYFD PDTAQLVISE                                 1410

SEQ ID NO: 12          moltype = AA  length = 1410
FEATURE                Location/Qualifiers
source                 1..1410
                       mol_type = protein
                       organism = Clostridium difficile
SEQUENCE: 12
NTLNAAFFIQ SLIEYNSSKE SLSNLSVAMK VQVYAQLFST GLNTITDAAK VVELVSTALD  60
```

```
ETIDLLPTLS EGLPVIATII DGVSLGAAIK ELSETSDPLL RQEIEAKIGI MAVNLTAATT  120
AIITSSLGIA SGFSILLVPL AGISAGIPSL VNNELILRDK ATKVVDYFSH ISLAESEGAF  180
TSLDDKIMMP QDDLVISEID FNNNSITLGK CEIWRMEGGS GHTVTDDIDH FFSAPSITYR  240
EPHLSIYDVL EVQKEELDLS KDLMVLPNAP NRVFAWETGW TPGLRSLEND GTKLLDRIRD  300
NYEGEFYWRY FAFIADALIT TLKPRYEDTN IRINLDSNTR SFIVPVITTE YIREKLSYSF  360
YGSGGTYALS LSQYNMNINI ELNENDTWVI DVDNVVRDVT IESDKIKKGD LIENILSKLS  420
IEDNKIILDN HEINFSGTLN GGNGFVSLTF SILEGINAVI EVDLLSKSYK VLISGELKTL  480
MANSNSVQQK IDYIGLNSEL QKNIPYSFMD DKGKENGFIN CSTKEGLFVS ELSDVVLISK  540
VYMDNSKPLF GYCSNDLKDV KVITKDDVII LTGYYLKDDI KISLSFTIQD ENTIKLNGVY  600
LDENGVAEIL KFMNKKGSTN TSDSLMSFLE SMNIKSIFIN SLQSNTKLIL DTNFIISGTT  660
SIGQFEFICD KDNNIQPYFI KFNTLETKYT LYVGNRQNMI VEPNYDLDDS GDISSTVINF  720
SQKYLYGIDS CVNKVIISPN IYTDEINITP IYEANNTYPE VIVLDTNYIS EKINININDL  780
SIRYVWSNDG SDFILMSTDE ENKVSQVKIR FTNVFKGNTI SDKISFNFSD KQDVSINKVI  840
STFTPSYYVE GLLNYDLGLI SLYNEKFYIN NFGMMVSGLV YINDSLYYFK PPIKNLITGF  900
TTIGDDKYYF NPDNGGAASV GETIIDGKNY YFSQNGVLQT GVFSTEDGFK YFAPADTLDE  960
NLEGEAIDFT GKLTIDENVY YFGDNYRAAI EWQTLDDEVY YFSTDTGRAF KGLNQIGDDK  1020
FYFNSDGIMQ KGFVNINDKT FYFDDSGVMK SGYTEIDGKY FYFAENGEMQ IGVFNTADGF  1080
KYFAHHDEDL GNEEGEALSY SGILNFNNKI YYFDDSFTAV VGWKDLEDGS KYYFDEDTAE  1140
AYIGISIIND GKYYFNDSGI MQIGFVTINN EVFYFSDSGI VESGMQNIDD NYFYIDENGL  1200
VQIGVFDTSD GYKYFAPANT VNDNIYGQAV EYSGLVRVGE DVYYFGETYT IETGWIYDME  1260
NESDKYYFDP ETKKAYKGIN VIDDIKYYFD ENGIMRTGLI TFEDNHYYFN EDGIMQYGYL  1320
NIEDKTFYFS EDGIMQIGVF NTPDGFKYFA HQNTLDENFE GESINYTGWL DLDEKRYYFT  1380
DEYIAATGSV IIDGEEYYFD PDTAQLVISE                                 1410

SEQ ID NO: 13          moltype = AA  length = 1600
FEATURE                Location/Qualifiers
source                 1..1600
                       mol_type = protein
                       organism = Clostridium difficile
SEQUENCE: 13
SIIKDISSKE YISFNPKENK ITVKSKNLPE LSTLLQEIRN NSNSSDIELE EKVMLTECEI  60
NVISNIDTQI VEERIEEAKN LTSDSINYIK DEFKLIESIS DALCDLKQQN ELEDSHFISF  120
EDISETDEGF SIRFINKETG ESIFVETEKT IFSEYANHIT EEISKIKGTI FDTVNGKLVK  180
KVNLDTTHEV NTLNAAFFIQ SLIEYNSSKE SLSNLSVAMK VQVYAQLFST GLNTITDAAK  240
VVELVSTALD ETIDLLPTLS EGLPIIATII DGVSLGAAIK ELSETSDPLL RQEIEAKIGI  300
MAVNLTTATT AIITSSLGIA SGFSILLVPL AGISAGIPSL VNNELVLRDK ATKVVDYFKH  360
VSLVETEGVF TLLDDKIMMP QDDLVISEID FNNNSIVLGK CEIWRMEGGS GHTVTDDIDH  420
FFSAPSITYR EPHLSIYDVL EVQKEELDLS KDLMVLPNAP NRVFAWETGW TPGLRSLEND  480
GTKLLDRIRD NYEGEFYWRY FAFIADALIT TLKPRYEDTN IRINLDSNTR SFIVPIITTE  540
YIREKLSYSF YGSGGTYALS LSQYNMGINI ELSESDVWII DVDNVVRDVT IESDKIKKGD  600
LIEGILSTLS IEENKIILNS HEINFSGEVN GSNGFVSLTF SILEGINAII EVDLLSKSYK  660
LLISGELKIL MLNSNHIQQK IDYIGFNSEL QKNIPYSFVD SEGKENGFIN GSTKEGLFVS  720
ELPDVVLISK VYMDDSKPSF GYYSNNLKDV KVITKDNVNI LTGYYLKDDI KISLSLTLQD  780
EKTIKLNSVH LDESGVAEIL KFMNRKGNTN TSDSLMSFLE SMNIKSIFVN FLQSNIKFIL  840
DANFIISGTT SIGQFEFICD ENDNIQPYFI KFNTLETNYT LYVGNRQNMI VEPNYDLDDS  900
GDISSTVINF SQKYLYGIDS CVNKVVISPN IYTDEINITP VYETNNTYPE VIVLDANYIN  960
EKINVNINDL SIRYVWSNDG NDFILMSTSE ENKVSQVKIR FVNVFKDKTL ANKLSFNFSD  1020
KQDVPVSEII LSFTPSYYED GLIGYDLGLV SLYNEKFYIN NFGMMVSGLI YINDSLYYFK  1080
PPVNNLITGF VTVGDDKYYF NPINGGAASI GETIIDDKNY YFNQSGVLQT GVFSTEDGFK  1140
YFAPANTLDE NLEGEAIDFT GKLIIDENIY YFDDNYRGAV EWKELDGEMH YFSPETGKAF  1200
KGLNQIGDYK YYFNSDGVMQ KGFVSINDNK HYFDDSGVMK VGYTEIDGKH FYFAENGEMQ  1260
IGVFNTEDGF KYFAHHNEDL GNEEGEEISY SGILNFNNKI YYFDDSFTAV VGWKDLEDGS  1320
KYYFDEDTAE AYIGLSLIND GQYYFNDDGI MQVGFVTIND KVFYFSDSGI IESGVQNIDD  1380
NYFYIDDNGI VQIGVFDTSD GYKYFAPANT VNDNIYGQAV EYSGLVRVGE DVYYFGETYT  1440
IETGWIYDME NESDKYYFNP ETKKACKGIN LIDDIKYYFD EKGIMRTGLI SFENNNYYFN  1500
ENGEMQFGYI NIEDKMFYFG EDGVMQIGVF NTPDGFKYFA HQNTLDENFE GESINYTGWL  1560
DLDEKRYYFT DEYIAATGSV IIDGEEYYFD PDTAQLVISE                      1600

SEQ ID NO: 14          moltype = AA  length = 1600
FEATURE                Location/Qualifiers
source                 1..1600
                       mol_type = protein
                       organism = Clostridium difficile
SEQUENCE: 14
SIIKDISSKE YISFNPKENK IIVKSKNLPE LSTLLQEIRN NSNSSDIELE EKVMLAECEI  60
NVISNIDTQV VEGRIEEAKS LTSDSINYIK NEFKLIESIS DALYDLKQQN ELEESHFISF  120
EDILETDEGF SIRFIDKETG ESIFVETEKA IFSEYANHIT EEISKIKGTI FDTVNGKLVK  180
KVNLDATHEV NTLNAAFFIQ SLIEYNSSKE SLSNLSVAMK VQVYAQLFST GLNTITDAAK  240
VVELVSTALD ETIDLLPTLS EGLPVIATII DGVSLGAAIK ELSETSDPLL RQEIEAKIGI  300
MAVNLTAATT AIITSSLGIA SGFSILLVPL AGISAGIPSL VNNELILRDK ATKVVDYFSH  360
ISLAESEGAF TSLDDKIMMP QDDLVISEID FNNNSITLGK CEIWRMEGGS GHTVTDDIDH  420
FFSAPSITYR EPHLSIYDVL EVQKEELDLS KDLMVLPNAP NRVFAWETGW TPGLRSLEND  480
GTKLLDRIRD NYEGEFYWRY FAFIADALIT TLKPRYEDTN IRINLDSNTR SFIVPVITTE  540
YIREKLSYSF YGSGGTYALS LSQYNMNINI ELNENDTWVI DVDNVVRDVT IESDKIKKGD  600
LIENILSKLS IEDNKIILDN HEINFSGTLN GGNGFVSLTF SILEGINAVI EVDLLSKSYK  660
VLISGELKTL MANSNSVQQK IDYIGLNSEL QKNIPYSFMD DKGKENGFIN CSTKEGLFVS  720
ELSDVVLISK VYMDNSKPLF GYCSNDLKDV KVITKDDVII LTGYYLKDDI KISLSFTIQD  780
ENTIKLNGVY LDENGVAEIL KFMNKKGSTN TSDSLMSFLE SMNIKSIFIN SLQSNTKLIL  840
DTNFIISGTT SIGQFEFICD KDNNIQPYFI KFNTLETKYT LYVGNRQNMI VEPNYDLDDS  900
```

```
GDISSTVINF SQKYLYGIDS CVNKVIISPN IYTDEINITP IYEANNTYPE VIVLDTNYIS  960
EKININDL SIRYVWSNDG SDFILMSTDE ENKVSQVKIR FTNVFKGNTI SDKISFNFSD  1020
KQDVSINKVI STFTPSYYVE GLLNYDLGLI SLYNEKFYIN NFGMMVSGLV YINDSLYYFK  1080
PPIKNLITGF TTIGDDKYYF NPDNGGAASV GETIIDGKNY YFSQNGVLQT GVFSTEDGFK  1140
YFAPADTLDE NLEGEAIDFT GKLTIDENVY YFGDNYRAAI EWQTLDDEVY YFSTDTGRAF  1200
KGLNQIGDDK FYFNSDGIMQ KGFVNINDKT FYFDDSGVMK SGYTEIDGKY FYFAENGEMQ  1260
IGVFNTADGF KYFAHHDEDL GNEEGEALSY SGILNFNNKI YYFDDSFTAV VGWKDLEDGS  1320
KYYFDEDTAE AYIGISIIND GKYYFNDSGI MQIGFVTINN EVFYFSDSGI VESGMQNIDD  1380
NYFYIDENGL VQIGVFDTSD GYKYFAPANT VNDNIYGQAV EYSGLVRVGE DVYYFGETYT  1440
IETGWIYDME NESDKYYFDP ETKKAYKGIN VIDDIKYYFD ENGIMRTGLI TFEDNHYYFN  1500
EDGIMQYGYL NIEDKTFYFS EDGIMQIGVF NTPDGFKYFA HQNTLDENFE GESINYTGWL  1560
DLDEKRYYFT DEYIAATGSV IIDGEEYYFD PDTAQLVISE                      1600

SEQ ID NO: 15          moltype = AA  length = 1756
FEATURE                Location/Qualifiers
source                 1..1756
                       mol_type = protein
                       organism = Clostridium difficile
SEQUENCE: 15
NTLNAAFFIQ SLIEYNSSKE SLSNLSVAMK VQVYAQLFST GLNTITDAAK VVELVSTALD  60
ETIDLLPTLS EGLPIIATII DGVSLGAAIK ELSETSDPLL RQEIEAKIGI MAVNLTTATT  120
AIITSSLGIA SGFSILLVPL AGISAGIPSL VNNELVLRDK ATKVVDYFKH VSLVETEGVF  180
TLLDDKIMMP QDDLVISEID FNNNSIVLGK CEIWRMEGGS GHTVTDDIDH FFSAPSITYR  240
EPHLSIYDVL EVQKEELDLS KDLMVLPNAP NRVFAWETGW TPGLRSLEND GTKLLDRIRD  300
NYEGEFYWRY FAFIADALIT TLKPRYEDTN IRINLDSNTR SFIVPIITTE YIREKLSYSF  360
YGSGGTYALS LSQYNMGINI ELSESDVWII DVDNVVRDVT IESDKIKKGD LIEGILSTLS  420
IEENKIILNS HEINFSGEVN GSNGFVSLTF SILEGINAII EVDLLSKSYK LLISGELKIL  480
MLNSNHIQQK IDYIGFNSEL QKNIPYSFVD SEGKENGFIN GSTKEGLFVS ELPDVVLISK  540
VYMDDSKPSF GYYSNNLKDV KVITKDNVNI LTGYYLKDDI KISLSLTLQD EKTIKLNSVH  600
LDESGVAEIL KFMNRKGNTN TSDSLMSFLE SMNIKSIFVN FLQSNIKFIL DANFIISGTT  660
SIGQFEFICD ENDNIQPYFI KFNTLETNYT LYVGNRQNMI VEPNYDLDDS GDISSTVINF  720
SQKYLYGIDS CVNKVVISPN IYTDEINITP VYETNNTYPE VIVLDANYIN EKINVNINDL  780
SIRYVWSNDG NDFILMSTSE ENKVSQVKIR FVNVFKDKTL ANKLSFNFSD KQDVPVSEII  840
LSFTPSYYED GLIGYDLGLV SLYNEKFYIN NFGMMVSGLI YINDSLYYFK PPVNNLVTGW  900
QTINGKKYYF DINTGAALIS YKIINGKHFY FNNDGVMQLG VFKGPDGFEY FAPANTQNNN  960
IEGQAIVYQS KFLTLNGKKY YFDNDSKAVT GWRIINNEKY YFNPNNAIAA VGLQVIDNNK  1020
YYFNPDTAII SKGWQTVNGS RYYFDTDTAI AFNGYKTIDG KHFYFDSDCV VKIGVFSTSN  1080
GFEYFAPANT YNNNIEGQAI VYQSKFLTLN GKKYYFDNNS KAVTGWQTID SKKYYFNTNT  1140
AEAATGWQTI DGKKYYFNTN TAEAATGWQT IDGKKYYFNT NTAIASTGYT IINGKHFYFN  1200
TDGIMQIGVF KGPNGFEYFA PANTDANNIE GQAILYQNEF LTLNGKKYYF GSDSKAVTGW  1260
RIINNKKYYF NPNNAIAAIH LCTINNDKYY FSYDGILQNG YITIERNNFY FDANNESKMV  1320
TGVFKGPNGF EYFAPANTHN NNIEGQAIVY QNKFLTLNGK KYYFDNDSKA VTGWQTIDGK  1380
KYYFNLNTAE AATGWQTIDG KKYYFNLNTA EAATGWQTID GKKYYFNTNT FIASTGYTSI  1440
NGKHFYFNTD GIMQIGVFKG PNGFEYFAPA NTHNNNIEGQ AILYQNKFLT LNGKKYYFGS  1500
DSKAVTGLRT IDGKKYYFNT NTAVAVTGWQ TINGKKYYFN TNTSIASTGY TIISGKHFYF  1560
NTDGIMQIGV FKGPDGFEYF APANTDANNI EGQAIRYQNR FLYLHDNIYY FGNNSKAATG  1620
WVTIDGNRYY FEPNTAMGAN GYKTIDNKNF YFRNGLPQIG VFKGSNGFEY FAPANTDANN  1680
IEGQAIRYQN RFLHLLGKIY YFGNNSKAVT GWQTINGKVY YFMPDTAMAA AGGLFEIDGV  1740
IYFFGVDGVK APGIYG                                                1756

SEQ ID NO: 16          moltype = AA  length = 1595
FEATURE                Location/Qualifiers
source                 1..1595
                       mol_type = protein
                       organism = Clostridium difficile
SEQUENCE: 16
IMSDLSSKEY IFFDSIDNKL KAKSKNIPGL ASISEDIKTL LLDASVSPDT KFILNNLKLN  60
IESSIGDYIY YEKLEPVKNI IHNSIDDLID EFNLLENVSD ELYELKKLNN LDEKYLISFE  120
DISKNNSTYS VRFINKSNGE SVYVETEKEI FSKYSEHITK EISTIKNSII TDVNGNLLDN  180
IQLDHTSQVN TLNAAFFIQS LIDYSSNKDV LNDLSTSVKV QLYAQLFSTG LNTIYDSIQL  240
VNLISNAVND TINVLPTITE GIPIVSTILD GINLGAAIKE LLDEHDPLLK KELEAKVGVL  300
AINMSLSIAA TVASIVGIGA EVTIFLLPIA GISAGIPSLV NNELILHDKA TSVVNYFNHL  360
SESKKYGPLK TEDDKILVPI DDLVISEIDF NNNSIKLGTC NILAMEGGSG HTVTGNIDHF  420
FSSPSISSHI PSLSIYSAIG IETENLDFSK KIMMLPNAPS RVFWWETGAV PGLRSLENDG  480
TRLLDSIRDL YPGKFYWRFY AFFDYAITTL KPVYEDTNIK IKLDKDTRNF IMPTITTNEI  540
RNKLSYSFDG AGGTYSLLLS SYPISTNINL SKDDLWIFNI DNEVREISIE NGTIKKGKLI  600
KDVLSKIDIN KNKLIIGNQT IDFSGDIDNK DRYIFLTCEL DDKISLIIEI NLVAKSYSLL  660
LSGDKNYLIS NLSNIIEKIN TLGLDSKNIA YNYTDESNNK YFGAISKTSQ KSIIHYKKDS  720
KNILEFYNDS TLEFNSKDFI AEDINVFMKD DINTITGKYY VDNNTDKSID FSISLVSKNQ  780
VKVNGLYLNE SVYSSYLDFV KNSDGHHNTS NFMNLFLDNI SFWKLFGFEN INFVIDKYFT  840
LVGKTNLGYV EFICDNNKNI DIYFGEWKTS SSKSTIFSGN GRNVVVEPIY NPDTGEDIST  900
SLDFSYEPLY GIDRYINKVL IAPDLYTSLI NINTNYYSNE YYPEIIVLNP NTFHKKVNIN  960
LDSSSFEYKW STEGSDFILV RYLEESNKKI LQKIRIKGIL SNTQSFNKMS IDFKDIKKLS  1020
LGYIMSNFKS FNSENELDRD HLGFKIIDNK TYYYDEDSKL VKGLININNS LFYFDPIEFN  1080
LITGFVTVGD DKYYFNPING GAASIGETII DDKNYYFNQS GVLQTGVFST EDGFKYFAPA  1140
NTLDENLEGE AIDFTGKLII DENIYYFDDN YRGAVEWKEL DGEMHYFSPE TGKAFKGLNQ  1200
IGDYKYYFNS DGVMQKGFVS INDNKHYFDD SGVMKVGYTE IDGKHFYFAE NGEMQIGVFN  1260
TEDGFKYFAH HNEDLGNEEG EEISYSGILN FNNKIYYFDD SFTAVVGWKD LEDGSKYYFD  1320
EDTAEAYIGL SLINDGQYYF NDDGIMQVGF VTINDKVFYF SDSGIIESGV QNIDDNYFYI  1380
```

```
DDNGIVQIGV FDTSDGYKYF APANTVNDNI YGQAVEYSGL VRVGEDVYYF GETYTIETGW  1440
IYDMENESDK YYFNPETKKA CKGINLIDDI KYYFDEKGIM RTGLISFENN NYYFNENGEM  1500
QFGYINIEDK MFYFGEDGVM QIGVFNTPDG FKYFAHQNTL DENFEGESIN YTGWLDLDEK  1560
RYYFTDEYIA ATGSVIIDGE EYYFDPDTAQ LVISE                             1595

SEQ ID NO: 17          moltype = AA  length = 1595
FEATURE                Location/Qualifiers
source                 1..1595
                       mol_type = protein
                       organism = Clostridium difficile
SEQUENCE: 17
IMSDLSSKEY IFFDSIDNKL KAKSKNIPGL ASISEDIKTL LLDASVSPDT KFILNNLKLN  60
IESSIGDYIY YEKLEPVKNI IHNSIDDLID EFNLLENVSD ELYELKKLNN LDEKYLISFE  120
DISKNNSTYS VRFINKSNGE SVYVETEKEI FSKYSEHITK EISTIKNSII TDVNGNLLDN  180
IQLDHTSQVN TLNAAFFIQS LIDYSSNKDV LNDLSTSVKV QLYAQLFSTG LNTIYDSIQL  240
VNLISNAVND TINVLPTITE GIPIVSTILD GINLGAAIKE LLDEHDPLLK KELEAKVGVL  300
AINMSLSIAA TVASIVGIGA EVTIFLLPIA GISAGIPSLV NNELILHDKA TSVVNYFNHL  360
SESKKYGPLK TEDDKILVPI DDLVISEIDF NNNSIKLGTC NILAMEGGSG HTVTGNIDHF  420
FSSPSISSHI PSLSIYSAIG IETENLDFSK KIMMLPNAPS RVFWWETGAV PGLRSLENDG  480
TRLLDSIRDL YPGKFYWRFY AFFDYAITTL KPVYEDTNIK IKLDKDTRNF IMPTITTNEI  540
RNKLSYSFDG AGGTYSLLLS SYPISTNINL SKDDLWIFNI DNEVREISIE NGTIKKGKLI  600
KDVLSKIDIN KNKLIIGNQT IDFSGDIDNK DRYIFLTCEL DDKISLIIEI NLVAKSYSLL  660
LSGDKNYLIS NLSNIIEKIN TLGLDSKNIA YNYTDESNNK YFGAISKTSQ KSIIHYKKDS  720
KNILEFYNDS TLEFNSKDFI AEDINVFMKD DINTITGKYY VDNNTDKSID FSISLVSKNQ  780
VKVNGLYLNE SVYSSYLDFV KNSDGHHNTS NFMNLFLDNI SFWKLFGFEN INFVIDKYFT  840
LVGKTNLGYV EFICDNNKNI DIYFGEWKTS SSKSTIFSGN GRNVVVEPIY NPDTGEDIST  900
SLDFSYEPLY GIDRYINKVL IAPDLYTSLI NINTNYYSNE YYPEIIVLNP NTFHKKVNIN  960
LDSSSFEYKW STEGSDFILV RYLEESNKKI LQKIRIKGIL SNTQSFNKMS IDFKDIKKLS  1020
LGYIMSNFKS FNSENELDRD HLGFKIIDNK TYYYDEDSKL VKGLININNS LFYFDPIEFN  1080
LITGFTTIGD DKYYFNPDNG GAASVGETII DGKNYYFSQN GVLQTGVFST EDGFKYFAPA  1140
DTLDENLEGE AIDFTGKLTI DENVYYFGDN YRAAIEWQTL DDEVYYFSTD TGRAFKGLNQ  1200
IGDDKFYFNS DGIMQKGFVN INDKTFYFDD SGVMKSGYTE IDGKYFYFAE NGEMQIGVFN  1260
TADGFKYFAH HDEDLGNEEG EALSYSGILN FNNKIYYFDD SFTAVVGWKD LEDGSKYYFD  1320
EDTAEAYIGI SIINDGKYYF NDSGIMQIGF VTINNEVFYF SDSGIVESGM QNIDDNYFYI  1380
DENGLVQIGV FDTSDGYKYF APANTVNDNI YGQAVEYSGL VRVGEDVYYF GETYTIETGW  1440
IYDMENESDK YYFDPETKKA YKGINVIDDI KYYFDENGIM RTGLITFEDN HYYFNEDGIM  1500
QYGYLNIEDK TFYFSEDGIM QIGVFNTPDG FKYFAHQNTL DENFEGESIN YTGWLDLDEK  1560
RYYFTDEYIA ATGSVIIDGE EYYFDPDTAQ LVISE                             1595

SEQ ID NO: 18          moltype = AA  length = 2493
FEATURE                Location/Qualifiers
REGION                 1..2493
                       note = Fusion protein
source                 1..2493
                       mol_type = protein
                       organism = synthetic construct
SEQUENCE: 18
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALV PRGSVTSLYK KAGSAAAPFT MIMSDLSSKE  540
YIFFDSIDNK LKAKSKNIPG LASISEDIKT LLLDASVSPD TKFILNNLKL NIESSIGDYI  600
YYEKLEPVKN IIHNSIDDLI DEFNLLENVS DELYELKKLN NLDEKYLISF EDISKNNSTY  660
SVRFINKSNG ESVYVETEKE IFSKYSEHIT KEISTIKNSI ITDVNGNLLD NIQLDHTSQV  720
NTLNAAFFIQ SLIDYSSNKD VLNDLSTSVK VQLYAQLFST GLNTIYDSIQ LVNLISNAVN  780
DTINVLPTIT EGIPIVSTIL DGINLGAAIK ELLDEHDPLL KKELEAKVGV LAINMSLSIA  840
ATVASIVGIG AEVTIFLLPI AGISAGIPSL VNNELILHDK ATSVVNYFNH LSESKKYGPL  900
KTEDDKILVP IDDLVISEID FNNNSIKLGT CNILAMEGGS GHTVTGNIDH FFSSPSISSH  960
IPSLSIYSAI GIETENLDFS KKIMMLPNAP SRVFWWETGA VPGLRSLEND GTRLLDSIRD  1020
LYPGKFYWRF YAFFDYAITT LKPVYEDTNI KIKLDKDTRN FIMPTITTNE IRNKLSYSFD  1080
GAGGTYSLLL SSYPISTNIN LSKDDLWIFN IDNEVREISI ENGTIKKGKL IKDVLSKIDI  1140
NKNKLIIGNQ TIDFSGDIDN KDRYIFLTCE LDDKISLIIE INLVAKSYSL LLSGDKNYLI  1200
SNLSNIIEKI NTLGLDSKNI AYNYTDESNN KYFGAISKTS QKSIIHYKKD SKNILEFYND  1260
STLEFNSKDF IAEDINVFMK DDINTITGKY YVDNNTDKSI DFSISLVSKN QVKVNGLYLN  1320
ESVYSSYLDF VKNSDGHHNT SNFMNLFLDN ISFWKLFGFE NINFVIDKYF TLVGKTNLGY  1380
VEFICDNNKN IDIYFGEWKT SSSKSTIFSG NGRNVVVEPI YNPDTGEDIS TSLDFSYEPL  1440
YGIDRYINKV LIAPDLYTSL ININTNYYSN EYYPEIIVLN PNTFHKKVNI NLDSSSFEYK  1500
WSTEGSDFIL VRYLEESNKK ILQKIRIKGI LSNTQSFNKM SIDFKDIKKL SLGYIMSNFK  1560
SFNSENELDR DHLGFKIIDN KTYYYDEDSK LVKGLININN SLFYFDPIEF NLVTGWQTIN  1620
GKKYYFDINT GAALISYKII NGKHFYFNND GVMQLGVFKG PDGFEYFAPA NTQNNNIEGQ  1680
AIVYQSKFLT LNGKKYYFDN DSKAVTGWRI INNEKYYFNP NNAIAAVGLQ VIDNNKYYFN  1740
PDTAIISKGW QTVNGSRYYF DTDTAIAFNG YKTIDGKHFY FDSDCVVKIG VFSTSNGFEY  1800
FAPANTYNNN IEGQAIVYQS KFLTLNGKKY YFDNNSKAVT GWQTIDSKKY YFNTNTAEAA  1860
TGWQTIDGKK YYFNTNTAEA ATGWQTIDGK KYYFNTNTAI ASTGYTIING KHFYFNTDGI  1920
```

-continued

```
MQIGVFKGPN GFEYFAPANT DANNIEGQAI LYQNEFLTLN GKKYYFGSDS KAVTGWRIIN  1980
NKKYYFNPNN AIAAIHLCTI NNDKYYFSYD GILQNGYITI ERNNFYFDAN NESKMVTGVF  2040
KGPNGFEYFA PANTHNNNIE GQAIVYQNKF LTLNGKKYYF DNDSKAVTGW QTIDGKKYYF  2100
NLNTAEAATG WQTIDGKKYY FNLNTAEAAT GWQTIDGKKY YFNTNTFIAS TGYTSINGKH  2160
FYFNTDGIMQ IGVFKGPNGF EYFAPANTHN NNIEGQAILY QNKFLTLNGK KYYFGSDSKA  2220
VTGLRTIDGK KYYFNTNTAV AVTGWQTING KKYYFNTNTS IASTGYTIIS GKHFYFNTDG  2280
IMQIGVFKGP DGFEYFAPAN TDANNIEGQA IRYQNRFLYL HDNIYYFGNN SKAATGWVTI  2340
DGNRYYFEPN TAMGANGYKT IDNKNFYFRN GLPQIGVFKG SNGFEYFAPA NTDANNIEGQ  2400
AIRYQNRFLH LLGKIYYFGN NSKAVTGWQT INGKVYYFMP DTAMAAAGGL FEIDGVIYFF  2460
GVDGVKAPGI YGGGSGGSLV PRGSGGSHHH HHH                              2493
```

```
SEQ ID NO: 19          moltype = AA  length = 2472
FEATURE                Location/Qualifiers
REGION                 1..2472
                       note = Fusion protein
source                 1..2472
                       mol_type = protein
                       organism = synthetic construct
SEQUENCE: 19
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALV PRGSVTSLYK KAGSAAAPFT MIMSDLSSKE  540
YIFFDSIDNK LKAKSKNIPG LASISEDIKT LLLDASVSPD TKFILNNLKL NIESSIGDYI  600
YYEKLEPVKN IIHNSIDDLI DEFNLLENVS DELYELKKLN NLDEKYLISF EDISKNNSTY  660
SVRFINKSNG ESVYVETEKE IFSKYSEHIT KEISTIKNSI ITDVNGNLLD NIQLDHTSQV  720
NTLNAAFFIQ SLIDYSSNKD VLNDLSTSVK VQLYAQLFST GLNTIYDSIQ LVNLISNAVN  780
DTINVLPTIT EGIPIVSTIL DGINLGAAIK ELLDEHDPLL KKELEAKVGV LAINMSLSIA  840
ATVASIVGIG AEVTIFLLPI AGISAGIPSL VNNELILHDK ATSVVNYFNH LSESKKYGPL  900
KTEDDKILVP IDDLVISEID FNNNSIKLGT CNILAMEGGS GHTVTGNIDH FFSSPSISSH  960
IPSLSIYSAI GIETENLDFS KKIMMLPNAP SRVFWWETGA VPGLRSLEND GTRLLDSIRD  1020
LYPGKFYWRF YAFFDYAITT LKPVYEDTNI KIKLDKDTRN FIMPTITTNE IRNKLSYSFD  1080
GAGGTYSLLL SSYPISTNIN LSKDDLWIFN IDNEVREISI ENGTIKKGKL IKDVLSKIDI  1140
NKNKLIIGNQ TIDFSGDIDN KDRYIFLTCE LDDKISLIIE INLVAKSYSL LLSGDKNYLI  1200
SNLSNIIEKI NTLGLDSKNI AYNYTDESNN KYFGAISKTS QKSIIHYKKD SKNILEFYND  1260
STLEFNSKDF IAEDINVFMK DDINTITGKY YVDNNTDKSI DFSISLVSKN QVKVNGLYLN  1320
ESVYSSYLDF VKNSDGHHNT SNFMNLFLDN ISFWKLFGFE NINFVIDKYF TLVGKTNLGY  1380
VEFICDNNKN IDIYFGEWKT SSSKSTIFSG NGRNVVVEPI YNPDTGEDIS TSLDFSYEPL  1440
YGIDRYINKV LIAPDLYTSL ININTNYYSN EYYPEIIVLN PNTFHKKVNI NLDSSSFEYK  1500
WSTEGSDFIL VRYLEESNKK ILQKIRIKGI LSNTQSFNKM SIDFKDIKKL SLGYIMSNFK  1560
SFNSENELDR DHLGFKIIDN KTYYYDEDSK LVKGLININN SLFYFDPIEF NLVTGWQTIN  1620
GKKYYFDINT GAALISYKII NGKHFYFNND GVMQLGVFKG PDGFEYFAPA NTQNNNIEGQ  1680
AIVYQSKFLT LNGKKYYFDN DSKAVTGWRI INNEKYYFNP NNAIAAVGLQ VIDNNKYYFN  1740
PDTAIISKGW QTVNGSRYYF DTDTAIAFNG YKTIDGKHFY FDSDCVVKIG VFSTSNGFEY  1800
FAPANTYNNN IEGQAIVYQS KFLTLNGKKY YFDNNSKAVT GWQTIDSKKY YFNTNTAEAA  1860
TGWQTIDGKK YYFNTNTAEA ATGWQTIDGK KYYFNTNTAI ASTGYTIING KHFYFNTDGI  1920
MQIGVFKGPN GFEYFAPANT DANNIEGQAI LYQNEFLTLN GKKYYFGSDS KAVTGWRIIN  1980
NKKYYFNPNN AIAAIHLCTI NNDKYYFSYD GILQNGYITI ERNNFYFDAN NESKMVTGVF  2040
KGPNGFEYFA PANTHNNNIE GQAIVYQNKF LTLNGKKYYF DNDSKAVTGW QTIDGKKYYF  2100
NLNTAEAATG WQTIDGKKYY FNLNTAEAAT GWQTIDGKKY YFNTNTFIAS TGYTSINGKH  2160
FYFNTDGIMQ IGVFKGPNGF EYFAPANTHN NNIEGQAILY QNKFLTLNGK KYYFGSDSKA  2220
VTGLRTIDGK KYYFNTNTAV AVTGWQTING KKYYFNTNTS IASTGYTIIS GKHFYFNTDG  2280
IMQIGVFKGP DGFEYFAPAN TDANNIEGQA IRYQNRFLYL HDNIYYFGNN SKAATGWVTI  2340
DGNRYYFEPN TAMGANGYKT IDNKNFYFRN GLPQIGVFKG SNGFEYFAPA NTDANNIEGQ  2400
AIRYQNRFLH LLGKIYYFGN NSKAVTGWQT INGKVYYFMP DTAMAAAGGL FEIDGVIYFF  2460
GVDGVKAPGI YG                                                     2472
```

```
SEQ ID NO: 20          moltype = AA  length = 2084
FEATURE                Location/Qualifiers
REGION                 1..2084
                       note = Fusion protein
source                 1..2084
                       mol_type = protein
                       organism = synthetic construct
SEQUENCE: 20
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LVPRGSVTSL YKKAGSAAAP FTMIMSDLSS KEYIFFDSID NKLKAKSKNI PGLASISEDI  180
KTLLLDASVS PDTKFILNNL KLNIESSIGD YIYYEKLEPV KNIIHNSIDD LIDEFNLLEN  240
VSDELYELKK LNNLDEKYLI SFEDISKNNS TYSVRFINKS NGESVYVETE KEIFSKYSEH  300
ITKEISTIKN SIITDVNGNL LDNIQLDHTS QVNTLNAAFF IQSLIDYSSN KDVLNDLSTS  360
VKVQLYAQLF STGLNTIYDS IQLVNLISNA VNDTINVLPT ITEGIPIVST ILDGINLGAA  420
IKELLDEHDP LLKKELEAKV GVLAINMSLS IAATVASIVG IGAEVTIFLL PIAGISAGIP  480
SLVNNELILH DKATSVVNYF NHLSESKKYG PLKTEDDKIL VPIDDLVISE IDFNNNSIKL  540
```

-continued

```
GTCNILAMEG GSGHTVTGNI DHFFSSPSIS SHIPSLSIYS AIGIETENLD FSKKIMMLPN  600
APSRVFWWET GAVPGLRSLE NDGTRLLDSI RDLYPGKFYW RFYAFFDYAI TTLKPVYEDT  660
NIKIKLDKDT RNFIMPTITT NEIRNKLSYS FDGAGGTYSL LLSSYPISTN INLSKDDLWI  720
FNIDNEVREI SIENGTIKKG KLIKDVLSKI DINKNKLIIG NQTIDFSGDI DNKDRYIFLT  780
CELDDKISLI IEINLVAKSY SLLLSGDKNY LISNLSNIIE KINTLGLDSK NIAYNYTDES  840
NNKYFGAISK TSQKSIIHYK KDSKNILEFY NDSTLEFNSK DFIAEDINVF MKDDINTITG  900
KYYVDNNTDK SIDFSISLVS KNQVKVNGLY LNESVYSSYL DFVKNSDGHH NTSNFMNLFL  960
DNISFWKLFG FENINFVIDK YFTLVGKTNL GYVEFICDNN KNIDIYFGEW KTSSSKSTIF  1020
SGNGRNVVVE PIYNPDTGED ISTSLDFSYE PLYGIDRYIN KVLIAPDLYT SLININTNYY  1080
SNEYYPEIIV LNPNTFHKKV NINLDSSSFE YKWSTEGSDF ILVRYLEESN KKILQKIRIK  1140
GILSNTQSFN KMSIDFKDIK KLSLGYIMSN FKSFNSENEL DRDHLGFKII DNKTYYYDED  1200
SKLVKGLINI NNSLFYFDPI EFNLVTGWQT INGKKYYFDI NTGAALISYK IINGKHFYFN  1260
NDGVMQLGVF KGPDGFEYFA PANTQNNNIE GQAIVYQSKF LTLNGKKYYF DNDSKAVTGW  1320
RIINNEKYYF NPNNAIAAVG LQVIDNNKYY FNPDTAIISK GWQTVNGSRY YFDTDTAIAF  1380
NGYKTIDGKH FYFDSDCVVK IGVFSTSNGF EYFAPANTYN NNIEGQAIVY QSKFLTLNGK  1440
KYYFDNNSKA VTGWQTIDSK KYYFNTNTAE AATGWQTIDG KKYYFNTNTA EAATGWQTID  1500
GKKYYFNTNT AIASTGYTII NGKHFYFNTD GIMQIGVFKG PNGFEYFAPA NTDANNIEGQ  1560
AILYQNEFLT LNGKKYYFGS DSKAVTGWRI INNKKYYFNP NNAIAAIHLC TINNDKYYFS  1620
YDGILQNGYI TIERNNFYFD ANNESKMVTG VFKGPNGFEY FAPANTHNNN IEGQAIVYQN  1680
KFLTLNGKKY YFDNDSKAVT GWQTIDGKKY YFNLNTAEAA TGWQTIDGKK YYFNLNTAEA  1740
ATGWQTIDGK KYYFNTNTFI ASTGYTSING KHFYFNTDGI MQIGVFKGPN GFEYFAPANT  1800
HNNNIEGQAI LYQNKFLTLN GKKYYFGSDS KAVTGLRTID GKKYYFNTNT AVAVTGWQTI  1860
NGKKYYFNTN TSIASTGYTI ISGKHFYFNT DGIMQIGVFK GPDGFEYFAP ANTDANNIEG  1920
QAIRYQNRFL YLHDNIYYFG NNSKAATGWV TIDGNRYYFE PNTAMGANGY KTIDNKNFYF  1980
RNGLPQIGVF KGSNGFEYFA PANTDANNIE GQAIRYQNRF LHLLGKIYYF GNNSKAVTGW  2040
QTINGKVYYF MPDTAMAAAG GLFEIDGVIY FFGVDGVKAP GIYG                   2084

SEQ ID NO: 21           moltype = AA  length = 1723
FEATURE                 Location/Qualifiers
REGION                  1..1723
                        note = Fusion protein
source                  1..1723
                        mol_type = protein
                        organism = synthetic construct
SEQUENCE: 21
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LVPRGSVTSL YKKAGSAAAP FTMESKKYGP LKTEDDKILV PIDDLVISEI DFNNNSIKLG  180
TCNILAMEGG SGHTVTGNID HFFSSPSISS HIPSLSIYSA IGIETENLDF SKKIMMLPNA  240
PSRVFWWETG AVPGLRSLEN DGTRLLDSIR DLYPGKFYWR FYAFFDYAIT TLKPVYEDTN  300
IKIKLDKDTR NFIMPTITTN EIRNKLSYSF DGAGGTYSLL LSSYPISTNI NLSKDDLWIF  360
NIDNEVREIS IENGTIKKGK LIKDVLSKID INKNKLIIGN QTIDFSGDID NKDRYIFLTC  420
ELDDKISLII EINLVAKSYS LLLSGDKNYL ISNLSNIIEK INTLGLDSKN IAYNYTDESN  480
NKYFGAISKT SQKSIIHYKK DSKNILEFYN DSTLEFNSKD FIAEDINVFM KDDINTITGK  540
YYVDNNTDKS IDFSISLVSK NQVKVNGLYL NESVYSSYLD FVKNSDGHHN TSNFMNLFLD  600
NISFWKLFGF ENINFVIDKY FTLVGKTNLG YVEFICDNNK NIDIYFGEWK TSSSKSTIFS  660
GNGRNVVVEP IYNPDTGEDI STSLDFSYEP LYGIDRYINK VLIAPDLYTS LININTNYYS  720
NEYYPEIIVL NPNTFHKKVN INLDSSSFEY KWSTEGSDFI LVRYLEESNK KILQKIRIKG  780
ILSNTQSFNK MSIDFKDIKK LSLGYIMSNF KSFNSENELD RDHLGFKIID NKTYYYDEDS  840
KLVKGLININ NSLFYFDPIE FNLVTGWQTI NGKKYYFDIN TGAALISYKI INGKHFYFNN  900
DGVMQLGVFK GPDGFEYFAP ANTQNNNIEG QAIVYQSKFL TLNGKKYYFD NDSKAVTGWR  960
IINNEKYYFN PNNAIAAVGL QVIDNNKYYF NPDTAIISKG WQTVNGSRYY FDTDTAIAFN  1020
GYKTIDGKHF YFDSDCVVKI GVFSTSNGFE YFAPANTYNN NIEGQAIVYQ SKFLTLNGKK  1080
YYFDNNSKAV TGWQTIDSKK YYFNTNTAEA ATGWQTIDGK KYYFNTNTAE AATGWQTIDG  1140
KKYYFNTNTA IASTGYTIIN GKHFYFNTDG IMQIGVFKGP NGFEYFAPAN TDANNIEGQA  1200
ILYQNEFLTL NGKKYYFGSD SKAVTGWRII NNKKYYFNPN NAIAAIHLCT INNDKYYFSY  1260
DGILQNGYIT IERNNFYFDA NNESKMVTGV FKGPNGFEYF APANTHNNNI EGQAIVYQNK  1320
FLTLNGKKYY FDNDSKAVTG WQTIDGKKYY FNLNTAEAAT GWQTIDGKKY YFNLNTAEAA  1380
TGWQTIDGKK YYFNTNTFIA STGYTSINGK HFYFNTDGIM QIGVFKGPNG FEYFAPANTH  1440
NNNIEGQAIL YQNKFLTLNG KKYYFGSDSK AVTGLRTIDG KKYYFNTNTA VAVTGWQTIN  1500
GKKYYFNTNT SIASTGYTII SGKHFYFNTD GIMQIGVFKG PDGFEYFAPA NTDANNIEGQ  1560
AIRYQNRFLY LHDNIYYFGN NSKAATGWVT IDGNRYYFEP NTAMGANGYK TIDNKNFYFR  1620
NGLPQIGVFK GSNGFEYFAP ANTDANNIEG QAIRYQNRFL HLLGKIYYFG NNSKAVTGWQ  1680
TINGKVYYFM PDTAMAAAGG LFEIDGVIYF FGVDGVKAPG IYG                   1723

SEQ ID NO: 22           moltype = AA  length = 2111
FEATURE                 Location/Qualifiers
REGION                  1..2111
                        note = Fusion protein
source                  1..2111
                        mol_type = protein
                        organism = synthetic construct
SEQUENCE: 22
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
```

```
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALV PRGSVTSLYK KAGSAAAPFT MESKKYGPLK  540
TEDDKILVPI DDLVISEIDF NNNSIKLGTC NILAMEGGSG HTVTGNIDHF FSSPSISSHI  600
PSLSIYSAIG IETENLDFSK KIMMLPNAPS RVFWWETGAV PGLRSLENDG TRLLDSIRDL  660
YPGKFYWRFY AFFDYAITTL KPVYEDTNIK IKLDKDTRNF IMPTITTNEI RNKLSYSFDG  720
AGGTYSLLLS SYPISTNINL SKDDLWIFNI DNEVREISIE NGTIKKGKLI KDVLSKIDIN  780
KNKLIIGNQT IDFSGDIDNK DRYIFLTCEL DDKISLIIEI NLVAKSYSLL LSGDKNYLIS  840
NLSNIIEKIN TLGLDSKNIA YNYTDESNNK YFGAISKTSQ KSIIHYKKDS KNILEFYNDS  900
TLEFNSKDFI AEDINVFMKD DINTITGKYY VDNNTDKSID FSISLVSKNQ VKVNGLYLNE  960
SVYSSYLDFV KNSDGHHNTS NFMNLFLDNI SFWKLFGFEN INFVIDKYFT LVGKTNLGYV  1020
EFICDNNKNI DIYFGEWKTS SSKSTIFSGN GRNVVVEPIY NPDTGEDIST SLDFSYEPLY  1080
GIDRYINKVL IAPDLYTSLI NINTNYYSNE YYPEIIVLNP NTFHKKVNIN LDSSSFEYKW  1140
STEGSDFILV RYLEESNKKI LQKIRIKGIL SNTQSFNKMS IDFKDIKKLS LGYIMSNFKS  1200
FNSENELDRD HLGFKIIDNK TYYYDEDSKL VKGLININNS LFYFDPIEFN LVTGWQTING  1260
KKYYFDINTG AALISYKIIN GKHFYFNNDG VMQLGVFKGP DGFEYFAPAN TQNNNIEGQA  1320
IVYQSKFLTL NGKKYYFDND SKAVTGWRII NNEKYYFNPN NAIAAVGLQV IDNNKYYFNP  1380
DTAIISKGWQ TVNGSRYYFD TDTAIAFNGY KTIDGKHFYF DSDCVVKIGV FSTSNGFEYF  1440
APANTYNNNI EGQAIVYQSK FLTLNGKKYY FDNNSKAVTG WQTIDSKKYY FNTNTAEAAT  1500
GWQTIDGKKY YFNTNTAEAA TGWQTIDGKK YYFNTNTAIA STGYTIINGK HFYFNTDGIM  1560
QIGVFKGPNG FEYFAPANTD ANNIEGQAIL YQNEFLTLNG KKYYFGSDSK AVTGWRIINN  1620
KKYYFNPNNA IAAIHLCTIN NDKYYFSYDG ILQNGYITIE RNNFYFDANN ESKMVTGVFK  1680
GPNGFEYFAP ANTHNNNIEG QAIVYQNKFL TLNGKKYYFD NDSKAVTGWQ TIDGKKYYFN  1740
LNTAEAATGW QTIDGKKYYF NLNTAEAATG WQTIDGKKYY FNTNTFIAST GYTSINGKHF  1800
YFNTDGIMQI GVFKGPNGFE YFAPANTHNN NIEGQAILYQ NKFLTLNGKK YYFGSDSKAV  1860
TGLRTIDGKK YYFNTNTAVA VTGWQTINGK KYYFNTNTSI ASTGYTIISG KHFYFNTDGI  1920
MQIGVFKGPD GFEYFAPANT DANNIEGQAI RYQNRFLYLH DNIYYFGNNS KAATGWVTID  1980
GNRYYFEPNT AMGANGYKTI DNKNFYFRNG LPQIGVFKGS NGFEYFAPAN TDANNIEGQA  2040
IRYQNRFLHL LGKIYYFGNN SKAVTGWQTI NGKVYYFMPD TAMAAAGGLF EIDGVIYFFG  2100
VDGVKAPGIY G                                                       2111

SEQ ID NO: 23          moltype = AA  length = 2138
FEATURE                Location/Qualifiers
REGION                 1..2138
                       note = Fusion protein
source                 1..2138
                       mol_type = protein
                       organism = synthetic construct
SEQUENCE: 23
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALV PRGSVTSLYK KAGSAAAPFT MSIIKDISSK  540
EYISFNPKEN KITVKSKNLP ELSTLLQEIR NNSNSSDIEL EEKVMLTECE INVISNIDTQ  600
IVEERIEEAK NLTSDSINYI KDEFKLIESI SDALCDLKQQ NELEDSHFIS FEDISETDEG  660
FSIRFINKET GESIFVETEK TIFSEYANHI TEEISKIKGT IFDTVNGKLV KKVNLDTTHE  720
VNTLNAAFFI QSLIEYNSSK ESLSNLSVAM KVQVYAQLFS TGLNTITDAA KVVELVSTAL  780
DETIDLLPTL SEGLPIIATI IDGVSLGAAI KELSETSDPL LRQEIEAKIG IMAVNLTTAT  840
TAIITSSLGI ASGFSILLVP LAGISAGIPS LVNNELVLRD KATKVVDYFK HVSLVETEGV  900
FTLLDDKIMM PQDDLVISEI DFNNNSIVLG KCEIWRMEGG SGHTVTDDID HFFSAPSITY  960
REPHLSIYDV LEVQKEELDL SKDLMVLPNA PNRVFAWETG WTPGLRSLEN DGTKLLDRIR  1020
DNYEGEFYWR YFAFIADALI TTLKPRYEDT NIRINLDSNT RSFIVPIITT EYIREKLSYS  1080
FYGSGGTYAL SLSQYNMGIN IELSESDVWI IDVDNVVRDV TIESDKIKKG DLIEGILSTL  1140
SIEENKIILN SHEINFSGEV NGSNGFVSLT FSILEGINAI IEVDLLSKSY KLLISGELKI  1200
LMLNSNHIQQ KIDYIGFNSE LQKNIPYSFV DSEGKENGFI NGSTKEGLFV SELPDVVLIS  1260
KVYMDDSKPS FGYYSNNLKD VKVITKDNVN ILTGYYLKDD IKISLSLTLQ DEKTIKLNSV  1320
HLDESGVAEI LKFMNRKGNT NTSDSLMSFL ESMNIKSIFV NFLQSNIKFI LDANFIISGT  1380
TSIGQFEFIC DENDNIQPYF IKFNTLETNY TLYVGNRQNM IVEPNYDLDD SGDISSTVIN  1440
FSQKYLYGID SCVNKVVISP NIYTDEINIT PVYETNNTYP EVIVLDANYI NEKINVNIND  1500
LSIRYVWSND GNDFILMSTS EENKVSQVKI RFVNVFKDKT LANKLSFNFS DKQDVPVSEI  1560
ILSFTPSYYE DGLIGYDLGL VSLYNEKFYI NNFGMMVSGL IYINDSLYYF KPPVNNLITG  1620
FVTVGDDKYY FNPINGGAAS IGETIIDDKN YYFNQSGVLQ TGVFSTEDGF KYFAPANTLD  1680
ENLEGEAIDF TGKLIIDENI YYFDDNYRGA VEWKELDGEM HYFSPETGKA FKGLNQIGDY  1740
KYYFNSDGVM QKGFVSINDN KHYFDDSGVM KVGYTEIDGK HFYFAENGEM QIGVFNTEDG  1800
FKYFAHHNED LGNEEGEEIS YSGILNFNNK IYYFDDSFTA VVGWKDLEDG SKYYFDEDTA  1860
EAYIGLSLIN DGQYYFNDDG IMQVGFVTIN DKVFYFSDSG IIESGVQNID DNYFYIDDNG  1920
IVQIGVFDTS DGYKYFAPAN TVNDNIYGQA VEYSGLVRVG EDVYYFGETY TIETGWIYDM  1980
ENESDKYYFN PETKKACKGI NLIDDIKYYF DEKGIMRTGL ISFENNNYYF NENGEMQFGY  2040
INIEDKMFYF GEDGVMQIGV FNTPDGFKYF AHQNTLDENF EGESINYTGW LDLDEKRYYF  2100
TDEYIAATGS VIIDGEEYYF DPDTAQLVIS EGHHHHHH                           2138

SEQ ID NO: 24          moltype = AA  length = 2131
FEATURE                Location/Qualifiers
REGION                 1..2131
```

```
                         note = Fusion protein
source                   1..2131
                         mol_type = protein
                         organism = synthetic construct
SEQUENCE: 24
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALV PRGSVTSLYK KAGSAAAPFT MSIIKDISSK  540
EYISFNPKEN KITVKSKNLP ELSTLLQEIR NNSNSSDIEL EEKVMLTECE INVISNIDTQ  600
IVEERIEEAK NLTSDSINYI KDEFKLIESI SDALCDLKQQ NELEDSHFIS FEDISETDEG  660
FSIRFINKET GESIFVETEK TIFSEYANHI TEEISKIKGT IFDTVNGKLV KKVNLDTTHE  720
VNTLNAAFFI QSLIEYNSSK ESLSNLSVAM KVQVYAQLFS TGLNTITDAA KVVELVSTAL  780
DETIDLLPTL SEGLPIIATI IDGVSLGAAI KELSETSDPL LRQEIEAKIG IMAVNLTTAT  840
TAIITSSLGI ASGFSILLVP LAGISAGIPS LVNNELVLRD KATKVVDYFK HVSLVETEGV  900
FTLLDDKIMM PQDDLVISEI DFNNNSIVLG KCEIWRMEGG SGHTVTDDID HFFSAPSITY  960
REPHLSIYDV LEVQKEELDL SKDLMVLPNA PNRVFAWETG WTPGLRSLEN DGTKLLDRIR  1020
DNYEGEFYWR YFAFIADALI TTLKPRYEDT NIRINLDSNT RSFIVPIITT EYIREKLSYS  1080
FYGSGGTYAL SLSQYNMGIN IELSESDVWI IDVDNVVRDV TIESDKIKKG DLIEGILSTL  1140
SIEENKIILN SHEINFSGEV NGSNGFVSLT FSILEGINAI IEVDLLSKSY KLLISGELKI  1200
LMLNSNHIQQ KIDYIGFNSE LQKNIPYSFV DSEGKENGFI NGSTKEGLFV SELPDVVLIS  1260
KVYMDDSKPS FGYYSNNLKD VKVITKDNVN ILTGYYLKDD IKISLSLTLQ DEKTIKLNSV  1320
HLDESGVAEI LKFMNRKGNT NTSDSLMSFL ESMNIKSIFV NFLQSNIKFI LDANFIISGT  1380
TSIGQFEFIC DENDNIQPYF IKFNTLETNY TLYVGNRQNM IVEPNYDLDD SGDISSTVIN  1440
FSQKYLYGID SCVNKVVISP NIYTDEINIT PVYETNNTYP EVIVLDANYI NEKINVNIND  1500
LSIRYVWSND GNDFILMSTS EENKVSQVKI RFVNVFKDKT LANKLSFNFS DKQDVPVSEI  1560
ILSFTPSYYE DGLIGYDLGL VSLYNEKFYI NNFGMMVSGL IYINDSLYYF KPPVNNLITG  1620
FVTVGDDKYY FNPINGGAAS IGETIIDDKN YYFNQSGVLQ TGVFSTEDGF KYFAPANTLD  1680
ENLEGEAIDF TGKLIIDENI YYFDDNYRGA VEWKELDGEM HYFSPETGKA FKGLNQIGDY  1740
KYYFNSDGVM QKGFVSINDN KHYFDDSGVM KVGYTEIDGK HFYFAENGEM QIGVFNTEDG  1800
FKYFAHHNED LGNEEGEEIS YSGILNFNNK IYYFDDSFTA VVGWKDLEDG SKYYFDEDTA  1860
EAYIGLSLIN DGQYYFNDDG IMQVGFVTIN DKVFYFSDSG IIESGVQNID DNYFYIDDNG  1920
IVQIGVFDTS DGYKYFAPAN TVNDNIYGQA VEYSGLVRVG EDVYYFGETY TIETGWIYDM  1980
ENESDKYYFN PETKKACKGI NLIDDIKYYF DEKGIMRTGL ISFENNNYYF NENGEMQFGY  2040
INIEDKMFYF GEDGVMQIGV FNTPDGFKYF AHQNTLDENF EGESINYTGW LDLDEKRYYF  2100
TDEYIAATGS VIIDGEEYYF DPDTAQLVIS E                                2131

SEQ ID NO: 25            moltype = AA  length = 1743
FEATURE                  Location/Qualifiers
REGION                   1..1743
                         note = Fusion protein
source                   1..1743
                         mol_type = protein
                         organism = synthetic construct
SEQUENCE: 25
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LVPRGSVTSL YKKAGSAAAP FTMSIIKDIS SKEYISFNPK ENKITVKSKN LPELSTLLQE  180
IRNNSNSSDI ELEEKVMLTE CEINVISNID TQIVEERIEE AKNLTSDSIN YIKDEFKLIE  240
SISDALCDLK QQNELEDSHF ISFEDISETD EGFSIRFINK ETGESIFVET EKTIFSEYAN  300
HITEEISKIK GTIFDTVNGK LVKKVNLDTT HEVNTLNAAF FIQSLIEYNS SKESLSNLSV  360
AMKVQVYAQL FSTGLNTITD AAKVVELVST ALDETIDLLP TLSEGLPIIA TIIDGVSLGA  420
AIKELSETSD PLLRQEIEAK IGIMAVNLTT ATTAIITSSL GIASGFSILL VPLAGISAGI  480
PSLVNNELVL RDKATKVVDY FKHVSLVETE GVFTLLDDKI MMPQDDLVIS EIDFNNNSIV  540
LGKCEIWRME GGSGHTVTDD IDHFFSAPSI TYREPHLSIY DVLEVQKEEL DLSKDLMVLP  600
NAPNRVFAWE TGWTPGLRSL ENDGTKLLDR IRDNYEGEFY WRYFAFIADA LITTLKPRYE  660
DTNIRINLDS NTRSFIVPII TTEYIREKLS YSFYGSGGTY ALSLSQYNMG INIELSESDV  720
WIIDVDNVVR DVTIESDKIK KGDLIEGILS TLSIEENKII LNSHEINFSG EVNGSNGFVS  780
LTFSILEGIN AIIEVDLLSK SYKLLISGEL KILMLNSNHI QQKIDYIGFN SELQKNIPYS  840
FVDSEGKENG FINGSTKEGL FVSELPDVVL ISKVYMDDSK PSFGYYSNNL KDVKVITKDN  900
VNILTGYYLK DDIKISLSLT LQDEKTIKLN SVHLDESGVA EILKFMNRKG NTNTSDSLMS  960
FLESMNIKSI FVNFLQSNIK FILDANFIIS GTTSIGQFEF ICDENDNIQP YFIKFNTLET  1020
NYTLYVGNRQ NMIVEPNYDL DDSGDISSTV INFSQKYLYG IDSCVNKVVI SPNIYTDEIN  1080
ITPVYETNNT YPEVIVLDAN YINEKINVNI NDLSIRYVWS NDGNDFILMS TSEENKVSQV  1140
KIRFVNVFKD KTLANKLSFN FSDKQDVPVS EIILSFTPSY YEDGLIGYDL GLVSLYNEKF  1200
YINNFGMMVS GLIYINDSLY YFKPPVNNLI TGFVTVGDDK YYFNPINGGA ASIGETIIDD  1260
KNYYFNQSGV LQTGVFSTED GFKYFAPANT LDENLEGEAI DFTGKLIIDE NIYYFDDNYR  1320
GAVEWKELDG EMHYFSPETG KAFKGLNQIG DYKYYFNSDG VMQKGFVSIN DNKHYFDDSG  1380
VMKVGYTEID GKHFYFAENG EMQIGVFNTE DGFKYFAHHN EDLGNEEGEE ISYSGILNFN  1440
NKIYYFDDSF TAVVGWKDLE DGSKYYFDED TAEAYIGLSL INDGQYYFND DGIMQVGFVT  1500
INDKVFYFSD SGIIESGVQN IDDNYFYIDD NGIVQIGVFD TSDGYKYFAP ANTVNDNIYG  1560
QAVEYSGLVR VGEDVYYFGE TYTIETGWIY DMENESDKYY FNPETKKACK GINLIDDIKY  1620
YFDEKGIMRT GLISFENNNY YFNENGEMQF GYINIEDKMF YFGEDGVMQI GVFNTPDGFK  1680
YFAHQNTLDE NFEGESINYT GWLDLDEKRY YFTDEYIAAT GSVIIDGEEY YFDPDTAQLV  1740
```

```
ISE                                                                       1743

SEQ ID NO: 26           moltype = AA  length = 1751
FEATURE                 Location/Qualifiers
REGION                  1..1751
                        note = Fusion protein
source                  1..1751
                        mol_type = protein
                        organism = synthetic construct
SEQUENCE: 26
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALV PRGSVTSLYK KAGSAAGGSM PQDDLVISEI  540
DFNNNSIVLG KCEIWRMEGG SGHTVTDDID HFFSAPSITY REPHLSIYDV LEVQKEELDL  600
SKDLMVLPNA PNRVFAWETG WTPGLRSLEN DGTKLLDRIR DNYEGEFYWR YFAFIADALI  660
TTLKPRYEDT NIRINLDSNT RSFIVPIITT EYIREKLSYS FYGSGGTYAL SLSQYNMGIN  720
IELSESDVWI IDVDNVVRDV TIESDKIKKG DLIEGILSTL SIEENKIILN SHEINFSGEV  780
NGSNGFVSLT FSILEGINAI IEVDLLSKSY KLLISGELKI LMLNSNHIQQ KIDYIGFNSE  840
LQKNIPYSFV DSEGKENGFI NGSTKEGLFV SELPDVVLIS KVYMDDSKPS FGYYSNNLKD  900
VKVITKDNVN ILTGYYLKDD IKISLSLTLQ DEKTIKLNSV HLDESGVAEI LKFMNRKGNT  960
NTSDSLMSFL ESMNIKSIFV NFLQSNIKFI LDANFIISGT TSIGQFEFIC DENDNIQPYF  1020
IKFNTLETNY TLYVGNRQNM IVEPNYDLDD SGDISSTVIN FSQKYLYGID SCVNKVVISP  1080
NIYTDEINIT PVYETNNTYP EVIVLDANYI NEKINVNIND LSIRYVWSND GNDFILMSTS  1140
EENKVSQVKI RFVNVFKDKT LANKLSFNFS DKQDVPVSEI ILSFTPSYYE DGLIGYDLGL  1200
VSLYNEKFYI NNFGMMVSGL IYINDSLYYF KPPVNNLITG FVTVGDDKYY FNPINGGAAS  1260
IGETIIDDKN YYFNQSGVLQ TGVFSTEDGF KYFAPANTLD ENLEGEAIDF TGKLIIDENI  1320
YYFDDNYRGA VEWKELDGEM HYFSPETGKA FKGLNQIGDY KYYFNSDGVM QKGFVSINDN  1380
KHYFDDSGVM KVGYTEIDGK HFYFAENGEM QIGVFNTEDG FKYFAHHNED LGNEEGEEIS  1440
YSGILNFNNK IYYFDDSFTA VVGWKDLEDG SKYYFDEDTA EAYIGLSLIN DGQYYFNDDG  1500
IMQVGFVTIN DKVFYFSDSG IIESGVQNID DNYFYIDDNG IVQIGVFDTS DGYKYFAPAN  1560
TVNDNIYGQA VEYSGLVRVG EDVYYFGETY TIETGWIYDM ENESDKYYFN PETKKACKGI  1620
NLIDDIKYYF DEKGIMRTGL ISFENNNYYF NENGEMQFGY INIEDKMFYF GEDGVMQIGV  1680
FNTPDGFKYF AHQNTLDENF EGESINYTGW LDLDEKRYYF TDEYIAATGS VIIDGEEYYF  1740
DPDTAQLVIS E                                                      1751

SEQ ID NO: 27           moltype = AA  length = 1363
FEATURE                 Location/Qualifiers
REGION                  1..1363
                        note = Fusion protein
source                  1..1363
                        mol_type = protein
                        organism = synthetic construct
SEQUENCE: 27
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LVPRGSVTSL YKKAGSAAGG SMPQDDLVIS EIDFNNNSIV LGKCEIWRME GGSGHTVTDD  180
IDHFFSAPSI TYREPHLSIY DVLEVQKEEL DLSKDLMVLP NAPNRVFAWE TGWTPGLRSL  240
ENDGTKLLDR IRDNYEGEFY WRYFAFIADA LITTLKPRYE DTNIRINLDS NTRSFIVPII  300
TTEYIREKLS YSFYGSGGTY ALSLSQYNMG INIELSESDV WIIDVDNVVR DVTIESDKIK  360
KGDLIEGILS TLSIEENKII LNSHEINFSG EVNGSNGFVS LTFSILEGIN AIIEVDLLSK  420
SYKLLISGEL KILMLNSNHI QQKIDYIGFN SELQKNIPYS FVDSEGKENG FINGSTKEGL  480
FVSELPDVVL ISKVYMDDSK PSFGYYSNNL KDVKVITKDN VNILTGYYLK DDIKISLSLT  540
LQDEKTIKLN SVHLDESGVA EILKFMNRKG NTNTSDSLMS FLESMNIKSI FVNFLQSNIK  600
FILDANFIIS GTTSIGQFEF ICDENDNIQP YFIKFNTLET NYTLYVGNRQ NMIVEPNYDL  660
DDSGDISSTV INFSQKYLYG IDSCVNKVVI SPNIYTDEIN ITPVYETNNT YPEVIVLDAN  720
YINEKINVNI NDLSIRYVWS NDGNDFILMS TSEENKVSQV KIRFVNVFKD KTLANKLSFN  780
FSDKQDVPVS EIILSFTPSY YEDGLIGYDL GLVSLYNEKF YINNFGMMVS GLIYINDSLY  840
YFKPPVNNLI TGFVTVGDDK YYFNPINGGA ASIGETIIDD KNYYFNQSGV LQTGVFSTED  900
GFKYFAPANT LDENLEGEAI DFTGKLIIDE NIYYFDDNYR GAVEWKELDG EMHYFSPETG  960
KAFKGLNQIG DYKYYFNSDG VMQKGFVSIN DNKHYFDDSG VMKVGYTEID GKHFYFAENG  1020
EMQIGVFNTE DGFKYFAHHN EDLGNEEGEE ISYSGILNFN NKIYYFDDSF TAVVGWKDLE  1080
DGSKYYFDED TAEAYIGLSL INDGQYYFND DGIMQVGFVT INDKVFYFSD SGIIESGVQN  1140
IDDNYFYIDD NGIVQIGVFD TSDGYKYFAP ANTVNDNIYG QAVEYSGLVR VGEDVYYFGE  1200
TYTIETGWIY DMENESDKYY FNPETKKACK GINLIDDIKY YFDEKGIMRT GLISFENNNY  1260
YFNENGEMQF GYINIEDKMF YFGEDGVMQI GVFNTPDGFK YFAHQNTLDE NFEGESINYT  1320
GWLDLDEKRY YFTDEYIAAT GSVIIDGEEY YFDPDTAQLV ISE                   1363

SEQ ID NO: 28           moltype = AA  length = 2504
FEATURE                 Location/Qualifiers
REGION                  1..2504
                        note = Fusion protein
source                  1..2504
                        mol_type = protein
```

```
                         organism = synthetic construct
SEQUENCE: 28
HHHHHHHHHG GSGGSGGSGG SGGSGGSGGS GGSGGSGGSH MASNKEILAV VEAVSNEKAL  60
PREKIFEALE SALATATKKK YEQEIDVRVQ IDRKSGDFDT FRRWLVVDEV TQPTKEITLE  120
AARYEDESLN LGDYVEDQIE SVTFDRITTQ TAKQVIVQKV REAERAMVVD QFREHEGEII  180
TGVVKKVNRD NISLDLGNNA EAVILREDML PRENFRPGDR VRGVLYSVRP EARGAQLFVT  240
RSKPEMLIEL FRIEVPEIGE EVIEIKAAAR DPGSRAKIAV KTNDKRIDPV GACVGMRGAR  300
VQAVSTELGG ERIDIVLWDD NPAQFVINAM APADVASIVV DEDKHTMDIA VEAGNLAQAI  360
GRNGQNVRLA SQLSGWELNV MTVDDLQAKH QAEAHAAIDT FTKYLDIDED FATVLVEEGF  420
STLEELAYVP MKELLEIEGL DEPTVEALRE RAKNALATIA QAQEESLGDN KPADDLLNLE  480
GVDRDLAFKL AARGVCTLED LAEQGIDDLA DIEGLTDEKA GALIMAARNI CWFGDEASGA  540
LVPRGSVTSL YKKAGSAAAP FTMIMSDLSS KEYIFFDSID NKLKAKSKNI PGLASISEDI  600
KTLLLDASVS PDTKFILNNL KLNIESSIGD YIYYEKLEPV KNIIHNSIDD LIDEFNLLEN  660
VSDELYELKK LNNLDEKYLI SFEDISKNNS TYSVRFINKS NGESVYVETE KEIFSKYSEH  720
ITKEISTIKN SIITDVNGNL LDNIQLDHTS QVNTLNAAFF IQSLIDYSSN KDVLNDLSTS  780
VKVQLYAQLF STGLNTIYDS IQLVNLISNA VNDTINVLPT ITEGIPIVST ILDGINLGAA  840
IKELLDEHDP LLKKELEAKV GVLAINMSLS IAATVASIVG IGAEVTIFLL PIAGISAGIP  900
SLVNNELILH DKATSVVNYF NHLSESKKYG PLKTEDDKIL VPIDDLVISE IDFNNNSIKL  960
GTCNILAMEG GSGHTVTGNI DHFFSSPSIS SHIPSLSIYS AIGIETENLD FSKKIMMLPN  1020
APSRVFWWET GAVPGLRSLE NDGTRLLDSI RDLYPGKFYW RFYAFFDYAI TTLKPVYEDT  1080
NIKIKLDKDT RNFIMPTITT NEIRNKLSYS FDGAGGTYSL LLSSYPISTN INLSKDDLWI  1140
FNIDNEVREI SIENGTIKKG KLIKDVLSKI DINKNKLIIG NQTIDFSGDI DNKDRYIFLT  1200
CELDDKISLI IEINLVAKSY SLLLSGDKNY LISNLSNIIE KINTLGLDSK NIAYNYTDES  1260
NNKYFGAISK TSQKSIIHYK KDSKNILEFY NDSTLEFNSK DFIAEDINVF MKDDINTITG  1320
KYYVDNNTDK SIDFSISLVS KNQVKVNGLY LNESVYSSYL DFVKNSDGHH NTSNFMNLFL  1380
DNISFWKLFG FENINFVIDK YFTLVGKTNL GYVEFICDNN KNIDIYFGEW KTSSSKSTIF  1440
SGNGRNVVVE PIYNPDTGED ISTSLDFSYE PLYGIDRYIN KVLIAPDLYT SLININTNYY  1500
SNEYYPEIIV LNPNTFHKKV NINLDSSSFE YKWSTEGSDF ILVRYLEESN KKILQKIRIK  1560
GILSNTQSFN KMSIDFKDIK KLSLGYIMSN FKSFNSENEL DRDHLGFKII DNKTYYYDED  1620
SKLVKGLINI NNSLFYFDPI EFNLVTGWQT INGKKYYFDI NTGAALISYK IINGKHFYFN  1680
NDGVMQLGVF KGPDGFEYFA PANTQNNNIE GQAIVYQSKF LTLNGKKYYF DNDSKAVTGW  1740
RIINNEKYYF NPNNAIAAVG LQVIDNNKYY FNPDTAIISK GWQTVNGSRY YFDTDTAIAF  1800
NGYKTIDGKH FYFDSDCVVK IGVFSTSNGF EYFAPANTYN NNIEGQAIVY QSKFLTLNGK  1860
KYYFDNNSKA VTGWQTIDSK KYYFNTNTAE AATGWQTIDG KKYYFNTNTA EAATGWQTID  1920
GKKYYFNTNT AIASTGYTII NGKHFYFNTD GIMQIGVFKG PNGFEYFAPA NTDANNIEGQ  1980
AILYQNEFLT LNGKKYYFGS DSKAVTGWRI INNKKYYFNP NNAIAAIHLC TINNDKYYFS  2040
YDGILQNGYI TIERNNFYFD ANNESKMVTG VFKGPNGFEY FAPANTHNNN IEGQAIVYQN  2100
KFLTLNGKKY YFDNDSKAVT GWQTIDGKKY YFNLNTAEAA TGWQTIDGKK YYFNLNTAEA  2160
ATGWQTIDGK KYYFNTNTFI ASTGYTSING KHFYFNTDGI MQIGVFKGPN GFEYFAPANT  2220
HNNNIEGQAI LYQNKFLTLN GKKYYFGSDS KAVTGLRTID GKKYYFNTNT AVAVTGWQTI  2280
NGKKYYFNTN TSIASTGYTI ISGKHFYFNT DGIMQIGVFK GPDGFEYFAP ANTDANNIEG  2340
QAIRYQNRFL YLHDNIYYFG NNSKAATGWV TIDGNRYYFE PNTAMGANGY KTIDNKNFYF  2400
RNGLPQIGVF KGSNGFEYFA PANTDANNIE GQAIRYQNRF LHLLGKIYYF GNNSKAVTGW  2460
QTINGKVYYF MPDTAMAAAG GLFEIDGVIY FFGVDGVKAP GIYG                 2504

SEQ ID NO: 29            moltype = AA  length = 2511
FEATURE                  Location/Qualifiers
REGION                   1..2511
                         note = Fusion protein
source                   1..2511
                         mol_type = protein
                         organism = synthetic construct
SEQUENCE: 29
HHHHHHHHHH GGSLAEAAAK EAAAKEAAAK EAAAKEAAAK AAAGGSHMAS NKEILAVVEA  60
VSNEKALPRE KIFEALESAL ATATKKKYEQ EIDVRVQIDR KSGDFDTFRR WLVVDEVTQP  120
TKEITLEAAR YEDESLNLGD YVEDQIESVT FDRITTQTAK QVIVQKVREA ERAMVVDQFR  180
EHEGEIITGV VKKVNRDNIS LDLGNNAEAV ILREDMLPRE NFRPGDRVRG VLYSVRPEAR  240
GAQLFVTRSK PEMLIELFRI EVPEIGEEVI EIKAAARDPG SRAKIAVKTN DKRIDPVGAC  300
VGMRGARVQA VSTELGGERI DIVLWDDNPA QFVINAMAPA DVASIVVDED KHTMDIAVEA  360
GNLAQAIGRN GQNVRLASQL SGWELNVMTV DDLQAKHQAE AHAAIDTFTK YLDIDEDFAT  420
VLVEEGFSTL EELAYVPMKE LLEIEGLDEP TVEALRERAK NALATIAQAQ EESLGDNKPA  480
DDLLNLEGVD RDLAFKLAAR GVCTLEDLAE QGIDDLADIE GLTDEKAGAL IMAARNICWF  540
GDEASGALVP RGSVTSLYKK AGSAAAPFTM IMSDLSSKEY IFFDSIDNKL KAKSKNIPGL  600
ASISEDIKTL LLDASVSPDT KFILNNLKLN IESSIGDYIY YEKLEPVKNI IHNSIDDLID  660
EFNLLENVSD ELYELKKLNN LDEKYLISFE DISKNNSTYS VRFINKSNGE SVYVETEKEI  720
FSKYSEHITK EISTIKNSII TDVNGNLLDN IQLDHTSQVN TLNAAFFIQS LIDYSSNKDV  780
LNDLSTSVKV QLYAQLFSTG LNTIYDSIQL VNLISNAVND TINVLPTITE GIPIVSTILD  840
GINLGAAIKE LLDEHDPLLK KELEAKVGVL AINMSLSIAA TVASIVGIGA EVTIFLLPIA  900
GISAGIPSLV NNELILHDKA TSVVNYFNHL SESKKYGPLK TEDDKILVPI DDLVISEIDF  960
NNNSIKLGTC NILAMEGGSG HTVTGNIDHF FSSPSISSHI PSLSIYSAIG IETENLDFSK  1020
KIMMLPNAPS RVFWWETGAV PGLRSLENDG TRLLDSIRDL YPGKFYWRFY AFFDYAITTL  1080
KPVYEDTNIK IKLDKDTRNF IMPTITTNEI RNKLSYSFDG AGGTYSLLLS SYPISTNINL  1140
SKDDLWIFNI DNEVREISIE NGTIKKGKLI KDVLSKIDIN KNKLIIGNQT IDFSGDIDNK  1200
DRYIFLTCEL DDKISLIIEI NLVAKSYSLL LSGDKNYLIS NLSNIIEKIN TLGLDSKNIA  1260
YNYTDESNNK YFGAISKTSQ KSIIHYKKDS KNILEFYNDS TLEFNSKDFI AEDINVFMKD  1320
DINTITGKYY VDNNTDKSID FSISLVSKNQ VKVNGLYLNE SVYSSYLDFV KNSDGHHNTS  1380
NFMNLFLDNI SFWKLFGFEN INFVIDKYFT LVGKTNLGYV EFICDNNKNI DIYFGEWKTS  1440
SSKSTIFSGN GRNVVVEPIY NPDTGEDIST SLDFSYEPLY GIDRYINKVL IAPDLYTSLI  1500
NINTNYYSNE YYPEIIVLNP NTFHKKVNIN LDSSSFEYKW STEGSDFILV RYLEESNKKI  1560
```

```
LQKIRIKGIL SNTQSFNKMS IDFKDIKKLS LGYIMSNFKS FNSENELDRD HLGFKIIDNK  1620
TYYYDEDSKL VKGLININNS LFYFDPIEFN LVTGWQTING KKYYFDINTG AALISYKIIN  1680
GKHFYFNNDG VMQLGVFKGP DGFEYFAPAN TQNNNIEGQA IVYQSKFLTL NGKKYYFDND  1740
SKAVTGWRII NNEKYYFNPN NAIAAVGLQV IDNNKYYFNP DTAIISKGWQ TVNGSRYYFD  1800
TDTAIAFNGY KTIDGKHFYF DSDCVVKIGV FSTSNGFEYF APANTYNNNI EGQAIVYQSK  1860
FLTLNGKKYY FDNNSKAVTG WQTIDSKKYY FNTNTAEAAT GWQTIDGKKY YFNTNTAEAA  1920
TGWQTIDGKK YYFNTNTAIA STGYTIINGK HFYFNTDGIM QIGVFKGPNG FEYFAPANTD  1980
ANNIEGQAIL YQNEFLTLNG KKYYFGSDSK AVTGWRIINN KKYYFNPNNA IAAIHLCTIN  2040
NDKYYFSYDG ILQNGYITIE RNNFYFDANN ESKMVTGVFK GPNGFEYFAP ANTHNNNIEG  2100
QAIVYQNKFL TLNGKKYYFD NDSKAVTGWQ TIDGKKYYFN LNTAEAATGW QTIDGKKYYF  2160
NLNTAEAATG WQTIDGKKYY FNTNTFIAST GYTSINGKHF YFNTDGIMQI GVFKGPNGFE  2220
YFAPANTHNN NIEGQAILYQ NKFLTLNGKK YYFGSDSKAV TGLRTIDGKK YYFNTNTAVA  2280
VTGWQTINGK KYYFNTNTSI ASTGYTIISG KHFYFNTDGI MQIGVFKGPD GFEYFAPANT  2340
DANNIEGQAI RYQNRFLYLH DNIYYFGNNS KAATGWVTID GNRYYFEPNT AMGANGYKTI  2400
DNKNFYFRNG LPQIGVFKGS NGFEYFAPAN TDANNIEGQA IRYQNRFLHL LGKIYYFGNN  2460
SKAVTGWQTI NGKVYYFMPD TAMAAAGGLF EIDGVIYFFG VDGVKAPGIY G           2511

SEQ ID NO: 30          moltype = AA  length = 2492
FEATURE                Location/Qualifiers
REGION                 1..2492
                       note = Fusion protein
source                 1..2492
                       mol_type = protein
                       organism = synthetic construct
SEQUENCE: 30
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALG GSGGSGGSGG SGGSGGSGGS GGSGGSLVPR  540
GSGSAAAPFT MIMSDLSSKE YIFFDSIDNK LKAKSKNIPG LASISEDIKT LLLDASVSPD  600
TKFILNNLKL NIESSIGDYI YYEKLEPVKN IIHNSIDDLI DEFNLLENVS DELYELKKLN  660
NLDEKYLISF EDISKNNSTY SVRFINKSNG ESVYVETEKE IFSKYSEHIT KEISTIKNSI  720
ITDVNGNLLD NIQLDHTSQV NTLNAAFFIQ SLIDYSSNKD VLNDLSTSVK VQLYAQLFST  780
GLNTIYDSIQ LVNLISNAVN DTINVLPTIT EGIPIVSTIL DGINLGAAIK ELLDEHDPLL  840
KKELEAKVGV LAINMSLSIA ATVASIVGIG AEVTIFLLPI AGISAGIPSL VNNELILHDK  900
ATSVVNYFNH LSESKKYGPL KTEDDKILVP IDDLVISEID FNNNSIKLGT CNILAMEGGS  960
GHTVTGNIDH FFSSPSISSH IPSLSIYSAI GIETENLDFS KKIMMLPNAP SRVFWWETGA  1020
VPGLRSLEND GTRLLDSIRD LYPGKFYWRF YAFFDYAITT LKPVYEDTNI KIKLDKDTRN  1080
FIMPTITTNE IRNKLSYSFD GAGGTYSLLL SSYPISTNIN LSKDDLWIFN IDNEVREISI  1140
ENGTIKKGKL IKDVLSKIDI NKNKLIIGNQ TIDFSGDIDN KDRYIFLTCE LDDKISLIIE  1200
INLVAKSYSL LLSGDKNYLI SNLSNIIEKI NTLGLDSKNI AYNYTDESNN KYFGAISKTS  1260
QKSIIHYKKD SKNILEFYND STLEFNSKDF IAEDINVFMK DDINTITGKY YVDNNTDKSI  1320
DFSISLVSKN QVKVNGLYLN ESVYSSYLDF VKNSDGHHNT SNFMNLFLDN ISFWKLFGFE  1380
NINFVIDKYF TLVGKTNLGY VEFICDNNKN IDIYFGEWKT SSSKSTIFSG NGRNVVVEPI  1440
YNPDTGEDIS TSLDFSYEPL YGIDRYINKV LIAPDLYTSL ININTNYYSN EYYPEIIVLN  1500
PNTFHKKVNI NLDSSSFEYK WSTEGSDFIL VRYLEESNKK ILQKIRIKGI LSNTQSFNKM  1560
SIDFKDIKKL SLGYIMSNFK SFNSENELDR DHLGFKIIDN KTYYYDEDSK LVKGLININN  1620
SLFYFDPIEF NLVTGWQTIN GKKYYFDINT GAALISYKII NGKHFYFNND GVMQLGVFKG  1680
PDGFEYFAPA NTQNNNIEGQ AIVYQSKFLT LNGKKYYFDN DSKAVTGWRI INNEKYYFNP  1740
NNAIAAVGLQ VIDNNKYYFN PDTAIISKGW QTVNGSRYYF DTDTAIAFNG YKTIDGKHFY  1800
FDSDCVVKIG VFSTSNGFEY FAPANTYNNN IEGQAIVYQS KFLTLNGKKY YFDNNSKAVT  1860
GWQTIDSKKY YFNTNTAEAA TGWQTIDGKK YYFNTNTAEA ATGWQTIDGK KYYFNTNTAI  1920
ASTGYTIING KHFYFNTDGI MQIGVFKGPN GFEYFAPANT DANNIEGQAI LYQNEFLTLN  1980
GKKYYFGSDS KAVTGWRIIN NKKYYFNPNN AIAAIHLCTI NNDKYYFSYD GILQNGYITI  2040
ERNNFYFDAN NESKMVTGVF KGPNGFEYFA PANTHNNNIE GQAIVYQNKF LTLNGKKYYF  2100
DNDSKAVTGW QTIDGKKYYF NLNTAEAATG WQTIDGKKYY FNLNTAEAAT GWQTIDGKKY  2160
YFNTNTFIAS TGYTSINGKH FYFNTDGIMQ IGVFKGPNGF EYFAPANTHN NNIEGQAILY  2220
QNKFLTLNGK KYYFGSDSKA VTGLRTIDGK KYYFNTNTAV AVTGWQTING KKYYFNTNTS  2280
IASTGYTIIS GKHFYFNTDG IMQIGVFKGP DGFEYFAPAN TDANNIEGQA IRYQNRFLYL  2340
HDNIYYFGNN SKAATGWVTI DGNRYYFEPN TAMGANGYKT IDNKNFYFRN GLPQIGVFKG  2400
SNGFEYFAPA NTDANNIEGQ AIRYQNRFLH LLGKIYYFGN NSKAVTGWQT INGKVYYFMP  2460
DTAMAAAGGL FEIDGVIYFF GVDGVKAPGI YG                               2492

SEQ ID NO: 31          moltype = AA  length = 2498
FEATURE                Location/Qualifiers
REGION                 1..2498
                       note = Fusion protein
source                 1..2498
                       mol_type = protein
                       organism = synthetic construct
SEQUENCE: 31
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
```

-continued

ENFRPGDRVR GVLYSVRPEA RGAQLFVTRS KPEMLIELFR IEVPEIGEEV IEIKAAARDP 240
GSRAKIAVKT NDKRIDPVGA CVGMRGARVQ AVSTELGGER IDIVLWDDNP AQFVINAMAP 300
ADVASIVVDE DKHTMDIAVE AGNLAQAIGR NGQNVRLASQ LSGWELNVMT VDDLQAKHQA 360
EAHAAIDTFT KYLDIDEDFA TVLVEEGFST LEELAYVPMK ELLEIEGLDE PTVEALRERA 420
KNALATIAQA QEESLGDNKP ADDLLNLEGV DRDLAFKLAA RGVCTLEDLA EQGIDDLADI 480
EGLTDEKAGA LIMAARNICW FGDEASGALL AEAAAKEAAA KEAAAKEAAA KEAAAKAAAG 540
GSLVPRGSGS AAAPFTMIMS DLSSKEYIFF DSIDNKLKAK SKNIPGLASI SEDIKTLLLD 600
ASVSPDTKFI LNNLKLNIES SIGDYIYYEK LEPVKNIIHN SIDDLIDEFN LLENVSDELY 660
ELKKLNNLDE KYLISFEDIS KNNSTYSVRF INKSNGESVY VETEKEIFSK YSEHITKEIS 720
TIKNSIITDV NGNLLDNIQL DHTSQVNTLN AAFFIQSLID YSSNKDVLND LSTSVKVQLY 780
AQLFSTGLNT IYDSIQLVNL ISNAVNDTIN VLPTITEGIP IVSTILDGIN LGAAIKELLD 840
EHDPLLKKEL EAKVGVLAIN MSLSIAATVA SIVGIGAEVT IFLLPIAGIS AGIPSLVNNE 900
LILHDKATSV VNYFNHLSES KKYGPLKTED DKILVPIDDL VISEIDFNNN SIKLGTCNIL 960
AMEGGSGHTV TGNIDHFFSS PSISSHIPSL SIYSAIGIET ENLDFSKKIM MLPNAPSRVF 1020
WWETGAVPGL RSLENDGTRL LDSIRDLYPG KFYWRFYAFF DYAITTLKPV YEDTNIKIKL 1080
DKDTRNFIMP TITTNEIRNK LSYSFDGAGG TYSLLLSSYP ISTNINLSKD DLWIFNIDNE 1140
VREISIENGT IKKGKLIKDV LSKIDINKNK LIIGNQTIDF SGDIDNKDRY IFLTCELDDK 1200
ISLIIEINLV AKSYSLLLSG DKNYLISNLS NIIEKINTLG LDSKNIAYNY TDESNNKYFG 1260
AISKTSQKSI IHYKKDSKNI LEFYNDSTLE FNSKDFIAED INVFMKDDIN TITGKYYVDN 1320
NTDKSIDFSI SLVSKNQVKV NGLYLNESVY SSYLDFVKNS DGHHNTSNFM NLFLDNISFW 1380
KLFGFENINF VIDKYFTLVG KTNLGYVEFI CDNNKNIDIY FGEWKTSSSK STIFSGNGRN 1440
VVVEPIYNPD TGEDISTSLD FSYEPLYGID RYINKVLIAP DLYTSLININ TNYYSNEYYP 1500
EIIVLNPNTF HKKVNINLDS SSFEYKWSTE GSDFILVRYL EESNKKILQK IRIKGILSNT 1560
QSFNKMSIDF KDIKKLSLGY IMSNFKSFNS ENELDRDHLG FKIIDNKTYY YDEDSKLVKG 1620
LININNSLFY FDPIEFNLVT GWQTINGKKY YFDINTGAAL ISYKIINGKH FYFNNDGVMQ 1680
LGVFKGPDGF EYFAPANTQN NNIEGQAIVY QSKFLTLNGK KYYFDNDSKA VTGWRIINNE 1740
KYYFNPNNAI AAVGLQVIDN NKYYFNPDTA IISKGWQTVN GSRYYFDTDT AIAFNGYKTI 1800
DGKHFYFDSD CVVKIGVFST SNGFEYFAPA NTYNNNIEGQ AIVYQSKFLT LNGKKYYFDN 1860
NSKAVTGWQT IDSKKYYFNT NTAEAATGWQ TIDGKKYYFN TNTAEAATGW QTIDGKKYYF 1920
NTNTAIASTG YTIINGKHFY FNTDGIMQIG VFKGPNGFEY FAPANTDANN IEGQAILYQN 1980
EFLTLNGKKY YFGSDSKAVT GWRIINNKKY YFNPNNAIAA IHLCTINNDK YYFSYDGILQ 2040
NGYITIERNN FYFDANNESK MVTGVFKGPN GFEYFAPANT HNNNIEGQAI VYQNKFLTLN 2100
GKKYYFDNDS KAVTGWQTID GKKYYFNLNT AEAATGWQTI DGKKYYFNLN TAEAATGWQT 2160
IDGKKYYFNT NTFIASTGYT SINGKHFYFN TDGIMQIGVF KGPNGFEYFA PANTHNNNIE 2220
GQAILYQNKF LTLNGKKYYF GSDSKAVTGL RTIDGKKYYF NTNTAVAVTG WQTINGKKYY 2280
FNTNTSIAST GYTIISGKHF YFNTDGIMQI GVFKGPDGFE YFAPANTDAN NIEGQAIRYQ 2340
NRFLYLHDNI YYFGNNSKAA TGWVTIDGNR YYFEPNTAMG ANGYKTIDNK NFYFRNGLPQ 2400
IGVFKGSNGF EYFAPANTDA NNIEGQAIRY QNRFLHLLGK IYYFGNNSKA VTGWQTINGK 2460
VYYFMPDTAM AAAGGLFEID GVIYFFGVDG VKAPGIYG 2498

SEQ ID NO: 32 moltype = AA length = 2143
FEATURE Location/Qualifiers
REGION 1..2143
note = Fusion protein
source 1..2143
mol_type = protein
organism = synthetic construct
SEQUENCE: 32
HHHHHHHHHG GSGGSGGSGG SGGSGGSGGS GGSGGSGGSH MASNKEILAV VEAVSNEKAL 60
PREKIFEALE SALATATKKK YEQEIDVRVQ IDRKSGDFDT FRRWLVVDEV TQPTKEITLE 120
AARYEDESLN LGDYVEDQIE SVTFDRITTQ TAKQVIVQKV REAERAMVVD QFREHEGEII 180
TGVVKKVNRD NISLDLGNNA EAVILREDML PRENFRPGDR VRGVLYSVRP EARGAQLFVT 240
RSKPEMLIEL FRIEVPEIGE EVIEIKAAAR DPGSRAKIAV KTNDKRIDPV GACVGMRGAR 300
VQAVSTELGG ERIDIVLWDD NPAQFVINAM APADVASIVV DEDKHTMDIA VEAGNLAQAI 360
GRNGQNVRLA SQLSGWELNV MTVDDLQAKH QAEAHAAIDT FTKYLDIDED FATVLVEEGF 420
STLEELAYVP MKELLEIEGL DEPTVEALRE RAKNALATIA QAQEESLGDN KPADDLLNLE 480
GVDRDLAFKL AARGVCTLED LAEQGIDDLA DIEGLTDEKA GALIMAARNI CWFGDEASGA 540
LVPRGSVTSL YKKAGSAAAP FTMESKKYGP LKTEDDKILV PIDDLVISEI DFNNNSIKLG 600
TCNILAMEGG SGHTVTGNID HFFSSPSISS HIPSLSIYSA IGIETENLDF SKKIMMLPNA 660
PSRVFWWETG AVPGLRSLEN DGTRLLDSIR DLYPGKFYWR FYAFFDYAIT TLKPVYEDTN 720
IKIKLDKDTR NFIMPTITTN EIRNKLSYSF DGAGGTYSLL LSSYPISTNI NLSKDDLWIF 780
NIDNEVREIS IENGTIKKGK LIKDVLSKID INKNKLIIGN QTIDFSGDID NKDRYIFLTC 840
ELDDKISLII EINLVAKSYS LLLSGDKNYL ISNLSNIIEK INTLGLDSKN IAYNYTDESN 900
NKYFGAISKT SQKSIIHYKK DSKNILEFYN DSTLEFNSKD FIAEDINVFM KDDINTITGK 960
YYVDNNTDKS IDFSISLVSK NQVKVNGLYL NESVYSSYLD FVKNSDGHHN TSNFMNLFLD 1020
NISFWKLFGF ENINFVIDKY FTLVGKTNLG YVEFICDNNK NIDIYFGEWK TSSSKSTIFS 1080
GNGRNVVVEP IYNPDTGEDI STSLDFSYEP LYGIDRYINK VLIAPDLYTS LININTNYYS 1140
NEYYPEIIVL NPNTFHKKVN INLDSSSFEY KWSTEGSDFI LVRYLEESNK KILQKIRIKG 1200
ILSNTQSFNK MSIDFKDIKK LSLGYIMSNF KSFNSENELD RDHLGFKIID NKTYYYDEDS 1260
KLVKGLININ NSLFYFDPIE FNLVTGWQTI NGKKYYFDIN TGAALISYKI INGKHFYFNN 1320
DGVMQLGVFK GPDGFEYFAP ANTQNNNIEG QAIVYQSKFL TLNGKKYYFD NDSKAVTGWR 1380
IINNEKYYFN PNNAIAAVGL QVIDNNKYYF NPDTAIISKG WQTVNGSRYY FDTDTAIAFN 1440
GYKTIDGKHF YFDSDCVVKI GVFSTSNGFE YFAPANTYNN NIEGQAIVYQ SKFLTLNGKK 1500
YYFDNNSKAV TGWQTIDSKK YYFNTNTAEA ATGWQTIDGK KYYFNTNTAE AATGWQTIDG 1560
KKYYFNTNTA IASTGYTIIN GKHFYFNTDG IMQIGVFKGP NGFEYFAPAN TDANNIEGQA 1620
ILYQNEFLTL NGKKYYFGSD SKAVTGWRII NNKKYYFNPN NAIAAIHLCT INNDKYYFSY 1680
DGILQNGYIT IERNNFYFDA NNESKMVTGV FKGPNGFEYF APANTHNNNI EGQAIVYQNK 1740
FLTLNGKKYY FDNDSKAVTG WQTIDGKKYY FNLNTAEAAT GWQTIDGKKY YFNLNTAEAA 1800
TGWQTIDGKK YYFNTNTFIA STGYTSINGK HFYFNTDGIM QIGVFKGPNG FEYFAPANTH 1860

```
NNNIEGQAIL YQNKFLTLNG KKYYFGSDSK AVTGLRTIDG KKYYFNTNTA VAVTGWQTIN  1920
GKKYYFNTNT SIASTGYTII SGKHFYFNTD GIMQIGVFKG PDGFEYFAPA NTDANNIEGQ  1980
AIRYQNRFLY LHDNIYYFGN NSKAATGWVT IDGNRYYFEP NTAMGANGYK TIDNKNFYFR  2040
NGLPQIGVFK GSNGFEYFAP ANTDANNIEG QAIRYQNRFL HLLGKIYYFG NNSKAVTGWQ  2100
TINGKVYYFM PDTAMAAAGG LFEIDGVIYF FGVDGVKAPG IYG                    2143

SEQ ID NO: 33          moltype = AA  length = 2150
FEATURE                Location/Qualifiers
REGION                 1..2150
                       note = Fusion protein
source                 1..2150
                       mol_type = protein
                       organism = synthetic construct
SEQUENCE: 33
HHHHHHHHHH GGSLAEAAAK EAAAKEAAAK EAAAKEAAAK AAAGGSHMAS NKEILAVVEA  60
VSNEKALPRE KIFEALESAL ATATKKKYEQ EIDVRVQIDR KSGDFDTFRR WLVVDEVTQP  120
TKEITLEAAR YEDESLNLGD YVEDQIESVT FDRITTQTAK QVIVQKVREA ERAMVVDQFR  180
EHEGEIITGV VKKVNRDNIS LDLGNNAEAV ILREDMLPRE NFRPGDRVRG VLYSVRPEAR  240
GAQLFVTRSK PEMLIELFRI EVPEIGEEVI EIKAAARDPG SRAKIAVKTN DKRIDPVGAC  300
VGMRGARVQA VSTELGGERI DIVLWDDNPA QFVINAMAPA DVASIVVDED KHTMDIAVEA  360
GNLAQAIGRN GQNVRLASQL SGWELNVMTV DDLQAKHQAE AHAAIDTFTK YLDIDEDFAT  420
VLVEEGFSTL EELAYVPMKE LLEIEGLDEP TVEALRERAK NALATIAQAQ EESLGDNKPA  480
DDLLNLEGVD RDLAFKLAAR GVCTLEDLAE QGIDDLADIE GLTDEKAGAL IMAARNICWF  540
GDEASGALVP RGSVTSLYKK AGSAAAPFTM ESKKYGPLKT EDDKILVPID DLVISEIDFN  600
NNSIKLGTCN ILAMEGGSGH TVTGNIDHFF SSPSISSHIP SLSIYSAIGI ETENLDFSKK  660
IMMLPNAPSR VFWWETGAVP GLRSLENDGT RLLDSIRDLY PGKFYWRFYA FFDYAITTLK  720
PVYEDTNIKI KLDKDTRNFI MPTITTNEIR NKLSYSFDGA GGTYSLLLSS YPISTNINLS  780
KDDLWIFNID NEVREISIEN GTIKKGKLIK DVLSKIDINK NKLIIGNQTI DFSGDIDNKD  840
RYIFLTCELD DKISLIIEIN LVAKSYSLLL SGDKNYLISN LSNIIEKINT LGLDSKNIAY  900
NYTDESNNKY FGAISKTSQK SIIHYKKDSK NILEFYNDST LEFNSKDFIA EDINVFMKDD  960
INTITGKYYV DNNTDKSIDF SISLVSKNQV KVNGLYLNES VYSSYLDFVK NSDGHHNTSN  1020
FMNLFLDNIS FWKLFGFENI NFVIDKYFTL VGKTNLGYVE FICDNNKNID IYFGEWKTSS  1080
SKSTIFSGNG RNVVVEPIYN PDTGEDISTS LDFSYEPLYG IDRYINKVLI APDLYTSLIN  1140
INTNYYSNEY YPEIIVLNPN TFHKKVNINL DSSSFEYKWS TEGSDFILVR YLEESNKKIL  1200
QKIRIKGILS NTQSFNKMSI DFKDIKKLSL GYIMSNFKSF NSENELDRDH LGFKIIDNKT  1260
YYYDEDSKLV KGLININNSL FYFDPIEFNL VTGWQTINGK KYYFDINTGA ALISYKIING  1320
KHFYFNNDGV MQLGVFKGPD GFEYFAPANT QNNNIEGQAI VYQSKFLTLN GKKYYFDNDS  1380
KAVTGWRIIN NEKYYFNPNN AIAAVGLQVI DNNKYYFNPD TAIISKGWQT VNGSRYYFDT  1440
DTAIAFNGYK TIDGKHFYFD SDCVVKIGVF STSNGFEYFA PANTYNNNIE GQAIVYQSKF  1500
LTLNGKKYYF DNNSKAVTGW QTIDSKKYYF NTNTAEAATG WQTIDGKKYY FNTNTAEAAT  1560
GWQTIDGKKY YFNTNTAIAS TGYTIINGKH FYFNTDGIMQ IGVFKGPNGF EYFAPANTDA  1620
NNIEGQAILY QNEFLTLNGK KYYFGSDSKA VTGWRIINNK KYYFNPNNAI AAIHLCTINN  1680
DKYYFSYDGI LQNGYITIER NNFYFDANNE SKMVTGVFKG PNGFEYFAPA NTHNNNIEGQ  1740
AIVYQNKFLT LNGKKYYFDN DSKAVTGWQT IDGKKYYFNL NTAEAATGWQ TIDGKKYYFN  1800
LNTAEAATGW QTIDGKKYYF NTNTFIASTG YTSINGKHFY FNTDGIMQIG VFKGPNGFEY  1860
FAPANTHNNN IEGQAILYQN KFLTLNGKKY YFGSDSKAVT GLRTIDGKKY YFNTNTAVAV  1920
TGWQTINGKK YYFNTNTSIA STGYTIISGK HFYFNTDGIM QIGVFKGPDG FEYFAPANTD  1980
ANNIEGQAIR YQNRFLYLHD NIYYFGNNSK AATGWVTIDG NRYYFEPNTA MGANGYKTID  2040
NKNFYFRNGL PQIGVFKGSN GFEYFAPANT DANNIEGQAI RYQNRFLHLL GKIYYFGNNS  2100
KAVTGWQTIN GKVYYFMPDT AMAAAGGLFE IDGVIYFFGV DGVKAPGIYG             2150

SEQ ID NO: 34          moltype = AA  length = 2131
FEATURE                Location/Qualifiers
REGION                 1..2131
                       note = Fusion protein
source                 1..2131
                       mol_type = protein
                       organism = synthetic construct
SEQUENCE: 34
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALG GSGGSGGSGG SGGSGGSGGS GGSGGSLVPR  540
GSGSAAAPFT MESKKYGPLK TEDDKILVPI DDLVISEIDF NNNSIKLGTC NILAMEGGSG  600
HTVTGNIDHF FSSPSISSHI PSLSIYSAIG IETENLDFSK KIMMLPNAPS RVFWWETGAV  660
PGLRSLENDG TRLLDSIRDL YPGKFYWRFY AFFDYAITTL KPVYEDTNIK IKLDKDTRNF  720
IMPTITTNEI RNKLSYSFDG AGGTYSLLLS SYPISTNINL SKDDLWIFNI DNEVREISIE  780
NGTIKKGKLI KDVLSKIDIN KNKLIIGNQT IDFSGDIDNK DRYIFLTCEL DDKISLIIEI  840
NLVAKSYSLL LSGDKNYLIS NLSNIIEKIN TLGLDSKNIA YNYTDESNNK YFGAISKTSQ  900
KSIIHYKKDS KNILEFYNDS TLEFNSKDFI AEDINVFMKD DINTITGKYY VDNNTDKSID  960
FSISLVSKNQ VKVNGLYLNE SVYSSYLDFV KNSDGHHNTS NFMNLFLDNI SFWKLFGFEN  1020
INFVIDKYFT LVGKTNLGYV EFICDNNKNI DIYFGEWKTS SSKSTIFSGN GRNVVVEPIY  1080
NPDTGEDIST SLDFSYEPLY GIDRYINKVL IAPDLYTSLI NINTNYYSNE YYPEIIVLNP  1140
NTFHKKVNIN LDSSSFEYKW STEGSDFILV RYLEESNKKI LQKIRIKGIL SNTQSFNKMS  1200
```

```
IDFKDIKKLS LGYIMSNFKS FNSENELDRD HLGFKIIDNK TYYYDEDSKL VKGLININNS  1260
LFYFDPIEFN LVTGWQTING KKYYFDINTG AALISYKIIN GKHFYFNNDG VMQLGVFKGP  1320
DGFEYFAPAN TQNNNIEGQA IVYQSKFLTL NGKKYYFDND SKAVTGWRII NNEKYYFNPN  1380
NAIAAVGLQV IDNNKYYFNP DTAIISKGWQ TVNGSRYYFD TDTAIAFNGY KTIDGKHFYF  1440
DSDCVVKIGV FSTSNGFEYF APANTYNNNI EGQAIVYQSK FLTLNGKKYY FDNNSKAVTG  1500
WQTIDSKKYY FNTNTAEAAT GWQTIDGKKY YFNTNTAEAA TGWQTIDGKK YYFNTNTAIA  1560
STGYTIINGK HFYFNTDGIM QIGVFKGPNG FEYFAPANTD ANNIEGQAIL YQNEFLTLNG  1620
KKYYFGSDSK AVTGWRIINN KKYYFNPNNA IAAIHLCTIN NDKYYFSYDG ILQNGYITIE  1680
RNNFYFDANN ESKMVTGVFK GPNGFEYFAP ANTHNNNIEG QAIVYQNKFL TLNGKKYYFD  1740
NDSKAVTGWQ TIDGKKYYFN LNTAEAATGW QTIDGKKYYF NLNTAEAATG WQTIDGKKYY  1800
FNTNTFIAST GYTSINGKHF YFNTDGIMQI GVFKGPNGFE YFAPANTHNN NIEGQAILYQ  1860
NKFLTLNGKK YYFGSDSKAV TGLRTIDGKK YYFNTNTAVA VTGWQTINGK KYYFNTNTSI  1920
ASTGYTIISG KHFYFNTDGI MQIGVFKGPD GFEYFAPANT DANNIEGQAI RYQNRFLYLH  1980
DNIYYFGNNS KAATGWVTID GNRYYFEPNT AMGANGYKTI DNKNFYFRNG LPQIGVFKGS  2040
NGFEYFAPAN TDANNIEGQA IRYQNRFLHL LGKIYYFGNN SKAVTGWQTI NGKVYYFMPD  2100
TAMAAAGGLF EIDGVIYFFG VDGVKAPGIY G                                2131

SEQ ID NO: 35          moltype = AA  length = 2137
FEATURE                Location/Qualifiers
REGION                 1..2137
                       note = Fusion protein
source                 1..2137
                       mol_type = protein
                       organism = synthetic construct
SEQUENCE: 35
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALL AEAAAKEAAA KEAAAKEAAA KEAAAKAAAG  540
GSLVPRGSGS AAAPFTMESK KYGPLKTEDD KILVPIDDLV ISEIDFNNNS IKLGTCNILA  600
MEGGSGHTVT GNIDHFFSSP SISSHIPSLS IYSAIGIETE NLDFSKKIMM LPNAPSRVFW  660
WETGAVPGLR SLENDGTRLL DSIRDLYPGK FYWRFYAFFD YAITTLKPVY EDTNIKIKLD  720
KDTRNFIMPT ITTNEIRNKL SYSFDGAGGT YSLLLSSYPI STNINLSKDD LWIFNIDNEV  780
REISIENGTI KKGKLIKDVL SKIDINKNKL IIGNQTIDFS GDIDNKDRYI FLTCELDDKI  840
SLIIEINLVA KSYSLLLSGD KNYLISNLSN IIEKINTLGL DSKNIAYNYT DESNNKYFGA  900
ISKTSQKSII HYKKDSKNIL EFYNDSTLEF NSKDFIAEDI NVFMKDDINT ITGKYYVDNN  960
TDKSIDFSIS LVSKNQVKVN GLYLNESVYS SYLDFVKNSD GHHNTSNFMN LFLDNISFWK  1020
LFGFENINFV IDKYFTLVGK TNLGYVEFIC DNNKNIDIYF GEWKTSSSKS TIFSGNGRNV  1080
VVEPIYNPDT GEDISTSLDF SYEPLYGIDR YINKVLIAPD LYTSLININT NYYSNEYYPE  1140
IIVLNPNTFH KKVNINLDSS SFEYKWSTEG SDFILVRYLE ESNKKILQKI RIKGILSNTQ  1200
SFNKMSIDFK DIKKLSLGYI MSNFKSFNSE NELDRDHLGF KIIDNKTYYY DEDSKLVKGL  1260
INNNSLFYF DPIEFNLVTG WQTINGKKYY FDINTGAALI SYKIINGKHF YFNNDGVMQL  1320
GVFKGPDGFE YFAPANTQNN NIEGQAIVYQ SKFLTLNGKK YYFDNDSKAV TGWRIINNEK  1380
YYFNPNNAIA AVGLQVIDNN KYYFNPDTAI ISKGWQTVNG SRYYFDTDTA IAFNGYKTID  1440
GKHFYFDSDC VVKIGVFSTS NGFEYFAPAN TYNNNIEGQA IVYQSKFLTL NGKKYYFDNN  1500
SKAVTGWQTI DSKKYYFNTN TAEAATGWQT IDGKKYYFNT NTAEAATGWQ TIDGKKYYFN  1560
TNTAIASTGY TIINGKHFYF NTDGIMQIGV FKGPNGFEYF APANTDANNI EGQAILYQNE  1620
FLTLNGKKYY FGSDSKAVTG WRIINNKKYY FNPNNAIAAI HLCTINNDKY YFSYDGILQN  1680
GYITIERNNF YFDANNESKM VTGVFKGPNG FEYFAPANTH NNNIEGQAIV YQNKFLTLNG  1740
KKYYFDNDSK AVTGWQTIDG KKYYFNLNTA EAATGWQTID GKKYYFNLNT AEAATGWQTI  1800
DGKKYYFNTN TFIASTGYTS INGKHFYFNT DGIMQIGVFK GPNGFEYFAP ANTHNNNIEG  1860
QAILYQNKFL TLNGKKYYFG SDSKAVTGLR TIDGKKYYFN TNTAVAVTGW QTINGKKYYF  1920
NTNTSIASTG YTIISGKHFY FNTDGIMQIG VFKGPDGFEY FAPANTDANN IEGQAIRYQN  1980
RFLYLHDNIY YFGNNSKAAT GWVTIDGNRY YFEPNTAMGA NGYKTIDNKN FYFRNGLPQI  2040
GVFKGSNGFE YFAPANTDAN NIEGQAIRYQ NRFLHLLGKI YYFGNNSKAV TGWQTINGKV  2100
YYFMPDTAMA AAGGLFEIDG VIYFFGVDGV KAPGIYG                          2137

SEQ ID NO: 36          moltype = AA  length = 2116
FEATURE                Location/Qualifiers
REGION                 1..2116
                       note = Fusion protein
source                 1..2116
                       mol_type = protein
                       organism = synthetic construct
SEQUENCE: 36
HHHHHHHHHG GSGGSGGSGG SGGSGGSGGS GGSGGSGGSH MASDKIIHLT DDSFDTDVLK  60
ADGAILVDFW AEWCGPCKMI APILDEIADE YQGKLTVAKL NIDQNPGTAP KYGIRGIPTL  120
LLFKNGEVAA TKVGALSKGQ LKEFLDANLA RALVPRGSVT SLYKKAGSAA APFTMIMSDL  180
SSKEYIFFDS IDNKLKAKSK NIPGLASISE DIKTLLLDAS VSPDTKFILN NLKLNIESSI  240
GDYIYYEKLE PVKNIIHNSI DDLIDEFNLL ENVSDELYEL KKLNNLDEKY LISFEDISKN  300
NSTYSVRFIN KSNGESVYVE TEKEIFSKYS EHITKEISTI KNSIITDVNG NLLDNIQLDH  360
TSQVNTLNAA FFIQSLIDYS SNKDVLNDLS TSVKVQLYAQ LFSTGLNTIY DSIQLVNLIS  420
NAVNDTINVL PTITEGIPIV STILDGINLG AAIKELLDEH DPLLKKELEA KVGVLAINMS  480
LSIAATVASI VGIGAEVTIF LLPIAGISAG IPSLVNNELI LHDKATSVVN YFNHLSESKK  540
```

```
YGPLKTEDDK ILVPIDDLVI SEIDFNNNSI KLGTCNILAM EGGSGHTVTG NIDHFFSSPS  600
ISSHIPSLSI YSAIGIETEN LDFSKKIMML PNAPSRVFWW ETGAVPGLRS LENDGTRLLD  660
SIRDLYPGKF YWRFYAFFDY AITTLKPVYE DTNIKIKLDK DTRNFIMPTI TTNEIRNKLS  720
YSFDGAGGTY SLLLSSYPIS TNINLSKDDL WIFNIDNEVR EISIENGTIK KGKLIKDVLS  780
KIDINKNKLI IGNQTIDFSG DIDNKDRYIF LTCELDDKIS LIIEINLVAK SYSLLLSGDK  840
NYLISNLSNI IEKINTLGLD SKNIAYNYTD ESNNKYFGAI SKTSQKSIIH YKKDSKNILE  900
FYNDSTLEFN SKDFIAEDIN VFMKDDINTI TGKYYVDNNT DKSIDFSISL VSKNQVKVNG  960
LYLNESVYSS YLDFVKNSDG HHNTSNFMNL FLDNISFWKL FGFENINFVI DKYFTLVGKT  1020
NLGYVEFICD NNKNIDIYFG EWKTSSSKST IFSGNGRNVV VEPIYNPDTG EDISTSLDFS  1080
YEPLYGIDRY INKVLIAPDL YTSLININTN YYSNEYYPEI IVLNPNTFHK KVNINLDSSS  1140
FEYKWSTEGS DFILVRYLEE SNKKILQKIR IKGILSNTQS FNKMSIDFKD IKKLSLGYIM  1200
SNFKSFNSEN ELDRDHLGFK IIDNKTYYYD EDSKLVKGLI NINNSLFYFD PIEFNLVTGW  1260
QTINGKKYYF DINTGAALIS YKIINGKHFY FNNDGVMQLG VFKGPDGFEY FAPANTQNNN  1320
IEGQAIVYQS KFLTLNGKKY YFDNDSKAVT GWRIINNEKY YFNPNNAIAA VGLQVIDNNK  1380
YYFNPDTAII SKGWQTVNGS RYYFDTDTAI AFNGYKTIDG KHFYFDSDCV VKIGVFSTSN  1440
GFEYFAPANT YNNNIEGQAI VYQSKFLTLN GKKYYFDNNS KAVTGWQTID SKKYYFNTNT  1500
AEAATGWQTI DGKKYYFNTN TAEAATGWQT IDGKKYYFNT NTAIASTGYT IINGKHFYFN  1560
TDGIMQIGVF KGPNGFEYFA PANTDANNIE GQAILYQNEF LTLNGKKYYF GSDSKAVTGW  1620
RIINNKKYYF NPNNAIAAIH LCTINNDKYY FSYDGILQNG YITIERNNFY FDANNESKMV  1680
TGVFKGPNGF EYFAPANTHN NNIEGQAIVY QNKFLTLNGK KYYFDNDSKA VTGWQTIDGK  1740
KYYFNLNTAE AATGWQTIDG KKYYFNLNTA EAATGWQTID GKKYYFNTNT FIASTGYTSI  1800
NGKHFYFNTD GIMQIGVFKG PNGFEYFAPA NTHNNNIEGQ AILYQNKFLT LNGKKYYFGS  1860
DSKAVTGLRT IDGKKYYFNT NTAVAVTGWQ TINGKKYYFN TNTSIASTGY TIISGKHFYF  1920
NTDGIMQIGV FKGPDGFEYF APANTDANNI EGQAIRYQNR FLYLHDNIYY FGNNSKAATG  1980
WVTIDGNRYY FEPNTAMGAN GYKTIDNKNF YFRNGLPQIG VFKGSNGFEY FAPANTDANN  2040
IEGQAIRYQN RFLHLLGKIY YFGNNSKAVT GWQTINGKVY YFMPDTAMAA AGGLFEIDGV  2100
IYFFGVDGVK APGIYG                                                  2116
```

```
SEQ ID NO: 37           moltype = AA  length = 2123
FEATURE                 Location/Qualifiers
REGION                  1..2123
                        note = Fusion protein
source                  1..2123
                        mol_type = protein
                        organism = synthetic construct
SEQUENCE: 37
HHHHHHHHHH GGSLAEAAAK EAAAKEAAAK EAAAKEAAAK AAAGGSHMAS DKIIHLTDDS  60
FDTDVLKADG AILVDFWAEW CGPCKMIAPI LDEIADEYQG KLTVAKLNID QNPGTAPKYG  120
IRGIPTLLLF KNGEVAATKV GALSKGQLKE FLDANLARAL VPRGSVTSLY KKAGSAAAPF  180
TMIMSDLSSK EYIFFDSIDN KLKAKSKNIP GLASISEDIK TLLLDASVSP DTKFILNNLK  240
LNIESSIGDY IYYEKLEPVK NIIHNSIDDL IDEFNLLENV SDELYELKKL NNLDEKYLIS  300
FEDISKNNST YSVRFINKSN GESVYVETEK EIFSKYSEHI TKEISTIKNS IITDVNGNLL  360
DNIQLDHTSQ VNTLNAAFFI QSLIDYSSNK DVLNDLSTSV KVQLYAQLFS TGLNTIYDSI  420
QLVNLISNAV NDTINVLPTI TEGIPIVSTI LDGINLGAAI KELLDEHDPL LKKELEAKVG  480
VLAINMSLSI AATVASIVGI GAEVTIFLLP IAGISAGIPS LVNNELILHD KATSVVNYFN  540
HLSESKKYGP LKTEDDKILV PIDDLVISEI DFNNNSIKLG TCNILAMEGG SGHTVTGNID  600
HFFSSPSISS HIPSLSIYSA IGIETENLDF SKKIMMLPNA PSRVFWWETG AVPGLRSLEN  660
DGTRLLDSIR DLYPGKFYWR FYAFFDYAIT TLKPVYEDTN IKIKLDKDTR NFIMPTITTN  720
EIRNKLSYSF DGAGGTYSLL LSSYPISTNI NLSKDDLWIF NIDNEVREIS IENGTIKKGK  780
LIKDVLSKID INKNKLIIGN QTIDFSGDID NKDRYIFLTC ELDDKISLII EINLVAKSYS  840
LLLSGDKNYL ISNLSNIIEK INTLGLDSKN IAYNYTDESN NKYFGAISKT SQKSIIHYKK  900
DSKNILEFYN DSTLEFNSKD FIAEDINVFM KDDINTITGK YYVDNNTDKS IDFSISLVSK  960
NQVKVNGLYL NESVYSSYLD FVKNSDGHHN TSNFMNLFLD NISFWKLFGF ENINFVIDKY  1020
FTLVGKTNLG YVEFICDNNK NIDIYFGEWK TSSSKSTIFS GNGRNVVVEP IYNPDTGEDI  1080
STSLDFSYEP LYGIDRYINK VLIAPDLYTS LININTNYYS NEYYPEIIVL NPNTFHKKVN  1140
INLDSSSFEY KWSTEGSDFI LVRYLEESNK KILQKIRIKG ILSNTQSFNK MSIDFKDIKK  1200
LSLGYIMSNF KSFNSENELD RDHLGFKIID NKTYYYDEDS KLVKGLININ NSLFYFDPIE  1260
FNLVTGWQTI NGKKYYFDIN TGAALISYKI INGKHFYFNN DGVMQLGVFK GPDGFEYFAP  1320
ANTQNNNIEG QAIVYQSKFL TLNGKKYYFD NDSKAVTGWR IINNEKYYFN PNNAIAAVGL  1380
QVIDNNKYYF NPDTAIISKG WQTVNGSRYY FDTDTAIAFN GYKTIDGKHF YFDSDCVVKI  1440
GVFSTSNGFE YFAPANTYNN NIEGQAIVYQ SKFLTLNGKK YYFDNNSKAV TGWQTIDSKK  1500
YYFNTNTAEA ATGWQTIDGK KYYFNTNTAE AATGWQTIDG KKYYFNTNTA IASTGYTIIN  1560
GKHFYFNTDG IMQIGVFKGP NGFEYFAPAN TDANNIEGQA ILYQNEFLTL NGKKYYFGSD  1620
SKAVTGWRII NNKKYYFNPN NAIAAIHLCT INNDKYYFSY DGILQNGYIT IERNNFYFDA  1680
NNESKMVTGV FKGPNGFEYF APANTHNNNI EGQAIVYQNK FLTLNGKKYY FDNDSKAVTG  1740
WQTIDGKKYY FNLNTAEAAT GWQTIDGKKY YFNLNTAEAA TGWQTIDGKK YYFNTNTFIA  1800
STGYTSINGK HFYFNTDGIM QIGVFKGPNG FEYFAPANTH NNNIEGQAIL YQNKFLTLNG  1860
KKYYFGSDSK AVTGLRTIDG KKYYFNTNTA VAVTGWQTIN GKKYYFNTNT SIASTGYTII  1920
SGKHFYFNTD GIMQIGVFKG PDGFEYFAPA NTDANNIEGQ AIRYQNRFLY LHDNIYYFGN  1980
NSKAATGWVT IDGNRYYFEP NTAMGANGYK TIDNKNFYFR NGLPQIGVFK GSNGFEYFAP  2040
ANTDANNIEG QAIRYQNRFL HLLGKIYYFG NNSKAVTGWQ TINGKVYYFM PDTAMAAAGG  2100
LFEIDGVIYF FGVDGVKAPG IYG                                         2123
```

```
SEQ ID NO: 38           moltype = AA  length = 2104
FEATURE                 Location/Qualifiers
REGION                  1..2104
                        note = Fusion protein
source                  1..2104
                        mol_type = protein
```

```
                         organism = synthetic construct
SEQUENCE: 38
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LGGSGGSGGS GGSGGSGGSG GSGGSGGSLV PRGSGSAAAP FTMIMSDLSS KEYIFFDSID  180
NKLKAKSKNI PGLASISEDI KTLLLDASVS PDTKFILNNL KLNIESSIGD YIYYEKLEPV  240
KNIIHNSIDD LIDEFNLLEN VSDELYELKK LNNLDEKYLI SFEDISKNNS TYSVRFINKS  300
NGESVYVETE KEIFSKYSEH ITKEISTIKN SIITDVNGNL LDNIQLDHTS QVNTLNAAFF  360
IQSLIDYSSN KDVLNDLSTS VKVQLYAQLF STGLNTIYDS IQLVNLISNA VNDTINVLPT  420
ITEGIPIVST ILDGINLGAA IKELLDEHDP LLKKELEAKV GVLAINMSLS IAATVASIVG  480
IGAEVTIFLL PIAGISAGIP SLVNNELILH DKATSVVNYF NHLSESKKYG PLKTEDDKIL  540
VPIDDLVISE IDFNNNSIKL GTCNILAMEG GSGHTVTGNI DHFFSSPSIS SHIPSLSIYS  600
AIGIETENLD FSKKIMMLPN APSRVFWWET GAVPGLRSLE NDGTRLLDSI RDLYPGKFYW  660
RFYAFFDYAI TTLKPVYEDT NIKIKLDKDT RNFIMPTITT NEIRNKLSYS FDGAGGTYSL  720
LLSSYPISTN INLSKDDLWI FNIDNEVREI SIENGTIKKG KLIKDVLSKI DINKNKLIIG  780
NQTIDFSGDI DNKDRYIFLT CELDDKISLI IEINLVAKSY SLLLSGDKNY LISNLSNIIE  840
KINTLGLDSK NIAYNYTDES NNKYFGAISK TSQKSIIHYK KDSKNILEFY NDSTLEFNSK  900
DFIAEDINVF MKDDINTITG KYYVDNNTDK SIDFSISLVS KNQVKVNGLY LNESVYSSYL  960
DFVKNSDGHH NTSNFMNLFL DNISFWKLFG FENINFVIDK YFTLVGKTNL GYVEFICDNN  1020
KNIDIYFGEW KTSSSKSTIF SGNGRNVVVE PIYNPDTGED ISTSLDFSYE PLYGIDRYIN  1080
KVLIAPDLYT SLININTNYY SNEYYPEIIV LNPNTFHKKV NINLDSSSFE YKWSTEGSDF  1140
ILVRYLEESN KKILQKIRIK GILSNTQSFN KMSIDFKDIK KLSLGYIMSN FKSFNSENEL  1200
DRDHLGFKII DNKTYYYDED SKLVKGLINI NNSLFYFDPI EFNLVTGWQT INGKKYYFDI  1260
NTGAALISYK IINGKHFYFN NDGVMQLGVF KGPDGFEYFA PANTQNNNIE GQAIVYQSKF  1320
LTLNGKKYYF DNDSKAVTGW RIINNEKYYF NPNNAIAAVG LQVIDNNKYY FNPDTAIISK  1380
GWQTVNGSRY YFDTDTAIAF NGYKTIDGKH FYFDSDCVVK IGVFSTSNGF EYFAPANTYN  1440
NNIEGQAIVY QSKFLTLNGK KYYFDNNSKA VTGWQTIDSK KYYFNTNTAE AATGWQTIDG  1500
KKYYFNTNTA EAATGWQTID GKKYYFNTNT AIASTGYTII NGKHFYFNTD GIMQIGVFKG  1560
PNGFEYFAPA NTDANNIEGQ AILYQNEFLT LNGKKYYFGS DSKAVTGWRI INNKKYYFNP  1620
NNAIAAIHLC TINNDKYYFS YDGILQNGYI TIERNNFYFD ANNESKMVTG VFKGPNGFEY  1680
FAPANTHNNN IEGQAIVYQN KFLTLNGKKY YFDNDSKAVT GWQTIDGKKY YFNLNTAEAA  1740
TGWQTIDGKK YYFNLNTAEA ATGWQTIDGK KYYFNTNTFI ASTGYTSING KHFYFNTDGI  1800
MQIGVFKGPN GFEYFAPANT HNNNIEGQAI LYQNKFLTLN GKKYYFGSDS KAVTGLRTID  1860
GKKYYFNTNT AVAVTGWQTI NGKKYYFNTN TSIASTGYTI ISGKHFYFNT DGIMQIGVFK  1920
GPDGFEYFAP ANTDANNIEG QAIRYQNRFL YLHDNIYYFG NNSKAATGWV TIDGNRYYFE  1980
PNTAMGANGY KTIDNKNFYF RNGLPQIGVF KGSNGFEYFA PANTDANNIE GQAIRYQNRF  2040
LHLLGKIYYF GNNSKAVTGW QTINGKVYYF MPDTAMAAAG GLFEIDGVIY FFGVDGVKAP  2100
GIYG                                                               2104

SEQ ID NO: 39            moltype = AA  length = 2110
FEATURE                  Location/Qualifiers
REGION                   1..2110
                         note = Fusion protein
source                   1..2110
                         mol_type = protein
                         organism = synthetic construct
SEQUENCE: 39
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LLAEAAAKEA AAKEAAAKEA AAKEAAAKAA AGGSLVPRGS GSAAAPFTMI MSDLSSKEYI  180
FFDSIDNKLK AKSKNIPGLA SISEDIKTLL LDASVSPDTK FILNNLKLNI ESSIGDYIYY  240
EKLEPVKNII HNSIDDLIDE FNLLENVSDE LYELKKLNNL DEKYLISFED ISKNNSTYSV  300
RFINKSNGES VYVETEKEIF SKYSEHITKE ISTIKNSIIT DVNGNLLDNI QLDHTSQVNT  360
LNAAFFIQSL IDYSSNKDVL NDLSTSVKVQ LYAQLFSTGL NTIYDSIQLV NLISNAVNDT  420
INVLPTITEG IPIVSTILDG INLGAAIKEL LDEHDPLLKK ELEAKVGVLA INMSLSIAAT  480
VASIVGIGAE VTIFLLPIAG ISAGIPSLVN NELILHDKAT SVVNYFNHLS ESKKYGPLKT  540
EDDKILVPID DLVISEIDFN NNSIKLGTCN ILAMEGGSGH TVTGNIDHFF SSPSISSHIP  600
SLSIYSAIGI ETENLDFSKK IMMLPNAPSR VFWWETGAVP GLRSLENDGT RLLDSIRDLY  660
PGKFYWRFYA FFDYAITTLK PVYEDTNIKI KLDKDTRNFI MPTITTNEIR NKLSYSFDGA  720
GGTYSLLLSS YPISTNINLS KDDLWIFNID NEVREISIEN GTIKKGKLIK DVLSKIDINK  780
NKLIIGNQTI DFSGDIDNKD RYIFLTCELD DKISLIIEIN LVAKSYSLLL SGDKNYLISN  840
LSNIIEKINT LGLDSKNIAY NYTDESNNKY FGAISKTSQK SIIHYKKDSK NILEFYNDST  900
LEFNSKDFIA EDINVFMKDD INTITGKYYV DNNTDKSIDF SISLVSKNQV KVNGLYLNES  960
VYSSYLDFVK NSDGHHNTSN FMNLFLDNIS FWKLFGFENI NFVIDKYFTL VGKTNLGYVE  1020
FICDNNKNID IYFGEWKTSS SKSTIFSGNG RNVVVEPIYN PDTGEDISTS LDFSYEPLYG  1080
IDRYINKVLI APDLYTSLIN INTNYYSNEY YPEIIVLNPN TFHKKVNINL DSSSFEYKWS  1140
TEGSDFILVR YLEESNKKIL QKIRIKGILS NTQSFNKMSI DFKDIKKLSL GYIMSNFKSF  1200
NSENELDRDH LGFKIIDNKT YYYDEDSKLV KGLININNSL FYFDPIEFNL VTGWQTINGK  1260
KYYFDINTGA ALISYKIING KHFYFNNDGV MQLGVFKGPD GFEYFAPANT QNNNIEGQAI  1320
VYQSKFLTLN GKKYYFDNDS KAVTGWRIIN NEKYYFNPNN AIAAVGLQVI DNNKYYFNPD  1380
TAIISKGWQT VNGSRYYFDT DTAIAFNGYK TIDGKHFYFD SDCVVKIGVF STSNGFEYFA  1440
PANTYNNNIE GQAIVYQSKF LTLNGKKYYF DNNSKAVTGW QTIDSKKYYF NTNTAEAATG  1500
WQTIDGKKYY FNTNTAEAAT GWQTIDGKKY YFNTNTAIAS TGYTIINGKH FYFNTDGIMQ  1560
IGVFKGPNGF EYFAPANTDA NNIEGQAILY QNEFLTLNGK KYYFGSDSKA VTGWRIINNK  1620
KYYFNPNNAI AAIHLCTINN DKYYFSYDGI LQNGYITIER NNFYFDANNE SKMVTGVFKG  1680
PNGFEYFAPA NTHNNNIEGQ AIVYQNKFLT LNGKKYYFDN DSKAVTGWQT IDGKKYYFNL  1740
NTAEAATGWQ TIDGKKYYFN LNTAEAATGW QTIDGKKYYF NTNTFIASTG YTSINGKHFY  1800
FNTDGIMQIG VFKGPNGFEY FAPANTHNNN IEGQAILYQN KFLTLNGKKY YFGSDSKAVT  1860
GLRTIDGKKY YFNTNTAVAV TGWQTINGKK YYFNTNTSIA STGYTIISGK HFYFNTDGIM  1920
```

```
QIGVFKGPDG FEYFAPANTD ANNIEGQAIR YQNRFLYLHD NIYYFGNNSK AATGWVTIDG  1980
NRYYFEPNTA MGANGYKTID NKNFYFRNGL PQIGVFKGSN GFEYFAPANT DANNIEGQAI  2040
RYQNRFLHLL GKIYYFGNNS KAVTGWQTIN GKVYYFMPDT AMAAAGGLFE IDGVIYFFGV  2100
DGVKAPGIYG                                                        2110

SEQ ID NO: 40          moltype = AA  length = 1755
FEATURE                Location/Qualifiers
REGION                 1..1755
                       note = Fusion protein
source                 1..1755
                       mol_type = protein
                       organism = synthetic construct
SEQUENCE: 40
HHHHHHHHHG GSGGSGGSGG SGGSGGSGGS GGSGGSGGSH MASDKIIHLT DDSFDTDVLK  60
ADGAILVDFW AEWCGPCKMI APILDEIADE YQGKLTVAKL NIDQNPGTAP KYGIRGIPTL  120
LLFKNGEVAA TKVGALSKGQ LKEFLDANLA RALVPRGSVT SLYKKAGSAA APFTMESKKY  180
GPLKTEDDKI LVPIDDLVIS EIDFNNNSIK LGTCNILAME GGSGHTVTGN IDHFFSSPSI  240
SSHIPSLSIY SAIGIETENL DFSKKIMMLP NAPSRVFWWE TGAVPGLRSL ENDGTRLLDS  300
IRDLYPGKFY WRFYAFFDYA ITTLKPVYED TNIKIKLDKD TRNFIMPTIT TNEIRNKLSY  360
SFDGAGGTYS LLLSSYPIST NINLSKDDLW IFNIDNEVRE ISIENGTIKK GKLIKDVLSK  420
IDINKNKLII GNQTIDFSGD IDNKDRYIFL TCELDDKISL IIEINLVAKS YSLLLSGDKN  480
YLISNLSNII EKINTLGLDS KNIAYNYTDE SNNKYFGAIS KTSQKSIIHY KKDSKNILEF  540
YNDSTLEFNS KDFIAEDINV FMKDDINTIT GKYYVDNNTD KSIDFSISLV SKNQVKVNGL  600
YLNESVYSSY LDFVKNSDGH HNTSNFMNLF LDNISFWKLF GFENINFVID KYFTLVGKTN  660
LGYVEFICDN NKNIDIYFGE WKTSSSKSTI FSGNGRNVVV EPIYNPDTGE DISTSLDFSY  720
EPLYGIDRYI NKVLIAPDLY TSLININTNY YSNEYYPEII VLNPNTFHKK VNINLDSSSF  780
EYKWSTEGSD FILVRYLEES NKKILQKIRI KGILSNTQSF NKMSIDFKDI KKLSLGYIMS  840
NFKSFNSENE LDRDHLGFKI IDNKTYYYDE DSKLVKGLIN INNSLFYFDP IEFNLVTGWQ  900
TINGKKYYFD INTGAALISY KIINGKHFYF NNDGVMQLGV FKGPDGFEYF APANTQNNNI  960
EGQAIVYQSK FLTLNGKKYY FDNDSKAVTG WRIINNEKYY FNPNNAIAAV GLQVIDNNKY  1020
YFNPDTAIIS KGWQTVNGSR YYFDTDTAIA FNGYKTIDGK HFYFDSDCVV KIGVFSTSNG  1080
FEYFAPANTY NNNIEGQAIV YQSKFLTLNG KKYYFDNNSK AVTGWQTIDS KKYYFNTNTA  1140
EAATGWQTID GKKYYFNTNT AEAATGWQTI DGKKYYFNTN TAIASTGYTI INGKHFYFNT  1200
DGIMQIGVFK GPNGFEYFAP ANTDANNIEG QAILYQNEFL TLNGKKYYFG SDSKAVTGWR  1260
IINNKKYYFN PNNAIAAIHL CTINNDKYYF SYDGILQNGY ITIERNNFYF DANNESKMVT  1320
GVFKGPNGFE YFAPANTHNN NIEGQAIVYQ NKFLTLNGKK YYFDNDSKAV TGWQTIDGKK  1380
YYFNLNTAEA ATGWQTIDGK KYYFNLNTAE AATGWQTIDG KKYYFNTNTF IASTGYTSIN  1440
GKHFYFNTDG IMQIGVFKGP NGFEYFAPAN THNNNIEGQA ILYQNKFLTL NGKKYYFGSD  1500
SKAVTGLRTI DGKKYYFNTN TAVAVTGWQT INGKKYYFNT NTSIASTGYT IISGKHFYFN  1560
TDGIMQIGVF KGPDGFEYFA PANTDANNIE GQAIRYQNRF LYLHDNIYYF GNNSKAATGW  1620
VTIDGNRYYF EPNTAMGANG YKTIDNKNFY FRNGLPQIGV FKGSNGFEYF APANTDANNI  1680
EGQAIRYQNR FLHLLGKIYY FGNNSKAVTG WQTINGKVYY FMPDTAMAAA GGLFEIDGVI  1740
YFFGVDGVKA PGIYG                                                  1755

SEQ ID NO: 41          moltype = AA  length = 1762
FEATURE                Location/Qualifiers
REGION                 1..1762
                       note = Fusion protein
source                 1..1762
                       mol_type = protein
                       organism = synthetic construct
SEQUENCE: 41
HHHHHHHHHH GGSLAEAAAK EAAAKEAAAK EAAAKEAAAK AAAGGSHMAS DKIIHLTDDS  60
FDTDVLKADG AILVDFWAEW CGPCKMIAPI LDEIADEYQG KLTVAKLNID QNPGTAPKYG  120
IRGIPTLLLF KNGEVAATKV GALSKGQLKE FLDANLARAL VPRGSVTSLY KKAGSAAAPF  180
TMESKKYGPL KTEDDKILVP IDDLVISEID FNNNSIKLGT CNILAMEGGS GHTVTGNIDH  240
FFSSPSISSH IPSLSIYSAI GIETENLDFS KKIMMLPNAP SRVFWWETGA VPGLRSLEND  300
GTRLLDSIRD LYPGKFYWRF YAFFDYAITT LKPVYEDTNI KIKLDKDTRN FIMPTITTNE  360
IRNKLSYSFD GAGGTYSLLL SSYPISTNIN LSKDDLWIFN IDNEVREISI ENGTIKKGKL  420
IKDVLSKIDI NKNKLIIGNQ TIDFSGDIDN KDRYIFLTCE LDDKISLIIE INLVAKSYSL  480
LLSGDKNYLI SNLSNIIEKI NTLGLDSKNI AYNYTDESNN KYFGAISKTS QKSIIHYKKD  540
SKNILEFYND STLEFNSKDF IAEDINVFMK DDINTITGKY YVDNNTDKSI DFSISLVSKN  600
QVKVNGLYLN ESVYSSYLDF VKNSDGHHNT SNFMNLFLDN ISFWKLFGFE NINFVIDKYF  660
TLVGKTNLGY VEFICDNNKN IDIYFGEWKT SSSKSTIFSG NGRNVVVEPI YNPDTGEDIS  720
TSLDFSYEPL YGIDRYINKV LIAPDLYTSL ININTNYYSN EYYPEIIVLN PNTFHKKVNI  780
NLDSSSFEYK WSTEGSDFIL VRYLEESNKK ILQKIRIKGI LSNTQSFNKM SIDFKDIKKL  840
SLGYIMSNFK SFNSENELDR DHLGFKIIDN KTYYYDEDSK LVKGLININN SLFYFDPIEF  900
NLVTGWQTIN GKKYYFDINT GAALISYKII NGKHFYFNND GVMQLGVFKG PDGFEYFAPA  960
NTQNNNIEGQ AIVYQSKFLT LNGKKYYFDN DSKAVTGWRI INNEKYYFNP NNAIAAVGLQ  1020
VIDNNKYYFN PDTAIISKGW QTVNGSRYYF DTDTAIAFNG YKTIDGKHFY FDSDCVVKIG  1080
VFSTSNGFEY FAPANTYNNN IEGQAIVYQS KFLTLNGKKY YFDNNSKAVT GWQTIDSKKY  1140
YFNTNTAEAA TGWQTIDGKK YYFNTNTAEA ATGWQTIDGK KYYFNTNTAI ASTGYTIING  1200
KHFYFNTDGI MQIGVFKGPN GFEYFAPANT DANNIEGQAI LYQNEFLTLN GKKYYFGSDS  1260
KAVTGWRIIN NKKYYFNPNN AIAAIHLCTI NNDKYYFSYD GILQNGYITI ERNNFYFDAN  1320
NESKMVTGVF KGPNGFEYFA PANTHNNNIE GQAIVYQNKF LTLNGKKYYF DNDSKAVTGW  1380
QTIDGKKYYF NLNTAEAATG WQTIDGKKYY FNLNTAEAAT GWQTIDGKKY YFNTNTFIAS  1440
TGYTSINGKH FYFNTDGIMQ IGVFKGPNGF EYFAPANTHN NNIEGQAILY QNKFLTLNGK  1500
KYYFGSDSKA VTGLRTIDGK KYYFNTNTAV AVTGWQTING KKYYFNTNTS IASTGYTIIS  1560
GKHFYFNTDG IMQIGVFKGP DGFEYFAPAN TDANNIEGQA IRYQNRFLYL HDNIYYFGNN  1620
```

```
SKAATGWVTI DGNRYYFEPN TAMGANGYKT IDNKNFYFRN GLPQIGVFKG SNGFEYFAPA  1680
NTDANNIEGQ AIRYQNRFLH LLGKIYYFGN NSKAVTGWQT INGKVYYFMP DTAMAAAGGL  1740
FEIDGVIYFF GVDGVKAPGI YG                                          1762

SEQ ID NO: 42          moltype = AA  length = 1743
FEATURE                Location/Qualifiers
REGION                 1..1743
                       note = Fusion protein
source                 1..1743
                       mol_type = protein
                       organism = synthetic construct
SEQUENCE: 42
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LGGSGGSGGS GGSGGSGGSG GSGGSGGSLV PRGSGSAAAP FTMESKKYGP LKTEDDKILV  180
PIDDLVISEI DFNNNSIKLG TCNILAMEGG SGHTVTGNID HFFSSPSISS HIPSLSIYSA  240
IGIETENLDF SKKIMMLPNA PSRVFWWETG AVPGLRSLEN DGTRLLDSIR DLYPGKFYWR  300
FYAFFDYAIT TLKPVYEDTN IKIKLDKDTR NFIMPTITTN EIRNKLSYSF DGAGGTYSLL  360
LSSYPISTNI NLSKDDLWIF NIDNEVREIS IENGTIKKGK LIKDVLSKID INKNKLIIGN  420
QTIDFSGDID NKDRYIFLTC ELDDKISLII EINLVAKSYS LLLSGDKNYL ISNLSNIIEK  480
INTLGLDSKN IAYNYTDESN NKYFGAISKT SQKSIIHYKK DSKNILEFYN DSTLEFNSKD  540
FIAEDINVFM KDDINTITGK YYVDNNTDKS IDFSISLVSK NQVKVNGLYL NESVYSSYLD  600
FVKNSDGHHN TSNFMNLFLD NISFWKLFGF ENINFVIDKY FTLVGKTNLG YVEFICDNNK  660
NIDIYFGEWK TSSSKSTIFS GNGRNVVVEP IYNPDTGEDI STSLDFSYEP LYGIDRYINK  720
VLIAPDLYTS LININTNYYS NEYYPEIIVL NPNTFHKKVN INLDSSSFEY KWSTEGSDFI  780
LVRYLEESNK KILQKIRIKG ILSNTQSFNK MSIDFKDIKK LSLGYIMSNF KSFNSENELD  840
RDHLGFKIID NKTYYYDEDS KLVKGLININ NSLFYFDPIE FNLVTGWQTI NGKKYYFDIN  900
TGAALISYKI INGKHFYFNN DGVMQLGVFK GPDGFEYFAP ANTQNNNIEG QAIVYQSKFL  960
TLNGKKYYFD NDSKAVTGWR IINNEKYYFN PNNAIAAVGL QVIDNNKYYF NPDTAIISKG  1020
WQTVNGSRYY FDTDTAIAFN GYKTIDGKHF YFDSDCVVKI GVFSTSNGFE YFAPANTYNN  1080
NIEGQAIVYQ SKFLTLNGKK YYFDNNSKAV TGWQTIDSKK YYFNTNTAEA ATGWQTIDGK  1140
KYYFNTNTAE AATGWQTIDG KKYYFNTNTA IASTGYTIIN GKHFYFNTDG IMQIGVFKGP  1200
NGFEYFAPAN TDANNIEGQA ILYQNEFLTL NGKKYYFGSD SKAVTGWRII NNKKYYFNPN  1260
NAIAAIHLCT INNDKYYFSY DGILQNGYIT IERNNFYFDA NNESKMVTGV FKGPNGFEYF  1320
APANTHNNNI EGQAIVYQNK FLTLNGKKYY FDNDSKAVTG WQTIDGKKYY FNLNTAEAAT  1380
GWQTIDGKKY YFNLNTAEAA TGWQTIDGKK YYFNTNTFIA STGYTSINGK HFYFNTDGIM  1440
QIGVFKGPNG FEYFAPANTH NNNIEGQAIL YQNKFLTLNG KKYYFGSDSK AVTGLRTIDG  1500
KKYYFNTNTA VAVTGWQTIN GKKYYFNTNT SIASTGYTII SGKHFYFNTD GIMQIGVFKG  1560
PDGFEYFAPA NTDANNIEGQ AIRYQNRFLY LHDNIYYFGN NSKAATGWVT IDGNRYYFEP  1620
NTAMGANGYK TIDNKNFYFR NGLPQIGVFK GSNGFEYFAP ANTDANNIEG QAIRYQNRFL  1680
HLLGKIYYFG NNSKAVTGWQ TINGKVYYFM PDTAMAAAGG LFEIDGVIYF FGVDGVKAPG  1740
IYG                                                               1743

SEQ ID NO: 43          moltype = AA  length = 1749
FEATURE                Location/Qualifiers
REGION                 1..1749
                       note = Fusion protein
source                 1..1749
                       mol_type = protein
                       organism = synthetic construct
SEQUENCE: 43
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LLAEAAAKEA AAKEAAAKEA AAKEAAAKAA AGGSLVPRGS GSAAAPFTME SKKYGPLKTE  180
DDKILVPIDD LVISEIDFNN NSIKLGTCNI LAMEGGSGHT VTGNIDHFFS SPSISSHIPS  240
LSIYSAIGIE TENLDFSKKI MMLPNAPSRV FWWETGAVPG LRSLENDGTR LLDSIRDLYP  300
GKFYWRFYAF FDYAITTLKP VYEDTNIKIK LDKDTRNFIM PTITTNEIRN KLSYSFDGAG  360
GTYSLLLSSY PISTNINLSK DDLWIFNIDN EVREISIENG TIKKGKLIKD VLSKIDINKN  420
KLIIGNQTID FSGDIDNKDR YIFLTCELDD KISLIIEINL VAKSYSLLLS GDKNYLISNL  480
SNIIEKINTL GLDSKNIAYN YTDESNNKYF GAISKTSQKS IIHYKKDSKN ILEFYNDSTL  540
EFNSKDFIAE DINVFMKDDI NTITGKYYVD NNTDKSIDFS ISLVSKNQVK VNGLYLNESV  600
YSSYLDFVKN SDGHHNTSNF MNLFLDNISF WKLFGFENIN FVIDKYFTLV GKTNLGYVEF  660
ICDNNKNIDI YFGEWKTSSS KSTIFSGNGR NVVVEPIYNP DTGEDISTSL DFSYEPLYGI  720
DRYINKVLIA PDLYTSLINI NTNYYSNEYY PEIIVLNPNT FHKKVNINLD SSSFEYKWST  780
EGSDFILVRY LEESNKKILQ KIRIKGILSN TQSFNKMSID FKDIKKLSLG YIMSNFKSFN  840
SENELDRDHL GFKIIDNKTY YYDEDSKLVK GLININNSLF YFDPIEFNLV TGWQTINGKK  900
YYFDINTGAA LISYKIINGK HFYFNNDGVM QLGVFKGPDG FEYFAPANTQ NNNIEGQAIV  960
YQSKFLTLNG KKYYFDNDSK AVTGWRIINN EKYYFNPNNA IAAVGLQVID NNKYYFNPDT  1020
AIISKGWQTV NGSRYYFDTD TAIAFNGYKT IDGKHFYFDS DCVVKIGVFS TSNGFEYFAP  1080
ANTYNNNIEG QAIVYQSKFL TLNGKKYYFD NNSKAVTGWQ TIDSKKYYFN TNTAEAATGW  1140
QTIDGKKYYF NTNTAEAATG WQTIDGKKYY FNTNTAIAST GYTIINGKHF YFNTDGIMQI  1200
GVFKGPNGFE YFAPANTDAN NIEGQAILYQ NEFLTLNGKK YYFGSDSKAV TGWRIINNKK  1260
YYFNPNNAIA AIHLCTINND KYYFSYDGIL QNGYITIERN NFYFDANNES KMVTGVFKGP  1320
NGFEYFAPAN THNNNIEGQA IVYQNKFLTL NGKKYYFDND SKAVTGWQTI DGKKYYFNLN  1380
TAEAATGWQT IDGKKYYFNL NTAEAATGWQ TIDGKKYYFN TNTFIASTGY TSINGKHFYF  1440
NTDGIMQIGV FKGPNGFEYF APANTHNNNI EGQAILYQNK FLTLNGKKYY FGSDSKAVTG  1500
LRTIDGKKYY FNTNTAVAVT GWQTINGKKY YFNTNTSIAS TGYTIISGKH FYFNTDGIMQ  1560
IGVFKGPDGF EYFAPANTDA NNIEGQAIRY QNRFLYLHDN IYYFGNNSKA ATGWVTIDGN  1620
RYYFEPNTAM GANGYKTIDN KNFYFRNGLP QIGVFKGSNG FEYFAPANTD ANNIEGQAIR  1680
```

```
YQNRFLHLLG KIYYFGNNSK AVTGWQTING KVYYFMPDTA MAAAGGLFEI DGVIYFFGVD  1740
GVKAPGIYG                                                         1749

SEQ ID NO: 44          moltype = AA  length = 2163
FEATURE                Location/Qualifiers
REGION                 1..2163
                       note = Fusion protein
source                 1..2163
                       mol_type = protein
                       organism = synthetic construct
SEQUENCE: 44
HHHHHHHHHG GSGGSGGSGG SGGSGGSGGS GGSGGSGGSH MASNKEILAV VEAVSNEKAL  60
PREKIFEALE SALATATKKK YEQEIDVRVQ IDRKSGDFDT FRRWLVVDEV TQPTKEITLE  120
AARYEDESLN LGDYVEDQIE SVTFDRITTQ TAKQVIVQKV REAERAMVVD QFREHEGEII  180
TGVVKKVNRD NISLDLGNNA EAVILREDML PRENFRPGDR VRGVLYSVRP EARGAQLFVT  240
RSKPEMLIEL FRIEVPEIGE EVIEIKAAAR DPGSRAKIAV KTNDKRIDPV GACVGMRGAR  300
VQAVSTELGG ERIDIVLWDD NPAQFVINAM APADVASIVV DEDKHTMDIA VEAGNLAQAI  360
GRNGQNVRLA SQLSGWELNV MTVDDLQAKH QAEAHAAIDT FTKYLDIDED FATVLVEEGF  420
STLEELAYVP MKELLEIEGL DEPTVEALRE RAKNALATIA QAQEESLGDN KPADDLLNLE  480
GVDRDLAFKL AARGVCTLED LAEQGIDDLA DIEGLTDEKA GALIMAARNI CWFGDEASGA  540
LVPRGSVTSL YKKAGSAAAP FTMSIIKDIS SKEYISFNPK ENKITVKSKN LPELSTLLQE  600
IRNNSNSSDI ELEEKVMLTE CEINVISNID TQIVEERIEE AKNLTSDSIN YIKDEFKLIE  660
SISDALCDLK QQNELEDSHF ISFEDISETD EGFSIRFINK ETGESIFVET EKTIFSEYAN  720
HITEEISKIK GTIFDTVNGK LVKKVNLDTT HEVNTLNAAF FIQSLIEYNS SKESLSNLSV  780
AMKVQVYAQL FSTGLNTITD AAKVVELVST ALDETIDLLP TLSEGLPIIA TIIDGVSLGA  840
AIKELSETSD PLLRQEIEAK IGIMAVNLTT ATTAIITSSL GIASGFSILL VPLAGISAGI  900
PSLVNNELVL RDKATKVVDY FKHVSLVETE GVFTLLDDKI MMPQDDLVIS EIDFNNNSIV  960
LGKCEIWRME GGSGHTVTDD IDHFFSAPSI TYREPHLSIY DVLEVQKEEL DLSKDLMVLP  1020
NAPNRVFAWE TGWTPGLRSL ENDGTKLLDR IRDNYEGEFY WRYFAFIADA LITTLKPRYE  1080
DTNIRINLDS NTRSFIVPII TTEYIREKLS YSFYGSGGTY ALSLSQYNMG INIELSESDV  1140
WIIDVDNVVR DVTIESDKIK KGDLIEGILS TLSIEENKII LNSHEINFSG EVNGSNGFVS  1200
LTFSILEGIN AIIEVDLLSK SYKLLISGEL KILMLNSNHI QQKIDYIGFN SELQKNIPYS  1260
FVDSEGKENG FINGSTKEGL FVSELPDVVL ISKVYMDDSK PSFGYYSNNL KDVKVITKDN  1320
VNILTGYYLK DDIKISLSLT LQDEKTIKLN SVHLDESGVA EILKFMNRKG NTNTSDSLMS  1380
FLESMNIKSI FVNFLQSNIK FILDANFIIS GTTSIGQFEF ICDENDNIQP YFIKFNTLET  1440
NYTLYVGNRQ NMIVEPNYDL DDSGDISSTV INFSQKYLYG IDSCVNKVVI SPNIYTDEIN  1500
ITPVYETNNT YPEVIVLDAN YINEKINVNI NDLSIRYVWS NDGNDFILMS TSEENKVSQV  1560
KIRFVNVFKD KTLANKLSFN FSDKQDVPVS EIILSFTPSY YEDGLIGYDL GLVSLYNEKF  1620
YINNFGMMVS GLIYINDSLY YFKPPVNNLI TGFVTVGDDK YYFNPINGGA ASIGETIIDD  1680
KNYYFNQSGV LQTGVFSTED GFKYFAPANT LDENLEGEAI DFTGKLIIDE NIYYFDDNYR  1740
GAVEWKELDG EMHYFSPETG KAFKGLNQIG DYKYYFNSDG VMQKGFVSIN DNKHYFDDSG  1800
VMKVGYTEID GKHFYFAENG EMQIGVFNTE DGFKYFAHHN EDLGNEEGEE ISYSGILNFN  1860
NKIYYFDDSF TAVVGWKDLE DGSKYYFDED TAEAYIGLSL INDGQYYFND DGIMQVGFVT  1920
INDKVFYFSD SGIIESGVQN IDDNYFYIDD NGIVQIGVFD TSDGYKYFAP ANTVNDNIYG  1980
QAVEYSGLVR VGEDVYYFGE TYTIETGWIY DMENESDKYY FNPETKKACK GINLIDDIKY  2040
YFDEKGIMRT GLISFENNNY YFNENGEMQF GYINIEDKMF YFGEDGVMQI GVFNTPDGFK  2100
YFAHQNTLDE NFEGESINYT GWLDLDEKRY YFTDEYIAAT GSVIIDGEEY YFDPDTAQLV  2160
ISE                                                               2163

SEQ ID NO: 45          moltype = AA  length = 2151
FEATURE                Location/Qualifiers
REGION                 1..2151
                       note = Fusion protein
source                 1..2151
                       mol_type = protein
                       organism = synthetic construct
SEQUENCE: 45
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALG GSGGSGGSGG SGGSGGSGGS GGSGGSLVPR  540
GSGSAAAPFT MSIIKDISSK EYISFNPKEN KITVKSKNLP ELSTLLQEIR NNSNSSDIEL  600
EEKVMLTECE INVISNIDTQ IVEERIEEAK NLTSDSINYI KDEFKLIESI SDALCDLKQQ  660
NELEDSHFIS FEDISETDEG FSIRFINKET GESIFVETEK TIFSEYANHI TEEISKIKGT  720
IFDTVNGKLV KKVNLDTTHE VNTLNAAFFI QSLIEYNSSK ESLSNLSVAM KVQVYAQLFS  780
TGLNTITDAA KVVELVSTAL DETIDLLPTL SEGLPIIATI IDGVSLGAAI KELSETSDPL  840
LRQEIEAKIG IMAVNLTTAT TAIITSSLGI ASGFSILLVP LAGISAGIPS LVNNELVLRD  900
KATKVVDYFK HVSLVETEGV FTLLDDKIMM PQDDLVISEI DFNNNSIVLG KCEIWRMEGG  960
SGHTVTDDID HFFSAPSITY REPHLSIYDV LEVQKEELDL SKDLMVLPNA PNRVFAWETG  1020
WTPGLRSLEN DGTKLLDRIR DNYEGEFYWR YFAFIADALI TTLKPRYEDT NIRINLDSNT  1080
RSFIVPIITT EYIREKLSYS FYGSGGTYAL SLSQYNMGIN IELSESDVWI IDVDNVVRDV  1140
TIESDKIKKG DLIEGILSTL SIEENKIILN SHEINFSGEV NGSNGFVSLT FSILEGINAI  1200
IEVDLLSKSY KLLISGELKI LMLNSNHIQQ KIDYIGFNSE LQKNIPYSFV DSEGKENGFI  1260
NGSTKEGLFV SELPDVVLIS KVYMDDSKPS FGYYSNNLKD VKVITKDNVN ILTGYYLKDD  1320
```

```
IKISLSLTLQ DEKTIKLNSV HLDESGVAEI LKFMNRKGNT NTSDSLMSFL ESMNIKSIFV  1380
NFLQSNIKFI LDANFIISGT TSIGQFEFIC DENDNIQPYF IKFNTLETNY TLYVGNRQNM  1440
IVEPNYDLDD SGDISSTVIN FSQKYLYGID SCVNKVVISP NIYTDEINIT PVYETNNTYP  1500
EVIVLDANYI NEKINVNIND LSIRYVWSND GNDFILMSTS EENKVSQVKI RFVNVFKDKT  1560
LANKLSFNFS DKQDVPVSEI ILSFTPSYYE DGLIGYDLGL VSLYNEKFYI NNFGMMVSGL  1620
IYINDSLYYF KPPVNNLITG FVTVGDDKYY FNPINGGAAS IGETIIDDKN YYFNQSGVLQ  1680
TGVFSTEDGF KYFAPANTLD ENLEGEAIDF TGKLIIDENI YYFDDNYRGA VEWKELDGEM  1740
HYFSPETGKA FKGLNQIGDY KYYFNSDGVM QKGFVSINDN KHYFDDSGVM KVGYTEIDGK  1800
HFYFAENGEM QIGVFNTEDG FKYFAHHNED LGNEEGEEIS YSGILNFNNK IYYFDDSFTA  1860
VVGWKDLEDG SKYYFDEDTA EAYIGLSLIN DGQYYFNDDG IMQVGFVTIN DKVFYFSDSG  1920
IIESGVQNID DNYFYIDDNG IVQIGVFDTS DGYKYFAPAN TVNDNIYGQA VEYSGLVRVG  1980
EDVYYFGETY TIETGWIYDM ENESDKYYFN PETKKACKGI NLIDDIKYYF DEKGIMRTGL  2040
ISFENNNYYF NENGEMQFGY INIEDKMFYF GEDGVMQIGV FNTPDGFKYF AHQNTLDENF  2100
EGESINYTGW LDLDEKRYYF TDEYIAATGS VIIDGEEYYF DPDTAQLVIS E           2151

SEQ ID NO: 46          moltype = AA  length = 2170
FEATURE                Location/Qualifiers
REGION                 1..2170
                       note = Fusion protein
source                 1..2170
                       mol_type = protein
                       organism = synthetic construct
SEQUENCE: 46
HHHHHHHHHH GGSLAEAAAK EAAAKEAAAK EAAAKEAAAK AAAGGSHMAS NKEILAVVEA  60
VSNEKALPRE KIFEALESAL ATATKKKYEQ EIDVRVQIDR KSGDFDTFRR WLVVDEVTQP  120
TKEITLEAAR YEDESLNLGD YVEDQIESVT FDRITTQTAK QVIVQKVREA ERAMVVDQFR  180
EHEGEIITGV VKKVNRDNIS LDLGNNAEAV ILREDMLPRE NFRPGDRVRG VLYSVRPEAR  240
GAQLFVTRSK PEMLIELFRI EVPEIGEEVI EIKAAARDPG SRAKIAVKTN DKRIDPVGAC  300
VGMRGARVQA VSTELGGERI DIVLWDDNPA QFVINAMAPA DVASIVVDED KHTMDIAVEA  360
GNLAQAIGRN GQNVRLASQL SGWELNVMTV DDLQAKHQAE AHAAIDTFTK YLDIDEDFAT  420
VLVEEGFSTL EELAYVPMKE LLEIEGLDEP TVEALRERAK NALATIAQAQ EESLGDNKPA  480
DDLLNLEGVD RDLAFKLAAR GVCTLEDLAE QGIDDLADIE GLTDEKAGAL IMAARNICWF  540
GDEASGALVP RGSVTSLYKK AGSAAAPFTM SIIKDISSKE YISFNPKENK ITVKSKNLPE  600
LSTLLQEIRN NSNSSDIELE EKVMLTECEI NVISNIDTQI VEERIEEAKN LTSDSINYIK  660
DEFKLIESIS DALCDLKQQN ELEDSHFISF EDISETDEGF SIRFINKETG ESIFVETEKT  720
IFSEYANHIT EEISKIKGTI FDTVNGKLVK KVNLDTTHEV NTLNAAFFIQ SLIEYNSSKE  780
SLSNLSVAMK VQVYAQLFST GLNTITDAAK VVELVSTALD ETIDLLPTLS EGLPIIATII  840
DGVSLGAAIK ELSETSDPLL RQEIEAKIGI MAVNLTTATT AIITSSLGIA SGFSILLVPL  900
AGISAGIPSL VNNELVLRDK ATKVVDYFKH VSLVETEGVF TLLDDKIMMP QDDLVISEID  960
FNNNSIVLGK CEIWRMEGGS GHTVTDDIDH FFSAPSITYR EPHLSIYDVL EVQKEELDLS  1020
KDLMVLPNAP NRVFAWETGW TPGLRSLEND GTKLLDRIRD NYEGEFYWRY FAFIADALIT  1080
TLKPRYEDTN IRINLDSNTR SFIVPIITTE YIREKLSYSF YGSGGTYALS LSQYNMGINI  1140
ELSESDVWII DVDNVVRDVT IESDKIKKGD LIEGILSTLS IEENKIILNS HEINFSGEVN  1200
GSNGFVSLTF SILEGINAII EVDLLSKSYK LLISGELKIL MLNSNHIQQK IDYIGFNSEL  1260
QKNIPYSFVD SEGKENGFIN GSTKEGLFVS ELPDVVLISK VYMDDSKPSF GYYSNNLKDV  1320
KVITKDNVNI LTGYYLKDDI KISLSLTLQD EKTIKLNSVH LDESGVAEIL KFMNRKGNTN  1380
TSDSLMSFLE SMNIKSIFVN FLQSNIKFIL DANFIISGTT SIGQFEFICD ENDNIQPYFI  1440
KFNTLETNYT LYVGNRQNMI VEPNYDLDDS GDISSTVINF SQKYLYGIDS CVNKVVISPN  1500
IYTDEINITP VYETNNTYPE VIVLDANYIN EKINVNINDL SIRYVWSNDG NDFILMSTSE  1560
ENKVSQVKIR FVNVFKDKTL ANKLSFNFSD KQDVPVSEII LSFTPSYYED GLIGYDLGLV  1620
SLYNEKFYIN NFGMMVSGLI YINDSLYYFK PPVNNLITGF VTVGDDKYYF NPINGGAASI  1680
GETIIDDKNY YFNQSGVLQT GVFSTEDGFK YFAPANTLDE NLEGEAIDFT GKLIIDENIY  1740
YFDDNYRGAV EWKELDGEMH YFSPETGKAF KGLNQIGDYK YYFNSDGVMQ KGFVSINDNK  1800
HYFDDSGVMK VGYTEIDGKH FYFAENGEMQ IGVFNTEDGF KYFAHHNEDL GNEEGEEISY  1860
SGILNFNNKI YYFDDSFTAV VGWKDLEDGS KYYFDEDTAE AYIGLSLIND GQYYFNDDGI  1920
MQVGFVTIND KVFYFSDSGI IESGVQNIDD NYFYIDDNGI VQIGVFDTSD GYKYFAPANT  1980
VNDNIYGQAV EYSGLVRVGE DVYYFGETYT IETGWIYDME NESDKYYFNP ETKKACKGIN  2040
LIDDIKYYFD EKGIMRTGLI SFENNNYYFN ENGEMQFGYI NIEDKMFYFG EDGVMQIGVF  2100
NTPDGFKYFA HQNTLDENFE GESINYTGWL DLDEKRYYFT DEYIAATGSV IIDGEEYYFD  2160
PDTAQLVISE                                                         2170

SEQ ID NO: 47          moltype = AA  length = 2157
FEATURE                Location/Qualifiers
REGION                 1..2157
                       note = Fusion protein
source                 1..2157
                       mol_type = protein
                       organism = synthetic construct
SEQUENCE: 47
HHHHHHSHMA SNKEILAVVE AVSNEKALPR EKIFEALESA LATATKKKYE QEIDVRVQID  60
RKSGDFDTFR RWLVVDEVTQ PTKEITLEAA RYEDESLNLG DYVEDQIESV TFDRITTQTA  120
KQVIVQKVRE AERAMVVDQF REHEGEIITG VVKKVNRDNI SLDLGNNAEA VILREDMLPR  180
ENFRPGDRVR GVLYSVRPEA RGAQLFVTRS KPEMLIELFR IEVPEIGEEV IEIKAAARDP  240
GSRAKIAVKT NDKRIDPVGA CVGMRGARVQ AVSTELGGER IDIVLWDDNP AQFVINAMAP  300
ADVASIVVDE DKHTMDIAVE AGNLAQAIGR NGQNVRLASQ LSGWELNVMT VDDLQAKHQA  360
EAHAAIDTFT KYLDIDEDFA TVLVEEGFST LEELAYVPMK ELLEIEGLDE PTVEALRERA  420
KNALATIAQA QEESLGDNKP ADDLLNLEGV DRDLAFKLAA RGVCTLEDLA EQGIDDLADI  480
EGLTDEKAGA LIMAARNICW FGDEASGALL AEAAAKEAAA KEAAAKEAAA KEAAAKAAAG  540
GSLVPRGSGS AAAPFTMSII KDISSKEYIS FNPKENKITV KSKNLPELST LLQEIRNNSN  600
```

```
SSDIELEEKV MLTECEINVI SNIDTQIVEE RIEEAKNLTS DSINYIKDEF KLIESISDAL  660
CDLKQQNELE DSHFISFEDI SETDEGFSIR FINKETGESI FVETEKTIFS EYANHITEEI  720
SKIKGTIFDT VNGKLVKKVN LDTTHEVNTL NAAFFIQSLI EYNSSKESLS NLSVAMKVQV  780
YAQLFSTGLN TITDAAKVVE LVSTALDETI DLLPTLSEGL PIIATIIDGV SLGAAIKELS  840
ETSDPLLRQE IEAKIGIMAV NLTTATTAII TSSLGIASGF SILLVPLAGI SAGIPSLVNN  900
ELVLRDKATK VVDYFKHVSL VETEGVFTLL DDKIMMPQDD LVISEIDFNN NSIVLGKCEI  960
WRMEGGSGHT VTDDIDHFFS APSITYREPH LSIYDVLEVQ KEELDLSKDL MVLPNAPNRV  1020
FAWETGWTPG LRSLENDGTK LLDRIRDNYE GEFYWRYFAF IADALITTLK PRYEDTNIRI  1080
NLDSNTRSFI VPIITTEYIR EKLSYSFYGS GGTYALSLSQ YNMGINIELS ESDVWIIDVD  1140
NVVRDVTIES DKIKKGDLIE GILSTLSIEE NKIILNSHEI NFSGEVNGSN GFVSLTFSIL  1200
EGINAIIEVD LLSKSYKLLI SGELKILMLN SNHIQQKIDY IGFNSELQKN IPYSFVDSEG  1260
KENGFINGST KEGLFVSELP DVVLISKVYM DDSKPSFGYY SNNLKDVKVI TKDNVNILTG  1320
YYLKDDIKIS LSLTLQDEKT IKLNSVHLDE SGVAEILKFM NRKGNTNTSD SLMSFLESMN  1380
IKSIFVNFLQ SNIKFILDAN FIISGTTSIG QFEFICDEND NIQPYFIKFN TLETNYTLYV  1440
GNRQNMIVEP NYDLDDSGDI SSTVINFSQK YLYGIDSCVN KVVISPNIYT DEINITPVYE  1500
TNNTYPEVIV LDANYINEKI NVNINDLSIR YVWSNDGNDF ILMSTSEENK VSQVKIRFVN  1560
VFKDKTLANK LSFNFSDKQD VPVSEIILSF TPSYYEDGLI GYDLGLVSLY NEKFYINNFG  1620
MMVSGLIYIN DSLYYFKPPV NNLITGFVTV GDDKYYFNPI NGGAASIGET IIDDKNYYFN  1680
QSGVLQTGVF STEDGFKYFA PANTLDENLE GEAIDFTGKL IIDENIYYFD DNYRGAVEWK  1740
ELDGEMHYFS PETGKAFKGL NQIGDYKYYF NSDGVMQKGF VSINDNKHYF DDSGVMKVGY  1800
TEIDGKHFYF AENGEMQIGV FNTEDGFKYF AHHNEDLGNE EGEEISYSGI LNFNNKIYYF  1860
DDSFTAVVGW KDLEDGSKYY FDEDTAEAYI GLSLINDGQY YFNDDGIMQV GFVTINDKVF  1920
YFSDSGIIES GVQNIDDNYF YIDDNGIVQI GVFDTSDGYK YFAPANTVND NIYGQAVEYS  1980
GLVRVGEDVY YFGETYTIET GWIYDMENES DKYYFNPETK KACKGINLID DIKYYFDEKG  2040
IMRTGLISFE NNNYYFNENG EMQFGYINIE DKMFYFGEDG VMQIGVFNTP DGFKYFAHQN  2100
TLDENFEGES INYTGWLDLD EKRYYFTDEY IAATGSVIID GEEYYFDPDT AQLVISE     2157

SEQ ID NO: 48          moltype = AA  length = 1776
FEATURE                Location/Qualifiers
REGION                 1..1776
                       note = Fusion protein
source                 1..1776
                       mol_type = protein
                       organism = synthetic construct
SEQUENCE: 48
HHHHHHHHHH GGSGGSGGSG GSGGSGGSGG SGGSGGSGGS HMASDKIIHL TDDSFDTDVL  60
KADGAILVDF WAEWCGPCKM IAPILDEIAD EYQGKLTVAK LNIDQNPGTA PKYGIRGIPT  120
LLLFKNGEVA ATKVGALSKG QLKEFLDANL ARALVPRGSV TSLYKKAGSA AAPFTMSIIK  180
DISSKEYISF NPKENKITVK SKNLPELSTL LQEIRNNSNS SDIELEEKVM LTECEINVIS  240
NIDTQIVEER IEEAKNLTSD SINYIKDEFK LIESISDALC DLKQQNELED SHFISFEDIS  300
ETDEGFSIRF INKETGESIF VETEKTIFSE YANHITEEIS KIKGTIFDTV NGKLVKKVNL  360
DTTHEVNTLN AAFFIQSLIE YNSSKESLSN LSVAMKVQVY AQLFSTGLNT ITDAAKVVEL  420
VSTALDETID LLPTLSEGLP IIATIIDGVS LGAAIKELSE TSDPLLRQEI EAKIGIMAVN  480
LTTATTAIIT SSLGIASGFS ILLVPLAGIS AGIPSLVNNE LVLRDKATKV VDYFKHVSLV  540
ETEGVFTLLD DKIMMPQDDL VISEIDFNNN SIVLGKCEIW RMEGGSGHTV TDDIDHFFSA  600
PSITYREPHL SIYDVLEVQK EELDLSKDLM VLPNAPNRVF AWETGWTPGL RSLENDGTKL  660
LDRIRDNYEG EFYWRYFAFI ADALITTLKP RYEDTNIRIN LDSNTRSFIV PIITTEYIRE  720
KLSYSFYGSG GTYALSLSQY NMGINIELSE SDVWIIDVDN VVRDVTIESD KIKKGDLIEG  780
ILSTLSIEEN KIILNSHEIN FSGEVNGSNG FVSLTFSILE GINAIIEVDL LSKSYKLLIS  840
GELKILMLNS NHIQQKIDYI GFNSELQKNI PYSFVDSEGK ENGFINGSTK EGLFVSELPD  900
VVLISKVYMD DSKPSFGYYS NNLKDVKVIT KDNVNILTGY YLKDDIKISL SLTLQDEKTI  960
KLNSVHLDES GVAEILKFMN RKGNTNTSDS LMSFLESMNI KSIFVNFLQS NIKFILDANF  1020
IISGTTSIGQ FEFICDENDN IQPYFIKFNT LETNYTLYVG NRQNMIVEPN YDLDDSGDIS  1080
STVINFSQKY LYGIDSCVNK VVISPNIYTD EINITPVYET NNTYPEVIVL DANYINEKIN  1140
VNINDLSIRY VWSNDGNDFI LMSTSEENKV SQVKIRFVNV FKDKTLANKL SFNFSDKQDV  1200
PVSEIILSFT PSYYEDGLIG YDLGLVSLYN EKFYINNFGM MVSGLIYIND SLYYFKPPVN  1260
NLITGFVTVG DDKYYFNPIN GGAASIGETI IDDKNYYFNQ SGVLQTGVFS TEDGFKYFAP  1320
ANTLDENLEG EAIDFTGKLI IDENIYYFDD NYRGAVEWKE LDGEMHYFSP ETGKAFKGLN  1380
QIGDYKYYFN SDGVMQKGFV SINDNKHYFD DSGVMKVGYT EIDGKHFYFA ENGEMQIGVF  1440
NTEDGFKYFA HHNEDLGNEE GEEISYSGIL NFNNKIYYFD DSFTAVVGWK DLEDGSKYYF  1500
DEDTAEAYIG LSLINDGQYY FNDDGIMQVG FVTINDKVFY FSDSGIIESG VQNIDDNYFY  1560
IDDNGIVQIG VFDTSDGYKY FAPANTVNDN IYGQAVEYSG LVRVGEDVYY FGETYTIETG  1620
WIYDMENESD KYYFNPETKK ACKGINLIDD IKYYFDEKGI MRTGLISFEN NNYYFNENGE  1680
MQFGYINIED KMFYFGEDGV MQIGVFNTPD GFKYFAHQNT LDENFEGESI NYTGWLDLDE  1740
KRYYFTDEYI AATGSVIIDG EEYYFDPDTA QLVISE                            1776

SEQ ID NO: 49          moltype = AA  length = 1763
FEATURE                Location/Qualifiers
REGION                 1..1763
                       note = Fusion protein
source                 1..1763
                       mol_type = protein
                       organism = synthetic construct
SEQUENCE: 49
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LGGSGGSGGS GGSGGSGGSG GSGGSGGSLV PRGSGSAAAP FTMSIIKDIS SKEYISFNPK  180
ENKITVKSKN LPELSTLLQE IRNNSNSSDI ELEEKVMLTE CEINVISNID TQIVEERIEE  240
AKNLTSDSIN YIKDEFKLIE SISDALCDLK QQNELEDSHF ISFEDISETD EGFSIRFINK  300
```

```
ETGESIFVET EKTIFSEYAN HITEEISKIK GTIFDTVNGK LVKKVNLDTT HEVNTLNAAF  360
FIQSLIEYNS SKESLSNLSV AMKVQVYAQL FSTGLNTITD AAKVVELVST ALDETIDLLP  420
TLSEGLPIIA TIIDGVSLGA AIKELSETSD PLLRQEIEAK IGIMAVNLTT ATTAIITSSL  480
GIASGFSILL VPLAGISAGI PSLVNNELVL RDKATKVVDY FKHVSLVETE GVFTLLDDKI  540
MMPQDDLVIS EIDFNNNSIV LGKCEIWRME GGSGHTVTDD IDHFFSAPSI TYREPHLSIY  600
DVLEVQKEEL DLSKDLMVLP NAPNRVFAWE TGWTPGLRSL ENDGTKLLDR IRDNYEGEFY  660
WRYFAFIADA LITTLKPRYE DTNIRINLDS NTRSFIVPII TTEYIREKLS YSFYGSGGTY  720
ALSLSQYNMG INIELSESDV WIIDVDNVVR DVTIESDKIK KGDLIEGILS TLSIEENKII  780
LNSHEINFSG EVNGSNGFVS LTFSILEGIN AIIEVDLLSK SYKLLISGEL KILMLNSNHI  840
QQKIDYIGFN SELQKNIPYS FVDSEGKENG FINGSTKEGL FVSELPDVVL ISKVYMDDSK  900
PSFGYYSNNL KDVKVITKDN VNILTGYYLK DDIKISLSLT LQDEKTIKLN SVHLDESGVA  960
EILKFMNRKG NTNTSDSLMS FLESMNIKSI FVNFLQSNIK FILDANFIIS GTTSIGQFEF  1020
ICDENDNIQP YFIKFNTLET NYTLYVGNRQ NMIVEPNYDL DDSGDISSTV INFSQKYLYG  1080
IDSCVNKVVI SPNIYTDEIN ITPVYETNNT YPEVIVLDAN YINEKINVNI NDLSIRYVWS  1140
NDGNDFILMS TSEENKVSQV KIRFVNVFKD KTLANKLSFN FSDKQDVPVS EIILSFTPSY  1200
YEDGLIGYDL GLVSLYNEKF YINNFGMMVS GLIYINDSLY YFKPPVNNLI TGFVTVGDDK  1260
YYFNPINGGA ASIGETIIDD KNYYFNQSGV LQTGVFSTED GFKYFAPANT LDENLEGEAI  1320
DFTGKLIIDE NIYYFDDNYR GAVEWKELDG EMHYFSPETG KAFKGLNQIG DYKYYFNSDG  1380
VMQKGFVSIN DNKHYFDDSG VMKVGYTEID GKHFYFAENG EMQIGVFNTE DGFKYFAHHN  1440
EDLGNEEGEE ISYSGILNFN NKIYYFDDSF TAVVGWKDLE DGSKYYFDED TAEAYIGLSL  1500
INDGQYYFND DGIMQVGFVT INDKVFYFSD SGIIESGVQN IDDNYFYIDD NGIVQIGVFD  1560
TSDGYKYFAP ANTVNDNIYG QAVEYSGLVR VGEDVYYFGE TYTIETGWIY DMENESDKYY  1620
FNPETKKACK GINLIDDIKY YFDEKGIMRT GLISFENNNY YFNENGEMQF GYINIEDKMF  1680
YFGEDGVMQI GVFNTPDGFK YFAHQNTLDE NFEGESINYT GWLDLDEKRY YFTDEYIAAT  1740
GSVIIDGEEY YFDPDTAQLV ISE                                          1763

SEQ ID NO: 50          moltype = AA  length = 1782
FEATURE                Location/Qualifiers
REGION                 1..1782
                       note = Fusion protein
source                 1..1782
                       mol_type = protein
                       organism = synthetic construct
SEQUENCE: 50
HHHHHHHHHH GGSLAEAAAK EAAAKEAAAK EAAAKEAAAK AAAGGSHMAS DKIIHLTDDS  60
FDTDVLKADG AILVDFWAEW CGPCKMIAPI LDEIADEYQG KLTVAKLNID QNPGTAPKYG  120
IRGIPTLLLF KNGEVAATKV GALSKGQLKE FLDANLARAL VPRGSVTSLY KKAGSAAAPF  180
TMSIIKDISS KEYISFNPKE NKITVKSKNL PELSTLLQEI RNNSNSSDIE LEEKVMLTEC  240
EINVISNIDT QIVEERIEEA KNLTSDSINY IKDEFKLIES ISDALCDLKQ QNELEDSHFI  300
SFEDISETDE GFSIRFINKE TGESIFVETE KTIFSEYANH ITEEISKIKG TIFDTVNGKL  360
VKKVNLDTTH EVNTLNAAFF IQSLIEYNSS KESLSNLSVA MKVQVYAQLF STGLNTITDA  420
AKVVELVSTA LDETIDLLPT LSEGLPIIAT IIDGVSLGAA IKELSETSDP LLRQEIEAKI  480
GIMAVNLTTA TTAIITSSLG IASGFSILLV PLAGISAGIP SLVNNELVLR DKATKVVDYF  540
KHVSLVETEG VFTLLDDKIM MPQDDLVISE IDFNNNSIVL GKCEIWRMEG GSGHTVTDDI  600
DHFFSAPSIT YREPHLSIYD VLEVQKEELD LSKDLMVLPN APNRVFAWET GWTPGLRSLE  660
NDGTKLLDRI RDNYEGEFYW RYFAFIADAL ITTLKPRYED TNIRINLDSN TRSFIVPIIT  720
TEYIREKLSY SFYGSGGTYA LSLSQYNMGI NIELSESDVW IIDVDNVVRD VTIESDKIKK  780
GDLIEGILST LSIEENKIIL NSHEINFSGE VNGSNGFVSL TFSILEGINA IIEVDLLSKS  840
YKLLISGELK ILMLNSNHIQ QKIDYIGFNS ELQKNIPYSF VDSEGKENGF INGSTKEGLF  900
VSELPDVVLI SKVYMDDSKP SFGYYSNNLK DVKVITKDNV NILTGYYLKD DIKISLSLTL  960
QDEKTIKLNS VHLDESGVAE ILKFMNRKGN TNTSDSLMSF LESMNIKSIF VNFLQSNIKF  1020
ILDANFIISG TTSIGQFEFI CDENDNIQPY FIKFNTLETN YTLYVGNRQN MIVEPNYDLD  1080
DSGDISSTVI NFSQKYLYGI DSCVNKVVIS PNIYTDEINI TPVYETNNTY PEVIVLDANY  1140
INEKINVNIN DLSIRYVWSN DGNDFILMST SEENKVSQVK IRFVNVFKDK TLANKLSFNF  1200
SDKQDVPVSE IILSFTPSYY EDGLIGYDLG LVSLYNEKFY INNFGMMVSG LIYINDSLYY  1260
FKPPVNNLIT GFVTVGDDKY YFNPINGGAA SIGETIIDDK NYYFNQSGVL QTGVFSTEDG  1320
FKYFAPANTL DENLEGEAID FTGKLIIDEN IYYFDDNYRG AVEWKELDGE MHYFSPETGK  1380
AFKGLNQIGD YKYYFNSDGV MQKGFVSIND NKHYFDDSGV MKVGYTEIDG KHFYFAENGE  1440
MQIGVFNTED GFKYFAHHNE DLGNEEGEEI SYSGILNFNN KIYYFDDSFT AVVGWKDLED  1500
GSKYYFDEDT AEAYIGLSLI NDGQYYFNDD GIMQVGFVTI NDKVFYFSDS GIIESGVQNI  1560
DDNYFYIDDN GIVQIGVFDT SDGYKYFAPA NTVNDNIYGQ AVEYSGLVRV GEDVYYFGET  1620
YTIETGWIYD MENESDKYYF NPETKKACKG INLIDDIKYY FDEKGIMRTG LISFENNNYY  1680
FNENGEMQFG YINIEDKMFY FGEDGVMQIG VFNTPDGFKY FAHQNTLDEN FEGESINYTG  1740
WLDLDEKRYY FTDEYIAATG SVIIDGEEYY FDPDTAQLVI SE                     1782

SEQ ID NO: 51          moltype = AA  length = 1769
FEATURE                Location/Qualifiers
REGION                 1..1769
                       note = Fusion protein
source                 1..1769
                       mol_type = protein
                       organism = synthetic construct
SEQUENCE: 51
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LLAEAAAKEA AAKEAAAKEA AAKEAAAKAA AGGSLVPRGS GSAAAPFTMS IIKDISSKEY  180
ISFNPKENKI TVKSKNLPEL STLLQEIRNN SNSSDIELEE KVMLTECEIN VISNIDTQIV  240
EERIEEAKNL TSDSINYIKD EFKLIESISD ALCDLKQQNE LEDSHFISFE DISETDEGFS  300
IRFINKETGE SIFVETEKTI FSEYANHITE EISKIKGTIF DTVNGKLVKK VNLDTTHEVN  360
```

```
TLNAAFFIQS LIEYNSSKES LSNLSVAMKV QVYAQLFSTG LNTITDAAKV VELVSTALDE  420
TIDLLPTLSE GLPIIATIID GVSLGAAIKE LSETSDPLLR QEIEAKIGIM AVNLTTATTA  480
IITSSLGIAS GFSILLVPLA GISAGIPSLV NNELVLRDKA TKVVDYFKHV SLVETEGVFT  540
LLDDKIMMPQ DDLVISEIDF NNNSIVLGKC EIWRMEGGSG HTVTDDIDHF FSAPSITYRE  600
PHLSIYDVLE VQKEELDLSK DLMVLPNAPN RVFAWETGWT PGLRSLENDG TKLLDRIRDN  660
YEGEFYWRYF AFIADALITT LKPRYEDTNI RINLDSNTRS FIVPIITTEY IREKLSYSFY  720
GSGGTYALSL SQYNMGINIE LSESDVWIID VDNVVRDVTI ESDKIKKGDL IEGILSTLSI  780
EENKIILNSH EINFSGEVNG SNGFVSLTFS ILEGINAIIE VDLLSKSYKL LISGELKILM  840
LNSNHIQQKI DYIGFNSELQ KNIPYSFVDS EGKENGFING STKEGLFVSE LPDVVLISKV  900
YMDDSKPSFG YYSNNLKDVK VITKDNVNIL TGYYLKDDIK ISLSLTLQDE KTIKLNSVHL  960
DESGVAEILK FMNRKGNTNT SDSLMSFLES MNIKSIFVNF LQSNIKFILD ANFIISGTTS  1020
IGQFEFICDE NDNIQPYFIK FNTLETNYTL YVGNRQNMIV EPNYDLDDSG DISSTVINFS  1080
QKYLYGIDSC VNKVVISPNI YTDEINITPV YETNNTYPEV IVLDANYINE KINVNINDLS  1140
IRYVWSNDGN DFILMSTSEE NKVSQVKIRF VNVFKDKTLA NKLSFNFSDK QDVPVSEIIL  1200
SFTPSYYEDG LIGYDLGLVS LYNEKFYINN FGMMVSGLIY INDSLYYFKP PVNNLITGFV  1260
TVGDDKYYFN PINGGAASIG ETIIDDKNYY FNQSGVLQTG VFSTEDGFKY FAPANTLDEN  1320
LEGEAIDFTG KLIIDENIYY FDDNYRGAVE WKELDGEMHY FSPETGKAFK GLNQIGDYKY  1380
YFNSDGVMQK GFVSINDNKH YFDDSGVMKV GYTEIDGKHF YFAENGEMQI GVFNTEDGFK  1440
YFAHHNEDLG NEEGEEISYS GILNFNNKIY YFDDSFTAVV GWKDLEDGSK YYFDEDTAEA  1500
YIGLSLINDG QYYFNDDGIM QVGFVTINDK VFYFSDSGII ESGVQNIDDN YFYIDDNGIV  1560
QIGVFDTSDG YKYFAPANTV NDNIYGQAVE YSGLVRVGED VYYFGETYTI ETGWIYDMEN  1620
ESDKYYFNPE TKKACKGINL IDDIKYYFDE KGIMRTGLIS FENNNYYFNE NGEMQFGYIN  1680
IEDKMFYFGE DGVMQIGVFN TPDGFKYFAH QNTLDENFEG ESINYTGWLD LDEKRYYFTD  1740
EYIAATGSVI IDGEEYYFDP DTAQLVISE                                    1769

SEQ ID NO: 52          moltype = AA  length = 1402
FEATURE                Location/Qualifiers
REGION                 1..1402
                       note = Fusion protein
source                 1..1402
                       mol_type = protein
                       organism = synthetic construct
SEQUENCE: 52
HHHHHHHHHH GGSLAEAAAK EAAAKEAAAK EAAAKEAAAK AAAGGSHMAS DKIIHLTDDS  60
FDTDVLKADG AILVDFWAEW CGPCKMIAPI LDEIADEYQG KLTVAKLNID QNPGTAPKYG  120
IRGIPTLLLF KNGEVAATKV GALSKGQLKE FLDANLARAL VPRGSVTSLY KKAGSAAGGS  180
MPQDDLVISE IDFNNNSIVL GKCEIWRMEG GSGHTVTDDI DHFFSAPSIT YREPHLSIYD  240
VLEVQKEELD LSKDLMVLPN APNRVFAWET GWTPGLRSLE NDGTKLLDRI RDNYEGEFYW  300
RYFAFIADAL ITTLKPRYED TNIRINLDSN TRSFIVPIIT TEYIREKLSY SFYGSGGTYA  360
LSLSQYNMGI NIELSESDVW IIDVDNVVRD VTIESDKIKK GDLIEGILST LSIEENKIIL  420
NSHEINFSGE VNGSNGFVSL TFSILEGINA IIEVDLLSKS YKLLISGELK ILMLNSNHIQ  480
QKIDYIGFNS ELQKNIPYSF VDSEGKENGF INGSTKEGLF VSELPDVVLI SKVYMDDSKP  540
SFGYYSNNLK DVKVITKDNV NILTGYYLKD DIKISLSLTL QDEKTIKLNS VHLDESGVAE  600
ILKFMNRKGN TNTSDSLMSF LESMNIKSIF VNFLQSNIKF ILDANFIISG TTSIGQFEFI  660
CDENDNIQPY FIKFNTLETN YTLYVGNRQN MIVEPNYDLD DSGDISSTVI NFSQKYLYGI  720
DSCVNKVVIS PNIYTDEINI TPVYETNNTY PEVIVLDANY INEKINVNIN DLSIRYVWSN  780
DGNDFILMST SEENKVSQVK IRFVNVFKDK TLANKLSFNF SDKQDVPVSE IILSFTPSYY  840
EDGLIGYDLG LVSLYNEKFY INNFGMMVSG LIYINDSLYY FKPPVNNLIT GFVTVGDDKY  900
YFNPINGGAA SIGETIIDDK NYYFNQSGVL QTGVFSTEDG FKYFAPANTL DENLEGEAID  960
FTGKLIIDEN IYYFDDNYRG AVEWKELDGE MHYFSPETGK AFKGLNQIGD YKYYFNSDGV  1020
MQKGFVSIND NKHYFDDSGV MKVGYTEIDG KHFYFAENGE MQIGVFNTED GFKYFAHHNE  1080
DLGNEEGEEI SYSGILNFNN KIYYFDDSFT AVVGWKDLED GSKYYFDEDT AEAYIGLSLI  1140
NDGQYYFNDD GIMQVGFVTI NDKVFYFSDS GIIESGVQNI DDNYFYIDDN GIVQIGVFDT  1200
SDGYKYFAPA NTVNDNIYGQ AVEYSGLVRV GEDVYYFGET YTIETGWIYD MENESDKYYF  1260
NPETKKACKG INLIDDIKYY FDEKGIMRTG LISFENNNYY FNENGEMQFG YINIEDKMFY  1320
FGEDGVMQIG VFNTPDGFKY FAHQNTLDEN FEGESINYTG WLDLDEKRYY FTDEYIAATG  1380
SVIIDGEEYY FDPDTAQLVI SE                                           1402

SEQ ID NO: 53          moltype = AA  length = 1389
FEATURE                Location/Qualifiers
REGION                 1..1389
                       note = Fusion protein
source                 1..1389
                       mol_type = protein
                       organism = synthetic construct
SEQUENCE: 53
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LLAEAAAKEA AAKEAAAKEA AAKEAAAKAA AGGSLVPRGS GSAAGGSMPQ DDLVISEIDF  180
NNNSIVLGKC EIWRMEGGSG HTVTDDIDHF FSAPSITYRE PHLSIYDVLE VQKEELDLSK  240
DLMVLPNAPN RVFAWETGWT PGLRSLENDG TKLLDRIRDN YEGEFYWRYF AFIADALITT  300
LKPRYEDTNI RINLDSNTRS FIVPIITTEY IREKLSYSFY GSGGTYALSL SQYNMGINIE  360
LSESDVWIID VDNVVRDVTI ESDKIKKGDL IEGILSTLSI EENKIILNSH EINFSGEVNG  420
SNGFVSLTFS ILEGINAIIE VDLLSKSYKL LISGELKILM LNSNHIQQKI DYIGFNSELQ  480
KNIPYSFVDS EGKENGFING STKEGLFVSE LPDVVLISKV YMDDSKPSFG YYSNNLKDVK  540
VITKDNVNIL TGYYLKDDIK ISLSLTLQDE KTIKLNSVHL DESGVAEILK FMNRKGNTNT  600
SDSLMSFLES MNIKSIFVNF LQSNIKFILD ANFIISGTTS IGQFEFICDE NDNIQPYFIK  660
FNTLETNYTL YVGNRQNMIV EPNYDLDDSG DISSTVINFS QKYLYGIDSC VNKVVISPNI  720
YTDEINITPV YETNNTYPEV IVLDANYINE KINVNINDLS IRYVWSNDGN DFILMSTSEE  780
```

```
NKVSQVKIRF VNVFKDKTLA NKLSFNFSDK QDVPVSEIIL SFTPSYYEDG LIGYDLGLVS  840
LYNEKFYINN FGMMVSGLIY INDSLYYFKP PVNNLITGFV TVGDDKYYFN PINGGAASIG  900
ETIIDDKNYY FNQSGVLQTG VFSTEDGFKY FAPANTLDEN LEGEAIDFTG KLIIDENIYY  960
FDDNYRGAVE WKELDGEMHY FSPETGKAFK GLNQIGDYKY YFNSDGVMQK GFVSINDNKH  1020
YFDDSGVMKV GYTEIDGKHF YFAENGEMQI GVFNTEDGFK YFAHHNEDLG NEEGEEISYS  1080
GILNFNNKIY YFDDSFTAVV GWKDLEDGSK YYFDEDTAEA YIGLSLINDG QYYFNDDGIM  1140
QVGFVTINDK VFYFSDSGII ESGVQNIDDN YFYIDDNGIV QIGVFDTSDG YKYFAPANTV  1200
NDNIYGQAVE YSGLVRVGED VYYFGETYTI ETGWIYDMEN ESDKYYFNPE TKKACKGINL  1260
IDDIKYYFDE KGIMRTGLIS FENNNYYFNE NGEMQFGYIN IEDKMFYFGE DGVMQIGVFN  1320
TPDGFKYFAH QNTLDENFEG ESINYTGWLD LDEKRYYFTD EYIAATGSVI IDGEEYYFDP  1380
DTAQLVISE                                                         1389

SEQ ID NO: 54          moltype = AA  length = 1395
FEATURE                Location/Qualifiers
REGION                 1..1395
                       note = Fusion protein
source                 1..1395
                       mol_type = protein
                       organism = synthetic construct
SEQUENCE: 54
HHHHHHHHHG GSGGSGGSGG SGGSGGSGGS GGSGGSGGSH MASDKIIHLT DDSFDTDVLK  60
ADGAILVDFW AEWCGPCKMI APILDEIADE YQGKLTVAKL NIDQNPGTAP KYGIRGIPTL  120
LLFKNGEVAA TKVGALSKGQ LKEFLDANLA RALVPRGSVT SLYKKAGSAA GGSMPQDDLV  180
ISEIDFNNNS IVLGKCEIWR MEGGSGHTVT DDIDHFFSAP SITYREPHLS IYDVLEVQKE  240
ELDLSKDLMV LPNAPNRVFA WETGWTPGLR SLENDGTKLL DRIRDNYEGE FYWRYFAFIA  300
DALITTLKPR YEDTNIRINL DSNTRSFIVP IITTEYIREK LSYSFYGSGG TYALSLSQYN  360
MGINIELSES DVWIIDVDNV VRDVTIESDK IKKGDLIEGI LSTLSIEENK IILNSHEINF  420
SGEVNGSNGF VSLTFSILEG INAIIEVDLL SKSYKLLISG ELKILMLNSN HIQQKIDYIG  480
FNSELQKNIP YSFVDSEGKE NGFINGSTKE GLFVSELPDV VLISKVYMDD SKPSFGYYSN  540
NLKDVKVITK DNVNILTGYY LKDDIKISLS LTLQDEKTIK LNSVHLDESG VAEILKFMNR  600
KGNTNTSDSL MSFLESMNIK SIFVNFLQSN IKFILDANFI ISGTTSIGQF EFICDENDNI  660
QPYFIKFNTL ETNYTLYVGN RQNMIVEPNY DLDDSGDISS TVINFSQKYL YGIDSCVNKV  720
VISPNIYTDE INITPVYETN NTYPEVIVLD ANYINEKINV NINDLSIRYV WSNDGNDFIL  780
MSTSEENKVS QVKIRFVNVF KDKTLANKLS FNFSDKQDVP VSEIILSFTP SYYEDGLIGY  840
DLGLVSLYNE KFYINNFGMM VSGLIYINDS LYYFKPPVNN LITGFVTVGD DKYYFNPING  900
GAASIGETII DDKNYYFNQS GVLQTGVFST EDGFKYFAPA NTLDENLEGE AIDFTGKLII  960
DENIYYFDDN YRGAVEWKEL DGEMHYFSPE TGKAFKGLNQ IGDYKYYFNS DGVMQKGFVS  1020
INDNKHYFDD SGVMKVGYTE IDGKHFYFAE NGEMQIGVFN TEDGFKYFAH HNEDLGNEEG  1080
EEISYSGILN FNNKIYYFDD SFTAVVGWKD LEDGSKYYFD EDTAEAYIGL SLINDGQYYF  1140
NDDGIMQVGF VTINDKVFYF SDSGIIESGV QNIDDNYFYI DDNGIVQIGV FDTSDGYKYF  1200
APANTVNDNI YGQAVEYSGL VRVGEDVYYF GETYTIETGW IYDMENESDK YYFNPETKKA  1260
CKGINLIDDI KYYFDEKGIM RTGLISFENN NYYFNENGEM QFGYINIEDK MFYFGEDGVM  1320
QIGVFNTPDG FKYFAHQNTL DENFEGESIN YTGWLDLDEK RYYFTDEYIA ATGSVIIDGE  1380
EYYFDPDTAQ LVISE                                                  1395

SEQ ID NO: 55          moltype = AA  length = 1383
FEATURE                Location/Qualifiers
REGION                 1..1383
                       note = Fusion protein
source                 1..1383
                       mol_type = protein
                       organism = synthetic construct
SEQUENCE: 55
HHHHHHSHMA SDKIIHLTDD SFDTDVLKAD GAILVDFWAE WCGPCKMIAP ILDEIADEYQ  60
GKLTVAKLNI DQNPGTAPKY GIRGIPTLLL FKNGEVAATK VGALSKGQLK EFLDANLARA  120
LGGSGGSGGS GGSGGSGGSG GSGGSGGSLV PRGSGSAAGG SMPQDDLVIS EIDFNNNSIV  180
LGKCEIWRME GGSGHTVTDD IDHFFSAPSI TYREPHLSIY DVLEVQKEEL DLSKDLMVLP  240
NAPNRVFAWE TGWTPGLRSL ENDGTKLLDR IRDNYEGEFY WRYFAFIADA LITTLKPRYE  300
DTNIRINLDS NTRSFIVPII TTEYIREKLS YSFYGSGGTY ALSLSQYNMG INIELSESDV  360
WIIDVDNVVR DVTIESDKIK KGDLIEGILS TLSIEENKII LNSHEINFSG EVNGSNGFVS  420
LTFSILEGIN AIIEVDLLSK SYKLLISGEL KILMLNSNHI QQKIDYIGFN SELQKNIPYS  480
FVDSEGKENG FINGSTKEGL FVSELPDVVL ISKVYMDDSK PSFGYYSNNL KDVKVITKDN  540
VNILTGYYLK DDIKISLSLT LQDEKTIKLN SVHLDESGVA EILKFMNRKG NTNTSDSLMS  600
FLESMNIKSI FVNFLQSNIK FILDANFIIS GTTSIGQFEF ICDENDNIQP YFIKFNTLET  660
NYTLYVGNRQ NMIVEPNYDL DDSGDISSTV INFSQKYLYG IDSCVNKVVI SPNIYTDEIN  720
ITPVYETNNT YPEVIVLDAN YINEKINVNI NDLSIRYVWS NDGNDFILMS TSEENKVSQV  780
KIRFVNVFKD KTLANKLSFN FSDKQDVPVS EIILSFTPSY YEDGLIGYDL GLVSLYNEKF  840
YINNFGMMVS GLIYINDSLY YFKPPVNNLI TGFVTVGDDK YYFNPINGGA ASIGETIIDD  900
KNYYFNQSGV LQTGVFSTED GFKYFAPANT LDENLEGEAI DFTGKLIIDE NIYYFDDNYR  960
GAVEWKELDG EMHYFSPETG KAFKGLNQIG DYKYYFNSDG VMQKGFVSIN DNKHYFDDSG  1020
VMKVGYTEID GKHFYFAENG EMQIGVFNTE DGFKYFAHHN EDLGNEEGEE ISYSGILNFN  1080
NKIYYFDDSF TAVVGWKDLE DGSKYYFDED TAEAYIGLSL INDGQYYFND DGIMQVGFVT  1140
INDKVFYFSD SGIIESGVQN IDDNYFYIDD NGIVQIGVFD TSDGYKYFAP ANTVNDNIYG  1200
QAVEYSGLVR VGEDVYYFGE TYTIETGWIY DMENESDKYY FNPETKKACK GINLIDDIKY  1260
YFDEKGIMRT GLISFENNNY YFNENGEMQF GYINIEDKMF YFGEDGVMQI GVFNTPDGFK  1320
YFAHQNTLDE NFEGESINYT GWLDLDEKRY YFTDEYIAAT GSVIIDGEEY YFDPDTAQLV  1380
ISE                                                               1383

SEQ ID NO: 56          moltype = AA  length = 2317
```

```
FEATURE                 Location/Qualifiers
REGION                  1..2317
                        note = Fusion protein
source                  1..2317
                        mol_type = protein
                        organism = synthetic construct
SEQUENCE: 56
MGSSHHHHHH SHMASNKEIL AVVEAVSNEK ALPREKIFEA LESALATATK KKYEQEIDVR  60
VQIDRKSGDF DTFRRWLVVD EVTQPTKEIT LEAARYEDES LNLGDYVEDQ IESVTFDRIT  120
TQTAKQVIVQ KVREAERAMV VDQFREHEGE IITGVVKKVN RDNISLDLGN NAEAVILRED  180
MLPRENFRPG DRVRGVLYSV RPEARGAQLF VTRSKPEMLI ELFRIEVPEI GEEVIEIKAA  240
ARDPGSRAKI AVKTNDKRID PVGACVGMRG ARVQAVSTEL GGERIDIVLW DDNPAQFVIN  300
AMAPADVASI VVDEDKHTMD IAVEAGNLAQ AIGRNGQNVR LASQLSGWEL NVMTVDDLQA  360
KHQAEAHAAI DTFTKYLDID EDFATVLVEE GFSTLEELAY VPMKELLEIE GLDEPTVEAL  420
RERAKNALAT IAQAQEESLG DNKPADDLLN LEGVDRDLAF KLAARGVCTL EDLAEQGIDD  480
LADIEGLTDE KAGALIMAAR NICWFGDEAS GALRTRVKVV KNKALAEGTR IFDPVTGTTH  540
RIEDVVDGRK PIHVVAAAKD GTLHARPVVS WFDQGTRDVI GLRIAGGAIL WATPDHKVLT  600
EYGWRAAGEL RKGDRVAQPR RFDGFGDSAP IPARVQALAD ALDDKFLHDM LAEELRYSVI  660
REVLPTRRAR TFGLEVEELH TLVAEGVVVH NSSPPFKQAE FGSAAAPFTM SIIKDISSKE  720
YISFNPKENK ITVKSKNLPE LSTLLQEIRN NSNSSDIELE EKVMLTECEI NVISNIDTQI  780
VEERIEEAKN LTSDSINYIK DEFKLIESIS DALCDLKQQN ELEDSHFISF EDISETDEGF  840
SIRFINKETG ESIFVETEKT IFSEYANHIT EEISKIKGTI FDTVNGKLVK KVNLDTTHEV  900
NTLNAAFFIQ SLIEYNSSKE SLSNLSVAMK VQVYAQLFST GLNTITDAAK VVELVSTALD  960
ETIDLLPTLS EGLPIIATII DGVSLGAAIK ELSETSDPLL RQEIEAKIGI MAVNLTTATT  1020
AIITSSLGIA SGFSILLVPL AGISAGIPSL VNNELVLRDK ATKVVDYFKH VSLVETEGVF  1080
TLLDDKIMMP QDDLVISEID FNNNSIVLGK CEIWRMEGGS GHTVTDDIDH FFSAPSITYR  1140
EPHLSIYDVL EVQKEELDLS KDLMVLPNAP NRVFAWETGW TPGLRSLEND GTKLLDRIRD  1200
NYEGEFYWRY FAFIADALIT TLKPRYEDTN IRINLDSNTR SFIVPIITTE YIREKLSYSF  1260
YGSGGTYALS LSQYNMGINI ELSESDVWII DVDNVVRDVT IESDKIKKGD LIEGILSTLS  1320
IEENKIILNS HEINFSGEVN GSNGFVSLTF SILEGINAII EVDLLSKSYK LLISGELKIL  1380
MLNSNHIQQK IDYIGFNSEL QKNIPYSFVD SEGKENGFIN GSTKEGLFVS ELPDVVLISK  1440
VYMDDSKPSF GYYSNNLKDV KVITKDNVNI LTGYYLKDDI KISLSLTLQD EKTIKLNSVH  1500
LDESGVAEIL KFMNRKGNTN TSDSLMSFLE SMNIKSIFVN FLQSNIKFIL DANFIISGTT  1560
SIGQFEFICD ENDNIQPYFI KFNTLETNYT LYVGNRQNMI VEPNYDLDDS GDISSTVINF  1620
SQKYLYGIDS CVNKVVISPN IYTDEINITP VYETNNTYPE VIVLDANYIN EKINVNINDL  1680
SIRYVWSNDG NDFILMSTSE ENKVSQVKIR FVNVFKDKTL ANKLSFNFSD KQDVPVSEII  1740
LSFTPSYYED GLIGYDLGLV SLYNEKFYIN NFGMMVSGLI YINDSLYYFK PPVNNLITGF  1800
VTVGDDKYYF NPINGGAASI GETIIDDKNY YFNQSGVLQT GVFSTEDGFK YFAPANTLDE  1860
NLEGEAIDFT GKLIIDENIY YFDDNYRGAV EWKELDGEMH YFSPETGKAF KGLNQIGDYK  1920
YYFNSDGVMQ KGFVSINDNK HYFDDSGVMK VGYTEIDGKH FYFAENGEMQ IGVFNTEDGF  1980
KYFAHHNEDL GNEEGEEISY SGILNFNNKI YYFDDSFTAV VGWKDLEDGS KYYFDEDTAE  2040
AYIGLSLIND GQYYFNDDGI MQVGFVTIND KVFYFSDSGI IESGVQNIDD NYFYIDDNGI  2100
VQIGVFDTSD GYKYFAPANT VNDNIYGQAV EYSGLVRVGE DVYYFGETYT IETGWIYDME  2160
NESDKYYFNP ETKKACKGIN LIDDIKYYFD EKGIMRTGLI SFENNNYYFN ENGEMQFGYI  2220
NIEDKMFYFG EDGVMQIGVF NTPDGFKYFA HQNTLDENFE GESINYTGWL DLDEKRYYFT  2280
DEYIAATGSV IIDGEEYYFD PDTAQLVISE GHHHHHH                         2317

SEQ ID NO: 57           moltype = AA  length = 2321
FEATURE                 Location/Qualifiers
REGION                  1..2321
                        note = Fusion protein
source                  1..2321
                        mol_type = protein
                        organism = synthetic construct
SEQUENCE: 57
MGSSHHHHHH SHMASNKEIL AVVEAVSNEK ALPREKIFEA LESALATATK KKYEQEIDVR  60
VQIDRKSGDF DTFRRWLVVD EVTQPTKEIT LEAARYEDES LNLGDYVEDQ IESVTFDRIT  120
TQTAKQVIVQ KVREAERAMV VDQFREHEGE IITGVVKKVN RDNISLDLGN NAEAVILRED  180
MLPRENFRPG DRVRGVLYSV RPEARGAQLF VTRSKPEMLI ELFRIEVPEI GEEVIEIKAA  240
ARDPGSRAKI AVKTNDKRID PVGACVGMRG ARVQAVSTEL GGERIDIVLW DDNPAQFVIN  300
AMAPADVASI VVDEDKHTMD IAVEAGNLAQ AIGRNGQNVR LASQLSGWEL NVMTVDDLQA  360
KHQAEAHAAI DTFTKYLDID EDFATVLVEE GFSTLEELAY VPMKELLEIE GLDEPTVEAL  420
RERAKNALAT IAQAQEESLG DNKPADDLLN LEGVDRDLAF KLAARGVCTL EDLAEQGIDD  480
LADIEGLTDE KAGALIMAAR NICWFGDEAS GALEVFGEFG SGKAFARDTE VYYENDTVPH  540
MESIEEMYSK YASMNGELPF DNGYAVPLDN VFVYTLDIAS GEIKKTRASY IYREKVEKLI  600
EIKLSSGYSL KVTPSHPVLL FRDGLQWVPA AEVKPGDVVV GVREEVLRRR IISKGELEFH  660
EVSSVRIIDY NNWVYDLVIP ETHNFIAPNG LVLHNTQLAH TLAVMGSAAA PFTMSIIKDI  720
SSKEYISFNP KENKITVKSK NLPELSTLLQ EIRNNSNSSD IELEEKVMLT ECEINVISNI  780
DTQIVEERIE EAKNLTSDSI NYIKDEFKLI ESISDALCDL KQQNELEDSH FISFEDISET  840
DEGFSIRFIN KETGESIFVE TEKTIFSEYA NHITEEISKI KGTIFDTVNG KLVKKVNLDT  900
THEVNTLNAA FFIQSLIEYN SSKESLSNLS VAMKVQVYAQ LFSTGLNTIT DAAKVVELVS  960
TALDETIDLL PTLSEGLPII ATIIDGVSLG AAIKELSETS DPLLRQEIEA KIGIMAVNLT  1020
TATTAIITSS LGIASGFSIL LVPLAGISAG IPSLVNNELV LRDKATKVVD YFKHVSLVET  1080
EGVFTLLDDK IMMPQDDLVI SEIDFNNNSI VLGKCEIWRM EGGSGHTVTD DIDHFFSAPS  1140
ITYREPHLSI YDVLEVQKEE LDLSKDLMVL PNAPNRVFAW ETGWTPGLRS LENDGTKLLD  1200
RIRDNYEGEF YWRYFAFIAD ALITTLKPRY EDTNIRINLD SNTRSFIVPI ITTEYIREKL  1260
SYSFYGSGGT YALSLSQYNM GINIELSESD VWIIDVDNVV RDVTIESDKI KKGDLIEGIL  1320
STLSIEENKI ILNSHEINFS GEVNGSNGFV SLTFSILEGI NAIIEVDLLS KSYKLLISGE  1380
LKILMLNSNH IQQKIDYIGF NSELQKNIPY SFVDSEGKEN GFINGSTKEG LFVSELPDVV  1440
```

```
LISKVYMDDS KPSFGYYSNN LKDVKVITKD NVNILTGYYL KDDIKISLSL TLQDEKTIKL  1500
NSVHLDESGV AEILKFMNRK GNTNTSDSLM SFLESMNIKS IFVNFLQSNI KFILDANFII  1560
SGTTSIGQFE FICDENDNIQ PYFIKFNTLE TNYTLYVGNR QNMIVEPNYD LDDSGDISST  1620
VINFSQKYLY GIDSCVNKVV ISPNIYTDEI NITPVYETNN TYPEVIVLDA NYINEKINVN  1680
INDLSIRYVW SNDGNDFILM STSEENKVSQ VKIRFVNVFK DKTLANKLSF NFSDKQDVPV  1740
SEIILSFTPS YYEDGLIGYD LGLVSLYNEK FYINNFGMMV SGLIYINDSL YYFKPPVNNL  1800
ITGFVTVGDD KYYFNPINGG AASIGETIID DKNYYFNQSG VLQTGVFSTE DGFKYFAPAN  1860
TLDENLEGEA IDFTGKLIID ENIYYFDDNY RGAVEWKELD GEMHYFSPET GKAFKGLNQI  1920
GDYKYYFNSD GVMQKGFVSI NDNKHYFDDS GVMKVGYTEI DGKHFYFAEN GEMQIGVFNT  1980
EDGFKYFAHH NEDLGNEEGE EISYSGILNF NNKIYYFDDS FTAVVGWKDL EDGSKYYFDE  2040
DTAEAYIGLS LINDGQYYFN DDGIMQVGFV TINDKVFYFS DSGIIESGVQ NIDDNYFYID  2100
DNGIVQIGVF DTSDGYKYFA PANTVNDNIY GQAVEYSGLV RVGEDVYYFG ETYTIETGWI  2160
YDMENESDKY YFNPETKKAC KGINLIDDIK YYFDEKGIMR TGLISFENNN YYFNENGEMQ  2220
FGYINIEDKM FYFGEDGVMQ IGVFNTPDGF KYFAHQNTLD ENFEGESINY TGWLDLDEKR  2280
YYFTDEYIAA TGSVIIDGEE YYFDPDTAQL VISEGHHHHH H                      2321

SEQ ID NO: 58          moltype = AA  length = 2099
FEATURE                Location/Qualifiers
source                 1..2099
                       mol_type = protein
                       organism = Clostridium difficile
SEQUENCE: 58
MGSSHHHHHH SHMASDKIIH LTDDSFDTDV LKADGAILVD FWAEWCGPCK MIAPILDEIA  60
DEYQGKLTVA KLNIDQNPGT APKYGIRGIP TLLLFKNGEV AATKVGALSK GQLKEFLDAN  120
LARALEVLFQ GPGGSADARA KAQFEEYKRN YFEGAGGSIM SDLSSKEYIF FDSIDNKLKA  180
KSKNIPGLAS ISEDIKTLLL DASVSPDTKF ILNNLKLNIE SSIGDYIYYE KLEPVKNIIH  240
NSIDDLIDEF NLLENVSDEL YELKKLNNLD EKYLISFEDI SKNNSTYSVR FINKSNGESV  300
YVETEKEIFS KYSEHITKEI STIKNSIITD VNGNLLDNIQ LDHTSQVNTL NAAFFIQSLI  360
DYSSNKDVLN DLSTSVKVQL YAQLFSTGLN TIYDSIQLVN LISNAVNDTI NVLPTITEGI  420
PIVSTILDGI NLGAAIKELL DEHDPLLKKE LEAKVGVLAI NMSLSIAATV ASIVGIGAEV  480
TIFLLPIAGI SAGIPSLVNN ELILHDKATS VVNYFNHLSE SKKYGPLKTE DDKILVPIDD  540
LVISEIDFNN NSIKLGTCNI LAMEGGSGHT VTGNIDHFFS SPSISSHIPS LSIYSAIGIE  600
TENLDFSKKI MMLPNAPSRV FWWETGAVPG LRSLENDGTR LLDSIRDLYP GKFYWRFYAF  660
FDYAITTLKP VYEDTNIKIK LDKDTRNFIM PTITTNEIRN KLSYSFDGAG GTYSLLLSSY  720
PISTNINLSK DDLWIFNIDN EVREISIENG TIKKGKLIKD VLSKIDINKN KLIIGNQTID  780
FSGDIDNKDR YIFLTCELDD KISLIIEINL VAKSYSLLLS GDKNYLISNL SNIIEKINTL  840
GLDSKNIAYN YTDESNNKYF GAISKTSQKS IIHYKKDSKN ILEFYNDSTL EFNSKDFIAE  900
DINVFMKDDI NTITGKYYVD NNTDKSIDFS ISLVSKNQVK VNGLYLNESV YSSYLDFVKN  960
SDGHHNTSNF MNLFLDNISF WKLFGFENIN FVIDKYFTLV GKTNLGYVEF ICDNNKNIDI  1020
YFGEWKTSSS KSTIFSGNGR NVVVEPIYNP DTGEDISTSL DFSYEPLYGI DRYINKVLIA  1080
PDLYTSLINI NTNYYSNEYY PEIIVLNPNT FHKKVNINLD SSSFEYKWST EGSDFILVRY  1140
LEESNKKILQ KIRIKGILSN TQSFNKMSID FKDIKKLSLG YIMSNFKSFN SENELDRDHL  1200
GFKIIDNKTY YYDEDSKLVK GLININNSLF YFDPIEFNLV TGWQTINGKK YYFDINTGAA  1260
LISYKIINGK HFYFNNDGVM QLGVFKGPDG FEYFAPANTQ NNNIEGQAIV YQSKFLTLNG  1320
KKYYFDNDSK AVTGWRIINN EKYYFNPNNA IAAVGLQVID NNKYYFNPDT AIISKGWQTV  1380
NGSRYYFDTD TAIAFNGYKT IDGKHFYFDS DCVVKIGVFS TSNGFEYFAP ANTYNNNIEG  1440
QAIVYQSKFL TLNGKKYYFD NNSKAVTGWQ TIDSKKYYFN TNTAEAATGW QTIDGKKYYF  1500
NTNTAEAATG WQTIDGKKYY FNTNTAIAST GYTIINGKHF YFNTDGIMQI GVFKGPNGFE  1560
YFAPANTDAN NIEGQAILYQ NEFLTLNGKK YYFGSDSKAV TGWRIINNKK YYFNPNNAIA  1620
AIHLCTINND KYYFSYDGIL QNGYITIERN NFYFDANNES KMVTGVFKGP NGFEYFAPAN  1680
THNNNIEGQA IVYQNKFLTL NGKKYYFDND SKAVTGWQTI DGKKYYFNLN TAEAATGWQT  1740
IDGKKYYFNL NTAEAATGWQ TIDGKKYYFN TNTFIASTGY TSINGKHFYF NTDGIMQIGV  1800
FKGPNGFEYF APANTHNNNI EGQAILYQNK FLTLNGKKYY FGSDSKAVTG LRTIDGKKYY  1860
FNTNTAVAVT GWQTINGKKY YFNTNTSIAS TGYTIISGKH FYFNTDGIMQ IGVFKGPDGF  1920
EYFAPANTDA NNIEGQAIRY QNRFLYLHDN IYYFGNNSKA ATGWVTIDGN RYYFEPNTAM  1980
GANGYKTIDN KNFYFRNGLP QIGVFKGSNG FEYFAPANTD ANNIEGQAIR YQNRFLHLLG  2040
KIYYFGNNSK AVTGWQTING KVYYFMPDTA MAAAGGLFEI DGVIYFFGVD GVKAPGIYG   2099

SEQ ID NO: 59          moltype = AA  length = 1783
FEATURE                Location/Qualifiers
source                 1..1783
                       mol_type = protein
                       organism = Clostridium difficile
SEQUENCE: 59
MGSSHHHHHH SHMASDKIIH LTDDSFDTDV LKADGAILVD FWAEWCGPCK MIAPILDEIA  60
DEYQGKLTVA KLNIDQNPGT APKYGIRGIP TLLLFKNGEV AATKVGALSK GQLKEFLDAN  120
LARALVPRGS GGSADARAKA QFEEYKRNYF EGAGGSAAAP FTMIMSDLSS KEYIFFDSID  180
NKLKAKSKNI PGLASISEDI KTLLLDASVS PDTKFILNNL KLNIESSIGD YIYYEKLEPV  240
KNIIHNSIDD LIDEFNLLEN VSDELYELKK LNNLDEKYLI SFEDISKNNS TYSVRFINKS  300
NGESVYVETE KEIFSKYSEH ITKEISTIKN SIITDVNGNL LDNIQLDHTS QVNTLNAAFF  360
IQSLIDYSSN KDVLNDLSTS VKVQLYAQLF STGLNTIYDS IQLVNLISNA VNDTINVLPT  420
ITEGIPIVST ILDGINLGAA IKELLDEHDP LLKKELEAKV GVLAINMSLS IAATVASIVG  480
IGAEVTIFLL PIAGISAGIP SLVNNELILH DKATSVVNYF NHLSESKKYG PLKTEDDKIL  540
VPIDDLVISE IDFNNNSIKL GTCNILAMEG GSGHTVTGNI DHFFSSPSIS SHIPSLSIYS  600
AIGIETENLD FSKKIMMLPN APSRVFWWET GAVPGLRSLE NDGTRLLDSI RDLYPGKFYW  660
RFYAFFDYAI TTLKPVYEDT NIKIKLDKDT RNFIMPTITT NEIRNKLSYS FDGAGGTYSL  720
LLSSYPISTN INLSKDDLWI FNIDNEVREI SIENGTIKKG KLIKDVLSKI DINKNKLIIG  780
NQTIDFSGDI DNKDRYIFLT CELDDKISLI IEINLVAKSY SLLLSGDKNY LISNLSNIIE  840
KINTLGLDSK NIAYNYTDES NNKYFGAISK TSQKSIIHYK KDSKNILEFY NDSTLEFNSK  900
```

```
DFIAEDINVF MKDDINTITG KYYVDNNTDK SIDFSISLVS KNQVKVNGLY LNESVYSSYL  960
DFVKNSDGHH NTSNFMNLFL DNISFWKLFG FENINFVIDK YFTLVGKTNL GYVEFICDNN  1020
KNIDIYFGEW KTSSSKSTIF SGNGRNVVVE PIYNPDTGED ISTSLDFSYE PLYGIDRYIN  1080
KVLIAPDLYT SLININTNYY SNEYYPEIIV LNPNTFHKKV NINLDSSSFE YKWSTEGSDF  1140
ILVRYLEESN KKILQKIRIK GILSNTQSFN KMSIDFKDIK KLSLGYIMSN FKSFNSENEL  1200
DRDHLGFKII DNKTYYYDED SKLVKGLINI NNSLFYFDPI EFNLVTGWQT INGKKYYFDI  1260
NTGAALISYK IINGKHFYFN NDGVMQLGVF KGPDGFEYFA PANTQNNNIE GQAIVYQSKF  1320
LTLNGKKYYF DNDSKAVTGW RIINNEKYYF NPNNAIAAVG LQVIDNNKYY FNPDTAIISK  1380
GWQTVNGSRY YFDTDTAIAF NGYKTIDGKH FYFDSDCVVK IGVFSTSNGF EYFAPANTYN  1440
NNIEGQAIVY QSKFLTLNGK KYYFDNNSKA VTGWQTIDSK KYYFNTNTAE AATGWQTIDG  1500
KKYYFNTNTA EAATGWQTID GKKYYFNTNT AIASTGYTII NGKHFYFNTD GIMQIGVFKG  1560
PNGFEYFAPA NTDANNIEGQ AILYQNEFLT LNGKKYYFGS DSKAVTGWRI INNKKYYFNP  1620
NNAIAAIHLC TINNDKYYFS YDGILQNGYI TIERNNFYFD ANNESKMVTG VFKGPNGFEY  1680
FAPANTHNNN IEGQAIVYQN KFLTLNGKKY YFDNDSKAVT GWQTIDGKKY YFNLNTAEAA  1740
TGWQTIDGKK YYFNLNTAEA ATGWQTIDGK KYYFNTNTFI AST                    1783

SEQ ID NO: 60          moltype = AA  length = 31
FEATURE                Location/Qualifiers
source                 1..31
                       mol_type = protein
                       organism = Clostridium difficile
SEQUENCE: 60
GVFKGPDGFE YFAPANTQNN NIEGQAIVYQ S                                 31

SEQ ID NO: 61          moltype = AA  length = 157
FEATURE                Location/Qualifiers
source                 1..157
                       mol_type = protein
                       organism = Clostridium difficile
SEQUENCE: 61
VTGWQTINGK KYYFDINTGA ALTSYKIING KHFYFNNDGV MQLGVFKGPD GFEYFAPANT  60
QNNNIEGQAI VYQSKFLTLN GKKYYFDNNS KAVTGWRIIN NEKYYFNPNN AIAAVGLQVI  120
DNNKYYFNPD TAIISKGWQT VNGSRYYFDT DTAIAFN                           157

SEQ ID NO: 62          moltype = AA  length = 31
FEATURE                Location/Qualifiers
source                 1..31
                       mol_type = protein
                       organism = Clostridium difficile
SEQUENCE: 62
GVFSTSNGFE YFAPANTYNN NIEGQAIVYQ S                                 31

SEQ ID NO: 63          moltype = AA  length = 134
FEATURE                Location/Qualifiers
source                 1..134
                       mol_type = protein
                       organism = Clostridium difficile
SEQUENCE: 63
GYKTIDGKHF YFDSDCVVKI GVFSTSNGFE YFAPANTYNN NIEGQAIVYQ SKFLTLNGKK  60
YYFDNNSKAV TGLQTIDSKK YYFNTNTAEA ATGWQTIDGK KYYFNTNTAE AATGWQTIDG  120
KKYYFNTNTA IAST                                                    134

SEQ ID NO: 64          moltype = AA  length = 31
FEATURE                Location/Qualifiers
source                 1..31
                       mol_type = protein
                       organism = Clostridium difficile
SEQUENCE: 64
GVFKGPNGFE YFAPANTDAN NIEGQAILYQ N                                 31

SEQ ID NO: 65          moltype = AA  length = 112
FEATURE                Location/Qualifiers
source                 1..112
                       mol_type = protein
                       organism = Clostridium difficile
SEQUENCE: 65
GYTIINGKHF YFNTDGIMQI GVFKGPNGFE YFAPANTDAN NIEGQAILYQ NEFLTLNGKK  60
YYFGSDSKAV TGWRIINNKK YYFNPNNAIA AIHLCTINND KYYFSYDGIL QN          112

SEQ ID NO: 66          moltype = AA  length = 31
FEATURE                Location/Qualifiers
source                 1..31
                       mol_type = protein
                       organism = Clostridium difficile
SEQUENCE: 66
GVFKGPNGFE YFAPANTHNN NIEGQAIVYQ N                                 31

SEQ ID NO: 67          moltype = AA  length = 136
FEATURE                Location/Qualifiers
```

```
source                  1..136
                        mol_type = protein
                        organism = Clostridium difficile
SEQUENCE: 67
GYITIERNNF YFDANNESKM VTGVFKGPNG FEYFAPANTH NNNIEGQAIV YQNKFLTLNG  60
KKYYFDNDSK AVTGWQTIDG KKYYFNLNTA EAATGWQTID GKKYYFNLNT AEAATGWQTI  120
DGKKYYFNTN TFIAST                                                  136

SEQ ID NO: 68           moltype = AA  length = 31
FEATURE                 Location/Qualifiers
source                  1..31
                        mol_type = protein
                        organism = Clostridium difficile
SEQUENCE: 68
GVFKGPNGFE YFAPANTDAN NIEGQAILYQ N                                 31

SEQ ID NO: 69           moltype = AA  length = 113
FEATURE                 Location/Qualifiers
source                  1..113
                        mol_type = protein
                        organism = Clostridium difficile
SEQUENCE: 69
GYTSINGKHF YFNTDGIMQI GVFKGPNGFE YFAPANTDAN NIEGQAILYQ NKFLTLNGKK  60
YYFGSDSKAV TGLRTIDGKK YYFNTNTAVA VTGWQTINGK KYYFNTNTSI AST         113

SEQ ID NO: 70           moltype = AA  length = 31
FEATURE                 Location/Qualifiers
source                  1..31
                        mol_type = protein
                        organism = Clostridium difficile
SEQUENCE: 70
GVFKGPDGFE YFAPANTDAN NIEGQAIRYQ N                                 31

SEQ ID NO: 71           moltype = AA  length = 92
FEATURE                 Location/Qualifiers
source                  1..92
                        mol_type = protein
                        organism = Clostridium difficile
SEQUENCE: 71
GYTIISGKHF YFNTDGIMQI GVFKGPDGFE YFAPANTDAN NIEGQAIRYQ NRFLYLHDNI  60
YYFGNNSKAA TGWVTIDGNR YYFEPNTAMG AN                                92

SEQ ID NO: 72           moltype = AA  length = 31
FEATURE                 Location/Qualifiers
source                  1..31
                        mol_type = protein
                        organism = Clostridium difficile
SEQUENCE: 72
GVFKGSNGFE YFAPANTDAN NIEGQAIRYQ N                                 31

SEQ ID NO: 73           moltype = AA  length = 116
FEATURE                 Location/Qualifiers
source                  1..116
                        mol_type = protein
                        organism = Clostridium difficile
SEQUENCE: 73
GYKTIDNKNF YFRNGLPQIG VFKGSNGFEY FAPANTDANN IEGQAIRYQN RFLHLLGKIY  60
YFGNNSKAVT GWQTINGKVY YFMPDTAMAA AGGLFEIDGV IYFFGVDGVK APGIYG      116

SEQ ID NO: 74           moltype = AA  length = 147
FEATURE                 Location/Qualifiers
source                  1..147
                        mol_type = protein
                        organism = Clostridium difficile
SEQUENCE: 74
DDKYYFNPIN GGAASIGETI IDDKNYYFNQ SGVLQTGVFS TEDGFKYFAP ANTLDENLEG  60
EAIDFTGKLI IDENIYYFDD NYRGAVEWKE LDGEMHYFSP ETGKAFKGLN QIGDYKYYFN  120
SDGVMQKGFV SINDNKHYFD DSGVMKV                                      147

SEQ ID NO: 75           moltype = AA  length = 147
FEATURE                 Location/Qualifiers
source                  1..147
                        mol_type = protein
                        organism = Clostridium difficile
SEQUENCE: 75
DDKYYFNPIN GGAASIGETI IDDKNYYFNQ SGVLQTGVFS TEDGFKYFAP ANTLDENLEG  60
EAIDFTGKLI IDENIYYFDD NYRGAVEWKE LDGEMHYFSP ETGKAFKGLN QIGDYKYYFN  120
SDGVMQKGFV SINDNKHYFD DSGVMKV                                      147
```

-continued

```
SEQ ID NO: 76          moltype = AA  length = 30
FEATURE                Location/Qualifiers
source                 1..30
                       mol_type = protein
                       organism = Clostridium difficile
SEQUENCE: 76
GVFNTEDGFK YFAHHNEDLG NEEGEEISYS                                   30

SEQ ID NO: 77          moltype = AA  length = 132
FEATURE                Location/Qualifiers
source                 1..132
                       mol_type = protein
                       organism = Clostridium difficile
SEQUENCE: 77
GYTEIDGKHF YFAENGEMQI GVFNTEDGFK YFAHHNEDLG NEEGEEISYS GILNFNNKIY  60
YFDDSFTAVV GWKDLEDGSK YYFDEDTAEA YIGLSLINDG QYYFNDDGIM QVGFVTINDK  120
VFYFSDSGII ES                                                      132

SEQ ID NO: 78          moltype = AA  length = 30
FEATURE                Location/Qualifiers
source                 1..30
                       mol_type = protein
                       organism = Clostridium difficile
SEQUENCE: 78
GVFDTSDGYK YFAPANTVND NIYGQAVEYS                                   30

SEQ ID NO: 79          moltype = AA  length = 134
FEATURE                Location/Qualifiers
source                 1..134
                       mol_type = protein
                       organism = Clostridium difficile
SEQUENCE: 79
GVQNIDDNYF YIDDNGIVQI GVFDTSDGYK YFAPANTVND NIYGQAVEYS GLVRVGEDVY  60
YFGETYTIET GWIYDMENES DKYYFNPETK KACKGINLID DIKYYFDEKG IMRTGLISFE  120
NNNYYFNENG EMQF                                                    134

SEQ ID NO: 80          moltype = AA  length = 30
FEATURE                Location/Qualifiers
source                 1..30
                       mol_type = protein
                       organism = Clostridium difficile
SEQUENCE: 80
GVFNTPDGFK YFAHQNTLDE NFEGESINYT                                   30

SEQ ID NO: 81          moltype = AA  length = 93
FEATURE                Location/Qualifiers
source                 1..93
                       mol_type = protein
                       organism = Clostridium difficile
SEQUENCE: 81
GYINIEDKMF YFGEDGVMQI GVFNTPDGFK YFAHQNTLDE NFEGESINYT GWLDLDEKRY  60
YFTDEYIAAT GSVIIDGEEY YFDPDTAQLV ISE                               93
```

*CLOSTRIDIUM DIFFICILE* ANTIGENS

CROSS-REFERENCES TO RELATED APPLICATIONS

This application is a continuation of U.S. application Ser. No. 17/224,404, filed Apr. 7, 2021, which is a division of U.S. application Ser. No. 16/511,503, filed Jul. 15, 2019, now abandoned, which is a division of U.S. application Ser. No. 13/878,150, filed Jun. 25, 2013, now U.S. Pat. No. 10,369,206, issued Aug. 6, 2019, which is the National Stage of International Application No. PCT/GB2011/051910, filed Oct. 5, 2011, which claims the benefit of GB Application No. 1016742.7, filed Oct. 5, 2010.

STATEMENT REGARDING SEQUENCE LISTING

The Sequence Listing XML associated with this application is provided in XML format and is hereby incorporated by reference into the specification. The name of the XML file containing the sequence listing is 2677-P16USCON2_Seq_List_20220817. The XML file is 198 KB, was created on Aug. 17, 2022, and is being submitted electronically via Patent Center with the filing of the specification.

BACKGROUND

The present invention relates to antigens for the prevention/treatment/suppression of *Clostridium difficile* infection (CDI). Also provided are methods for generating said antigens, methods for generating antibodies that bind to said antigens, and the use of said antibodies for the prevention/treatment/suppression of CDI.

*Clostridium difficile* infection (CDI) is now a major problem in hospitals worldwide. The bacterium causes nosocomial, antibiotic-associated disease which manifests itself in several forms ranging from mild self-limiting diarrhoea to potentially life-threatening, severe colitis. Elderly patients are most at risk from these potentially life-threatening diseases and incidents of CDI have increased dramatically over the last 10 years. In 2010 in the UK there were over 21,000 cases of CDI with over 2,700 associated deaths. CDI costs the UK National Health Service in excess of £500M per annum.

The various strains of *C. difficile* may be classified by a number of methods. One of the most commonly used is polymerase chain reaction (PCR) ribotyping in which PCR is used to amplify the 16S-23S rRNA gene intergenic spacer region of *C. difficile*. Reaction products from this provide characteristic band patterns identifying the bacterial ribotype of isolates. Toxinotyping is another typing method in which the restriction patterns derived from DNA coding for the *C. difficile* toxins are used to identify strain toxinotype. The differences in restriction patterns observed between toxin genes of different strains are also indicative of sequence variation within the *C. difficile* toxin family. For example, there is an approximate 13% sequence difference with the C-terminal 60 kDa region of toxinotype 0 Toxin B compared to the same region in toxinotype III Toxin B.

Strains of *C. difficile* produce a variety of virulence factors, notable among which are several protein toxins: Toxin A, Toxin B and, in some strains, a binary toxin which is similar to *Clostridium perfringens* iota toxin. Toxin A is a large protein cytotoxin/enterotoxin which plays a role in the pathology of infection and may influence the gut colonisation process. Outbreaks of CDI have been reported with Toxin A-negative/Toxin B-positive strains, which indicates that Toxin B is also capable of playing a key role in the disease pathology.

The genetic sequences encoding Toxin A and Toxin B (Mw 308 k and Mw 269 k, respectively) are known—see, for example, Moncrief et al. (1997) Infect. Immun 63:1105-1108. The two toxins have high sequence homology and are believed to have arisen from gene duplication. The toxins also share a common structure (see FIG. 1), namely an N-terminal glucosyl transferase domain, a central hydrophobic region, four conserved cysteines, and a long series of C-terminal repeating units (RUs).

Toxin A comprises 39 contiguous repeating units (RUs), which span amino acid residues 1851-2710 of the Toxin A polypeptide sequence. Toxin B comprises fewer RUs (between 19 and 24) which span amino acid residues 1852-2366 of the Toxin B polypeptide sequence. For both Toxins A and B, the repeating units are of two different types: short repeats (SRs) of approximately 15-25 residues and long repeats (LRs) of approximately 30 residues. The LRs are separated from each other by 3 or 4 SRs, and the LRs together with the flanking SRs provide the binding sites for the carbohydrate receptor of the toxins. Toxin A has 7 LRs within its C-terminal domain, which are believed to provide 7 receptor binding sites (Greco et al. (2005) Nature Structural Biol. 13:460-461). Toxin B has 4 LRs, which are believed to provide 4 carbohydrate binding units. Examples of the Toxin A and Toxin B SR/LR clusters (also known as receptor-binding "Modules") vary in size from 92-141 amino acid residues, and are exemplified by reference to Tables 1 and 2.

Both Toxins A and B exert their mechanisms of action via multi-step mechanisms, which include binding to receptors on the cell surface, internalisation followed by translocation and release of the effector domain into the cell cytosol, and finally intracellular action. Said mechanism of action involves the inactivation of small GTPases of the Rho family. In this regard, the toxins catalyse the transfer of a glucose moiety (from UDP-glucose) onto an amino residue of the Rho protein. Toxins A and B also contain a second enzyme activity in the form of a cysteine protease, which appears to play a role in the release of the effector domain into the cytosol after translocation. The *C. difficile* binary toxin modifies cell actin by a mechanism which involves the transfer of an ADP-ribose moiety from NAD onto its target protein.

Current therapies for the treatment of *C. difficile* infection rely on the use of antibiotics, notably metronidazole and vancomycin. However, these antibiotics are not effective in all cases and 20-30% of patients suffer relapse of the disease. Of major concern is the appearance in the UK of more virulent strains, which were first identified in Canada in 2002. These strains, which include those belonging to PCR ribotype 027 and toxinotype III, cause CDI with a directly attributable mortality more than 3-fold that observed previously.

New therapeutics are therefore required especially urgently since the efficacy of current antibiotics appears to be decreasing.

An attractive alternative is the use of antibodies which bind to and neutralize the activity of Toxin A and Toxin B. This is based on the knowledge that strains of *C. difficile* that do not release these toxins, so called non-toxigenic strains, do not cause CDI. In one approach patients with CDI or subjects at risk of developing such infections can be immunised with antigens which result in an increase in circulating and mucosal antibodies directed against Toxin A and Toxin B. This is defined as active immunisation. Alternatively, animals, such as horses or sheep, can be immunised, their sera collected and the antibodies purified for administration to patients—passive immunisation.

A critical requirement for both active and passive immunisation is the availability of suitable antigens with which to immunise the patient or animal respectively. These can comprise the natural toxins which can be purified from the media in which suitable toxigenic strains of *C. difficile* have been cultured. There are several disadvantages to this approach. Both Toxin A and Toxin B are present in culture medium in only small amounts and are difficult to purify without incurring significant losses. Thus, it will be both costly and difficult to obtain the amounts necessary to meet world-wide needs. In addition, the natural toxins are unstable and, because of their toxicity, must be converted to their toxoids (inactivated toxins) prior to their use as immunogens.

The above mentioned problems have resulted in there being few available *C. difficile* vaccine candidates. To-date, the only CDI vaccine in late-stage development is based on a mixture of native (i.e., naturally occurring) Toxins A and B, which have been inactivated by chemical modification (Salnikova et al. (2008), J. Pharm. Sci., 97:3735-3752).

One alternative to the use of natural toxins and their toxoids, involves the design, development and use of recombinant fragments derived from Toxins A and B. Among their advantages are that such fragments can be expressed and purified in large amounts and at lower cost than the native toxins. Examples of existing antigens intended for use in treating/preventing a *C. difficile* infection include peptides based on the C-terminal repeating units (RUs) of Toxin A or Toxin B—see, for example, WO00/61762. A problem with such antigens, however, is that they are either poorly immunogenic (i.e., the antigens produce poor antibody titres), or, where higher antibody titres are produced, the antibodies demonstrate poor neutralising efficacy against *C. difficile* cytotoxic activity (i.e., insufficient neutralising antibodies are produced).

There is therefore a need in the art for new vaccines/therapies/therapeutics capable of specifically addressing *C. difficile* infection (CDI). This need is addressed by the present invention, which solves one or more of the above-mentioned problems.

In one embodiment, the present invention provides antigens that are able to induce a potent toxin-neutralising response against *C. difficile* Toxin A and/or B. The invention also provides methods for preparing recombinant antigens. In another embodiment, said antigens are used as immunogens to enable the large-scale preparation of therapeutic antibodies. In a further embodiment, said antibodies are able to induce a potent toxin-neutralising response against *C. difficile* Toxin A and/or B and therefore have prophylactic and/or therapeutic applications.

As mentioned above (see WO00/61762), previous studies describe vaccine preparations based on the C-terminal, repeating units (RUs) of Toxin A and/or Toxin B. Said RU fragments have a poor toxin-neutralising effect, and/or are difficult to manufacture in large quantities.

In contrast, the present invention provides a *C. difficile* antigen based on a Toxin A and/or a Toxin B repeat unit, and further includes an additional *C. difficile* toxin domain, which the present inventors believe provides an important 'scaffold' function to the antigen. Said antigens of the invention demonstrate good toxin-neutralising immune responses and/or are readily manufactured in large quantities.

The present inventors have surprisingly identified that the presence of a "scaffold" first amino acid sequence (as above) provides a protective (toxin-neutralising) immune response that is between 10-100 fold increased as compared to corresponding fragments comprising just the repeat regions of Toxin A or Toxin B. Tables 3-10 clearly show the superior capacity of fusion proteins of the present invention to elicit a toxin-neutralising immune response compared to fragments containing just the repeat domains of a *C. difficile* Toxin. Comparison of the data in Tables 5 and 6 confirms that the Toxin B-based constructs of the present invention elicit a considerably more potent toxin-neutralising immune response than that of a corresponding construct based solely on the C-terminal repeating units of Toxin B (designated TxB2). In more detail, after an 18-week immunisation period, the toxin-neutralising immune response provided by constructs of the present invention was approximately 128-fold higher than that provided by the TxB2 construct. Tables 9 and 10 show similar data for Toxin A-based constructs of the present invention. Comparison of the data in said Tables confirms that the Toxin A-based constructs of the present invention elicit a considerably more potent toxin-neutralising immune response than that of a corresponding construct based solely on the C-terminal repeating units of Toxin A (designated TxA2). In more detail, after an 18-week immunisation period, the toxin-neutralising immune response provided by constructs of the present invention was 12-fold higher than that provided by the TxA2 construct.

These findings are surprising for a number of reasons. Previous studies have shown that toxin fragments consisting of the *C. difficile* Toxin RUs fold correctly, readily crystallise to yield an ordered structure (Ho et al. (2005) Proc. Natl. Acad. Sci. USA, 102:18373-18378), and bind carbohydrate moieties that mimic the natural *C. difficile* Toxin receptors (Greco et al. (2006) Nature Structure & Molecular Biology, 13: 460-461). Thus, the scientific evidence to-date supports and is consistent with the prior art use (e.g., WO 00/61762) of fragments consisting of the *C. difficile* Toxin RUs in antigenic formulations. More importantly, however, a further study has confirmed that antibodies raised against a whole *C. difficile*, while recognising a fragment consisting of the entire RU region alone, failed to recognise a fragment consisting of a "scaffold" region based on residues 901-1750 of the *C. difficile* same toxin (Genth et al., (2000) Infect. Immun., 68:1094-1101). These data therefore suggest that domains within "scaffold" residues 901-1750 contribute no significant antibody-binding structural determinants. In this regard, other than at the peptide bond, there is no contact in the tertiary structure between "scaffold" toxin domains and the C-terminal repeat region residues—see Pruitt et al., (2010) Proc. Natl. Acad. Sci. USA, 1002199107 online publication. Collectively, it is therefore extremely surprising that the inclusion of a *C. difficile* "scaffold" region within recombinant immunogens of Toxins A and/or Toxin B has the effect of significantly enhancing the toxin-neutralising immune response.

A first aspect of the present invention provides a fusion protein, consisting of or comprising a first amino acid sequence and a second amino acid sequence, wherein:

1) the first amino acid sequence is provided by an amino acid sequence that has at least 80% sequence identity with an amino acid sequence consisting of residues 1500-1850 of a *C. difficile* Toxin A sequence; and 2) the second amino acid sequence is provided by an amino acid sequence that has at least 80% sequence identity with an amino acid sequence consisting of a long repeat unit located within amino acid residues 1851-2710 of a *C. difficile* Toxin A sequence;

with the proviso that the fusion protein is not a polypeptide comprising amino acid residues 543-2710 of a *C. difficile* Toxin A.

Reference to a *C. difficile* Toxin A sequence means the amino acid sequence of a naturally-occurring *C. difficile* Toxin A (also referred to as a *C. difficile* Toxin A reference sequence). Examples of such sequences are readily understood by a skilled person, and some of the more common naturally-occurring Toxin A sequences are identified in the present specification (see, for example, SEQ ID NOs: 1 and 3) as well as throughout the literature.

Reference to 'at least 80% sequence identity' throughout this specification is considered synonymous with the phrase 'based on' and may embrace one or more of at least 85%, at least 90%, at least 93%, at least 95%, at least 97%, at least 99%, and 100% sequence identity. When assessing sequence identity, a reference sequence having a defined number of contiguous amino acid residues is aligned with an amino acid sequence (having the same number of contiguous amino acid residues) from the corresponding portion of a fusion protein of the present invention.

In one embodiment, the first amino acid sequence is based on (i.e., has at least 80% sequence identity with) amino acid residues 544-1850 of a *C. difficile* Toxin A. In another embodiment, the first amino acid sequence is based on an N-terminal truncation of amino acid residues 544-1850 of a *C. difficile* Toxin A, such as amino acid residues 564-1850, amino acid residues 584-1850, amino acid residues 594-1850, amino acid residues 614-1850, amino acid residues 634-1850, amino acid residues 654-1850, amino acid residues 674-1850, amino acid residues 694-1850, amino acid residues 714-1850, amino acid residues 734-1850, amino acid residues 754-1850, amino acid residues 767-1850, amino acid residues 770-1850, amino acid residues 774-1850, amino acid residues 794-1850, amino acid residues 814-1850, amino acid residues 834-1850, amino acid residues 854-1850, amino acid residues 874-1850, amino acid residues 894-1850, amino acid residues 914-1850, amino acid residues 934-1850, amino acid residues 954-1850, amino acid residues 974-1850, amino acid residues 994-1850, amino acid residues 1014-1850, amino acid residues 1034-1850, amino acid residues 1054-1850, amino acid residues 1074-1850, amino acid residues 1094-1850, amino acid residues 1104-1850, amino acid residues 1124-1850, amino acid residues, amino acid residues 1131-1850, amino acid residues 1144-1850, amino acid residues 1164-1850, amino acid residues 1184-1850, amino acid residues 1204-1850, amino acid residues 1224-1850, amino acid residues 1244-1850, amino acid residues 1264-1850, amino acid residues 1284-1850, amino acid residues 1304-1850, amino acid residues 1324-1850, amino acid residues 1344-1850, amino acid residues 1364-1850, amino acid residues 1384-1850, amino acid residues 1404-1850, amino acid residues 1424-1850, amino acid residues 1444-1850, amino acid residues 1464-1850, or amino acid residues 1684-1850 of a *C. difficile* Toxin A; though always with the proviso that the fusion protein is not a polypeptide comprising amino acid residues 543-2710 of a *C. difficile* Toxin A. By way of example only, the above amino acid position numbering may refer to the *C. difficile* Toxin A sequences identified as SEQ ID NOs: 1 and/or 3.

In one embodiment, the second amino acid sequence is based on (i.e., has at least 80% sequence identity with) any one or more of the long repeat (LR) amino acid sequences from a *C. difficile* Toxin A sequence. By way of example only, said one or more LR sequences may be based on any of SEQ ID NOs: 60, 62, 64, 66, 68, 70 and/or 72. In another embodiment, the second amino acid sequence is based on an entire Module sequence of a *C. difficile* Toxin A sequence, which includes a LR amino acid sequence plus one or more of its (flanking) short repeat (SR) sequences. By way of example only, the second amino acid may be based on one or more of SEQ ID NOs: 61, 63, 65, 67, 69, 71 and/or 73. In another embodiment, the second amino acid sequence is based on a sequence consisting of or comprising the entire Module 1 amino acid sequence from a *C. difficile* Toxin A sequence (residues 1851-2007)—see, for example, the Module 1 as illustrated in Table 1. In another embodiment, the second amino acid sequence is based on a sequence consisting of or comprising the entire Module 1 plus Module 2 amino acid sequence from a *C. difficile* Toxin A sequence (e.g., residues 1851-2141 as illustrated in Table 1). In another embodiment, the second amino acid sequence is based on a sequence consisting of or comprising the entire Module 1 plus Module 2 plus Module 3 amino acid sequence from a *C. difficile* Toxin A sequence (e.g., residues 1851-2253 as illustrated in Table 1). In another embodiment, the second amino acid sequence is based on a sequence consisting of or comprising the entire Module 1 plus Module 2 plus Module 3 plus Module 4 amino acid sequence from a *C. difficile* Toxin A sequence (e.g., residues 1851-2389 as illustrated in Table 1). In another embodiment, the second amino acid sequence is based on a sequence consisting of or comprising the entire Module 1 plus Module 2 plus Module 3 plus Module 4 plus Module 5 amino acid sequence from a *C. difficile* Toxin A sequence (e.g., residues 1851-2502 as illustrated in Table 1). In another embodiment, the second amino acid sequence is based on a sequence consisting of or comprising the entire Module 1 plus Module 2 plus Module 3 plus Module 4 plus Module 5 plus Module 6 amino acid sequence from a *C. difficile* Toxin A sequence (e.g., residues 1851-2594 as illustrated in Table 1). In another embodiment, the second amino acid sequence is based on a sequence consisting of or comprising the entire Module 1 plus Module 2 plus Module 3 plus Module 4 plus Module 5 plus Module 6 plus Module 7 amino acid sequence from a *C. difficile* Toxin A sequence (e.g., residues 1851-2710 as illustrated in Table 1). By way of example only, the above amino acid position numbering may refer to the *C. difficile* Toxin A sequences identified as SEQ ID NOs: 1 and/or 3.

Any of the embodiments for the second amino acid sequence may be combined with any of the embodiments described for the first amino acid sequence.

In one embodiment a fusion protein is provided, which comprises or consists of a sequence based on amino acid residues 1851-2710 of a Toxin A sequence (or a portion thereof) and an N-terminal polypeptide based on amino acid residues 770-1850 of a Toxin A polypeptide (or a portion thereof).

In another embodiment a fusion protein is provided, which comprises or consists of a sequence based on amino acid residues 1851-2710 of a Toxin A sequence (or a portion thereof) and an N-terminal polypeptide based on amino acid residues 1131-1850 of a Toxin A polypeptide.

In another embodiment a fusion protein is provided, which comprises or consists of a sequence based on amino acid residues 770-2710 or 1131-2710 of a Toxin A polypeptide (e.g., SEQ ID NOs 5, 6, 7, 8, 18, 19, 20, 21, 22, 28, 29, 30, 31, 32, 33, 34, 35, 36, 37, 38, 39, 40, 41, 42, 43, or 58).

In another embodiment a fusion protein is provided, which comprises or consists of a sequence based on amino acid residues 770-2007, 770-2141, 770-2253, 770-2389 or 1131-2007, 1131-2141, 1131-2253 or 1131-2389 of a Toxin A polypeptide (e.g., SEQ ID NO 59).

A related first aspect of the present invention provides a fusion protein, consisting of or comprising a first amino acid sequence and a second amino acid sequence, wherein:

1) the first amino acid sequence is provided by an amino acid sequence that has at least 80% sequence identity with an amino acid sequence consisting of residues 1500-1851 of a *C. difficile* Toxin B sequence; and
2) the second amino acid sequence is provided by an amino acid sequence that has at least 80% sequence identity with an amino acid sequence consisting of a long repeat unit located within amino acid residues 1852-2366 of a *C. difficile* Toxin B sequence;

with the proviso that the fusion protein is not a polypeptide comprising amino acid residues 543-2366 of a *C. difficile* Toxin B.

Reference to a *C. difficile* Toxin B sequence means the amino acid sequence of a naturally-occurring *C. difficile* Toxin B (also referred to as a *C. difficile* Toxin B reference sequence). Examples of such sequences are readily understood by a skilled person, and some of the more common naturally-occurring Toxin B sequences are identified in the present specification (see, for example, SEQ ID NOs: 2 and 4) as well as throughout the literature.

In one embodiment, the first amino acid sequence is based on (i.e., has at least 80% sequence identity with) amino acid residues 544-1851 of a *C. difficile* Toxin B. In another embodiment, the first amino acid sequence is based on an N-terminal truncation of amino acid residues 544-1851 of a *C. difficile* Toxin B, such as amino acid residues 564-1851, amino acid residues 584-1851, amino acid residues 594-1851, amino acid residues 614-1851, amino acid residues 634-1851, amino acid residues 654-1851, amino acid residues 674-1851, amino acid residues 694-1851, amino acid residues 714-1851, amino acid residues 734-1851, amino acid residues 754-1851, amino acid residues 767-1851, amino acid residues 770-1851, amino acid residues 774-1851, amino acid residues 794-1851, amino acid residues 814-1851, amino acid residues 834-1851, amino acid residues 854-1851, amino acid residues 874-1851, amino acid residues 894-1851, amino acid residues 914-1851, amino acid residues 934-1851, amino acid residues 954-1851, amino acid residues 974-1851, amino acid residues 994-1851, amino acid residues 1014-1851, amino acid residues 1034-1851, amino acid residues 1054-1851, amino acid residues 1074-1851, amino acid residues 1094-1851, amino acid residues 1104-1851, amino acid residues 1124-1851, amino acid residues 1131-1851, amino acid residues 1144-1851, amino acid residues 1164-1851, amino acid residues 1184-1851, amino acid residues 1204-1851, amino acid residues 1224-1851, amino acid residues 1244-1851, amino acid residues 1264-1851, amino acid residues 1284-1851, amino acid residues 1304-1851, amino acid residues 1324-1851, amino acid residues 1344-1851, amino acid residues 1364-1851, amino acid residues 1384-1851, amino acid residues 1404-1851, amino acid residues 1424-1851, amino acid residues 1444-1851, amino acid residues 1464-1851, or amino acid residues 1684-1851 of a *C. difficile* Toxin B; though always with the proviso that the fusion protein is not a polypeptide comprising amino acid residues 543-2366 of a *C. difficile* Toxin B. By way of example only, the above amino acid position numbering may refer to the *C. difficile* Toxin B sequences identified as SEQ ID NOs: 2 and/or 4.

In one embodiment, the second amino acid sequence is based on (i.e., has at least 80% sequence identity with) any one or more of the long repeat (LR) amino acid sequences from a *C. difficile* Toxin B sequence. By way of example only, said one or more LR sequences may be based on any of SEQ ID NOs: 74, 76, 78 and/or 80. In another embodiment, the second amino acid sequence is based on an entire Module sequence of a *C. difficile* Toxin B sequence, which includes a LR amino acid sequence plus one or more of its (flanking) short repeat (SR) sequences. By way of example only, the second amino acid sequence may be based on one or more of SEQ ID NOs: 75, 77, 79 and/or 81. In another embodiment the second amino acid is based on a sequence consisting of or comprising the entire Module 1 amino acid sequence from a *C. difficile* Toxin B sequence (residues 1852-2007)—see, for example, the Module 1 as illustrated in Table 2. In another embodiment, the second amino acid sequence is based on a sequence consisting of or comprising the entire Module 1 plus Module 2 amino acid sequence from a *C. difficile* Toxin B sequence (e.g., residues 1852-2139 as illustrated in Table 2). In another embodiment, the second amino acid sequence is based on a sequence consisting of or comprising the entire Module 1 plus Module 2 plus Module 3 amino acid sequence from a *C. difficile* Toxin B sequence (e.g., residues 1851-2273 as illustrated in Table 2). In another embodiment, the second amino acid sequence is based on a sequence consisting of or comprising the entire Module 1 plus Module 2 plus Module 3 plus Module 4 amino acid sequence from a *C. difficile* Toxin B sequence (e.g., residues 1851-2366 as illustrated in Table 2). By way of example only, the above amino acid position numbering may refer to the *C. difficile* Toxin B sequences identified as SEQ ID NOs: 2 and/or 4.

Any of the embodiments for the second amino acid sequence may be combined with any of the embodiments described for the first amino acid sequence.

In one embodiment, when the first and second amino acid sequences are both based on Toxin B sequences, the fusion protein may consist of or comprise an amino acid sequence that is based on at least 871 or at least 876 or at least 881 or at least 886 or at least 891 or at least 896 or at least 901 contiguous amino acid residues (e.g., starting from the C-terminal amino acid residue) of a *C. difficile* Toxin B sequence, such as SEQ ID NOs: 2 and/or 4).

In one embodiment a fusion protein is provided, which comprises or consists of a sequence based on amino acid residues 1852-2366 of a Toxin B polypeptide (or a portion thereof) and an N-terminal polypeptide based on amino acid residues 767-1851 of a Toxin B polypeptide (or a portion thereof).

In another embodiment a fusion protein is provided, which comprises or consists of a sequence based on amino acid residues 1852-2366 of a Toxin B polypeptide (or a portion thereof) and an N-terminal polypeptide based on amino acid residues 1145-1851 of a Toxin B polypeptide (or a portion thereof).

In another embodiment a fusion protein is provided, which comprises or consists of a sequence based on amino acid residues 767-2366 or 957-2366 or 1138-2366 of a Toxin B polypeptide (e.g., SEQ ID NOs 9, 10, 11, 12, 13, 14, 23, 24, 25, 26, 27, 44, 45, 46, 47, 48, 49, 50, 51, 52, 53, 54, 55, 56 or 57).

The present invention also provides fusion proteins that are chimeras of Toxin A and B domains. For example, one or more long repeat unit (optionally including one or more short repeat unit; or one, more or all Modules) based on a Toxin B polypeptide may be combined with a "scaffold" region of a Toxin A polypeptide. Similarly, one or more long repeat unit (optionally including one or more short repeat unit; or one, more or all Modules) based on a Toxin A polypeptide may be combined with a "scaffold" region of a Toxin B polypeptide.

Thus, a further related aspect of the present invention provides a hybrid/chimera fusion protein, consisting of or comprising a first amino acid sequence and a second amino acid sequence, wherein:

1) the first amino acid sequence is provided by an amino acid sequence that has at least 80% sequence identity with an amino acid sequence consisting of residues 1500-1850 of a *C. difficile* Toxin A sequence; and
2) the second amino acid sequence is provided by an amino acid sequence that has at least 80% sequence identity with an amino acid sequence consisting of a long repeat unit located within amino acid residues 1852-2366 of a *C. difficile* Toxin B sequence;

with the proviso that the fusion protein is not a polypeptide comprising amino acid residues 543-2710 of a *C. difficile* Toxin A;

and with the proviso that the fusion protein is not a polypeptide comprising amino acid residues 543-2366 of a *C. difficile* Toxin B.

Embodiments of the first and second amino acid sequences are as detailed above.

For example, in one embodiment a fusion protein is provided, which comprises or consists of a sequence based on amino acid residues 1852-2366 of a Toxin B polypeptide (or a portion thereof) and an N-terminal polypeptide based on amino acid residues 770-1849 of a Toxin A polypeptide (or a portion thereof).

In another embodiment a fusion protein is provided, which comprises or consists of a sequence based on amino acid residues 1852-2366 of a Toxin B polypeptide (or a portion thereof) and an N-terminal polypeptide based on amino acid residues 1131-1849 of a Toxin A polypeptide (or a portion thereof).

In another embodiment, a fusion protein is provided, which comprises or consists of a sequence based on amino acid residues 1852-2366 of a Toxin B polypeptide (or a portion thereof) and an N-terminal polypeptide based on amino acid residues 1500-1849 of a Toxin A polypeptide (or a portion thereof). In one embodiment, said Toxin A polypeptide component is preferably based on a sequence that is shorter than residues 543-1849 of a Toxin A polypeptide.

Specific examples include fusion proteins consisting of or comprising an amino acid sequence based on any one or more of SEQ ID NOs: 16 or 17.

Similarly, a further related first aspect of the present invention provides a hybrid/chimera fusion protein, consisting of or comprising a first amino acid sequence and a second amino acid sequence, wherein:

1) the first amino acid sequence is provided by an amino acid sequence that has at least 80% sequence identity with an amino acid sequence consisting of residues 1500-1851 of a *C. difficile* Toxin B sequence; and
2) the second amino acid sequence is provided by an amino acid sequence that has at least 80% sequence identity with an amino acid sequence consisting of a long repeat unit located within amino acid residues 1851-2710 of a *C. difficile* Toxin A sequence;

with the proviso that the fusion protein is not a polypeptide comprising amino acid residues 543-2710 of a *C. difficile* Toxin A and with the proviso that the fusion protein is not a polypeptide comprising amino acid residues 543-2366 of a *C. difficile* Toxin B.

Embodiments of the first and second amino acid sequences are as detailed above.

In one embodiment a fusion protein is provided, which comprises or consists of a sequence based on amino acid residues 1850-2710 of a Toxin A polypeptide (or a portion thereof) and an N-terminal polypeptide based on amino acid residues 767-1851 of a Toxin B polypeptide (or a portion thereof).

In another embodiment a fusion protein is provided, which comprises or consists of a sequence based on amino acid residues 1850-2710 of a Toxin A polypeptide (or a portion thereof) and an N-terminal polypeptide based on amino acid residues 1145-1851 of a Toxin B polypeptide (or a portion thereof).

In another embodiment, a fusion protein is provided, which comprises or consists of a sequence based on amino acid residues 1850-2710 of a Toxin A polypeptide (or a portion thereof) and an N-terminal polypeptide based on 1500-1851 of a Toxin B polypeptide. In one embodiment, the Toxin B polypeptide component is preferably based on a sequence that is shorter than residues 543-1851 of a Toxin B polypeptide.

Specific examples include fusion proteins consisting of or comprising an amino acid sequence based on SEQ ID NO: 15.

As hereinbefore described, the present invention relates to fusion proteins based on a "scaffold" section plus a LR portion (of the C-terminal repeating units) of a *C. difficile* Toxin A and/or a *C. difficile* Toxin B. In this regard, the total portion(s) of said fusion proteins that is based on said *C. difficile* Toxin A and/or Toxin B sequences typically amounts to a maximum of 1940 contiguous amino acid residues (for example a maximum of 1890, or 1840, or 1790, or 1740, or 1690, or 1640, or 1590, or 1540, or 1490, 1440, or 1390, or 1340, or 1290, or 1240 contiguous amino acid residues).

In one embodiment, the fusion protein substantially lacks cysteine protease activity. In another (or the same) embodiment, the fusion protein substantially lacks glucosyl transferase activity. For example, part or all of the amino acid sequence(s) providing said activity (activities) are typically absent (e.g., deleted) from the fusion proteins of the present invention. These enzymatic activities are present in native Toxin A and/or Toxin B, and are associated with N-terminal domains of said Toxins (see FIG. 1).

In another embodiment, the fusion protein substantially lacks the glucosyl transferase domain (amino acid residues 1-542 Toxin A; amino acid residues 1-543 Toxin B) of a native *C. difficile* Toxin. In another (or the same) embodiment, the fusion protein substantially lacks the cysteine protease domain (amino acid residues 543-770 Toxin A; 544-767 Toxin B) of a native *C. difficile* Toxin. Said amino acid residue numbering refers to any Toxin A or Toxin B toxinotype, for example any one or more of the reference Toxin A and/or Toxin B toxinotype SEQ ID NOs recited in the present specification. Accordingly, said amino acid residue numbering may refer to any specific Toxin A and/or Toxin B reference SEQ ID NOs recited in the present specification including an amino acid sequence variant having at least 80%, at least 85%, at least 90%, at least 93%, at least 95%, at least 97%, or at least 99% thereto.

Fusion protein constructs of the invention may be derived from any Toxin A and/or B sequence (including any toxinotype sequence), such as those illustrated in the present specification. For example, in one embodiment, first and/or second amino acid sequences are derived from Toxins A and/or B of toxinotype 0 (SEQ ID NOs: 1 and 2, respectively). In another embodiment, first and/or second amino acid sequences are derived from Toxins A and/or B of toxinotype 3 (SEQ NOs: 3 and 4, respectively).

Fusion proteins of the invention may further comprise a fusion protein partner to facilitate soluble expression. Fusion protein partners may be attached at the N- or C-terminus of the antigen construct but are usually placed at the N-terminal end. Examples of fusion partners are: NusA, thioredoxin, maltose-binding protein, small ubiquitin-like molecules (Sumo™-tag). To facilitate removal of the fusion protein partner during purification, a unique protease site may be inserted between the fusion protein partner and the fusion protein per se. Such protease sites may include those for thrombin, factor Xa, enterokinase, PreScission™, Sumo™. Alternatively, removal of the fusion protein partner may be achieved via inclusion of an intein sequence between the fusion protein partner and the fusion protein per se. Inteins are self cleaving proteins and in response to a stimulus (e.g., lowered pH) are capable of self splicing at the junction between the intein and the antigen construct thus eliminating the need for the addition of specific proteases. Examples of inteins include domains derived from *Mycobacterium tuberculosis* (RecA), and *Pyrococcus horikoshii* (RadA) (Fong et al., (2010) Trends Biotechnol. 28:272-279).

To facilitate purification, fusion proteins of the invention may include one or more purification tags to enable specific chromatography steps (e.g., metal ion chelating, affinity chromatography) to be included in the purification processes. Such purification tags may, for example, include: repeat histidine residues (e.g., 6-10 histidine residues), maltose binding protein, glutathione S-transferase; and streptavidin. These tags may be attached at the N- and/or C-terminus of the antigen fusion proteins of the invention. To facilitate removal of such tags during purification, protease sites and/or inteins (examples above) may be inserted between the fusion protein and the purification tag(s).

Thus, a typical fusion protein construct of the invention (starting from the N-terminus) may comprise:

a first purification tag
a fusion protein partner (to facilitate expression)
a first (preferably specific) protease sequence or intein sequence
the Toxin A and/or B antigen sequence
an optional second (preferably specific) protease sequence or intein sequence
an optional second purification tag The first and second purification tags may be the same or different. Similarly, the first and second protease/intein sequence may be the same or different. The first and second options are preferably different to enable selective and controllable cleavage/purification.

Specific examples of such fusion protein constructs are show in SEQ ID NOs: 18-27.

In one embodiment spacers may be introduced to distance the purification tag from the fusion protein—this may help to increase binding efficiency to affinity purification column media. The spacer may be placed (immediately) after the purification tag or between the fusion protein partner and the fusion protein per se. Typical spacer sequences may consist of between 10-40 amino acid residues to give either a linear or alpha-helical structure.

Accordingly, in one embodiment, a fusion protein construct of the invention may comprise (starting from the N-terminus):

a first purification tag
an optional first spacer sequence
a fusion protein partner (to facilitate expression)
an optional second spacer sequence
a (preferably specific) protease sequence or intein sequence
the Toxin A and/or B derived antigen sequence
an optional second (preferably specific) protease sequence or intein sequence
an optional third spacer sequence
an optional second purification tag Specific examples of such protein fusion constructs are shown in SEQ ID Nos: 28-57.

Genes encoding the constructs of the invention may be generated by PCR from *C. difficile* genomic DNA and sequenced by standard methods to ensure integrity. Alternatively and preferably genes may be synthesised providing the optimal codon bias for the expression host (e.g., *E. coli, Bacillus megaterium*). Thus, the present invention provides corresponding nucleic acid sequences that encode the aforementioned fusion proteins of the present invention.

Accordingly, a second aspect of the present invention provides a method for expressing one or more of the aforementioned fusion proteins, said method comprising:

1) providing a nucleic acid sequence that encodes one or more of said fusion proteins in a host cell, wherein said nucleic acid sequence is operably linked to a promoter; and
2) expressing said nucleic acid sequence in the host cell Fusion proteins of the invention may be formulated as vaccines for human or animal use in a number of ways. For example, formulation may include treatment with an agent to introduce intra-molecular cross-links. One example of such an agent is formaldehyde, which may be incubated, for example, with antigen fusion proteins of the invention for between 1-24 hours. Alternatively, longer incubation times of, for example, up to 2, 4, 6, 8 or 10 days may be employed. Following treatment with such an agent, antigen fusions of the invention may be combined with a suitable adjuvant, which may differ depending on whether the antigen fusion protein is intended for human or animal use.

A human or animal vaccine formulation may contain Toxin A and/or Toxin B and/or corresponding hybrid/chimera antigen fusions of the present invention. Thus, in one embodiment, a vaccine formulation procedure of the present invention comprises the following steps:

providing a recombinant Toxin A and/or Toxin B and/or hybrid/chimera toxin fusion protein in suitable buffer system
optionally (preferably) treating said mixture with a toxoiding component such as formaldehyde
optionally transferring the fusion proteins to a new buffer system
combining the fusion proteins with one or more suitable adjuvants and optionally other excipients Accordingly, a third aspect of the present invention provides one or more of the aforementioned fusion proteins of the invention, for use in the generation of antibodies that bind to *C. difficile* Toxin A and/or Toxin B. In one embodiment, said antibodies bind to and neutralize *C. difficile* Toxin A and/or Toxin B.

For immunisation of animals, the *C. difficile* recombinant fusion protein antigens of the invention may be used as immunogens separately or in combination, either concurrently or sequentially, in order to produce antibodies specific for individual *C. difficile* toxins or combinations. For example, two or more recombinant antigens may be mixed together and used as a single immunogen. Alternatively a *C. difficile* toxin fusion protein antigen (e.g., Toxin A-derived) may be used separately as a first immunogen on a first animal group, and another *C. difficile* toxin antigen (e.g., Toxin B-derived) may be used separately on a second animal group. The antibodies produced by separate immunisation may be combined to yield an antibody composition directed against *C. difficile* toxins. Non-limiting examples of suitable adjuvants for animal/veterinary use include Freund's (complete and incomplete forms), alum (aluminium phosphate or aluminium hydroxide), saponin and its purified component Quil A.

A fourth (vaccine) aspect of the present invention provides one or more of the aforementioned fusion proteins of the invention, for use in the prevention, treatment or suppression of CDI (e.g., in a mammal such as man) Put another way, the present invention provides a method for the prevention, treatment or suppression of CDI (e.g., in a mammal such as man), said method comprising administration of a therapeutically effective amount of one or more of the aforementioned fusion proteins of the invention to a subject (e.g., a mammal such as man).

By way of example, a Toxin A-based fusion protein (any A toxinotype) may be employed alone or in combination with a Toxin B-based fusion protein (any B toxinotype). Similarly, a Toxin B-based fusion protein (any B toxinotype) may be employed alone or in combination with a Toxin A-based fusion protein (any A toxinotype). Said fusion proteins may be administered in a sequential or simultaneous manner Vaccine applications of the present invention may further include the combined use (e.g., prior, sequential or subsequent administration) of one or more antigens such as a *C. difficile* antigen (e.g., a non-Toxin antigen; or a *C. difficile* bacterium such as one that has been inactivated or attenuated), and optionally one or more nosocomial infection antigens (e.g., an antigen, notably a surface antigen, from a bacterium that causes nosocomial infection; and/or a bacterium that causes a nosocomial infection such as one that has been inactivated or attenuated). Examples of bacteria that cause nosocomial infection include one or more of: *E. coli, Klebsiella pneumonae, Staphylococcus aureus* such as MRSA, *Legionella, Pseudomonas aeruginosa, Serratia marcescens, Enterobacter* spp, *Citrobacter* spp, *Stenotrophomonas maltophilia, Acinetobacter* spp such as *Acinetobacter baumannii, Burkholderia cepacia*, and *Enterococcus* such as vancomycin-resistant *Enterococcus* (VRE).

In one embodiment, said vaccine application may be employed prophylactically, for example to treat a patient before said patient enters a hospital (or similar treatment facility) to help prevent hospital-acquired infection. Alternatively, said vaccine application may be administered to vulnerable patients as a matter of routine.

A related vaccine aspect of the invention provides one or more antibodies (comprising or consisting whole IgG and/or Fab and/or $F(ab')_2$ fragments) that binds to the one or more aforementioned fusion proteins of the invention, for use in the prevention, treatment or suppression of CDI (e.g., in a mammal such as man) Put another way, the present invention provides a method for the prevention, treatment or suppression of CDI (e.g., in a mammal such as man), said method comprising administration of a therapeutically effective amount of said antibody (or antibodies) to a subject (e.g., a mammal such as man).

By way of example, an anti-Toxin A-based fusion protein (any A toxinotype) antibody may be employed alone or in combination with an anti-Toxin B-based fusion protein (any B toxinotype).antibody. Similarly, an anti-Toxin B-based fusion protein (any B toxinotype) antibody may be employed alone or in combination with an anti-Toxin A-based fusion protein (any A toxinotype) antibody. Said antibodies may be administered in a sequential or simultaneous manner Vaccine applications of the present invention may further include the combined use (e.g., prior, sequential or subsequent administration) of one or more antibodies that bind to antigens such as a *C. difficile* antigen (e.g., a non-Toxin antigen; or a *C. difficile* bacterium), and optionally one or more antibodies that bind to one or more nosocomial infection antigens (e.g., an antigen, notably a surface antigen, from a bacterium that causes nosocomial infection; and/or a bacterium that causes a nosocomial infection). Examples of bacteria that cause nosocomial infection include one or more of: *E. coli, Klebsiella pneumonae, Staphylococcus aureus* such as MRSA, *Legionella, Pseudomonas aeruginosa, Serratia marcescens, Enterobacter* spp, *Citrobacter* spp, *Stenotrophomonas maltophilia, Acinetobacter* spp such as *Acinetobacter baumannii, Burkholderia cepacia*, and *Enterococcus* such as vancomycin-resistant *Enterococcus* (VRE).

In one embodiment, said vaccine application may be employed prophylactically, for example once a patient has entered hospital (or similar treatment facility). Alternatively, said vaccine application may be administered to patients in combination with one or more antibiotics.

In one embodiment, said antibodies have been generated by immunisation of an animal (e.g., a mammal such as man, or a non-human animal such as goat or sheep) with one or more of the aforementioned fusion proteins of the present invention.

In one embodiment, the antibodies of the present invention do not (substantially) bind to the effector domain and/or to the cysteine protease domain of a *C. difficile* Toxin A and/or Toxin B.

For the preparation of vaccines for human (or non-human animal) use, the active immunogenic ingredients (whether these be antigenic fusion protein/s of the present invention and/or corresponding antibodies of the invention that bind thereto) may be mixed with carriers or excipients, which are pharmaceutically acceptable and compatible with the active ingredient. Suitable carriers and excipients include, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

The vaccine may further comprise one or more adjuvants. One non-limiting example of an adjuvant with the scope of the invention is aluminium hydroxide. Other non-limiting examples of adjuvants include but are not limited to: N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Typically, the vaccines are prepared as injectables, either as liquid solutions or suspensions. Of course, solid forms suitable for solution in, or suspension in, liquid prior to injection may also be prepared. The preparation may also be emulsified, or the peptide encapsulated in liposomes or microcapsules.

Vaccine administration is generally by conventional routes e.g., intravenous, subcutaneous, intraperitoneal, or mucosal routes. The administration may be by parenteral injection, for example, a subcutaneous or intramuscular injection.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be particular to each subject.

The vaccine may be given in a single dose schedule, or optionally in a multiple dose schedule. A multiple dose schedule is one in which a primary course of vaccination may be with 1-6 separate doses, followed by other doses given at subsequent time intervals required to maintain and/or reinforce the immune response, for example, at 1-4 months for a second dose, and if needed, a subsequent dose(s) after several months. The dosage regimen will also, at least in part, be determined by the need of the individual and be dependent upon the judgment of the practitioner.

In addition, the vaccine containing the immunogenic antigen(s) may be administered in conjunction with other immunoregulatory agents, for example, immunoglobulins, antibiotics, interleukins (e.g., IL-2, IL-12), and/or cytokines (e.g., IFN gamma)

Additional formulations suitable for use with the present invention include microcapsules, suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of about 0.5% to 10%, including for instance, about 1%-2%.

Fusion proteins of the invention may also have uses as ligands for use in affinity chromatography procedures. In such procedures, fusion proteins of the invention may be covalently immobilised onto a matrix, such as Sepharose, e.g., using cyanogen bromide-activated Sepharose. Such affinity columns may then be used to purify antibody from antisera or partially purified solutions of immunoglobulins by passing them through the column and then eluting the bound IgG fraction (e.g., by low pH). Almost all of the antibody in the eluted fraction will be directed against the fusion proteins of the invention, with non-specific antibodies and other proteins having been removed. These affinity purified IgG fractions have applications both as immunotherapeutics and as reagents in diagnostics. For immunotherapeutics, affinity purified antibodies enable a lower dose to be administered making adverse side effects less likely. For diagnostics, affinity purified agents often give improved specificity and fewer false positive results.

Definitions Section

*Clostridium difficile* is a species of Gram-positive bacterium of the genus *Clostridium.*

*Clostridium difficile* infection (CDI) means a bacterial infection which affects humans and animals and which results in a range of symptoms from mild self-limiting diarrhoea to life-threatening conditions such as pseudomembranous colitis and cytotoxic megacolon. In this disease, *C. difficile* replaces some of the normal gut flora and starts to produce cytotoxins which attack and damage the gut epithelium. Primary risk factors for human CDI include: receiving broad-spectrum antibiotics, being over 65 years old and being hospitalised.

*Clostridium difficile* Toxin A is a family of protein cytotoxins/enterotoxins of approximately 300 kDa in size. Toxin A has an enzyme activity within the N-terminal region which acts to disrupt the cytoskeleton of the mammalian cell causing cell death. There a number of naturally occurring variants of Toxin A within the strains of *Clostridium difficile* which are called 'toxinotypes'. The various toxinotypes of Toxin A have variations within their primary sequence of usually <10% overall. Examples of suitable Toxin A sequences include SEQ ID NOs: 1 and 3.

*Clostridium difficile* Toxin B is a family of protein cytotoxins of approximately 270 kDa in size which are similar to Toxin A but significantly more cytotoxic. Like Toxin A, Toxin B has an enzyme activity within the N-terminal region which acts to disrupt the cytoskeleton of the mammalian cell causing cell death. There are a number of naturally occurring variants of Toxin B within the strains of *C. difficile* which are called 'toxinotypes'. The various toxinotypes of Toxin B have variations within their primary sequence of up to 15% overall. Examples of suitable Toxin B sequences include SEQ ID NOs: 2 and 4.

*C. difficile* repeat units are regions within the C-terminus of Toxin A and B that contain repeating motifs which were first identified by von Eichel-Streiber and Sauerborn (1990; Gene 30: 107-113). In the case of Toxin A there are 31 short repeats and 7 long repeats with each repeat consisting of a 0-hairpin followed by a loop. Toxin B consists of a similar structure but with fewer repeats. The repeat units of Toxin A are contained within residues 1850-2710 and those for Toxin B within residues 1852-2366. The repeat regions play a role in receptor binding. The receptor binding regions (i.e., that define the toxin's structural binding pockets) appear to be clustered around the long repeat regions to form 'binding modules' (see Tables 1 and 2).

Central domains of Toxin A and B are believed to play a role in translocation of the toxins into mammalian cells. The central domains of Toxin A are based on residues 543-1849 and those for Toxin B are based on residues 543-1851. Of the central domain regions of Toxins A and B, the first domain is a cysteine protease, which plays a role in the internalisation of the toxin's effector domain (which contains the glucosyl transferase activity).

Toxinotypes are often used to classify strains of *C. difficile*. Toxinotyping is based on a method which characterises the restriction patterns obtained with the toxin genes. Toxinotypes of Toxins A and B represent variants, by primary amino acid sequence, of these protein toxins. In one embodiment, the *C. difficile* toxin is selected from one of toxinotypes 0 to XV. Preferred Toxinotypes (plus example Ribotypes and Strains) are listed in the Table immediately below. The listed Toxinotypes are purely illustrative and are not intended to be limiting to the present invention

| Toxinotype | Example Ribotypes | Example Strains | Reference |
|---|---|---|---|
| 0 | 001, 106 | VPI10463 | Rupnik et al. |
| 1 | 003, 012, 102 | EX623 | (1998) |
| 2 | 103 | AC008 | J. Clinical |
| 3 | 027, 034, 075, 080 | R20291, QCD-32g58 | Microbiol. |
| 4 | 023, 034, 075, 080 | 55767 | 36: 2240-2247 |
| 5 | 066, 078 | SE881 | |
| 6 | 045, 063, 066 | 51377 | |
| 7 | 063 | 57267 | |

-continued

| Toxinotype | Example Ribotypes | Example Strains | Reference |
|---|---|---|---|
| 8 | 017, 047 | 1470 | |
| 9 | 019 | 51680 | |
| 10 | 036 | 8864 | |
| 11 | 033 | IS58, R11402 | Rupnik et al. |
| 12 | 056 | IS25 | (2001) |
| 13 | 070 | R9367 | Microbiology |
| 14 | 111 | R10870 | 147: 439-447 |
| 15 | 122 | R9385 | |

An "antibody" is used in the broadest sense and specifically covers polyclonal antibodies and antibody fragments so long as they exhibit the desired biological activity. For example, an antibody is a protein including at least one or two, heavy (H) chain variable regions (abbreviated herein as VHC), and at least one or two light (L) chain variable regions (abbreviated herein as VLC). The VHC and VLC regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al., J. Mol. Biol. 196:901-917, 1987, which are incorporated herein by reference). Preferably, each VHC and VLC is composed of three CDRs and four FRs, arranged from amino-terminus to carboxy-terminus in the following order: PR1, CDR1, FR2, CDR2, FR3, CDR3, FR4.

The VHC or VLC chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (CIq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

The term antibody, as used herein, also refers to a portion of an antibody that binds to a toxin of *C. difficile* (e.g., Toxin A or B), e.g., a molecule in which one or more immunoglobulin chains is not full length, but which binds to a toxin. Examples of binding portions encompassed within the term antibody include (i) a Fab fragment, a monovalent fragment consisting of the VLC, VHC, CL and CH1 domains; (ii) a $F(ab')_2$ fragment, a bivalent fragment comprising two Fab fragments linked by a disulfide bridge at the hinge region; (iii) a Fc fragment consisting of the VHC and CH1 domains; (iv) a Fv fragment consisting of the VLC and VHC domains of a single arm of an antibody, (v) a dAb fragment (Ward et al., (1989) Nature 341:544-546), which consists of a VHC domain; and (vi) an isolated complementarity determining region (CDR) having sufficient framework to bind, e.g., an antigen binding portion of a variable region. An antigen binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single-chain antibodies (as well as camelids) are also encompassed within the term antibody. These are obtained using conventional techniques known to those with skill in the art, and the portions are screened for utility in the same manner as are intact antibodies.

The term "fragment" means a peptide typically having at least seventy, preferably at least eighty, more preferably at least ninety percent of the consecutive amino acid sequence of the reference sequence.

The term "variant" means a peptide or peptide fragment having at least eighty, preferably at least eighty five, more preferably at least ninety percent amino acid sequence homology with a *C. difficile* toxin polypeptide. For sequence comparison, typically one sequence acts as a reference sequence, to which test sequences may be compared. When using a sequence comparison algorithm, test and reference sequences are input into a computer, subsequent coordinates are designated, if necessary, and sequence algorithm program parameters are designated. The sequence comparison algorithm then calculates the percentage sequence identity for the test sequence(s) relative to the reference sequence, based on the designated program parameters.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, (1994) Nucleic Acids Research 22(22):4673-4680; and iterative refinement, see, e.g., Osamu Gotoh, Significant Improvement in Accuracy of Multiple Protein. Sequence Alignments by Iterative Refinement as Assessed by Reference to Structural Alignments, (1996) J. Mol. Biol. 264(4):823-838. Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, (1992) CABIOS 8(5):501-509; Gibbs sampling, see, e.g., C. E. Lawrence et al., Detecting Subtle Sequence Signals: A Gibbs Sampling Strategy for Multiple Alignment, (1993) Science 262(5131):208-214; Align-M, see, e.g., Ivo Van Walle et al., Align-M—A New Algorithm for Multiple Alignment of Highly Divergent Sequences, (2004) Bioinformatics 20(9):1428-1435.

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

```
                                        (SEQ ID NO: 82)
A R N D C Q E G H I L K M F P S T W Y V

A 4

R -1 5

N -2 0 6

D -2 -2 1 6

C 0 -3 -3 -3 9

Q -1 1 0 0 -3 5

E -1 0 0 2 -4 2 5

G 0 -2 0 -1 -3 -2 -2 6

H -2 0 1 -1 -3 0 0 -2 8

I -1 -3 -3 -3 -1 -3 -3 -4 -3 4

L -1 -2 -3 -4 -1 -2 -3 -4 -3 2 4

K -1 2 0 -1 -3 1 1 -2 -1 -3 -2 5

M -1 -1 -2 -3 -1 0 -2 -3 -2 1 2 -1 5

F -2 -3 -3 -3 -2 -3 -3 -3 -1 0 0 -3 0 6

P -1 -2 -2 -1 -3 -1 -1 -2 -2 -3 -3 -1 -2 -4 7

S 1 -1 1 0 -1 0 0 0 -1 -2 -2 0 -1 -2 -1 4

T 0 -1 0 -1 -1 -1 -1 -2 -2 -1 -1 -1 -1 -2 -1 1 5

W -3 -3 -4 -4 -2 -2 -3 -2 -2 -3 -2 -3 -1 1 -4 -3
-2 1 1

Y -2 -2 -2 -3 -2 -1 -2 -3 2 -1 -1 -2 -1 3 -3 -2 -2
2 7

V 0 -3 -3 -3 -1 -2 -2 -3 -3 3 1 -2 1 -1 -2 -2 0 -3
-1 4
```

The percent identity is then calculated as:

$$\frac{\text{Total number of identical matches}}{\text{length of the longer sequence plus the number of gaps introduced into the longer sequence in order to align the two sequences]}}\times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

Basic: arginine
- lysine
- histidine

Acidic: glutamic acid
- aspartic acid

Polar: glutamine
- asparagine

Hydrophobic: leucine
- isoleucine
- valine

Aromatic: phenylalanine
- tryptophan
- tyrosine

Small: glycine
- alanine
- serine
- threonine
- methionine

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for clostridial polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g., the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenised polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Toxin-neutralising means the capacity of a substance to prevent the cytotoxic action of either Toxin A or B on a mammalian cell. In assays for toxin-neutralising activity, a fixed amount of toxin is mixed with various concentrations of a neutralising substance (e.g., an antibody) and the mixture applied to and incubated with a mammalian cell line (e.g., Vero cells) for a fixed time. The dilution of the substance (antibody) that completely protects the cells from the cytotoxic effects of either Toxin A or B (evident by cell rounding) may be defined as the neutralising titre.

EXAMPLES

Figure 1:
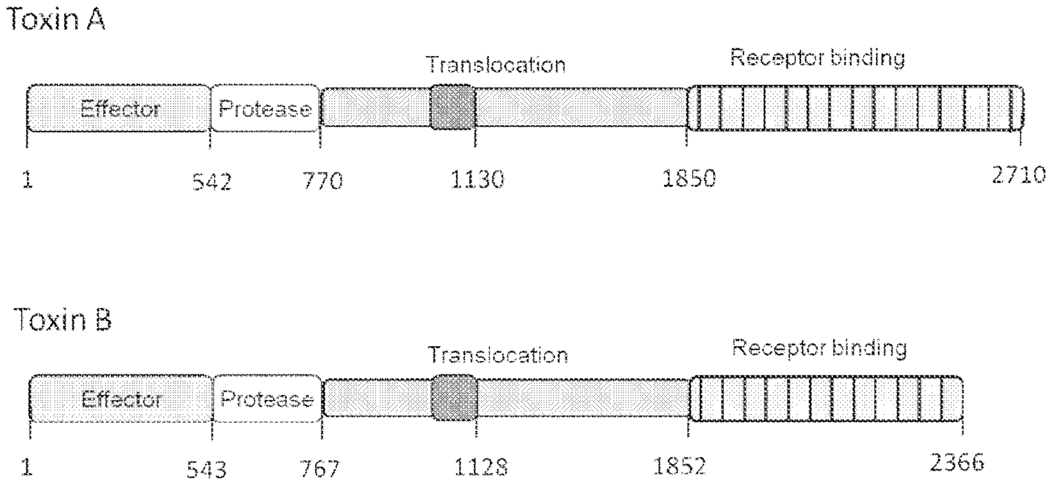
FIG. 1 illustrates the structures of *C. difficile* Toxins A and B showing amino acid residues at the various domain boundaries.

Example 1—Cloning and Expression of Antigens Derived from Toxins A and B

Genes encoding these peptides may be made commercially with codon bias for any desired expression host (e.g., *E. coli, Pichia pastoris*). Peptides are expressed from these genes using standard molecular biology methods (e.g., Sambrook et al. 1989, Molecular Cloning a Laboratory Manual, Second Edition, Cold Spring Harbor Laboratory Press, Cold Spring Harbor, New York). One convenient method of cloning is the Gateway® system (Invitrogen) which allow genetic constructs to be assembled in a modular fashion.

Protocol 1: The Gateway LR Recombination Reaction—a General Protocol

Materials: Antigen gene (Toxin A or B)) entry clones were synthesised by Entelechon. Gateway® LR Clonase™ II Enzyme Mix was purchased from Invitrogen. Gateway® Nova pET Destination vectors were purchased from Calbiochem Nova, part of Merck Chemicals Ltd.

Toxin A or B entry clone (1 μl), destination vector (1 μl) and TE buffer (6 μl) were mixed at room temperature in a 1.5 ml microcentrifuge tube. LR Clonase™ II was placed on ice for two minutes and mixed briefly with vortexing (2×2 s). The clonase enzyme (2 μl) was added to the microcentrifuge tube and the components mixed with gentle pipetting. Recombinations were incubated at 25° C. for 1 hour. Proteinase K solution (1 μl, 2 μg/μl) was added and the reactions incubated at 37° C. for 10 minutes. The resultant solution (1 μl) was used to transform chemically competent *E. coli*.

Protocol 2: Transformation of Chemically Competent Cells—a General Protocol

Materials: OneShot® BL21 Star™ (DE3) and One Shot® TOP10 chemically competent *E. coli* and SOC media were purchased from Invitrogen. Ampicillin was purchased from Sigma Aldrich.

LR recombination reaction or plasmid DNA (1 μl) was pipetted into an aliquot (50 μl) of BL21 Star™ or TOP10 chemically competent *E. coli*. The mixture was incubated on ice for 30 minutes and subsequently heat shocked in a water bath at 42° C. for 30 seconds. The cell aliquot was returned to the ice and SOC media (250 μl) added. Transformations were maintained in SOC media at 37° C. for 1 hour with orbital shaking (180 rpm). Transformation culture (100-200 μl) was plated out onto LB agar supplemented with ampicillin (100 μg/ml). The plates were incubated at 37° C. for 15 minutes, inverted and maintained at the same temperature overnight.

Example 2—Purification of Antigens of the Invention—Expression and Purification of *C. difficile* Toxin B Fragment TxB3

Toxin B-derived antigen TxB3(-h) (e.g., SEQ ID NO: 9) was expressed as a thioredoxin fusion protein (SEQ ID NO: 27).

An N-$his_6$-thioredoxin fusion of TxB3 was expressed in BL21 Star™ (DE3) *E. coli* harbouring plasmid pDest59TxB3. LB media (3×20 ml) supplemented with 100 μg/ml ampicillin and 0.5% glucose was inoculated from a glycerol cell stock (cell culture<$OD_{600}$ 1 [500 μl]+glycerol [125 μl]). Cultures were maintained at 37° C. for 6-7 hours with orbital shaking (180 rpm). Each culture was used to inoculate LB media (100 ml) supplemented with 100 μg/ml ampicillin and 0.5% glucose. Cultures were maintained at 37° C. for 1 hour with orbital shaking (180 rpm). Terrific Broth (3×1 L) supplemented with 100 μg/ml ampicillin and 0.1% glucose was inoculated with the LB culture (100 ml per litre) and maintained at 37° C. as before to an absorbance at 600 nm of 0.5. Expression was induced with the addition of IPTG to a final concentration of 1 mM and the cultures maintained at 16° C. overnight with orbital shaking (180 rpm). Cells were harvested by centrifugation for 30 minutes (3000 rpm, Sorvall RC3BP centrifuge, rotor #H6000A), resuspended in low imidazole buffer (100 ml, pH 7.4, 50 mM HEPES, 500 mM sodium chloride, 20 mM imidazole) and frozen at −80° C.

(i) Nickel Affinity Purification of the Thioredoxin TxB3 Fusion Protein

Cell paste was thawed at room temperature and then on ice until liquefied. Cells were disrupted with sonication (10 cycles of 30 s ON and 30 s OFF) and the resultant lysate cleared by centrifugation for 30 minutes (14,000 rpm, Sorvall RCSC centrifuge, rotor #SS-34). Cleared lysate was applied to fast flow chelating sepharose charged with nickel ions (40 ml bed volume) at a flow rate of 1 ml/min. The column was washed with low imidazole buffer (pH 7.4, 50 mM HEPES, 500 mM sodium chloride, 20 mM imidazole) until the absorbance of the flow through at 280 nM returned to near baseline levels. Bound material was eluted with sequential steps to 15, 25 and 70% high imidazole buffer (pH 7.4, 50 mM HEPES, 500 mM sodium chloride, 500 mM imidazole). Material eluted at 70% high imidazole buffer was pooled and dialysed into thrombin cleavage buffer (20 mM Tris-HCl pH 8.4, 150 mM sodium chloride, 2.5 mM calcium chloride) overnight.

(ii) Thrombin Digestion of the Thioredoxin TxB3 Fusion Protein

Human thrombin (Novagen, 1 U per mg of total protein) was added to the pooled nickel column fractions which had been dialysed into thrombin cleavage buffer. The digest was incubated at 25° C. for 4 hours and frozen at −80° C. to prevent continued cleavage.

(iii) Nickel Affinity Purification of TxB3

Figure 2:
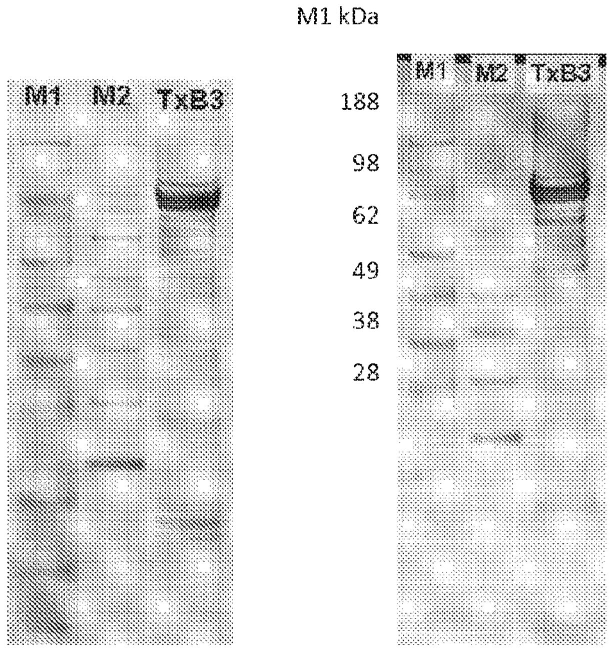
FIG. 2 illustrates TxB3 purification. The left-hand Figure shows a 4-12% SDS-PAGE analysis of TxB3. M1=SeeBlue® Plus2 Pre-Stained Standard, M2=MagicMark™ XP Standard. The right-hand Figure shows a Western blot analysis of TxB3 with ovine anti-TcdB polyclonal antibodies. M1 and M2 are as described for the left-hand Figure.

The thrombin digest was thawed on ice and p-Aminobenzamidine resin added (0.1 ml drained resin per 6U of thrombin). The mixture was gently rocked over ice for 30 minutes and the resin filtered off. The cleared filtrate was passed over fast flow chelating sepharose charge with nickel ions (6 ml bed volume) at a flow rate of 1 ml/min and the flow through pooled and dialysed into storage buffer (pH 7.4, 50 mM HEPES, 150 mM sodium chloride). The solution was sterile filtered into 1 ml aliquots. The total protein obtained was 10.5 mg, which was estimated to be 55% TxB3. Protein was also analysed by Western blotting with ovine anti-TcdB polyclonal antibodies (FIG. 2).

Example 3—Purification of Antigens of the Invention—Expression and Purification of *C. difficile* Toxin B Fragment TxB4

Large Scale Expression of the Nus TxB4 Fusion Protein

A bead from a −80° C. stock of BL21 Star™ (DE3) *E. coli* harbouring plasmid pDest57TxB4His was streaked onto L-agar supplemented with 100 μg/ml ampicillin and incubated at 37° C. overnight. A single colony was used to inoculate 2YT media (100 ml) supplemented with 100 μg/ml ampicillin and 0.5% glucose. The culture was maintained at 37° C. with orbital shaking (180 rpm) to an absorbance of 0.6 at 600 nm and used as a 5% inoculum for Terrific Broth (2×1 L) supplemented with 100 μg/ml ampicillin and 0.5% glucose. Cultures were maintained as before to an absorbance of 0.6 at 600 nm and the temperature lowered to 16° C. Protein expression was induced by the addition of IPTG to a final concentration of 1 mM following thermal equilibration and the culture maintained overnight. Cells were harvested by centrifugation for 30 minutes (3000 rpm, Sorvall RC3BP centrifuge, rotor #H6000A), resuspended in low imidazole buffer (1:4 cell paste to buffer w/v, 50 mM HEPES pH 7.4, 500 mM sodium chloride, 20 mM imidazole) and frozen at −80° C.

Nickel Affinity Purification of the Nus TxB4 Fusion Protein

Cell paste was thawed at room temperature and then on ice until liquefied. Cells were disrupted with sonication (15 cycles of 30 s ON and 30 s OFF) and the resultant lysate cleared by centrifugation for 30 minutes at 4° C. (16,000 rpm, Sorvall RCSC centrifuge, rotor #SS-34). Cleared lysate was applied to fast flow chelating sepharose charged with nickel ions (40 ml bed volume) at a flow rate of 2 ml/min. The column was washed with low imidazole buffer (pH 7.4, 50 mM HEPES, 500 mM sodium chloride, 20 mM imidazole) until the absorbance of the flow through at 280 nm returned to near baseline levels. Bound material was eluted with a step to 50% high imidazole buffer (pH 7.4, 50 mM HEPES, 500 mM sodium chloride, 500 mM imidazole). Material eluted from the column was analysed by SDS-PAGE and selected fractions pooled. Protein concentration was determined from the absorbance at 280 nm.

Thrombin Digestion of the Nus TxB4 Fusion Protein

To each 10 μg of protein, 5 μl of thrombin digest buffer (200 mM Tris-HCl pH 8.4, 1.5 M NaCl, 25 mM $CaCl_2$), 1 μl of Human thrombin (Novagen) diluted 200 fold in thrombin dilution buffer (50 mM sodium citrate, pH 6.5, 200 mM NaCl, 0.1% PEG-8000, 50% glycerol) and water to a volume of 50 μl were added. The protein was digested overnight at room temperature and dialysed into low imidazole buffer at 4° ° C.

Nickel Affinity Purification of TxB4

Figure 3:
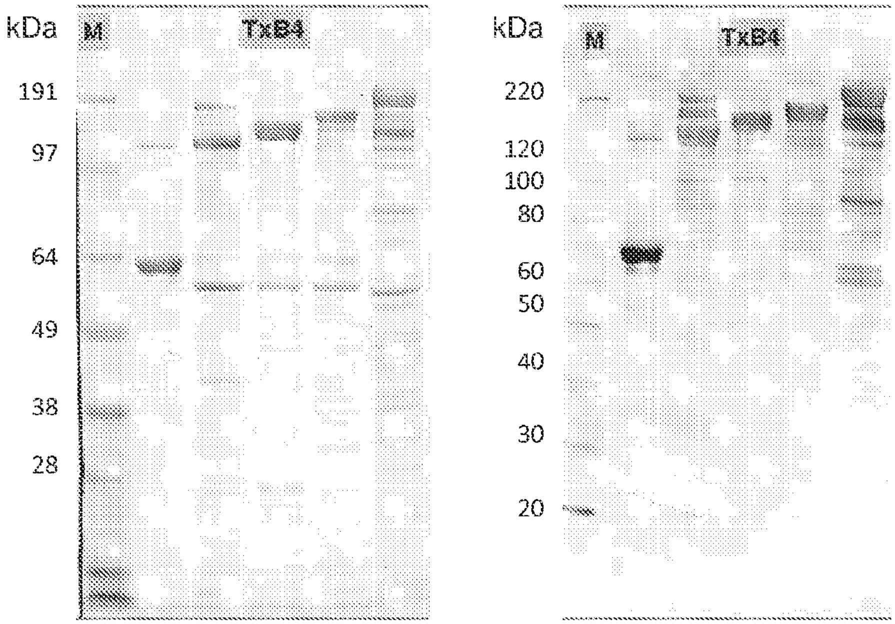
FIG. 3 illustrates TxB4 purification. The left-hand Figure shows a 4-12% SDS-PAGE analysis of TxB4. M=SeeBlue® Plus2 Pre-Stained Standard. The right-hand Figure shows a Western blot analysis of TxB4 with ovine anti-TcdB polyclonal antibodies, M=MagicMark™ XP Standard.

TxB4 in low imidazole buffer was applied to fast flow chelating sepharose charged with nickel ions (40 ml bed volume) at a flow rate of 3 ml/min. The column was washed with low imidazole buffer until the absorbance of the flow through at 280 nm returned to near baseline levels. The column was washed with 80 mM imidazole, protein eluting after the resultant initial peak in UV absorbance (280 nm) was collected and dialysed into storage buffer (50 mM HEPES pH 7.4, 150 mM sodium chloride). Protein was analysed by SDS-PAGE and Western blotting with ovine anti-TcdB polyclonal antibodies (FIG. 3).

Example 4—Expression and Purification of *C. difficile* Toxin B Fragment TxB5 (Residues 544-2366 of Toxin B)

Large Scale Expression of the Nus TxB5 Fusion Protein

An N-his$_6$-Nus fusion of TxB5 was expressed in BL21 Star™ (DE3) *E. coli* harbouring plasmid pDest57TxB5. An overnight culture in LB media supplemented with 100 μg/ml ampicillin was used as a 3% inoculum for Terrific Broth (3 L) supplemented with 100 μg/ml ampicillin. Cultures were maintained at 37° C. to an absorbance at 600 nm of 0.6 with orbital shaking (180 rpm). Expression was induced with the addition of IPTG to a final concentration of 1 mM and the cultures maintained at 16° C. overnight with orbital shaking (180 rpm). Cells (25 g) were harvested by centrifugation for 30 minutes (3000 rpm, Sorvall RC3BP centrifuge, rotor

#H6000A) and resuspended in low imidazole buffer (250 ml, pH 7.4, 50 mM HEPES, 500 mM sodium chloride, 20 mM imidazole).

Nickel Affinity Purification of the Nus TxB5 Fusion Protein

Lysozyme (10 mg) was added to the resuspended cells and the mixture stirred for 15 minutes. Cells were disrupted with sonication (10 cycles of 30 s ON and 30 s OFF) and the resultant lysate cleared by centrifugation for 30 minutes (14,000 rpm, Sorvall RCSC centrifuge, rotor #SS-34). Half of the cleared lysate was applied to fast flow chelating sepharose charged with nickel ions (40 ml bed volume) at a flow rate of 2 ml/min. The column was washed with low imidazole buffer until the UV absorbance of the flow through at 280 nm returned to near baseline levels. Protein, including Nus TxB5, was eluted with a step to 38% (200 mM imidazole) high imidazole buffer (pH 7.4, 50 mM HEPES, 500 mM sodium chloride, 500 mM imidazole). The second half of the lysate was processed in the same manner and the pooled eluted protein dialysed overnight into high salt HIC buffer (pH 7.4, 50 mM HEPES, 750 mM ammonium sulphate).

Butyl-s Hydrophobic Interaction Chromatography Purification of Nus TxB5

Half of the pooled protein solution in high salt HIC buffer was applied to a column containing butyl-s-sepharose 6 fast flow resin (9 ml bed volume). The column was washed with high salt HIC buffer (pH 7.4, 50 mM HEPES, 750 mM ammonium sulphate) until the UV absorbance of the flow through at 280 nm returned to near baseline levels. Protein was eluted from the column with a step to 100% low salt HIC buffer ((pH 7.4, 50 mM HEPES). The other half of the protein from the first nickel column was purified in the same manner. The eluted protein was pooled in preparation for digestion with thrombin.

Thrombin Digestion of the Nus TxB5 Fusion Protein

Pooled protein from the HIC column (69 mg, 30 ml) was added to a solution containing 10×thrombin cleavage buffer (15 ml, 200 mM Tris-HCl pH 8.4, 1.5 M sodium chloride, 25 mM calcium chloride), deionised water (105 ml) and human thrombin (Novagen, 40 U). The solution was incubated at room temperature for 4 hours and PMSF added to a final concentration of 1 mM. The resultant protein including the TxB5 was dialysed into high salt HIC buffer.

Butyl-s Hydrophobic Interaction Chromatography Purification of TxB5

The TxB5 from the thrombin digest was purified in two batches. Each batch was applied in high salt HIC buffer (pH 7.4, 50 mM HEPES, 750 mM ammonium sulphate) to a column containing butyl-s-sepharose 6 fast flow resin (9 ml bed volume) at a flow rate of 1 ml/mM The column was washed with high salt HIC buffer until the UV absorbance of the flow through at 280 nm returned to near baseline levels. Protein was eluted from the column with a step to 100% low salt HIC buffer (pH 7.4, 50 mM HEPES). The eluted material was dialysed against buffer (pH 7.4, 50 mM HEPES) overnight.

Q Sepharose Ion Exchange Chromatography Purification of TxB5

Figure 4:
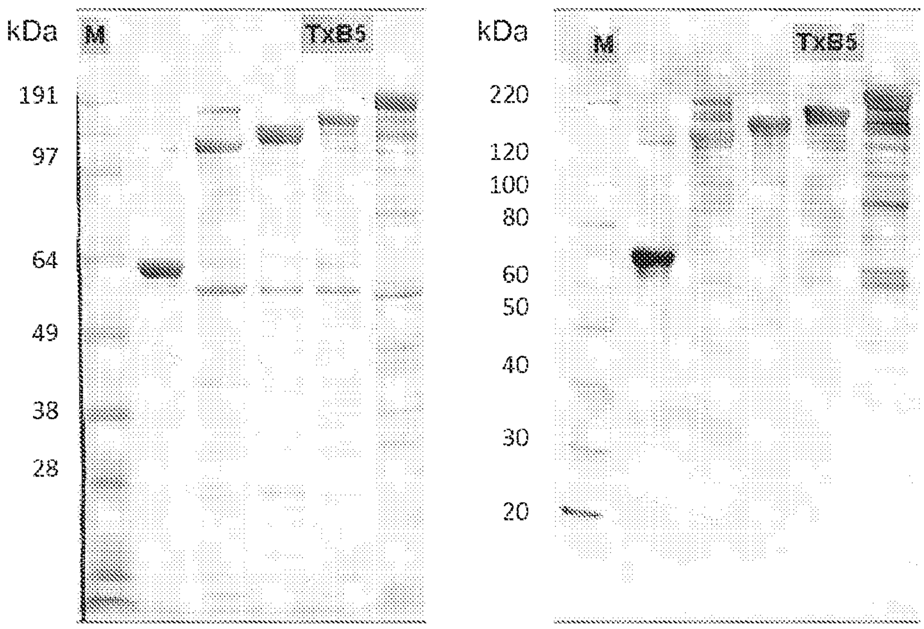
FIG. 4 illustrates TxB5 purification. The left-hand Figure shows a 4-12% SDS-PAGE analysis of TxB5. M=SeeBlue® Plus2 Pre-Stained Standard. The right-hand Figure shows a Western blot analysis of TxB5 with ovine anti-TcdB polyclonal antibodies, M=MagicMark™ XP Standard.

The TxB5 in buffer (pH 7.4, 50 mM HEPES) was run through a column containing Q sepharose fast flow resin (5 ml bed volume) at a flow rate of 1 ml/min. The flow through was pooled and dialysed into storage buffer (pH 7.4, 50 mM HEPES, 150 mM sodium chloride). Approximately 20 mg of protein was produced, of this 60% was TxB5 based on SDS-PAGE analysis. The protein was frozen in 1 ml aliquots at −80° C. Protein was analysed by SDS-PAGE and Western blotting with ovine anti-TcdB polyclonal antibodies (FIG. 4).

Example 5—Expression and Purification of *C. difficile* Toxin a Fragment TxA4 (Residues 770-2710 of Toxin A)

Expression

L-broth (100 ml) supplemented with 50 μg/ml kanamycin and 0.2% glucose was inoculated with a scrape from a glycerol freeze (BL21 (DE3) *E. coli* harbouring plasmid pET28aHis$_6$TrxHRV3CαNaturalTxA4) and maintained overnight at 30° C. and 180 rpm. The overnight culture was used as a 2% inoculum for Terrific Broth (4×0.5 L in 2 L unbaffled flasks) supplemented with 50 μg/ml kanamycin and 0.2% glucose. Cultures were maintained at 37° C. with orbital shaking (180 rpm) to an absorbance at 600 nm of 0.6. The temperature of the cultures was reduced to 16° C. and protein expression induced with the addition of 1 mM IPTG. The culture was maintained overnight at 16° C. with orbital shaking as before. Cell paste (23 g) was harvested by centrifugation (Sorvall RC3BP centrifuge, H6000A rotor, 4000 g, 20 minutes). The paste was recovered from the centrifuge pots by resuspension in low imidazole buffer (pH 7.5, 50 mM Hepes, 0.5 M sodium chloride, 20 mM Imidazole) and stored at −80° C.

Immobilised Nickel Affinity Purification of the TxA4 Precursor

Cells (23 g) resuspended with 85 ml of low imidazole buffer (pH7.5, 50 mM Hepes, 0.5 M NaCl 20 mM imidazole) was subjected to lysis using sonication. The lysate was cleared by centrifugation (Sorvall RCSC centrifuge, SS-34 rotor, 20,000 g, 20 minutes) and applied to a 20 ml nickel column (Ø26 mm) at a flow rate of 1.5 ml/min. The column was washed with ten column volumes of low imidazole buffer and bound protein eluted using a five column volume gradient to 100% high imidazole buffer (pH 7.5, 50 mM Hepes, 0.5 M NaCl, 0.5 M imidazole). Fractions were analysed on 4-12% NuPAGE Bis-Tris polyacrylamide gels with coomassie staining.

Cleavage of the Fusion Partner and His6-Tag

The purest fractions were pooled and dialysed against HRV3C cleavage buffer (2 L, pH 7.5, 20 mM Tris-HCl, 0.5 M NaCl) overnight at 4° C. HRV3C protease (10 U per mg of full length target protein) was added to the solution and incubated at 20° C. for five hours followed by 4° C. overnight.

Immobilised Nickel Affinity Purification of Post Cleavage TxA4

Figure 5:
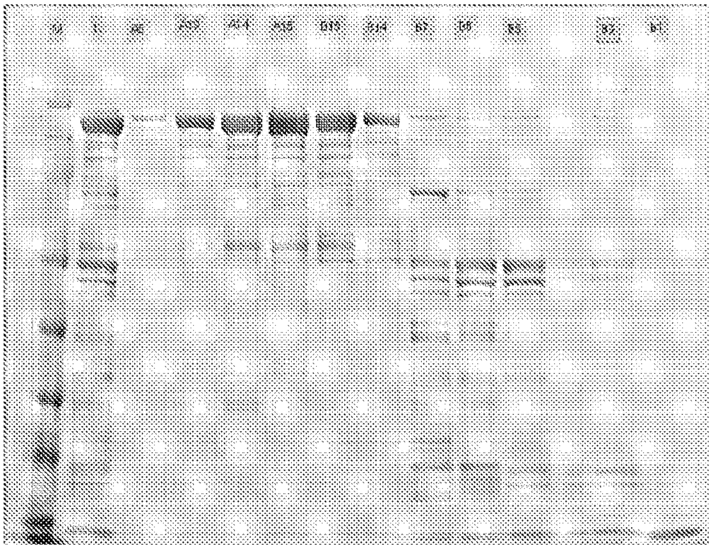
FIG. 5 illustrates TxA4 purification and SDS-PAGE analysis of the nickel affinity purification of HRV3C protease treated TxA4. M=Molecular weight markers, L=column load, A8=column flow-through. Fractions A14-B14 showed the purified TxA4.

The protein solution (pH 7.5 20 mM Tris-HCl, 0.5 M NaCl) was passed over a 20 ml nickel column (Ø 26 mm) at a flow rate of 1.5 ml/min. Some protein was seen to elute in the flow through as judged by the UV absorbance. The column was given a short wash with the HRV3C cleavage buffer and the TxA4 eluted with 5% high imidazole buffer (pH7.5, 50 mM Hepes, 0.5 M NaCl, 0.5 M imidazole) at an imidazole concentration of 25 mM. The remaining proteins were eluted from the column with a four column volume gradient to 100% high imidazole buffer. The purest fractions were pooled and dialysed into storage buffer (pH 7.5, 50 mM Hepes, 0.5 M NaCl). Fractions from the final purification column are shown in FIG. 5.

Example 6—Expression and Purification of *C. difficile* Toxin a Fragment TxA4 Truncated (Residues 770-2389 of Toxin A)

Expression

L-Broth (100 ml) supplemented with 100 μg/ml ampicillin and 0.5% glucose was inoculated with a colony (harbouring pET59His6TRXtcsanaturalTxA4truncate) from an overnight growth on a L-agar plate supplemented with 100 μg/ml ampicillin and maintained overnight at 37° C. and 180 rpm. This was used as an inoculum for Terrific Broth (6×1000 mls in 2000 ml unbaffled flasks) supplemented with 100 μg/ml ampicillin and 0.5% glucose. Cultures were maintained at 37° C. with orbital shaking (180 rpm) to an absorbance at 600 nm of 0.6. The temperature of the cultures was reduced to 16° C. and protein expression induced with the addition of IPTG to a final concentration of 1 mM. The culture was maintained overnight at 16° C. with orbital shaking as before. Cell paste was harvested by centrifugation (Sorvall RC3BP centrifuge, H6000A rotor, 4000 g, 30 minutes). The paste was recovered from the centrifuge pots by re-suspension in Hepes buffer (50 mM Hepes pH 7.4, 0.5 M sodium chloride) and stored at −20° C.

Immobilised Nickel Affinity Purification of the TxA4 Truncate Precursor

Cells (44 g) re-suspended with 180 ml of Hepes buffer (50 mM Hepes pH 7.4, 500 mM NaCl) were subject to lysis using sonication. The lysate was clarified by centrifugation at 4000 rpm for 20 minutes (Heraeus Multifuge). The supernatant was retained and applied to a 64 ml Zinc Sepharose column (XK26×12) at a flow rate of 5 ml/minute. The column was washed until the absorbance at 280 nm was reduced to the baseline. The bound protein was eluted using a gradient of 0-250 mM imidazole in 50 mM Hepes pH 7.4, 500 mM sodium chloride. The fractions were analysed on 4-12% NuPAGE® Bis-Tris polyacrylamide gels with coomassie staining.

Cleavage of the Fusion Partner and $His_6$-Tag

The purest fractions were pooled and dialysed against thrombin cleavage buffer (20 mM Tris/HCl pH 8.4+150 mM NaCl+2.5 mM $CaCl_2$) overnight at +4° C. Restriction grade thrombin (Novagen) was added at 1:2000 wt:wt with respect to the target protein. The mixture was incubated at room temperature overnight.

Immobilised Zinc Affinity Purification of Post Cleavage TxA4 Truncate

The protein solution (in 50 mM Hepes pH 7.4, 500 mM sodium chloride) was passed over a 24 ml zinc column (XK16×12) at a flow rate of 2 ml/minute. The column was washed with equilibration buffer (50 mM Hepes pH 7.4, 500 mM sodium chloride) until the absorbance at 280 nm was reduced to the baseline. The bound protein was eluted using a gradient of 0-250 mM imidazole in 50 mM Hepes pH 7.4, 500 mM sodium chloride.

Example 7—Formulation of Antigens of the Invention for Immunisation of Animals Purified *C. difficile* antigens at a concentration of between 0.5-2 mg/ml (nominally 1 mg/mi) were dialysed against a suitable buffer (e.g., 10 mM Hepes buffer pH 7.4 containing 150 mM NaCl) and then formaldehyde added to a final concentration of 0.2% and incubated for up to 7 days at 35° C. After incubation, the formaldehyde may optionally be removed by dialysis against a suitable buffer, e.g., phosphate buffered saline.

For sheep, 2 ml of buffer solution containing between 10 and 500 μg of the above *C. difficile* antigen is mixed with 2.6 ml of Freund's adjuvant to form an emulsion. Mixing with the adjuvant is carried out for several minutes to ensure a stable emulsion. The complete form of the adjuvant is used for the primary immunisation and incomplete Freund's adjuvant for all subsequent boosts.

Example 8—Generation of Antibodies to Antigens of the Invention

A number of conventional factors are taken into consideration during the preparation of antiserum in order to achieve the optimal humoral antibody response. These include: breed of animal; choice of adjuvant; number and location of immunisation sites; quantity of immunogen; and number of and interval between doses. With conventional optimisation of these parameters is routine to obtain specific antibody levels in excess of 6 g/litre of serum.

For sheep, an emulsion of the antigen with Freund's adjuvant was prepared as described as in Example 7. The complete form of the adjuvant is used for the primary immunisation and incomplete Freund's adjuvant for all subsequent boosts. About 4.2 ml of the antigen/adjuvant mixture was used to immunise each sheep by i.m. injection and spread across 6 sites including the neck and all the upper limbs. This was repeated every 28 days. Blood samples were taken 14 days after each immunisation.

For comparison of the toxin-neutralising immune response to the different antigens, 3 sheep were used per antigen. They were immunised as above using an identical protocol and the same protein dose per immunisation.

Example 9—Assessment of the Neutralising Efficacy of Antisera to Toxins Using the In Vitro Cell Assay The toxin neutralizing activity of the antisera against *C. difficile* Toxins was measured by cytotoxicity assays using Vero cells. A fixed amount of either purified *C. difficile* Toxin A or Toxin B was mixed with various dilutions of the antibodies, incubated for 30 min at 37° C. and then applied to Vero cells growing on 96-well tissue culture plates. Both Toxin A and B possess cytotoxic activity which results in a characteristic rounding of the Vero cells over a period of 24-72 h. In the presence of neutralising antibodies this activity is inhibited and the neutralising strength of an antibody preparation may be assessed by the dilution required to neutralize the effect of a designated quantity of either Toxin A or B.

Data demonstrating the neutralising activity of ovine antibody to various recombinant *C. difficile* Toxin B antigens are shown in Tables 3-6. In these experiments, various dilutions of ovine antibody were mixed with Toxin B at a final concentration of 0.5 ng/ml and incubated for 30 min at 37° C. and then applied to Vero cells as above and incubated at 37° and monitored over a period of 24-72 h. The antibody dilutions which completely protect the cells against the cytotoxic effects of the Toxin B were calculated. Similar data for Toxin A-derived antigens are shown in tables 7-10.

Collectively, the data in Tables 3-10 show the superior capacity of fusion proteins of the invention to elicit a toxin-neutralising immune response compared to fragments containing just the repeat domains of either Toxin A or B.

Example 10—Assessment of the In Vivo Efficacy of Antiserum Generated Using Recombinant Antigens of the Invention for Treating CDI To demonstrate the efficacy of the antisera generated, using recombinant antigens, to treat CDI in vivo, Syrian hamsters are passively immunised with antibodies which have neutralising activity against one or more of the toxins of *C. difficile*. For assessing the efficacy of a treatment formulation, hamsters will be given antibody either intravenously or by the intraperitoneal route at various times from 6 hours post-challenge to 240 hours post challenge with *C. difficile*

Prior to passively immunisation hamsters are administered a broad spectrum antibiotic (e.g., clindamycin) and 12-72 h later challenged with *C. difficile* spores by mouth. Animals are then monitored for up to 15 days for symptoms of *C. difficile*-associated disease. Control, non-immunised animals develop signs of the disease (e.g., diarrhoea, swollen abdomen, lethargy, ruffled fur) while those treated with ovine antibody appear normal.

Example 11—Vaccination by Peptide/Peptide Fragments of the Invention

A vaccine, represented by a peptide/peptide fragment of the invention is prepared by current Good Manufacturing Practice. Using such practices, peptides/peptide fragments of the invention may be bound to an adjuvant of aluminium hydroxide which is commercially available (e.g., Alhydrogel®). The vaccine would normally contain a combination of antigens of the invention derived from Toxin A and Toxin B but could also contain either Toxin A or B antigens. The vaccine may also contain Toxin A and B antigens in combination with other antigens of bacterial or viral origin.

Purified *C. difficile* Toxin A and/or Toxin B antigen of the invention may be treated with formaldehyde at a final concentration of 0.2% and incubated for up to 24 hours at 35° C. (as described in Example 7).

In addition to the antigens of the invention, a typical vaccine composition comprises:

A) A buffer (e.g., Hepes buffer between 5 and 20 mM and pH between 7.0 and 7.5;

B) A salt component to make the vaccine physiologically isotonic (e.g., between 100 and 150 mM NaCl);

C) An adjuvant (e.g., aluminium hydroxide at a final aluminium concentration of between 100 and 700 μg per vaccine dose); and D) A preservative (e.g., Thiomersal at 0.01% or formaldehyde at 0.01%).

Such vaccine compositions are administered to humans by a variety of different immunisation regimens, such as:

1. A single dose (e.g., 20 μg adsorbed fragment of the invention) in 0.5 ml administered sub-cutaneously.
2. Two doses (e.g., of 10 μg adsorbed fragment of the invention) in 0.5 mls administered at 0 and 4 weeks.
3. 3. Three doses (e.g., of 10 μg adsorbed fragment of the invention) in 0.5 mls administered at 0, 2 and 12 weeks.

These vaccination regimens confer levels of protection against exposure to the homologous serotypes of *C. difficile* toxins

Example 12—Affinity Purification of IgG Using Immobilised Constructs of the Invention Preparation of the Affinity Chromatography Medium The construct of the invention to be immobilised is dialysed against a suitable coupling buffer e.g., 0.1 M $NaHCO_3$ pH 8.3 containing 0.5 M NaCl. Approximately 5 ml of protein solution at 1-3 mg/ml is added per ml of CNBr-activated Sepharose 4B powder. The mixture is rotated end-over end for 1 h at room temperature or overnight at 4° C. Other gentle stirring methods may be employed. Excess ligand is then wash away excess with at least 5 medium (gel) volumes of coupling buffer. Any remaining active groups and then blocked. The medium is transferred to 0.1 M Tris-HCl buffer, pH 8.0 or 1 M ethanolamine, pH 8.0 and incubated 2 hours at room temperature. The gel is then washed with at least three cycles of alternating pH (at least 5 medium volumes of each buffer). Each cycle should consist of a wash with 0.1 M acetic acid/sodium acetate, pH 4.0 containing 0.5 M NaCl followed by a wash with. 0.1 M Tris-HCl, pH 8 containing 0.5 M NaCl. After washing the gel is transferred to a suitable storage buffer (e.g., 50 mM HEPES pH 7.4 containing 0.15 M NaCl and stored at 4° C. until use Purification of IgG Affinity columns are prepared as above using antigens of the invention derived from either Toxin A or B. For purification of antibodies to Toxin B, a construct such as TxB4 (residues 767-2366) could be used. For purification of antibodies to Toxin A, a construct such as TxA4 (residues 770-2710) could be used. For affinity purification of antibodies which bind toxin B, serum which contains antibodies to Toxin B is diluted 1:1 with a suitable buffer (e.g. 20 mM HEPES pH 7.4 buffer containing 0.5M NaCl) and the mixture applied to column containing immobilised TxB4 packed in a suitable column (2-6 ml mixture per ml of gel). After the unbound fraction (which contains serum albumin and non-specific IgG) is washed off with at least 10 column volumes of 20 mM HEPES pH 7.4 buffer containing 0.5M NaCl buffer, the bound fraction is eluted from the column with 5 column volumes of elution buffer (e.g., 100 mM glycine buffer, pH 2.5). The eluted fractions containing the IgG are then immediately neutralized to approximately pH 7.0 with of 1 M Tris-HCl pH 8.0. These fractions, which contain the IgG which binds Toxin B, are then dialysed against 50 mM HEPES pH 7.4 containing 0.15 m NaCl and stored frozen until required Affinity purified IgG fractions which bind and neutralizes either Toxin A or B may be used as therapeutic agents to either treatment of prevent CDI. They may also be used in assay systems such as enzyme-linked immunosorbant assay (ELISA) for the detection of Toxins A or B. In such diagnostic systems, affinity purified antibodies may provide assays of higher sensitivity and with reduced background interference.

FIGURES AND TABLES

TABLE 1

Toxin A Receptor-Binding Repeat Modules

| Toxin A Receptor-Binding Modules | Amino acid Sequence (Long Repeat regions shown in bold) |
|---|---|
| Module 1 LR = SEQ ID NO: 60 | **GVFKGPDGFEYFAPANTQNNNIEGQAIVYQS** |
| Module 1 (residues 1851-2007 = SEQ ID NO: 61) | VTGWQTINGKKYYFDINTGAALTSYKIINGKHF<br>YFNNDGVMQL**GVFKGPDGFEYFAPANTQNN**<br>**NIEGQAIVYQS**KFLTLNGKKYYFDNNSKAVTG<br>WRIINNEKYYFNPNNAIAAVGLQVIDNNKYYF<br>NPDTAIISKGWQTVNGSRYYFDTDTAIAFN |
| Module 2 LR = SEQ ID NO: 62 | **GVFSTSNGFEYFAPANTYNNNIEGQAIVYQS** |
| Module 2 (residues 2008-2141 = SEQ ID NO: 63) | GYKTIDGKHFYFDSDCVVKI**GVFSTSNGFEYF**<br>**APANTYNNNIEGQAIVYQS**KFLTLNGKKYYFD<br>NNSKAVTGLQTIDSKKYYFNTNTAEAATGWQT<br>IDGKKYYFNTNTAEAATGWQTIDGKKYYFNTN<br>TAIAST |
| Module 3 LR = SEQ ID NO: 64) | **GVFKGPNGFEYFAPANTDANNIEGQAILYQN** |
| Module 3 (residues 2142-2253 = SEQ ID NO: 65) | GYTIINGKHFYFNTDGIMQI**GVFKGPNGFEYF**<br>**APANTDANNIEGQAILYQN**EFLTLNGKKYYFG<br>SDSKAVTGWRIINNKKYYFNPNNAIAAIHLCTI<br>NNDKYYFSYDGILQN |
| Module 4 LR = SEQ ID NO: 66) | **GVFKGPNGFEYFAPANTHNNNIEGQAIVYQN** |
| Module 4 (residues 2254-2389 = SEQ ID NO: 67) | GYITIERNNFYFDANNESKMVT**GVFKGPNGFE**<br>**YFAPANTHNNNIEGQAIVYQN**KFLTLNGKKY<br>YFDNDSKAVTGWQTIDGKKYYFNLNTAEAAT<br>GWQTIDGKKYYFNLNTAEAATGWQTIDGKKY<br>YFNTNTFIAST |
| Module 5 LR = SEQ ID NO: 68) | **GVFKGPNGFEYFAPANTDANNIEGQAILYQN** |
| Module 5 (residues 2390-2502 = SEQ ID NO: 69) | GYTSINGKHFYFNTDGIMQI**GVFKGPNGFEYF**<br>**APANTDANNIEGQAILYQN**KFLTLNGKKYYF<br>GSDSKAVTGLRTIDGKKYYFNTNTAVAVTGW<br>QTINGKKYYFNTNTSIAST |
| Module 6 LR = SEQ ID NO: 70) | **GVFKGPDGFEYFAPANTDANNIEGQAIRYQN** |
| Module 6 (residues 2503-2594 = SEQ ID NO: 71) | GYTIISGKHFYFNTDGIMQI**GVFKGPDGFEYFA**<br>**PANTDANNIEGQAIRYQN**RFLYLHDNIYYFGN<br>NSKAATGWVTIDGNRYYFEPNTAMGAN |
| Module 7 LR = SEQ ID NO: 72) | **GVFKGSNGFEYFAPANTDANNIEGQAIRYQN** |
| Module 7 (residues 2595-2710 = SEQ ID NO: 73) | GYKTIDNKNFYFRNGLPQI**GVFKGSNGFEYFA**<br>**PANTDANNIEGQAIRYQN**RFLHLLGKIYYFGN<br>NSKAVTGWQTINGKVYYFMPDTAMAAAGGLF<br>EIDGVIYFFGVDGVKAPGIYG |

TABLE 2

Toxin B Receptor-Binding Repeat Modules

| Toxin B Receptor-Binding Modules | Amino acid Sequence (Long Repeat regions shown in bold) |
|---|---|
| Module 1 LR = SEQ ID NO: 74 | **GVFSTEDGFKYFAPANTLDENLEGEAIDFT** |
| Module 1 (residues 1852-2007 = SEQ ID NO: 75) | DDKYYFNPINGGAASIGETIIDDKNYYFNQSGV<br>LQT**GVFSTEDGFKYFAPANTLDENLEGEAID**<br>**FT**GKLIIDENIYYFDDNYRGAVEWKELDGEMH<br>YFSPETGKAFKGLNQIGDYKYYFNSDGVMQKG<br>FVSINDNKHYFDDSGVMKV |
| Module 2 LR = SEQ ID NO: 76 | **GVFNTEDGFKYFAHHNEDLGNEEGEEISYS** |
| Module 2 (residues 2008-2139 = SEQ ID NO: 77) | GYTEIDGKHFYFAENGEMQI**GVFNTEDGFKYF**<br>**AHHNEDLGNEEGEEISYS**GILNFNNKIYYFDD<br>SFTAVVGWKDLEDGSKYYFDEDTAEAYIGLSLI<br>NDGQYYFNDDGIMQVGFVTINDKVFYFSDSGII<br>ES |

TABLE 2-continued

Toxin B Receptor-Binding Repeat Modules

| Toxin B Receptor-Binding Modules | Amino acid Sequence (Long Repeat regions shown in bold) |
|---|---|
| Module 3 LR = SEQ ID NO: 78 | **GVFDTSDGYKYFAPANTVNDNIYGQAVEYS** |
| Module 3 (residues 2140-2273 = SEQ ID NO: 79) | GVQNIDDNYFYIDDNGIVQI**GVFDTSDGYKYF**<br>**APANTVNDNIYGQAVEYS**GLVRVGEDVYYFG<br>ETYTIETGWIYDMENESDKYYFNPETKKACKGI<br>NLIDDIKYYFDEKGIMRTGLISFENNNYYFNEN<br>GEMQF |
| Module 4 LR = SEQ ID NO: 80 | **GVFNTPDGFKYFAHQNTLDENFEGESINYT** |
| Module 4 (residues 2274-2366 = SEQ ID NO: 81) | GYINIEDKMFYFGEDGVMQI**GVFNTPDGFKYF**<br>**AHQNTLDENFEGESINYT**GWLDLDEKRYYFT<br>DEYIAATGSVIIDGEEYYFDPDTAQLVISE |

TABLE 3

Neutralisation titres obtained by immunisation of sheep with recombinant Toxin B-derived antigens (6 weeks time point; 2 doses of 100 g each)

| Toxin B-derived Antigen (amino acid sequence) | Neutralisation titre against Toxin B (0.5 ng/ml) |
|---|---|
| Recombinant Toxin B (1756-2366) | <10 |
| Recombinant Toxin B (1145-2366) | 960 |
| Recombinant Toxin B (767-2366) | 2,560 |
| Recombinant Toxin B (543-2366) | 1,280 |

TABLE 4

Neutralisation titres obtained by immunisation of sheep with recombinant Toxin B-derived antigens (18 weeks time point; 5 doses of 100 μg each)

| Toxin B- derived Antigen (amino acid sequence) | Neutralisation titre against Toxin B (0.5 ng/ml) |
|---|---|
| Recombinant Toxin B (1756-2366) | 80 |
| Recombinant Toxin B (1145-2366) | 5,120 |
| Recombinant Toxin B (767-2366) | 10,250 |
| Recombinant Toxin B (543-2366) | 5,120 |

TABLE 5

Neutralisation titres obtained by immunisation of sheep with a recombinant Toxin B-derived antigen (TxB4; residues 767-2366) of the invention

| Antigen | No of Doses | Immunisation period (weeks) | Neutralisation titre against Toxin B (0.5 ng/ml) |
|---|---|---|---|
| Recombinant Toxin B | 2 | 6 | 2,560 |
| (residues 767-2366) | 3 | 10 | 2,560 |
| at 100 μg/dose | 4 | 14 | 10,250 |
| | 5 | 18 | 10,250 |
| | 6 | 22 | 20,480 |

TABLE 6

Neutralisation titres obtained by immunisation of sheep with a recombinant Toxin B-derived antigen (TxB2, 1756-2366) representing the repeat regions

| Antigen | No of Doses | Immunisation period (weeks) | Neutralisation titre against Toxin B (0.5 ng/ml) |
|---|---|---|---|
| Recombinant Toxin B | 2 | 6 | <10 |
| (residues 1756-2366) | 3 | 10 | 10 |
| at 100 μg/dose | 4 | 14 | 10 |
| | 5 | 18 | 80 |

TABLE 7

Neutralisation titres obtained by immunisation of sheep with recombinant Toxin A-derived antigens (10 weeks time point)

| Toxin A-derived Antigen (amino acid sequence) | No of Doses (100 μg) | Neutralisation titre against Toxin A (50 ng/ml) |
|---|---|---|
| Recombinant Toxin A (1850-2710) | 3 | 640 |
| Recombinant Toxin A (770-2710) | 2 | 7,680 |
| Recombinant Toxin A (770-2389) | 3 | 10,240 |

TABLE 8

Neutralisation titres obtained by immunisation of sheep with recombinant Toxin A-derived antigens (18 weeks time point)

| Toxin A-derived Antigen (amino acid sequence) | No of Doses (100 μg) | Neutralisation titre against Toxin A (50 ng/ml) |
|---|---|---|
| Recombinant Toxin A (1850-2710) | 5 | 1,280 |
| Recombinant Toxin A (770-2710) | 4 | 15,360 |

TABLE 9

Neutralisation titres obtained by immunisation of sheep with a recombinant Toxin A-derived antigen (TxA4; residues 770-2710) of the invention

| Antigen | No of Doses | Immunisation period (weeks) | Neutralisation titre against Toxin A (50 ng/ml) |
|---|---|---|---|
| Recombinant Toxin A | 2 | 10 | 7,680 |
| (residues 770-2710) | 3 | 14 | 10,240 |
| at 100 μg/dose | 4 | 18 | 15,360 |

TABLE 10

Neutralisation titres obtained by immunisation of sheep with arecombinant Toxin A-derived antigen (TxA2; residues 1850-2710) representing the repeat region only

| Antigen | No of Doses | Immunisation period (weeks) | Neutralisation titre against Toxin A (50 ng/ml) |
|---|---|---|---|
| Recombinant Toxin A | 2 | 6 | 320 |
| (residues 1850-2710) | 3 | 10 | 630 |
| at 100 μg/dose | 4 | 14 | 1,280 |
| | 5 | 18 | 1,280 |

SEQ ID NOs

SEQ ID NO: 1 - *Clostridium difficile* Toxin A (Toxinotype 0)
MSLISKEELIKLAYSIRPRENEYKTILTNLDEYNKLTTNNNENKYLQLKKLNESID
VFMNKYKTSSRNRALSNLKKDILKEVILIKNSNTSPVEKNLHFVWIGGEVSDIALE
YIKQWADINAEYNIKLWYDSEAFLVNTLKKAIVESSTTEALQLLEEEIQNPQFDN
MKFYKKRMEFIYDRQKRFINYYKSQINKPTVPTIDDIIKSHLVSEYNRDETVLESY
RTNSLRKINSNHGIDIRANSLFTEQELLNIYSQELLNRGNLAAASDIVRLLALKNF
GGVYLDVDMLPGIHSDLFKTISRPSSIGLDRWEMIKLEAIMKYKKYINNYTSENF
DKLDQQLKDNFKLIIESKSEKSEIFSKLENLNVSDLEIKIAFALGSVINQALISKQGS
YLTNLVIEQVKNRYQFLNQHLNPAIESDNNFTDTTKIFHDSLFNSATAENSMFLTK
IAPYLQVGFMPEARSTISLSGPGAYASAYYDFINLQENTIEKTLKASDLIEFKFPEN
NLSQLTEQEINSLWSFDQASAKYQFEKYVRDYTGGSLSEDNGVDFNKNTALDKN
YLLNNKIPSNNVEEAGSKNYVHYIIQLQGDDISYEATCNLFSKNPKNSIIIQRNMN
ESAKSYFLSDDGESILELNKYRIPERLKNKEKVKVTFIGHGKDEFNTSEFARLSVD
SLSNEISSFLDTIKLDISPKNVEVNLLGCNMFSYDFNVEETYPGKLLLSIMDKITST
LPDVNKNSITIGANQYEVRINSEGRKELLAHSGKWINKEEAIMSDLSSKEYIFFDSI
DNKLKAKSKNIPGLASISEDIKTLLLDASVSPDTKFILNNLKLNIESSIGDYIYYEKL
EPVKNIIHNSIDDLIDEFNLLENVSDELYELKKLNNLDEKYLISFEDISKNNSTYSV
RFINKSNGESVYVETEKEIFSKYSEHITKEISTIKNSIITDVNGNLLDNIQLDHTSQV
NTLNAAFFIQSLIDYSSNKDVLNDLSTSVKVQLYAQLFSTGLNTIYDSIQLVNLISN
AVNDTINVLPTITEGIPIVSTILDGINLGAAIKELLDEHDPLLKKELEAKVGVLAIN
MSLSIAATVASIVGIGAEVTIFLLPIAGISAGIPSLVNNELILHDKATSVVNYFNHLS
ESKKYGPLKTEDDKILVPIDDLVISEIDFNNNSIKLGTCNILAMEGGSGHTVTGNID
HFFSSPSISSHIPSLSIYSAIGIETENLDFSKKIMMLPNAPSRVFWWETGAVPGLRSL
ENDGTRLLDSIRDLYPGKFYWRFYAFFDYAITTLKPVYEDTNIKIKLDKDTRNFIM
PTITTNEIRNKLSYSFDGAGGTYSLLLSSYPISTNINLSKDDLWIFNIDNEVREISIEN
GTIKKGKLIKDVLSKIDINKNKLIIGNQTIDFSGDIDNKDRYIFLTCELDDKISLIIEI
NLVAKSYSLLLSGDKNYLISNLSNTIEKINTLGLDSKNIAYNYTDESNNKYFGAIS
KTSQKSIIHYKKDSKNILEFYNDSTLEFNSKDFIAEDINVFMKDDINTITGKYYVD
NNTDKSIDFSISLVSKNQVKVNGLYLNESVYSSYLDFVKNSDGHHNTSNFMNLFL
DNISFWKLFGFENINFVIDKYFTLVGKTNLGYVEFICDNNKNIDIYFGEWKTSSSK
STIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIEFNLVTGWQTINGKKYYFDINTGAA
LTSYKIINGKHFYFNNDGVMQLGVFKGPDGFEYFAPANTQNNNIEGQAIVYQSKF
LTLNGKKYYFDNNSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNG
FEYFAPANTYNNNIEGQAIVYQSKFLTLNGKKYYFDNNSKAVTGLQTIDSKKYYF
NTNTAEAATGWQTIDGKKYYFNTNTAEAATGWQTIDGKKYYFNTNTAIASTGY
TIINGKHFYFNTDGIMQIGVFKGPNGFEYFAPANTDANNIEGQAILYQNEFLTLNG
KKYYFGSDSKAVTGWRIINNKKYYFNPNNAIAAIHLCTINNDKYYFSYDGILQNG
YITIERNNFYFDANNESKMVTGVFKGPNGFEYFAPANTHNNNIEGQAIVYQNKFL
TLNGKKYYFDNDSKAVTGWQTIDGKKYYFNLNTAEAATGWQTIDGKKYYFNL
NTAEAATGWQTIDGKKYYFNTNTFIASTGYTSINGKHFYFNTDGIMQIGVFKGPN
GFEYFAPANTDANNIEGQAILYQNKFLTLNGKKYYFGSDSKAVTGLRTIDGKKY
YFNTNTAVAVTGWQTINGKKYYFNTNTSIASTGYTIISGKHFYFNTDGIMQIGVF
KGPDGFEYFAPANTDANNIEGQAIRYQNRFLYLHDNIYYFGNNSKAATGWVTID
GNRYYFEPNTAMGANGYKTIDNKNFYFRNGLPQIGVFKGSNGFEYFAPANTDAN
NIEGQAIRYQNRFLHLLGKIYYFGNNSKAVTGWQTINGKVYYFMPDTAMAAAG
GLFEIDGVIYFFGVDGVKAPGIYG SEQ ID NO: 2 - *C. difficile* Toxin B (Toxinotype 0)
MSLVNRKQLEKMANVRFRTQEDEYVAILDALEEYHNMSENTVVEKYLKLKDIN
SLTDIYIDTYKKSGRNKALKKFKEYLVTEVLELKNNNLTPVEKNLHFVWIGGQIN
DTAINYINQWKDVNSDYNVNVFYDSNAFLINTLKKTVVESAINDTLESFRENLND
PRFDYNKFFRKRMEIIYDKQKNFINYYKAQREENPELIIDDIVKTYLSNEYSKEIDE
LNTYIEESLNKITQNSGNDVRNFEEFKNGESFNLYEQELVERWNLAAASDILRISA
LKEIGGMYLDVDMLPGIQPDLFESIEKPSSVTVDFWEMTKLEAIMKYKEYIPEYTS
EHFDMLDEEVQSSFESVLASKSDKSEIFSSLGDMEASPLEVKIAFNSKGIINQGLIS -continued SEQ ID NOs VKDSYCSNLIVKQIENRYKILNNSLNPAISEDNDFNTTTNTFIDSIMAEANADNGR
FMMELGKYLRVGFFPDVKTTINLSGPEAYAAAYQDLLMFKEGSMNIHLIEADLR
NFEISKTNISQSTEQEMASLWSFDDARAKAQFEEYKRNYFEGSLGEDDNLDFSQN
IVVDKEYLLEKISSLARSSERGYIHYIVQLQGDKISYEAACNLFAKTPYDSVLFQK
MEDSEIAYYYNPGDGEIQEIDKYKIPSIISDRPKIKLTFIGHGKDEFNTDIFAGFDV
DSLSTEIEAAIDLAKEDISPKSIEINLLGCNMFSYSINVEETYPGKLLLKVKDKISEL
MPSISQDSIIVSANQYEVRINSEGRRELLDHSGEWINKEESIIKDISSKEYISFNPKEN
KITVKSKNLPELSTLLQEIRNNSNSSDIELEEKVMLTECEINVISNIDTQIVEERIEEA
KNLTSDSINYIKDEFKLIESISDALCDLKQQNELEDSHFISFEDISETDEGFSIRFINK
ETGESIFVETEKTIFSEYANHITEEISKIKGTIFDTVNGKLVKKVNLDTTHEVNTLN
AAFFIQSLIEYNSSKESLSNLSVAMKVQVYAQLFSTGLNTITDAAKVVELVSTALD
ETIDLLPTLSEGLPIIATIIDGVSLGAAIKELSETSDPLLRQEIEAKIGIMAVNLTTAT
TAIITSSLGIASGFSILLVPLAGISAGIPSLVNNELVLRDKATKVVDYFKHVSLVETE
GVFTLLDDKIMMPQDDLVISEIDFNNNSIVLGKCEIWRMEGGSGHTVTDDIDHFF
SAPSITYREPHLSIYDVLEVQKEELDLSKDLMVLPNAPNRVFAWETGWTPGLRSL
ENDGTKLLDRIRDNYEGEFYWRYFAFIADALITTLKPRYEDTNIRINLDSNTRSFIV
PIITTEYIREKLSYSFYGSGGTYALSLSQYNMGINIELSESDVWIIDVDNVVRDVTI
ESDKIKKGDLIEGILSTLSIEENKIILNSHEINFSGEVNGSNGFVSLTFSILEGINAIIE
VDLLSKSYKLLISGELKILMLNSNHIQQKIDYIGFNSELQKNIPYSFVDSEGKENGF
INGSTKEGLFVSELPDVVLISKVYMDDSKPSFGYYSNNLKDVKVITKDNVNILTG
YYLKDDIKISLSLTLQDEKTIKLNSVHLDESGVAEILKFMNRKGNTNTSDSLMSFL
ESMNIKSIFVNFLQSNIKFILDANFIISGTTSIGQFEFICDENDNIQPYFIKFNTLETNY
TLYVGNRQNMIVEPNYDLDDSGDISSTVINFSQKYLYGIDSCVNKVVISPNIYTDE
INITPVYETNNTYPEVIVLDANYINEKINVNINDLSIRYVWSNDGNDFILMSTSEEN
KVSQVKIRFVNVFKDKTLANKLSFNFSDKQDVPVSEIILSFTPSYYEDGLIGYDLG
LVSLYNEKFYINNFGMMVSGLIYINDSLYYFKPPVNNLITGFVTVGD
DKYYFNPINGGAASIGETIIDDKNYYFNQSGVLQTGVFSTEDGFKYFAPANTLDE
NLEGEAIDFTGKLIIDENIYYPDDNYRGAVEWKELDGEMHYFSPETGKAFKGLNQ
IGDYKYYFNSDGVMQKGFVSINDNKHYFDDSGVMKVGYTEIDGKHFYFAENGE
MQIGVFNTEDGFKYFAHHNEDLGNEEGEEISYSGILNFNNKIYYFDDSFTAVVGW
KDLEDGSKYYFDEDTAEAYIGLSLINDGQYYFNDDGIMQVGFVTINDKVFYFSDS
GIIESGVQNIDDNYFYIDDNGIVQIGVFDTSDGYKYFAPANTVNDNIYGQAVEYS
GLVRVGEDVYYFGETYTIETGWIYDMENESDKYYFNPETKKACKGINLIDDIKYY
FDEKGIMRTGLISFENNNYYFNENGEMQFGYINIEDKMFYFGEDGVMQIGVFNTP
DGFKYFAHQNTLDENFEGESINYTGWLDLDEKRYYFTDEYIAATGSVIIDGEEYY
FDPDTAQLVISE SEQ ID NO: 3 - *C. difficile* Toxin A (Toxinotype 3)
MSLISKEELIKLAYSIRPRENEYKTILTNLDEYNKLTTNNNENKYLQLKKLNESID
VFMNKYKNSSRNRALSNLKKDILKEVILIKNSNTSPVEKNLHFVWIGGEVSDIALE
YIKQWADINAEYNIKLWYDSEAFLVNTLKKAIVESSTTEALQLLEEEIQNPQFDN
MKFYKKRMEFIYDRQKRFINYYKSQINKPTVPTIDDIIKSHLVSEYNRDETLLESY
RTNSLRKINSNHGIDIRANSLFTEQELLNIYSQELLNRGNLAAASDIVRLLALKNF
GGVYLDVDMLPGIHSDLFKTIPRPSSIGLDRWEMIKLEAIMKYKKYINNYTSENF
DKLDQQLKDNFKLIIESKSEKSEIFSKLENLNVSDLEIKIAFALGSVINQALISKQGS
YLTNLVIEQVKNRYQFLNQHLNPAIESDNNFTDTTKIFHDSLFNSATAENSMFLTK
IAPYLQVGFMPEARSTISLSGPGAYASAYYDFINLQENTIEKTLKASDLIEFKFPEN
NLSQLTEQEINSLWSFDQASAKYQFEKYVRDYTGGSLSEDNGVDFNKNTALDKN
YLLNNKIPSNNVEEAGSKNYVHYIIQLQGDDISYEATCNLFSKNPKNSIIIQRNMN
ESAKSYFLSDDGESILELNKYRIPERLKNKEKVKVTFIGHGKDEFNTSEFARLSVD
SLSNEISSFLDTIKLDISPKNVEVNLLGCNMFSYDFNVEETYPGKLLLSIMDKITST
LPDVNKDSITIGANQYEVRINSEGRKELLAHSGKWINKEEAIMSDLSSKEYIFFDSI
DNKLKAKSKNIPGLASISEDIKTLLLDASVSPDTKFILNNLKLNIESSIGDYIYYEKL
EPVKNIIHNSIDDLIDEFNLLENVSDELYELKKLNNLDEKYLISFEDISKNNSTYSV
RFINKSNGESVYVETEKEIFSKYSEHITKEISTIKNSIITDVNGNLLDNIQLDHTSQV
NTLNAAFFIQSLIDYSSNKDVLNDLSTSVKVQLYAQLFSTGLNTIYDSIQLVNLISN
AVNDTINVLPTITEGIPIVSTILDGINLGAAIKELLDEHDPLLKKELEAKVGVLAIN
MSLSIAATVASIVGIGAEVTIFLLPIAGISAGIPSLVNNELILHDKATSVVNYFNHLS
ESKKYGPLKTEDDKILVPIDDLVISEIDFNNNSIKLGTCNILAMEGGSGHTVTGNID
HFFSSPYISSHIPSLSVYSAIGIKTENLDFSKKIMMLPNAPSRVFWWETGAVPGLRS
LENNGTKLLDSIRDLYPGKFYWRFYAFFDYAITTLKPVYEDTNTKIKLDKDTRNFI
MPTITTDEIRNKLSYSFDGAGGTYSLLLSSYPISMNINLSKDDLWIFNIDNEVREISI
ENGTIKKGNLIEDVLSKIDINKNKLIIGNQTIDFSGDIDNKDRYIFLTCELDDKISLII
EINLVAKSYSLLLSGDKNYLISNLSNTIEKINTLGLDSKNIAYNYTDESNNKYFGAI
SKTSQKSIIHYKKDSKNILEFYNGSTLEFNSKDFIAEDINVFMKDDINTITGKYYVD
NNTDKSIDFSISLVSKNQVKVNGLYLNESVYSSYLDFVKNSDGHHNTSNFMNLFL
NNISFWKLFGFENINFVIDKYFTLVGKTNLGYVEFICDNNKNIDIYFGEWKTSSSK
STIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIESNLVTGWQTINGKKYYFDINTGAA
STSYKIINGKHFYFNNNGVMQLGVFKGPDGFEYFAPANTQNNNIEGQAIVYQSKF
LTLNGKKYYFDNDSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSGSNG
FEYFAPANTYNNNIEGQAIVYQSKFLTLNGKKYYFDNNSKAVTGWQTIDSKKYY
FNTNTAEAATGWQTIDGKKYYFNTNTAEAATGWQTIDGKKYYFNTNTSIASTGY
TIINGKYFYFNTDGIMQIGVFKVPNGFEYFAPANTHNNNIEGQAILYQNKFLTLNG -continued

| SEQ ID NOs |
|---|
| KKYYFGSDSKAITGWQTIDGKKYYFNPNNAIAATHLCTINNDKYYFSYDGILQN<br>GYITIERNNFYFDANNESKMVTGVFKGPNGFEYFAPANTHNNNIEGQAIVYQNKF<br>LTLNGKKYYFDNDSKAVTGWQTIDSKKYYFNLNTAVAVTGWQTIDGEKYYFNL<br>NTAEAATGWQTIDGKRYYFNTNTYIASTGYTIINGKHFYFNTDGIMQIGVFKGPD<br>GFEYFAPANTHNNNIEGQAILYQNKFLTLNGKKYYFGSDSKAVTGLRTIDGKKY<br>YFNTNTAVAVTGWQTINGKKYYFNTNTYIASTGYTIISGKHFYFNTDGIMQIGVF<br>KGPDGFEYFAPANTDANNIEGQAIRYQNRFLYLHDNIYYFGNDSKAATGWATID<br>GNRYYFEPNTAMGANGYKTIDNKNFYFRNGLPQIGVFKGPNGFEYFAPANTDAN<br>NIDGQAIRYQNRFLHLLGKIYYFGNNSKAVTGWQTINSKVYYFMPDTAMAAAG<br>GLFEIDGVIYFFGVDGVKAPGIYG<br><br>SEQ ID NO: 4 - *C. difficile* Toxin B (Toxinotype 3)<br>MSLVNRKQLEKMANVRFRVQEDEYVAILDALEEYHNMSENTVVEKYLKLKDIN<br>SLTDIYIDTYKKSGRNKALKKFKEYLVTEVLELKNNNLTPVEKNLHFVWIGGQIN<br>DTAINYINQWKDVNSDYNVNVFYDSNAFLINTLKKTIVESATNDTLESFRENLND<br>PRFDYNKFYRKRMEIIYDKQKNFINYYKTQREENPDLIIDDIVKIYLSNEYSKDIDE<br>LNSYIEESLNKVTENSGNDVRNFEEFKGGESFKLYEQELVERWNLAAASDILRISA<br>LKEVGGVYLDVDMLPGIQPDLFESIEKPSSVTVDFWEMVKLEAIMKYKEYIPGYT<br>SEHFDMLDEEVQSSFESVLASKSDKSEIFSSLGDMEASPLEVKIAFNSKGIINQGLI<br>SVKDSYCSNLIVKQIENRYKILNNSLNPAISEDNDFNTTTNAFIDSIMAEANADNG<br>RFMMELGKYLRVGFFPDVKTTINLSGPEAYAAAYQDLLMFKEGSMNIHLIEADL<br>RNFEISKTNISQSTEQEMASLWSFDDARAKAQFEEYKKNYFEGSLGEDDNLDFSQ<br>NTVVDKEYLLEKISSLARSSERGYIHYIVQLQGDKISYEAACNLFAKTPYDSVLFQ<br>KNIEDSEIAYYYNPGDGEIQEIDKYKIPSIISDRPKIKLTFIGHGKDEFNTDIFAGLD<br>VDSLSTEIETAIDLAKEDISPKSIEINLLGCNMFSYSVNVEETYPGKLLLRVKDKVS<br>ELMPSISQDSIIVSANQYEVRINSEGRRELLDHSGEWINKEESIIKDISSKEYISFNPK<br>ENKIIVKSKNLPELSTLLQEIRNNSNSSDIELEEKVMLAECEINVISNIDTQVVEGRI<br>EEAKSLTSDSINYIKNEFKLIESISDALYDLKQQNELEESHFISFEDILETDEGFSIRFI<br>DKETGESIFVETEKAIFSEYANHITEEISKIKGTIFDTVNGKLVKKVNLDATHEVNT<br>LNAAFFIQSLIEYNSSKESLSNLSVAMKVQVYAQLFSTGLNTITDAAKVVELVSTA<br>LDETIDLLPTLSEGLPVIATIIDGVSLGAAIKELSETSDPLLRQEIEAKIGIMAVNLT<br>AATTAIITSSLGIASGFSILLVPLAGISAGIPSLVNNELILRDKATKVVDYFSHISLAE<br>SEGAFTSLDDKIMMPQDDLVISEIDFNNNSITLGKCEIWRMEGGSGHTVTDDIDHF<br>FSAPSITYREPHLSIYDVLEVQKEELDLSKDLMVLPNAPNRVFAWETGWTPGLRS<br>LENDGTKLLDRIRDNYEGEFYWRYFAFIADALITTLKPRYEDTNIRINLDSNTRSFI<br>VPVITTEYIREKLSYSFYGSGGTYALSLSQYNMNINIELNENDTWVIDVDNVVRD<br>VTIESDKIKKGDLIENILSKLSIEDNKIILDNHEINFSGTLNGGNGFVSLTFSILEGIN<br>AVIEVDLLSKSYKVLISGELKTLMANSNSVQQKIDYIGLNSELQKNIPYSFMDDK<br>GKENGFINCSTKEGLFVSELSDVVLISKVYMDNSKPLFGYCSNDLKDVKVITKDD<br>VIILTGYYLKDDIKISLSFTIQDENTIKLNGVYLDENGVAEILKFMNKKGSTNTSDS<br>LMSFLESMNIKSIFINSLQSNTKLILDTNFIISGTTSIGQFEFICDKDNNIQPYFIKFNT<br>LETKYTLYVGNRQNMIVEPNYDLDDSGDISSTVINFSQKYLYGIDSCVNKVIISPNI<br>YTDEINITPIYEANNTYPEVIVLDTNYISEKININ􏰀INDLSIRYVWSNDGSDFILMSTD<br>EENKVSQVKIRFTNVFKGNTISDKISFNFSDKQDVSINKVISTFTPSYYVEGLLNYD<br>LGLISLYNEKFYINNFGMMVSGLVYINDSLYYFKPPIKNLITGFTTIGDDKYYFNP<br>DNGGAASVGETIIDGKNYYFSQNGVLQTGVFSTEDGFKYFAPADTLDENLEGEAI<br>DFTGKLTIDENVYYFGDNYRAAIEWQTLDDEVYYFSTDTGRAFKGLNQIGDDKF<br>YFNSDGIMQKGFVNINDKTFYFDDSGVMKSGYTEIDGKYFYFAENGEMQIGVFN<br>TADGFKYFAHHDEDLGNEEGEALSYSGILNFNNKIYYFDDSFTAVVGWKDLEDG<br>SKYYFDEDTAEAYIGISIINDGKYYFNDSGIMQIGFVTINNEVFYFSDSGIVESGMQ<br>NIDDNYFYIDENGLVQIGVFDTSDGYKYFAPANTVNDNIYGQAVEYSGLVRVGE<br>DVYYFGETYTIETGWIYDMENESDKYYFDPETKKAYKGINVIDDIKYYFDENGIM<br>RTGLITFEDNHYYFNEDGIMQYGYLNIEDKTFYFSEDGIMQIGVFNTPDGFKYFA<br>HQNTLDENFEGESINYTGWLDLDEKRYYFTDEYIAATGSVIIDGEEYYFDPDTAQ<br>LVISE<br><br>SEQ ID NO: 5 - Toxin A fragment - TxA3 (Toxinotype 0)(Residues 1131-2710)<br>ESKKYGPLKTEDDKILVPIDDLVISEIDFNNNSIKLGTCNILAMEGGSGHTVTGNID<br>HFFSSPSISSHIPSLSIYSAIGIETENLDFSKKIMMLPNAPSRVFWWETGAVPGLRSL<br>ENDGTRLLDSIRDLYPGKFYWRFYAFFDYAITTLKPVYEDTNIKIKLDKDTRNFIM<br>PTITTNEIRNKLSYSFDGAGGTYSLLLSSYPISTNINLSKDDLWIFNIDNEVREISIEN<br>GTIKKGKLIKDVLSKIDINKNKLIIGNQTIDFSGDIDNKDRYIFLTCELDDKISLIIEI<br>NLVAKSYSLLLSGDKNYLISNLSNIIEKINTLGLDSKNIAYNYTDESNNKYFGAISK<br>TSQKSIIHYKKDSKNILEFYNDSTLEFNSKDFIAEDINVFMKDDINTITGKYYVDN<br>NTDKSIDFSISLVSKNQVKVNGLYLNESVYSSYLDFVKNSDGHHNTSNFMNLFLD<br>NISFWKLFGFENINFVIDKYFTLVGKTNLGYVEFICDNNKNIDIYFGEWKTSSSKS<br>TIFSGNGRNVVVEPIYNPDTGEDISTSLDFSYEPLYGIDRYINKVLIAPDLYTSLINI<br>NTNYYSNEYYPEIIVLNPNTFHKKVNINLDSSSFEYKWSTEGSDFILVRYLEESNK<br>KILQKIRIKGILSNTQSFNKMSIDFKDIKKLSLGYIMSNFKSFNSENELDRDHLGFKI<br>IDNKTYYYDEDSKLVKGLININNSLFYFDPIEFNLVTGWQTINGKKYYFDINTGAA<br>LISYKIINGKHFYFNNDGVMQLGVFKGPDGFEYFAPANTQNNNIEGQAIVYQSKF<br>LTLNGKKYYFDNDSKAVTGWRIINNEKYYFNPNNAIAAVGLQVIDNNKYYFNPD<br>TAIISKGWQTVNGSRYYFDTDTAIAFNGYKTIDGKHFYFDSDCVVKIGVFSTSNG<br>FEYFAPANTYNNNIEGQAIVYQSKFLTLNGKKYYFDNNSKAVTGWQTIDSKKYY<br>FNTNTAEAATGWQTIDGKKYYFNTNTAEAATGWQTIDGKKYYFNTNTAIASTG<br>YTIINGKHFYFNTDGIMQIGVFKGPNGFEYFAPANTDANNIEGQAILYQNEFLTLN<br>GKKYYFGSDSKAVTGWRIINNKKYYFNPNNAIAAIHLCTINNDKYYFSYDGILQN |

-continued

| SEQ ID NOs |
|---|
| GYITIERNNFYFDANNESKMVTGVFKGPNGFEYFAPANTHNNNIEGQAIVYQNKF<br>LTLNGKKYYFDNDSKAVTGWQTIDGKKYYFNLNTAEAATGWQTIDGKKYYFNL<br>NTAEAATGWQTIDGKKYYFNTNTFIASTGYTSINGKHFYFNTDGIMQIGVFKGPN<br>GFEYFAPANTHNNNIEGQAILYQNKFLTLNGKKYYFGSDSKAVTGLRTIDGKKY<br>YFNTNTAVAVTGWQTINGKKYYFNTNTSIASTGYTIISGKHFYFNTDGIMQIGVF<br>KGPDGFEYFAPANTDANNIEGQAIRYQNRFLYLHDNIYYFGNNSKAATGWVTID<br>GNRYYFEPNTAMGANGYKTIDNKNFYFRNGLPQIGVFKGSNGFEYFAPANTDAN<br>NIEGQAIRYQNRFLHLLGKIYYFGNNSKAVTGWQTINGKVYYFMPDTAMAAAG<br>GLFEIDGVIYFFGVDGVKAPGIYG |
| SEQ ID NO: 6 - Toxin A fragment - TxA3 (Toxinotype 3)(Residues 1131-2710)<br>ESKKYGPLKTEDDKILVPIDDLVISEIDFNNNSIKLGTCNILAMEGGSGHTVTGNID<br>HFFSSPSISSHIPSLSIYSAIGIETENLDFSKKIMMLPNAPSRVFWWETGAVPGLRSL<br>ENDGTRLLDSIRDLYPGKFYWRFYAFFDYAITTLKPVYEDTNIKIKLDKDTRNFIM<br>PTITTNEIRNKLSYSFDGAGGTYSLLLSSYPISTNINLSKDDLWIFNIDNEVREISIEN<br>GTIKKGKLIKDVLSKIDINKNKLIIGNQTIDFSGDIDNKDRYIFLTCELDDKISLIIEI<br>NLVAKSYSLLLSGDKNYLISNLSNTIEKINTLGLDSKNIAYNYTDESNNKYFGAIS<br>KTSQKSIIHYKKDSKNILEFYNDSTLEFNSKDFIAEDINVFMKDDINTITGKYYVD<br>NNTDKSIDFSISLVSKNQVKVNGLYLNESVYSSYLDFVKNSDGHHNTSNFMNLFL<br>DNISFWKLFGFENINFVIDKYFTLVGKTNLGYVEFICDNNKNIDIYFGEWKTSSSK<br>STIFSGNGRNVVVEPIYNPDTGEDISTSLDFSYEPLYGIDRYINKVLIAPDLYTSLINI<br>NTNYYSNEYYPEIIVLNPNTFHKKVNINLDSSSFEYKWSTEGSDFILVRYLEESNK<br>KILQKIRIKGILSNTQSFNKMSIDFKDIKKLSLGYIMSNFKSFNSENELDRDHLGFKI<br>IDNKTYYYDEDSKLVKGLININNSLFYFDPIEFNLVTGWQTINGKKYYFDINTGAA<br>LTSYKIINGKHFYFNNDGVMQLGVFKGPDGFEYFAPANTQNNNIEGQAIVYQSKF<br>LTLNGKKYYFDNNSKAVTGWRIINNEKYYFNPNNAIAAVGLQVIDNNKYYFNPD<br>TAIISKGWQTVNGSRYYFDTDTAIAFNGYKTIDGKHFYFDSDCVVKIGVFSTSNG<br>FEYFAPANTYNNNIEGQAIVYQSKFLTLNGKKYYFDNNSKAVTGLQTIDSKKYYF<br>NTNTAEAATGWQTIDGKKYYFNTNTAEAATGWQTIDGKKYYFNTNTAIASTGY<br>TIINGKHFYFNTDGIMQIGVFKGPNGFEYFAPANTDANNIEGQAILYQNEFLTLNG<br>KKYYFGSDSKAVTGWRIINNKKYYFNPNNAIAAIHLCTINNDKYYFSYDGILQNG<br>YITIERNNFYFDANNESKMVTGVFKGPNGFEYFAPANTHNNNIEGQAIVYQNKFL<br>TLNGKKYYFDNDSKAVTGWQTIDGKKYYFNLNTAEAATGWQTIDGKKYYFNL<br>NTAEAATGWQTIDGKKYYFNTNTFIASTGYTSINGKHFYFNTDGIMQIGVFKGPN<br>GFEYFAPANTDANNIEGQAILYQNKFLTLNGKKYYFGSDSKAVTGLRTIDGKKY<br>YFNTNTAVAVTGWQTINGKKYYFNTNTSIASTGYTIISGKHFYFNTDGIMQIGVF<br>KGPDGFEYFAPANTDANNIEGQAIRYQNRFLYLHDNIYYFGNNSKAATGWVTID<br>GNRYYFEPNTAMGANGYKTIDNKNFYFRNGLPQIGVFKGSNGFEYFAPANTDAN<br>NIEGQAIRYQNRFLHLLGKIYYFGNNSKAVTGWQTINGKVYYFMPDTAMAAAG<br>GLFEIDGVIYFFGVDGVKAPGIYG |
| SEQ ID NO: 7 - Toxin A fragment - TxA4 (Toxinotype 0)(Residues 770-2710)<br>IMSDLSSKEYIFFDSIDNKLKAKSKNIPGLASISEDIKTLLLDASVSPDTKFILNNLK<br>LNIESSIGDYIYYEKLEPVKNIIHNSIDDLIDEFNLLENVSDELYELKKLNNLDEKY<br>LISFEDISKNNSTYSVRFINKSNGESVYVETEKEIFSKYSEHITKEISTIKNSIITDVN<br>GNLLDNIQLDHTSQVNTLNAAFFIQSLIDYSSNKDVLNDLSTSVKVQLYAQLFST<br>GLNTIYDSIQLVNLISNAVNDTINVLPTITEGIPIVSTILDGINLGAAIKELLDEHDPL<br>LKKELEAKVGVLAINMSLSIAATVASIVGIGAEVTIFLLPIAGISAGIPSLVNNELIL<br>HDKATSVVNYFNHLSESKKYGPLKTEDDKILVPIDDLVISEIDFNNNSIKLGTCNIL<br>AMEGGSGHTVTGNIDHFFSSPSISSHIPSLSIYSAIGIETENLDFSKKIMMLPNAPSR<br>VFWWETGAVPGLRSLENDGTRLLDSIRDLYPGKFYWRFYAFFDYAITTLKPVYE<br>DTNIKIKLDKDTRNFIMPTITTNEIRNKLSYSPDGAGGTYSLLLSSYPISTNINLSKD<br>DLWIFNIDNEVREISIENGTIKKGKLIKDVLSKIDINKNKLIIGNQTIDFSGDIDNKD<br>RYIFLTCELDDKISLIIEINLVAKSYSLLLSGDKNYLISNLSNIIEKINTLGLDSKNIA<br>YNYTDESNNKYFGAISKTSQKSIIHYKKDSKNILEFYNDSTLEFNSKDFIAEDINVF<br>MKDDINTITGKYYVDNNTDKSIDFSISLVSKNQVKVNGLYLNESVYSSYLDFVKN<br>SDGHHNTSNFMNLFLDNISFWKLFGFENINFVIDKYFTLVGKTNLGYVEFICDNN<br>KNIDIYFGEWKTSSSKSTIFSGNGRNVVVEPIYNPDTGEDISTSLDFSYEPLYGIDR<br>YINKVLIAPDLYTSLININTNYYSNEYYPEIIVLNPNTFHKKVNINLDSSSFEYKWS<br>TEGSDFILVRYLEESNKKILQKIRIKGILSNTQSFNKMSIDFKDIKKLSLGYIMSNFK<br>SFNSENELDRDHLGFKIIDNKTYYYDEDSKLVKGLININNSLFYFDPIEFNLVTGW<br>QTINGKKYYFDINTGAALISYKIINGKHFYFNNDGVMQLGVFKGPDGFEYFAPAN<br>TQNNNIEGQAIVYQSKFLTLNGKKYYFDNDSKAVTGWRIINNEKYYFNPNNAIA<br>AVGLQVIDNNKYYFNPDTAIISKGWQTVNGSRYYFDTDTAIAFNGYKTIDGKHF<br>YFDSDCVVKIGVFSTSNGFEYFAPANTYNNNIEGQAIVYQSKFLTLNGKKYYFDN<br>NSKAVTGWQTIDSKKYYFNTNTAEAATGWQTIDGKKYYFNTNTAEAATGWQTI<br>DGKKYYFNTNTAIASTGYTIINGKHFYFNTDGIMQIGVFKGPNGFEYFAPANTDA<br>NNIEGQAILYQNEFLTLNGKKYYFGSDSKAVTGWRIINNKKYYFNPNNAIAAIHL<br>CTINNDKYYFSYDGILQNGYITIERNNFYFDANNESKMVTGVFKGPNGFEYFAPA<br>NTHNNNIEGQAIVYQNKFLTLNGKKYYFDNDSKAVTGWQTIDGKKYYFNLNTA<br>EAATGWQTIDGKKYYFNLNTAEAATGWQTIDGKKYYFNTNTFIASTGYTSINGK<br>HFYFNTDGIMQIGVFKGPNGFEYFAPANTHNNNIEGQAILYQNKFLTLNGKKYYF<br>GSDSKAVTGLRTIDGKKYYFNTNTAVAVTGWQTINGKKYYFNTNTSIASTGYTII<br>SGKHFYFNTDGIMQIGVFKGPDGFEYFAPANTDANNIEGQAIRYQNRFLYLHDNI<br>YYFGNNSKAATGWVTIDGNRYYFEPNTAMGANGYKTIDNKNFYFRNGLPQIGV<br>FKGSNGFEYFAPANTDANNIEGQAIRYQNRFLHLLGKIYYFGNNSKAVTGWQTIN<br>GKVYYFMPDTAMAAAGGLFEIDGVIYFFGVDGVKAPGIYG |

-continued

| SEQ ID NOs |
|---|

SEQ ID NO: 8 - Toxin A fragment - TxA4 (Toxinotype 3)(Residues 770-2710)
IMSDLSSKEYIFFDSIDNKLKAKSKNIPGLASISEDIKTLLLDASVSPDTKFILNNLK
LNIESSIGDYIYYEKLEPVKNIIHNSIDDLIDEFNLLENVSDELYELKKLNNLDEKY
LISFEDISKNNSTYSVRFINKSNGESVYVETEKEIFSKYSEHITKEISTIKNSIITDVN
GNLLDNIQLDHTSQVNTLNAAFFIQSLIDYSSNKDVLNDLSTSVKVQLYAQLFST
GLNTIYDSIQLVNLISNAVNDTINVLPTITEGIPIVSTILDGINLGAAIKELLDEHDPL
LKKELEAKVGVLAINMSLSIAATVASIVGIGAEVTIFLLPIAGISAGIPSLVNNELIL
HDKATSVVNYFNHLSESKEYGPLKTEDDKILVPIDDLVISEIDFNNNSIKLGTCNIL
AMEGGSGHTVTGNIDHFFSSPYISSHIPSLSVYSAIGIKTENLDFSKKIMMLPNAPS
RVFWWETGAVPGLRSLENNGTKLLDSIRDLYPGKFYWRFYAFFDYAITTLKPVY
EDTNTKIKLDKDTRNFIMPTITTDEIRNKLSYSFDGAGGTYSLLLSSYPISMNINLS
KDDLWIFNIDNEVREISIENGTIKKGNLIEDVLSKIDINKNKLIIGNQTIDFSGDIDN
KDRYIFLTCELDDKISLIIEINLVAKSYSLLLSGDKNYLISNLSNTIEKINTLGLDSK
NIAYNYTDESNNKYFGAISKTSQKSIIHYKKDSKNILEFYNGSTLEFNSKDFIAEDI
NVFMKDDINTITGKYYVDNNTDKSIDFSISLVSKNQVKVNGLYLNESVYSSYLDF
VKNSDGHHNTSNFMNLFLNNISFWKLFGFENINFVIDKYFTLVGKTNLGYVEFIC
DNNKNIDIYFGEWKTSSSKSTIFSGNGRNVVVEPIYNPDTGEDISTSLDFSYEPLYG
IDRYINKVLIAPDLYTSLININTNYYSNEYYPEIIVLNPNTFHKKVNINLDSSSFEYK
WSTEGSDFILVRYLEESNKKILQKIRIKGILSNTQSFNKMSIDFKDIKKLSLGYIMS
NFKSFNSENELDRDHLGFKIIDNKTYYYDEDSKLVKGLININNSLFYFDPIESNLVT
GWQTINGKKYYPDINTGAASTSYKIINGKHFYFNNNGVMQLGVFKGPDGFEYFA
PANTQNNNIEGQAIVYQSKFLTLNGKKYYFDNDSKAVTGWRIINNEKYYFNPNN
AIAAVGLQVIDNNKYYFNPDTAIISKGWQTVNGSRYYFDTDTAIAFNGYKTIDGK
HFYFDSDCVVKIGVFSGSNGFEYFAPANTYNNNIEGQAIVYQSKFLTLNGKKYYF
DNNSKAVTGWQTIDSKKYYFNTNTAEAATGWQTIDGKKYYFNTNTAEAATGW
QTIDGKKYYFNTNTSIASTGYTIINGKYFYFNTDGIMQIGVFKVPNGFEYFAPANT
HNNNIEGQAILYQNKFLTLNGKKYYFGSDSKAITGWQTIDGKKYYFNPNNAIAA
THLCTINNDKYYFSYDGILQNGYITIERNNFYFDANNESKMVTGVFKGPNGFENF
APANTHNNNIEGQAIVYQNKFLTLNGKKYYPDNDSKAVTGWQTIDSKKYYFNL
NTAVAVTGWQTIDGEKYYFNLNTAEAATGWQTIDGKRYYFNTNTYIASTGYTII
NGKHFYFNTDGIMQIGVFKGPDGFEYFAPANTHNNNIEGQAILYQNKFLTLNGK
KYYFGSDSKAVTGLRTIDGKKYYFNTNTAVAVTGWQTINGKKYYFNTNTYIAST
GYTIISGKHFYFNTDGIMQIGVFKGPDGFEYFAPANTDANNIEGQAIRYQNRFLYL
HDNIYYFGNDSKAATGWATIDGNRYYFEPNTAMGANGYKTIDNKNFYFRNGLP
QIGVFKGPNGFEYFAPANTDANNIDGQAIRYQNRFLHLLGKIYYFGNNSKAVTG
WQTINSKVYYFMPDTAMAAAGGLFEIDGVIYFFGVDGVKAPGIYG SEQ ID NO: 9 - Toxin B fragment - TxB3(-h)(Toxinotype 0)(Residues 1145-2366)
MPQDDLVISEIDFNNNSIVLGKCEIWRMEGGSGHTVTDDIDHFFSAPSITYREPHL
SIYDVLEVQKEELDLSKDLMVLPNAPNRVFAWETGWTPGLRSLENDGTKLLDRI
RDNYEGEFYWRYFAFIADALITTLKPRYEDTNIRINLDSNTRSFIVPIITTEYIREKL
SYSFYGSGGTYALSLSQYNMGINIELSESDVWIIDVDNVVRDVTIESDKIKKGDLI
EGILSTLSIEENKIILNSHEINFSGEVNGSNGFVSLTFSILEGINAIIEVDLLSKSYKLL
ISGELKILMLNSNHIQQKIDYIGFNSELQKNIPYSFVDSEGKENGFINGSTKEGLFV
SELPDVVLISKVYMDDSKPSFGYYSNNLKDVKVITKDNVNILTGYYLKDDIKISLS
LTLQDEKTIKLNSVHLDESGVAEILKFMNRKGNTNTSDSLMSFLESMNIKSIFVNF
LQSNIKFILDANFIISGTTSIGQFEFICDENDNIQPYFIKFNTLETNYTLYVGNRQNM
IVEPNYDLDDSGDISSTVINFSQKYLYGIDSCVNKVVISPNIYTDEINITPVYETNNT
YPEVIVLDANYINEKINVNINDLSIRYVWSNDGNDFILMSTSEENKVSQVKIRFVN
VFKDKTLANKLSFNFSDKQDVPVSEIILSFTPSYYEDGLIGYDLGLVSLYNEKFYI
NNFGMMVSGLIYINDSLYYFKPPVNNLITGFVTVGDDKYYFNPINGGAASIGETII
DDKNYYFNQSGVLQTGVFSTEDGFKYFAPANTLDENLEGEAIDFTGKLIIDENIY
YFDDNYRGAVEWKELDGEMHYFSPETGKAFKGLNQIGDYKYYFNSDGVMQKG
FVSINDNKHYFDDSGVMKVGYTEIDGKHFYFAENGEMQIGVFNTEDGFKYFAHH
NEDLGNEEGEEISYSGILNFNNKIYYFDDSFTAVVGWKDLEDGSKYYFDEDTAEA
YIGLSLINDGQYYFNDDGIMQVGFVTINDKVFYFSDSGIIESGVQNIDDNYFYIDD
NGIVQIGVFDTSDGYKYFAPANTVNDNIYGQAVEYSGLVRVGEDVYYFGETYTI
ETGWIYDMENESDKYYFNPETKKACKGINLIDDIKYYFDEKGIMRTGLISFENNN
YYFNENGEMQFGYINIEDKMFYFGEDGVMQIGVFNTPDGFKYFAHQNTLDENFE
GESINYTGWLDLDEKRYYFTDEYIAATGSVIIDGEEYYPDPDTAQLVISE SEQ ID NO: 10 - Toxin B fragment - TxB3(-h)(Toxinotype 3)(Residues 1145-2366)
MPQDDLVISEIDFNNNSITLGKCEIWRMEGGSGHTVTDDIDHFFSAPSITYREPHLS
IYDVLEVQKEELDLSKDLMVLPNAPNRVFAWETGWTPGLRSLENDGTKLLDRIR
DNYEGEFYWRYFAFIADALITTLKPRYEDTNIRINLDSNTRSFIVPVITTEYIREKLS
YSFYGSGGTYALSLSQYNMNINIELNENDTWVIDVDNVVRDVTIESDKIKKGDLI
ENILSKLSIEDNKIILDNHEINFSGTLNGGNGFVSLTFSILEGINAVIEVDLLSKSYK
VLISGELKTLMANSNSVQQKIDYIGLNSELQKNIPYSFMDDKGKENGFINCSTKEG
LFVSELSDVVLISKVYMDNSKPLFGYCSNDLKDVKVITKDDVIILTGYYLKDDIKI
SLSFTIQDENTIKLNGVYLDENGVAEILKFMNKKGSTNTSDSLMSFLESMNIKSIFI
NSLQSNTKLILDTNFIISGTTSIGQFEFICDKDNNIQPYFIKFNTLETKYTLYVGNRQ
NMIVEPNYDLDDSGDISSTVINFSQKYLYGIDSCVNKVIISPNIYTDEINITPIYEAN
NTYPEVIVLDTNYISEKININIDLSIRYVWSNDGSDFILMSTDEENKVSQVKIRFT
NVFKGNTISDKISFNFSDKQDVSINKVISTFTPSYYVEGLLNYDLGLISLYNEKFYI
NNFGMMVSGLVYINDSLYYFKPPIKNLITGFTTIGDDKYYFNPDNGGAASVGETII
DGKNYYFSQNGVLQTGVFSTEDGFKYFAPADTLDENLEGEAIDFTGKLTIDENVY -continued SEQ ID NOs YFGDNYRAAIEWQTLDDEVYYFSTDTGRAFKGLNQIGDDKFYFNSDGIMQKGFV
NINDKTFYFDDSGVMKSGYTEIDGKYFYFAENGEMQIGVFNTADGFKYFAHHDE
DLGNEEGEALSYSGILNFNNKIYYFDDSFTAVVGWKDLEDGSKYYFDEDTAEAY
IGISIINDGKYYFNDSGIMQIGFVTINNEVFYFSDSGIVESGMQNIDDNYFYIDENG
LVQIGVFDTSDGYKYFAPANTVNDNIYGQAVEYSGLVRVGEDVYYFGETYTIET
GWIYDMENESDKYYPDPETKKAYKGINVIDDIKYYFDENGIMRTGLITFEDNHYY
FNEDGIMQYGYLNIEDKTFYFSEDGIMQIGVFNTPDGFKYFAHQNTLDENFEGESI
NYTGWLDLDEKRYYFTDEYIAATGSVIIDGEEYYPDPDTAQLVISE SEQ ID NO: 11 - Toxin B fragment - TxB3 (Toxinotype 0)(Residues 957-2366)
NTLNAAFFIQSLIEYNSSKESLSNLSVAMKVQVYAQLFSTGLNTITDAAKVVELVS
TALDETIDLLPTLSEGLPIIATIIDGVSLGAAIKELSETSDPLLRQEIEAKIGIMAVNL
TTATTAIITSSLGIASGFSILLVPLAGISAGIPSLVNNELVLRDKATKVVDYFKHVSL
VETEGVFTLLDDKIMMPQDDLVISEIDFNNNSIVLGKCEIWRMEGGSGHTVTDDI
DHFFSAPSITYREPHLSIYDVLEVQKEELDLSKDLMVLPNAPNRVFAWETGWTPG
LRSLENDGTKLLDRIRDNYEGEFYWRYFAFIADALITTLKPRYEDTNIRINLDSNT
RSFIVPIITTEYIREKLSYSFYGSGGTYALSLSQYNMGINIELSESDVWIIDVDNVVR
DVTIESDKIKKGDLIEGILSTLSIEENKIILNSHEINFSGEVNGSNGFVSLTFSILEGIN
AIIEVDLLSKSYKLLISGELKILMLNSNHIQQKIDYIGFNSELQKNIPYSFVDSEGKE
NGFINGSTKEGLFVSELPDVVLISKVYMDDSKPSFGYYSNNLKDVKVITKDNVNI
LTGYYLKDDIKISLSLTLQDEKTIKLNSVHLDESGVAEILKFMNRKGNTNTSDSL
MSFLESMNIKSIFVNFLQSNIKFILDANFIISGTTSIGQFEFICDENDNIQPYFIKFNTL
ETNYTLYVGNRQNMIVEPNYDLDDSGDISSTVINFSQKYLYGIDSCVNKVVISPNI
YTDEINITPVYETNNTYPEVIVLDANYINEKINVNINDLSIRYVWSNDGNDFILMST
SEENKVSQVKIRFVNVFKDKTLANKLSFNFSDKQDVPVSEIILSFTPSYYEDGLIG
YDLGLVSLYNEKFYINNFGMMVSGLIYINDSLYYFKPPVNNLITGFVTVGDDKYY
FNPINGGAASIGETIIDDKNYYFNQSGVLQTGVFSTEDGFKYFAPANTLDENLEGE
AIDFTGKLIIDENIYYFDDNYRGAVEWKELDGEMHYFSPETGKAFKGLNQIGDYK
YYFNSDGVMQKGFVSINDNKHYFDDSGVMKVGYTEIDGKHFYFAENGEMQIGV
FNTEDGFKYFAHHNEDLGNEEGEEISYSGILNFNNKIYYFDDSFTAVVGWKDLED
GSKYYFDEDTAEAYIGLSLINDGQYYFNDDGIMQVGFVTINDKVFYFSDSGIIESG
VQNIDDNYFYIDDNGIVQIGVFDTSDGYKYFAPANTVNDNIYGQAVEYSGLVRV
GEDVYYFGETYTIETGWIYDMENESDKYYFNPETKKACKGINLIDDIKYYFDEKG
IMRTGLISFENNNYYFNENGEMQFGYINIEDKMFYFGEDGVMQIGVFNTPDGFKY
FAHQNTLDENFEGESINYTGWLDLDEKRYYFTDEYIAATGSVIIDGEEYYPDPDT
AQLVISE SEQ ID NO: 12 - Toxin B fragment - TxB3 (Toxinotype 3)(Residues 957-2366)
NTLNAAFFIQSLIEYNSSKESLSNLSVAMKVQVYAQLFSTGLNTITDAAKVVELVS
TALDETIDLLPTLSEGLPVIATIIDGVSLGAAIKELSETSDPLLRQEIEAKIGIMAVN
LTAATTAIITSSLGIASGFSILLVPLAGISAGIPSLVNNELILRDKATKVVDYFSHISL
AESEGAFTSLDDKIMMPQDDLVISEIDFNNNSITLGKCEIWRMEGGSGHTVTDDID
HFFSAPSITYREPHLSIYDVLEVQKEELDLSKDLMVLPNAPNRVFAWETGWTPGL
RSLENDGTKLLDRIRDNYEGEFYWRYFAFIADALITTLKPRYEDTNIRINLDSNTR
SFIVPVITTEYIREKLSYSFYGSGGTYALSLSQYNMNINIELNENDTWVIDVDNVV
RDVTIESDKIKKGDLIENILSKLSIEDNKIILDNHEINFSGTLNGGNGFVSLTFSILEG
INAVIEVDLLSKSYKVLISGELKTLMANSNSVQQKIDYIGLNSELQKNIPYSFMDD
KGKENGFINCSTKEGLFVSELSDVVLISKVYMDNSKPLFGYCSNDLKDVKVITKD
DVIILTGYYLKDDIKISLSFTIQDENTIKLNGVYLDENGVAEILKFMNKKGSTNTSD
SLMSFLESMNIKSIFINSLQSNTKLILDTNFIISGTTSIGQFEFICDKDNNIQPYFIKFN
TLETKYTLYVGNRQNMIVEPNYDLDDSGDISSTVINFSQKYLYGIDSCVNKVIISP
NIYTDEINITPIYEANNTYPEVIVLDTNYISEKININIQNDLSIRYVWSNDGSDFILMST
DEENKVSQVKIRFTNVFKGNTISDKISFNFSDKQDVSINKVISTFTPSYYVEGLLNY
DLGLISLYNEKFYINNFGMMVSGLVYINDSLYYFKPPIKNLITGFTTIGDDKYYFN
PDNGGAASVGETIIDGKNYYFSQNGVLQTGVFSTEDGFKYFAPADTLDENLEGE
AIDFTGKLTIDENVYYFGDNYRAAIEWQTLDDEVYYFSTDTGRAFKGLNQIGDD
KFYFNSDGIMQKGFVNINDKTFYFDDSGVMKSGYTEIDGKYFYFAENGEMQIGV
FNTADGFKYFAHHDEDLGNEEGEALSYSGILNFNNKIYYFDDSFTAVVGWKDLE
DGSKYYFDEDTAEAYIGISIINDGKYYFNDSGIMQIGFVTINNEVFYFSDSGIVESG
MQNIDDNYFYIDENGLVQIGVFDTSDGYKYFAPANTVNDNIYGQAVEYSGLVRV
GEDVYYFGETYTIETGWIYDMENESDKYYFDPETKKAYKGINVIDDIKYYFDEN
GIMRTGLITFEDNHYYFNEDGIMQYGYLNIEDKTFYFSEDGIMQIGVFNTPDGFK
YFAHQNTLDENFEGESINYTGWLDLDEKRYYFTDEYIAATGSVIIDGEEYYFDPD
TAQLVISE SEQ ID NO: 13 - Toxin B fragment - TxB 4 (Toxinotype 0)(Residues 767-2366)
SIIKDISSKEYISFNPKENKITVKSKNLPELSTLLQEIRNNSNSSDIELEEKVMLTECE
INVISNIDTQIVEERIEEAKNLTSDSINYIKDEFKLIESISDALCDLKQQNELEDSHFI
SFEDISETDEGFSIRFINKETGESIFVETEKTIFSEYANHITEEISKIKGTIFDTVNGKL
VKKVNLDTTHEVNTLNAAFFIQSLIEYNSSKESLSNLSVAMKVQVYAQLFSTGLN
TITDAAKVVELVSTALDETIDLLPTLSEGLPIIATIIDGVSLGAAIKELSETSDPLLRQ
EIEAKIGIMAVNLTTATTAIITSSLGIASGFSILLVPLAGISAGIPSLVNNELVLRDKA
TKVVDYFKHVSLVETEGVFTLLDDKIMMPQDDLVISEIDFNNNSIVLGKCEIWRM
EGGSGHTVTDDIDHFFSAPSITYREPHLSIYDVLEVQKEELDLSKDLMVLPNAPNR
VFAWETGWTPGLRSLENDGTKLLDRIRDNYEGEFYWRYFAFIADALITTLKPRYE
DTNIRINLDSNTRSFIVPIITTEYIREKLSYSFYGSGGTYALSLSQYNMGINIELSESD
VWIIDVDNVVRDVTIESDKIKKGDLIEGILSTLSIEENKIILNSHEINFSGEVNGSNG -continued SEQ ID NOs FVSLTFSILEGINAIIEVDLLSKSYKLLISGELKILMLNSNHIQQKIDYIGFNSELQKN
IPYSFVDSEGKENGFINGSTKEGLFVSELPDVVLISKVYMDDSKPSFGYYSNNLKD
VKVITKDNVNILTGYYLKDDIKISLSLTLQDEKTIKLNSVHLDESGVAEILKFMNR
KGNTNTSDSLMSFLESMNIKSIFVNFLQSNIKFILDANFIISGTTSIGQFEFICDENDN
IQPYFIKFNTLETNYTLYVGNRQNMIVEPNYDLDDSGDISSTVINFSQKYLYGIDS
CVNKVVISPNIYTDEINITPVYETNNTYPEVIVLDANYINEKINVNINDLSIRYVWS
NDGNDFILMSTSEENKVSQVKIRFVNVFKDKTLANKLSFNFSDKQDVPVSEIILSF
TPSYYEDGLIGYDLGLVSLYNEKFYINNFGMMVSGLIYINDSLYYFKPPVNNLITG
FVTVGDDKYYFNPINGGAASIGETIIDDKNYYFNQSGVLQTGVFSTEDGFKYFAP
ANTLDENLEGEAIDFTGKLIIDENIYYFDDNYRGAVEWKELDGEMHYFSPETGKA
FKGLNQIGDYKYYFNSDGVMQKGFVSINDNKHYFDDSGVMKVGYTEIDGKHFY
FAENGEMQIGVFNTEDGFKYFAHHNEDLGNEEGEEISYSGILNFNNKIYYFDDSFT
AVVGWKDLEDGSKYYFDEDTAEAYIGLSLINDGQYYFNDDGIMQVGFVTINDK
VFYFSDSGIIESGVQNIDDNYFYIDDNGIVQIGVFDTSDGYKYFAPANTVNDNIYG
QAVEYSGLVRVGEDVYYFGETYTIETGWIYDMENESDKYYFNPETKKACKGINL
IDDIKYYFDEKGIMRTGLISFENNNYYFNENGEMQFGYINIEDKMFYFGEDGVMQ
IGVFNTPDGFKYFAHQNTLDENFEGESINYTGWLDLDEKRYYFTDEYIAATGSVII
DGEEYYFDPDTAQLVISE SEQ ID NO: 14 - Toxin B fragment - TxB 4 (Toxinotype 3)(Residues 767-2366)
SIIKDISSKEYISFNPKENKIIVKSKNLPELSTLLQEIRNNSNSSDIELEEKVMLAECE
INVISNIDTQVVEGRIEEAKSLTSDSINYIKNEFKLIESISDALYDLKQQNELEESHFI
SFEDILETDEGFSIRFIDKETGESIFVETEKAIFSEYANHITEEISKIKGTIFDTVNGKL
VKKVNLDATHEVNTLNAAFFIQSLIEYNSSKESLSNLSVAMKVQVYAQLFSTGLN
TITDAAKVVELVSTALDETIDLLPTLSEGLPVIATIIDGVSLGAAIKELSETSDPLLR
QEIEAKIGIMAVNLTAATTAIITSSLGIASGFSILLVPLAGISAGIPSLVNNELILRDK
ATKVVDYFSHISLAESEGAFTSLDDKIMMPQDDLVISEIDFNNNSITLGKCEIWRM
EGGSGHTVTDDIDHFFSAPSITYREPHLSIYDVLEVQKEELDLSKDLMVLPNAPNR
VFAWETGWTPGLRSLENDGTKLLDRIRDNYEGEFYWRYFAFIADALITTLKPRYE
DTNIRINLDSNTRSFIVPVITTEYIREKLSYSFYGSGGTYALSLSQYNMNINIELNEN
DTWVIDVDNVVRDVTIESDKIKKGDLIENILSKLSIEDNKIILDNHEINFSGTLNGG
NGFVSLTFSILEGINAVIEVDLLSKSYKVLISGELKTLMANSNSVQQKIDYIGLNSE
LQKNIPYSFMDDKGKENGFINCSTKEGLFVSELSDVVLISKVYMDNSKPLFGYCS
NDLKDVKVITKDDVIILTGYYLKDDIKISLSFTIQDENTIKLNGVYLDENGVAEILK
FMNKKGSTNTSDSLMSFLESMNIKSIFINSLQSNTKLILDTNFIISGTTSIGQFEFICD
KDNNIQPYFIKFNTLETKYTLYVGNRQNMIVEPNYDLDDSGDISSTVINFSQKYLY
GIDSCVNKVIISPNIYTDEINITPIYEANNTYPEVIVLDTNYISEKININININDLSIRYV
WSNDGSDFILMSTDEENKVSQVKIRFTNVFKGNTISDKISFNFSDKQDVSINKVIST
FTPSYYVEGLLNYDLGLISLYNEKFYINNFGMMVSGLVYINDSLYYFKPPIKNLIT
GFTTIGDDKYYFNPDNGGAASVGETIIDGKNYYFSQNGVLQTGVFSTEDGFKYFA
PADTLDENLEGEAIDFTGKLTIDENVYYFGDNYRAAIEWQTLDDEVYYFSTDTGR
AFKGLNQIGDDKFYFNSDGIMQKGFVNINDKTFYFDDSGVMKSGYTEIDGKYFY
FAENGEMQIGVFNTADGFKYFAHHDEDLGNEEGEALSYSGILNFNNKIYYFDDSF
TAVVGWKDLEDGSKYYFDEDTAEAYIGISIINDGKYYFNDSGIMQIGFVTINNEVF
YFSDSGIVESGMQNIDDNYFYIDENGLVQIGVFDTSDGYKYFAPANTVNDNIYGQ
AVEYSGLVRVGEDVYYFGETYTIETGWIYDMENESDKYYFDPETKKAYKGINVI
DDIKYYFDENGIMRTGLITFEDNHYYFNEDGIMQYGYLNIEDKTFYFSEDGIMQIG
VFNTPDGFKYFAHQNTLDENFEGESINYTGWLDLDEKRYYFTDEYIAATGSVIID
GEEYYFDPDTAQLVISE SEQ ID NO: 15 - Toxin B fragment - Toxin B-A hybrid (toxinotype 0)
NTLNAAFFIQSLIEYNSSKESLSNLSVAMKVQVYAQLFSTGLNTITDAAKVVELVS
TALDETIDLLPTLSEGLPIIATIIDGVSLGAAIKELSETSDPLLRQEIEAKIGIMAVNL
TTATTAIITSSLGIASGFSILLVPLAGISAGIPSLVNNELVLRDKATKVVDYFKHVSL
VETEGVFTLLDDKIMMPQDDLVISEIDFNNNSIVLGKCEIWRMEGGSGHTVTDDI
DHFFSAPSITYREPHLSIYDVLEVQKEELDLSKDLMVLPNAPNRVFAWETGWTPG
LRSLENDGTKLLDRIRDNYEGEFYWRYFAFIADALITTLKPRYEDTNIRINLDSNT
RSFIVPIITTEYIREKLSYSFYGSGGTYALSLSQYNMGINIELSESDVWIIDVDNVVR
DVTIESDKIKKGDLIEGILSTLSIEENKIILNSHEINFSGEVNGSNGFVSLTFSILEGIN
AIIEVDLLSKSYKLLISGELKILMLNSNHIQQKIDYIGFNSELQKNIPYSFVDSEGKE
NGFINGSTKEGLFVSELPDVVLISKVYMDDSKPSFGYYSNNLKDVKVITKDNVNI
LTGYYLKDDIKISLSLTLQDEKTIKLNSVHLDESGVAEILKFMNRKGNTNTSDSL
MSFLESMNIKSIFVNFLQSNIKFILDANFIISGTTSIGQFEFICDENDNIQPYFIKFNTL
ETNYTLYVGNRQNMIVEPNYDLDDSGDISSTVINFSQKYLYGIDSCVNKVVISPNI
YTDEINITPVYETNNTYPEVIVLDANYINEKINVNINDLSIRYVWSNDGNDFILMST
SEENKVSQVKIRFVNVFKDKTLANKLSFNFSDKQDVPVSEIILSFTPSYYEDGLIG
YDLGLVSLYNEKFYINNFGMMVSGLIYINDSLYYFKPPVNNLVTGWQTINGKKY
YFDINTGAALISYKIINGKHFYFNNDGVMQLGVFKGPDGFEYFAPANTQNNNIEG
QAIVYQSKFLTLNGKKYYFDNDSKAVTGWRIINNEKYYFNPNNAIAAVGLQVID
NNKYYFNPDTAIISKGWQTVNGSRYYFDTDTAIAFNGYKTIDGKHFYFDSDCVV
KIGVFSTSNGFEYFAPANTYNNNIEGQAIVYQSKFLTLNGKKYYFDNNSKAVTG
WQTIDSKKYYFNTNTAEAATGWQTIDGKKYYFNTNTAEAATGWQTIDGKKYYF
NTNTAIASTGYTIINGKHFYFNTDGIMQIGVFKGPNGFEYFAPANTDANNIEGQAI
LYQNEFLTLNGKKYYFGSDSKAVTGWRIINNKKYYFNPNNAIAAIHLCTINNDKY
YFSYDGILQNGYITIERNNFYFDANNESKMVTGVFKGPNGFEYFAPANTHNNNIE
GQAIVYQNKFLTLNGKKYYFDNDSKAVTGWQTIDGKKYYFNLNTAEAATGWQ
TIDGKKYYFNLNTAEAATGWQTIDGKKYYFNTNTFIASTGYTSINGKHFYFNTDG -continued

| SEQ ID NOs |
|---|
| IMQIGVFKGPNGFEYFAPANTHNNNIEGQAILYQNKFLTLNGKKYYFGSDSKAVT<br>GLRTIDGKKYYFNTNTAVAVTGWQTINGKKYYFNTNTSIASTGYTIISGKHFYFN<br>TDGIMQIGVFKGPDGFEYFAPANTDANNIEGQAIRYQNRFLYLHDNIYYFGNNSK<br>IAATGWVTIDGNRYYFEPNTAMGANGYKTIDNKNFYFRNGLPQIGVFKGSNGFEY<br>FAPANTDANNIEGQAIRYQNRFLHLLGKIYYFGNNSKAVTGWQTINGKVYYFMP<br>DTAMAAAGGLFEIDGVIYFFGVDGVKAPGIYG |
| SEQ ID NO: 16 - Toxin B fragment - Toxin A-B hybrid (toxinotype 0)<br>IMSDLSSKEYIFFDSIDNKLKAKSKNIPGLASISEDIKTLLLDASVSPDTKFILNNLK<br>LNIESSIGDYIYYEKLEPVKNIIHNSIDDLIDEFNLLENVSDELYELKKLNNLDEKY<br>LISFEDISKNNSTYSVRFINKSNGESVYVETEKEIFSKYSEHITKEISTIKNSIITDVN<br>GNLLDNIQLDHTSQVNTLNAAFFIQSLIDYSSNKDVLNDLSTSVKVQLYAQLFST<br>GLNTIYDSIQLVNLISNAVNDTINVLPTITEGIPIVSTILDGINLGAAIKELLDEHDPL<br>ILKKELEAKVGVLAINMSLSIAATVASIVGIGAEVTIFLLPIAGISAGIPSLVNNELIL<br>HDKATSVVNYFNHLSESKKYGPLKTEDDKILVPIDDLVISEIDFNNNSIKLGTCNIL<br>AMEGGSGHTVTGNIDHFFSSPSISSHIPSLSIYSAIGIETENLDFSKKIMMLPNAPSR<br>VFWWETGAVPGLRSLENDGTRLLDSIRDLYPGKFYWRFYAFFDYAITTLKPVYE<br>DTNIKIKLDKDTRNFIMPTITTNEIRNKLSYSPDGAGGTYSLLLSSYPISTNINLSKD<br>DLWIFNIDNEVREISIENGTIKKGKLIKDVLSKIDINKNKLIIGNQTIDFSGDIDNKD<br>RYIFLTCELDDKISLIIEINLVAKSYSLLLSGDKNYLISNLSNIIEKINTLGLDSKNIA<br>YNYTDESNNKYFGAISKTSQKSIIHYKKDSKNILEFYNDSTLEFNSKDFIAEDINVF<br>MKDDINTITGKYYVDNNTDKSIDFSISLVSKNQVKVNGLYLNESVYSSYLDFVKN<br>SDGHHNTSNFMNLFLDNISFWKLFGFENINFVIDKYFTLVGKTNLGYVEFICDNN<br>IKNIDIYFGEWKTSSSKSTIFSGNGRNVVVEPIYNPDTGEDISTSLDFSYEPLYGIDR<br>YINKVLIAPDLYTSLININTNYYSNEYYPEIIVLNPNTFHKKVNINLDSSSFEYKWS<br>TEGSDFILVRYLEESNKKILQKIRIKGILSNTQSFNKMSIDFKDIKKLSLGYIMSNFK<br>SFNSENELDRDHLGFKIIDNKTYYYDEDSKLVKGLININNSLFYFDPIEFNLITGFV<br>TVGDDKYYFNPINGGAASIGETIIDDKNYYFNQSGVLQTGVFSTEDGFKYFAPAN<br>TLDENLEGEAIDFTGKLIIDENIYYFDDNYRGAVEWKELDGEMHYFSPETGKAFK<br>GLNQIGDYKYYFNSDGVMQKGFVSINDNKHYFDDSGVMKVGYTEIDGKHFYFA<br>ENGEMQIGVFNTEDGFKYFAHHNEDLGNEEGEEISYSGILNFNNKIYYFDDSFTA<br>VVGWKDLEDGSKYYFDEDTAEAYIGLSLINDGQYYFNDDGIMQVGFVTINDKVF<br>YFSDSGRESGVQNIDDNYFYIDDNGIVQIGVFDTSDGYKYFAPANTVNDNIYGQA<br>VEYSGLVRVGEDVYYFGETYTIETGWIYDMENESDKYYFNPETKKACKGINLID<br>DIKYYFDEKGIMRTGLISFENNNYYFNENGEMQFGYINIEDKMFYFGEDGVMQIG<br>VFNTPDGFKYFAHQNTLDENFEGESINYTGWLDLDEKRYYFTDEYIAATGSVIID<br>GEEYYFDPDTAQLVISE |
| SEQ ID NO: 17 - Toxin B fragment - Toxin A-B hybrid (toxinotype 0 and 3)<br>IMSDLSSKEYIFFDSIDNKLKAKSKNIPGLASISEDIKTLLLDASVSPDTKFILNNLK<br>LNIESSIGDYIYYEKLEPVKNIIHNSIDDLIDEFNLLENVSDELYELKKLNNLDEKY<br>LISFEDISKNNSTYSVRFINKSNGESVYVETEKEIFSKYSEHITKEISTIKNSIITDVN<br>GNLLDNIQLDHTSQVNTLNAAFFIQSLIDYSSNKDVLNDLSTSVKVQLYAQLFST<br>GLNTIYDSIQLVNLISNAVNDTINVLPTITEGIPIVSTILDGINLGAAIKELLDEHDPL<br>LKKELEAKVGVLAINMSLSIAATVASIVGIGAEVTIFLLPIAGISAGIPSLVNNELIL<br>HDKATSVVNYFNHLSESKKYGPLKTEDDKILVPIDDLVISEIDFNNNSIKLGTCNIL<br>AMEGGSGHTVTGNIDHFFSSPSISSHIPSLSIYSAIGIETENLDFSKKIMMLPNAPSR<br>VFWWETGAVPGLRSLENDGTRLLDSIRDLYPGKFYWRFYAFFDYAITTLKPVYE<br>DTNIKIKLDKDTRNFIMPTITTNEIRNKLSYS14DGAGGTYSLLLSSYPISTNINLSKD<br>DLWIFNIDNEVREISIENGTIKKGKLIKDVLSKIDINKNKLIIGNQTIDFSGDIDNKD<br>RYIFLTCELDDKISLIIEINLVAKSYSLLLSGDKNYLISNLSNIIEKINTLGLDSKNIA<br>YNYTDESNNKYFGAISKTSQKSIIHYKKDSKNILEFYNDSTLEFNSKDFIAEDINVF<br>MKDDINTITGKYYVDNNTDKSIDFSISLVSKNQVKVNGLYLNESVYSSYLDFVKN<br>SDGHHNTSNFMNLFLDNISFWKLFGFENINFVIDKYFTLVGKTNLGYVEFICDNN<br>KNIDIYFGEWKTSSSKSTIFSGNGRNVVVEPIYNPDTGEDISTSLDFSYEPLYGIDR<br>YINKVLIAPDLYTSLININTNYYSNEYYPEIIVLNPNTFHKKVNINLDSSSFEYKWS<br>TEGSDFILVRYLEESNKKILQKIRIKGILSNTQSFNKMSIDFKDIKKLSLGYIMSNFK<br>SFNSENELDRDHLGFKIIDNKTYYYDEDSKLVKGLININNSLFYFDPIEFNLITGFT<br>TIGDDKYYFNPDNGGAASVGETIIDGKNYYFSQNGVLQTGVFSTEDGFKYFAPA<br>DTLDENLEGEAIDFTGKLTIDENVYYFGDNYRAAIEWQTLDDEVYYFSTDTGRAF<br>KGLNQIGDDKFYFNSDGIMQKGFVNINDKTFYFDDSGVMKSGYTEIDGKYFYFA<br>ENGEMQIGVFNTADGFKYFAHHDEDLGNEEGEALSYSGILNFNNKIYYFDDSFTA<br>VVGWKDLEDGSKYYFDEDTAEAYIGISIINDGKYYFNDSGIMQIGFVTINNEVFYF<br>SDSGIVESGMQNIDDNYFYIDENGLVQIGVFDTSDGYKYFAPANTVNDNIYGQAV<br>EYSGLVRVGEDVYYFGETYTIETGWIYDMENESDKYYFDPETKKAYKGINVIDDI<br>KYYFDENGIMRTGLITFEDNHYYFNEDGIMQYGYLNIEDKTFYFSEDGIMQIGVF<br>NTPDGFKYFAHQNTLDENFEGESINYTGWLDLDEKRYYFTDEYIAATGSVIIDGE<br>EYYFDPDTAQLVISE |
| SEQ ID NO: 18 - Toxin A-derived recombinant antigen His-NusA-[thrombin site]-TxA4-His<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI |

SEQ ID NOs

GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALVPRGSVTSLYKKAGSAAAPFTMIMSDLSSKEYIFFD
SIDNKLKAKSKNIPGLASISEDIKTLLLDASVSPDTKFILNNLKLNIESSIGDYIYYE
KLEPVKNIIHNSIDDLIDEFNLLENVSDELYELKKLNNLDEKYLISFEDISKNNSTY
SVRFINKSNGESVYVETEKEIFSKYSEHITKEISTIKNSIITDVNGNLLDNIQLDHTS
QVNTLNAAFFIQSLIDYSSNKDVLNDLSTSVKVQLYAQLFSTGLNTIYDSIQLVNL
ISNAVNDTINVLPTITEGIPIVSTILDGINLGAAIKELLDEHDPLLKKELEAKVGVLA
INMSLSIAATVASIVGIGAEVTIFLLPIAGISAGIPSLVNNELILHDKATSVVNYFNH
LSESKKYGPLKTEDDKILVPIDDLVISEIDFNNNSIKLGTCNILAMEGGSGHTVTGN
IDHFFSSPSISSHIPSLSIYSAIGIETENLDFSKKIMMLPNAPSRVFWWETGAVPGLR
SLENDGTRLLDSIRDLYPGKFYWRFYAFFDYAITTLKPVYEDTNIKIKLDKDTRNF
IMPTITTNEIRNKLSYSFDGAGGTYSLLLSSYPISTNINLSKDDLWIFNIDNEVREISI
ENGTIKKGKLIKDVLSKIDINKNKLIIGNQTIDFSGDIDNKDRYIFLTCELDDKISLII
EINLVAKSYSLLLSGDKNYLISNLSNIIEKINTLGLDSKNIAYNYTDESNNKYFGAI
SKTSQKSIIHYKKDSKNILEFYNDSTLEFNSKDFIAEDINVFMKDDINTITGKYYVD
NNTDKSIDFSISLVSKNQVKVNGLYLNESVYSSYLDFVKNSDGHHNTSNFMNLFL
DNISFWKLFGFENINFVIDKYFTLVGKTNLGYVEFICDNNKNIDIYFGEWKTSSSK
ISTIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIEFNLVTGWQTINGKKYYFDINTGAA
LISYKIINGKHFYFNNDGVMQLGVFKGPDGFEYFAPANTQNNNIEGQAIVYQSKF
LTLNGKKYYFDNDSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNG
FEYFAPANTYNNNIEGQAIVYQSKFLTLNGKKYYFDNNSKAVTGWQTIDSKKYY
FNTNTAEAATGWQTIDGKKYYFNTNTAEAATGWQTIDGKKYYFNTNTAIASTG
YTIINGKHFYFNTDGIMQIGVFKGPNGFEYFAPANTDANNIEGQAILYQNEFLTLN
IGKKYYFGSDSKAVTGWRIINNKKYYFNPNNAIAAIHLCTINNDKYYFSYDGILQN
GYITIERNNFYFDANNESKMVTGVFKGPNGFEYFAPANTHNNNIEGQAIVYQNKF
LTLNGKKYYFDNDSKAVTGWQTIDGKKYYFNLNTAEAATGWQTIDGKKYYFNL
NTAEAATGWQTIDGKKYYFNTNTFIASTGYTSINGKHFYFNTDGIMQIGVFKGPN
GFEYFAPANTHNNNIEGQAILYQNKFLTLNGKKYYFGSDSKAVTGLRTIDGKKY
YFNTNTAVAVTGWQTINGKKYYFNTNTSIASTGYTIISGKHFYFNTDGIMQIGVF
KGPDGFEYFAPANTDANNIEGQAIRYQNRFLYLHDNIYYFGNNSKAATGWVTID
GNRYYFEPNTAMGANGYKTIDNKNFYFRNGLPQIGVFKGSNGFEYFAPANTDAN
NIEGQAIRYQNRFLHLLGKIYYFGNNSKAVTGWQTINGKVYYFMPDTAMAAAG
GLFEIDGVIYFFGVDGVKAPGIYGGGSGGSLVPRGSGGSHHHHHH

SEQ ID NO: 19 - Toxin A-derived recombinant antigen His-NusA-[thrombin site]-TxA4
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALVPRGSVTSLYKKAGSAAAPFTMIMSDLSSKEYIFFD
SIDNKLKAKSKNIPGLASISEDIKTLLLDASVSPDTKFILNNLKLNIESSIGDYIYYE
KLEPVKNIIHNSIDDLIDEFNLLENVSDELYELKKLNNLDEKYLISFEDISKNNSTY
SVRFINKSNGESVYVETEKEIFSKYSEHITKEISTIKNSIITDVNGNLLDNIQLDHTS
QVNTLNAAFFIQSLIDYSSNKDVLNDLSTSVKVQLYAQLFSTGLNTIYDSIQLVNL
ISNAVNDTINVLPTITEGIPIVSTILDGINLGAAIKELLDEHDPLLKKELEAKVGVLA
INMSLSIAATVASIVGIGAEVTIFLLPIAGISAGIPSLVNNELILHDKATSVVNYFNH
LSESKKYGPLKTEDDKILVPIDDLVISEIDFNNNSIKLGTCNILAMEGGSGHTVTGN
IDHFFSSPSISSHIPSLSIYSAIGIETENLDFSKKIMMLPNAPSRVFWWETGAVPGLR
SLENDGTRLLDSIRDLYPGKFYWRFYAFFDYAITTLKPVYEDTNIKIKLDKDTRNF
IMPTITTNEIRNKLSYSFDGAGGTYSLLLSSYPISTNINLSKDDLWIFNIDNEVREISI
ENGTIKKGKLIKDVLSKIDINKNKLIIGNQTIDFSGDIDNKDRYIFLTCELDDKISLII
EINLVAKSYSLLLSGDKNYLISNLSNIIEKINTLGLDSKNIAYNYTDESNNKYFGAI
SKTSQKSIIHYKKDSKNILEFYNDSTLEFNSKDFIAEDINVFMKDDINTITGKYYVD
NNTDKSIDFSISLVSKNQVKVNGLYLNESVYSSYLDFVKNSDGHHNTSNFMNLFL
DNISFWKLFGFENINFVIDKYFTLVGKTNLGYVEFICDNNKNIDIYFGEWKTSSSK
STIFSGNGRNVVVEPIYNPDTGEDISTSLDFSYEPLYGIDRYINKVLIAPDLYTSLINI
NTNYYSNEYYPEIIVLNPNTFHKKVNINLDSSSFEYKWSTEGSDFILVRYLEESNK
KILQKIRIKGILSNTQSFNKMSIDFKDIKKLSLGYIMSNFKSFNSENELDRDHLGFKI
IDNKTYYYDEDSKLVKGLININNSLFYFDPIEFNLVTGWQTINGKKYYFDINTGAA
LISYKIINGKHFYFNNDGVMQLGVFKGPDGFEYFAPANTQNNNIEGQAIVYQSKF
LTLNGKKYYFDNDSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNG
FEYFAPANTYNNNIEGQAIVYQSKFLTLNGKKYYFDNNSKAVTGWQTIDSKKYY
FNTNTAEAATGWQTIDGKKYYFNTNTAEAATGWQTIDGKKYYFNTNTAIASTG
YTIINGKHFYFNTDGIMQIGVFKGPNGFEYFAPANTDANNIEGQAILYQNEFLTLN
GKKYYFGSDSKAVTGWRIINNKKYYFNPNNAIAAIHLCTINNDKYYFSYDGILQN -continued

| SEQ ID NOs |
| --- |
| GYITIERNNFYFDANNESKMVTGVFKGPNGFEYFAPANTHNNNIEGQAIVYQNKF<br>LTLNGKKYYFDNDSKAVTGWQTIDGKKYYFNLNTAEAATGWQTIDGKKYYFNL<br>NTAEAATGWQTIDGKKYYFNTNTFIASTGYTSINGKHFYFNTDGIMQIGVFKGPN<br>GFEYFAPANTHNNNIEGQAILYQNKFLTLNGKKYYFGSDSKAVTGLRTIDGKKY<br>YFNTNTAVAVTGWQTINGKKYYFNTNTSIASTGYTIISGKHFYFNTDGIMQIGVF<br>KGPDGFEYFAPANTDANNIEGQAIRYQNRFLYLHDNIYYFGNNSKAATGWVTID<br>GNRYYFEPNTAMGANGYKTIDNKNFYFRNGLPQIGVFKGSNGFEYFAPANTDAN<br>NIEGQAIRYQNRFLHLLGKIYYFGNNSKAVTGWQTINGKVYYFMPDTAMAAAG<br>GLFEIDGVIYFFGVDGVKAPGIYG |
| SEQ ID NO: 20 - Toxin A-derived recombinant antigen - His-Thioredoxin-[thrombin site]-TxA4<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALVPRGSVTSLYKKAGSAAAPFTMIMSDLSSKEYIFFDSIDNKLK<br>AKSKNIPGLASISEDIKTLLLDASVSPDTKFILNNLKLNIESSIGDYIYYEKLEPVKN<br>IIHNSIDDLIDEFNLLENVSDELYELKKLNNLDEKYLISFEDISKNNSTYSVRFINKS<br>NGESVYVETEKEIFSKYSEHITKEISTIKNSIITDVNGNLLDNIQLDHTSQVNTLNA<br>AFFIQSLIDYSSNKDVLNDLSTSVKVQLYAQLFSTGLNTIYDSIQLVNLISNAVNDT<br>INVLPTITEGIPIVSTILDGINLGAAIKELLDEHDPLLKKELEAKVGVLAINMSLSIA<br>ATVASIVGIGAEVTIFLLPIAGISAGIPSLVNNELILHDKATSVVNYFNHLSESKKY<br>GPLKTEDDKILVPIDDLVISEIDFNNNSIKLGTCNILAMEGGSGHTVTGNIDHFFSS<br>PSISSHIPSLSIYSAIGIETENLDFSKKIMMLPNAPSRVFWWETGAVPGLRSLENDG<br>TRLLDSIRDLYPGKFYWRFYAFFDYAITTLKPVYEDTNIKIKLDKDTRNFIMPTITT<br>NEIRNKLSYSFDGAGGTYSLLLSSYPISTNINLSKDDLWIFNIDNEVREISIENGTIK<br>KGKLIKDVLSKIDINKNKLIIGNQTIDFSGDIDNKDRYIFLTCELDDKISLIIEINLVA<br>KSYSLLLSGDKNYLISNLSNIIEKINTLGLDSKNIAYNYTDESNNKYFGAISKTSQK<br>SIIHYKKDSKNILEFYNDSTLEFNSKDFIAEDINVFMKDDINTITGKYYVDNNTDK<br>SIDFSISLVSKNQVKVNGLYLNESVYSSYLDFVKNSDGHHNTSNFMNLFLDNISF<br>WKLFGFENINFVIDKYFTLVGKTNLGYVEFICDNNKNIDIYFGEWKTSSSKSTIFS<br>GNGRNVVVEPIYNPDTGEDISTSLDFSYEPLYGIDRYINKVLIAPDLYTSLININTN<br>YYSNEYYPEIIVLNPNTFHKKVNINLDSSSFENKWSTEGSDFILVRYLEESNKKILQ<br>KIRIKGILSNTQSFNKMSIDFKDIKKLSLGYIMSNFKSFNSENELDRDHLGFKIIDN<br>KTYYYDEDSKLVKGLININNSLFYFDPIEFNLVTGWQTINGKKYYFDINTGAALIS<br>YKIINGKHFYFNNDGVMQLGVFKGPDGFEYFAPANTQNNNIEGQAIVYQSKFLTL<br>NGKKYYFDNDSKAVTGWRIINNEKYYFNPNNAIAAVGLQVIDNNKYYFNPDTAI<br>ISKGWQTVNGSRYYFDTDTAIAFNGYKTIDGKHFYFDSDCVVKIGVFSTSNGFEN<br>FAPANTYNNNIEGQAIVYQSKFLTLNGKKYYFDNNSKAVTGWQTIDSKKYYFNT<br>NTAEAATGWQTIDGKKYYFNTNTAEAATGWQTIDGKKYYFNTNTAIASTGYTII<br>NGKHFYFNTDGIMQIGVFKGPNGFEYFAPANTDANNIEGQAILYQNEFLTLNGKK<br>YYFGSDSKAVTGWRIINNKKYYFNPNNAIAAIHLCTINNDKYYFSYDGILQNGYI<br>TIERNNFYFDANNESKMVTGVFKGPNGFEYFAPANTHNNNIEGQAIVYQNKFLTL<br>NGKKYYFDNDSKAVTGWQTIDGKKYYFNLNTAEAATGWQTIDGKKYYFNLNT<br>AEAATGWQTIDGKKYYFNTNTFIASTGYTSINGKHFYFNTDGIMQIGVFKGPNGF<br>EYFAPANTHNNNIEGQAILYQNKFLTLNGKKYYFGSDSKAVTGLRTIDGKKYYF<br>NTNTAVAVTGWQTINGKKYYFNTNTSIASTGYTIISGKHFYFNTDGIMQIGVFKG<br>PDGFEYFAPANTDANNIEGQAIRYQNRFLYLHDNIYYFGNNSKAATGWVTIDGN<br>RYYFEPNTAMGANGYKTIDNKNFYFRNGLPQIGVFKGSNGFEYFAPANTDANNI<br>EGQAIRYQNRFLHLLGKIYYFGNNSKAVTGWQTINGKVYYFMPDTAMAAAGGL<br>FEIDGVIYFFGVDGVKAPGIYG |
| SEQ ID NO: 21 - Toxin A-derived recombinant antigen - His-Thioredoxin-[thrombin site]-TxA3<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALVPRGSVTSLYKKAGSAAAPFTMESKKYGPLKTEDDKILVPIDD<br>LVISEIDFNNNSIKLGTCNILAMEGGSGHTVTGNIDHFFSSPSISSHIPSLSIYSAIGIE<br>TENLDFSKKIMMLPNAPSRVFWWETGAVPGLRSLENDGTRLLDSIRDLYPGKFY<br>WRFYAFFDYAITTLKPVYEDTNIKIKLDKDTRNFIMPTITTNEIRNKLSYSFDGAG<br>GTYSLLLSSYPISTNINLSKDDLWIFNIDNEVREISIENGTIKKGKLIKDVLSKIDINK<br>NKLIIGNQTIDFSGDIDNKDRYIFLTCELDDKISLIIEINLVAKSYSLLLSGDKNYLIS<br>NLSNIIEKINTLGLDSKNIAYNYTDESNNKYFGAISKTSQKSIIHYKKDSKNILEFY<br>NDSTLEFNSKDFIAEDINVFMKDDINTITGKYYVDNNTDKSIDFSISLVSKNQVKV<br>NGLYLNESVYSSYLDFVKNSDGHHNTSNFMNLFLDNISFWKLFGFENINFVIDKY<br>FTLVGKTNLGYVEFICDNNKNIDIYFGEWKTSSSKSTIFSGNGRNVVVEPIYNPDT<br>GEDISTSLDFSYEPLYGIDRYINKVLIAPDLYTSLININTNYYSNEYYPEIIVLNPNTF<br>HKKVNINLDSSSFEYKWSTEGSDFILVRYLEESNKKILQKIRIKGILSNTQSFNKMS<br>IDFKDIKKLSLGYIMSNFKSFNSENELDRDHLGFKIIDNKTYYYDEDSKLVKGLINI<br>NNSLFYFDPIEFNLVTGWQTINGKKYYFDINTGAALISYKIINGKHFYFNNDGVM<br>QLGVFKGPDGFEYFAPANTQNNNIEGQAIVYQSKFLTLNGKKYYFDNDSKAVTG<br>WRIINNEKYYFNPNNAIAAVGLQVIDNNKYYFNPDTAIISKGWQTVNGSRYYFDT<br>DTAIAFNGYKTIDGKHFYFDSDCVVKIGVFSTSNGFEYFAPANTYNNNIEGQAIV<br>YQSKFLTLNGKKYYFDNNSKAVTGWQTIDSKKYYFNTNTAEAATGWQTIDGKK<br>YYFNTNTAEAATGWQTIDGKKYYFNTNTAIASTGYTIINGKHFYFNTDGIMQIGV<br>FKGPNGFENFAPANTDANNIEGQAILYQNEFLTLNGKKYYFGSDSKAVTGWRIIN<br>NKKYYFNPNNAIAAIHLCTINNDKYYFSYDGILQNGYITIERNNFYFDANNESKM<br>VTGVFKGPNGFEYFAPANTHNNNIEGQAIVYQNKFLTLNGKKYYFDNDSKAVTG |

-continued

| SEQ ID NOs |
|---|
| WQTIDGKKYYFNLNTAEAATGWQTIDGKKYYFNLNTAEAATGWQTIDGKKYYF<br>NTNTFIASTGYTSINGKHFYFNTDGIMQIGVFKGPNGFEYFAPANTHNNNIEGQAI<br>LYQNKFLTLNGKKYYFGSDSKAVTGLRTIDGKKYYFNTNTAVAVTGWQTINGK<br>KYYFNTNTSIASTGYTIISGKHFYFNTDGIMQIGVFKGPDGFEYFAPANTDANNIE<br>GQAIRYQNRFLYLHDNIYYFGNNSKAATGWVTIDGNRYYFEPNTAMGANGYKTI<br>DNKNFYFRNGLPQIGVFKGSNGFEYFAPANTDANNIEGQAIRYQNRFLHLLGKIY<br>YFGNNSKAVTGWQTINGKVYYFMPDTAMAAAGGLFEIDGVIYFFGVDGVKAPG<br>IYG |
| SEQ ID NO: 22 - Toxin A-derived recombinant antigen - His-NusA-[thrombin site]-TxA3<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALVPRGSVTSLYKKAGSAAAPFTMESKKYGPLKTEDD<br>KILVPIDDLVISEIDFNNNSIKLGTCNILAMEGGSGHTVTGNIDHFFSSPSISSHIPSL<br>SIYSAIGIETENLDFSKKIMMLPNAPSRVFWWETGAVPGLRSLENDGTRLLDSIRD<br>LYPGKFYWRFYAFFDYAITTLKPVYEDTNIKIKLDKDTRNFIMPTITTNEIRNKLS<br>YSPDGAGGTYSLLLSSYPISTNINLSKDDLWIFNIDNEVREISIENGTIKKGKLIKDV<br>LSKIDINKNKLIIGNQTIDFSGDIDNKDRYIFLTCELDDKISLIIEINLVAKSYSLLLS<br>GDKNYLISNLSNIIEKINTLGLDSKNIAYNYTDESNNKYFGAISKTSQKSIIHYKKD<br>SKNILEFYNDSTLEFNSKDFIAEDINVFMKDDINTITGKYYVDNNTDKSIDFSISLV<br>SKNQVKVNGLYLNESVYSSYLDFVKNSDGHHNTSNFMNLFLDNISFWKLFGFEN<br>INFVIDKYFTLVGKTNLGYVEFICDNNKNIDIYFGEWKTSSSKSTIFSGNGRNVVV<br>EPIYNPDTGEDISTSLDFSYEPLYGIDRYINKVLIAPDLYTSLININTNYYSNEYYPEI<br>IVLNPNTFHKKVNINLDSSSFEYKWSTEGSDFILVRYLEESNKKILQKIRIKGILSNT<br>QSFNKMSIDFKDIKKLSLGYIMSNFKSFNSENELDRDHLGFKIIDNKTYYYDEDSK<br>LVKGLININNSLFYFDPIEFNLVTGWQTINGKKYYFDINTGAALISYKIINGKHFYF<br>NNDGVMQLGVFKGPDGFEYFAPANTQNNNIEGQAIVYQSKFLTLNGKKYYFDN<br>DSKAVTGWRIINNEKYYFNPNNAIAAVGLQVIDNNKYYFNPDTAIISKGWQTVN<br>GSRYYPDTDTAIAFNGYKTIDGKHFYFDSDCVVKIGVFSTSNGFEYFAPANTYNN<br>NIEGQAIVYQSKFLTLNGKKYYIDNNSKAVTGWQTIDSKKYYFNTNTAEAATG<br>WQTIDGKKYYFNTNTAEAATGWQTIDGKKYYFNTNTAIASTGYTIINGKHFYFN<br>TDGIMQIGVFKGPNGFEYFAPANTDANNIEGQAILYQNEFLTLNGKKYYFGSDSK<br>AVTGWRIINNKKYYFNPNNAIAAIHLCTINNDKYYFSYDGILQNGYITIERNNFYF<br>DANNESKMVTGVFKGPNGFEYFAPANTHNNNIEGQAIVYQNKFLTLNGKKYYF<br>DNDSKAVTGWQTIDGKKYYFNLNTAEAATGWQTIDGKKYYFNLNTAEAATGW<br>QTIDGKKYYFNTNTFIASTGYTSINGKHFYFNTDGIMQIGVFKGPNGFEYFAPANT<br>HNNNIEGQAILYQNKFLTLNGKKYYFGSDSKAVTGLRTIDGKKYYFNTNTAVAV<br>TGWQTINGKKYYFNTNTSIASTGYTIISGKHFYFNTDGIMQIGVFKGPDGFEYFAP<br>ANTDANNIEGQAIRYQNRFLYLHDNIYYFGNNSKAATGWVTIDGNRYYFEPNTA<br>MGANGYKTIDNKNFYFRNGLPQIGVFKGSNGFEYFAPANTDANNIEGQAIRYQN<br>RFLHLLGKIYYFGNNSKAVTGWQTINGKVYYFMPDTAMAAAGGLFEIDGVIYFF<br>GVDGVKAPGIYG |
| SEQ ID NO: 23 - Toxin B-derived recombinant antigen - His-NusA-[thrombin site]-TxB4-<br>His<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALVPRGSVTSLYKKAGSAAAPFTMSIIKDISSKEYISFN<br>PKENKITVKSKNLPELSTLLQEIRNNSNSSDIELEEKVMLTECEINVISNIDTQIVEE<br>RIEEAKNLTSDSINYIKDEFKLIESISDALCDLKQQNELEDSHFISFEDISETDEGFSI<br>RFINKETGESIFVETEKTIFSEYANHITEEISKIKGTIFDTVNGKLVKKVNLDTTHEV<br>NTLNAAFFIQSLIEYNSSKESLSNLSVAMKVQVYAQLFSTGLNTITDAAKVVELVS<br>TALDETIDLLPTLSEGLPIIATIIDGVSLGAAIKELSETSDPLLRQEIEAKIGIMAVNL<br>TTATTAIITSSLGIASGFSILLVPLAGISAGIPSLVNNELVLRDKATKVVDYFKHVSL<br>VETEGVFTLLDDKIMMPQDDLVISEIDFNNNSIVLGKCEIWRMEGGSGHTVTDDI<br>DHFFSAPSITYREPHLSIYDVLEVQKEELDLSKDLMVLPNAPNRVFAWETGWTPG<br>LRSLENDGTKLLDRIRDNYEGEFYWRYFAFIADALITTLKPRYEDTNIRINLDSNT<br>RSFIVPIITTEYIREKLSYSFYGSGGTYALSLSQYNMGINIELSESDVWIIDVDNVVR<br>DVTIESDKIKKGDLIEGILSTLSIEENKIILNSHEINFSGEVNGSNGFVSLTFSILEGIN<br>AIIEVDLLSKSYKLLISGELKILMLNSNHIQQKIDYIGFNSELQKNIPYSFVDSEGKE<br>NGFINGSTKEGLFVSELPDVVLISKVYMDDSKPSFGYYSNNLKDVKVITKDNVNI<br>LTGYYLKDDIKISLSLTLQDEKTIKLNSVHLDESGVAEILKFMNRKGNTNTSDSL<br>MSFLESMNIKSIFVNFLQSNIKFILDANFIISGTTSIGQFEFICDENDNIQPYFIKFNTL |

-continued

| SEQ ID NOs |
|---|
| ETNYTLYVGNRQNMIVEPNYDLDDSGDISSTVINFSQKYLYGIDSCVNKVVISPNI<br>YTDEINITPVYETNNTYPEVIVLDANYINEKINVNINDLSIRYVWSNDGNDFILMST<br>SEENKVSQVKIRFVNVFKDKTLANKLSFNFSDKQDVPVSEIILSFTPSYYEDGLIG<br>YDLGLVSLYNEKFYINNFGMMVSGLIYINDSLYYFKPPVNNLITGFVTVGDDKYY<br>FNPINGGAASIGETIIDDKNYYFNQSGVLQTGVFSTEDGFKYFAPANTLDENLEGE<br>AIDFTGKLIIDENIYYFDDNYRGAVEWKELDGEMHYFSPETGKAFKGLNQIGDYK<br>YYFNSDGVMQKGFVSINDNKHYFDDSGVMKVGYTEIDGKHFYFAENGEMQIGV<br>FNTEDGFKYFAHHNEDLGNEEGEEISYSGILNFNNKIYYFDDSFTAVVGWKDLED<br>GSKYYFDEDTAEAYIGLSLINDGQYYFNDDGIMQVGFVTINDKVFYFSDSGIIESG<br>VQNIDDNYFYIDDNGIVQIGVFDTSDGYKYFAPANTVNDNIYGQAVEYSGLVRV<br>GEDVYYFGETYTIETGWIYDMENESDKYYFNPETKKACKGINLIDDIKYYFDEKG<br>IMRTGLISFENNNYYFNENGEMQFGYINIEDKMFYFGEDGVMQIGVFNTPDGFKY<br>FAHQNTLDENFEGESINYTGWLDLDEKRYYFTDEYIAATGSVIIDGEEYYPDPDT<br>AQLVISEGHHHHHH |
| SEQ ID NO: 24 - Toxin B-derived recombinant antigen - His-NusA-[thrombin site]-TxB4<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALVPRGSVTSLYKKAGSAAAPFTMSIIKDISSKEYISFN<br>PKENKITVKSKNLPELSTLLQEIRNNSNSSDIELEEKVMLTECEINVISNIDTQIVEE<br>RIEEAKNLTSDSINYIKDEFKLIESISDALCDLKQQNELEDSHFISFEDISETDEGFSI<br>RFINKETGESIFVETEKTIFSEYANHITEEISKIKGTIFDTVNGKLVKKVNLDTTHEV<br>NTLNAAFFIQSLIEYNSSKESLSNLSVAMKVQVYAQLFSTGLNTITDAAKVVELVS<br>TALDETIDLLPTLSEGLPIIATIIDGVSLGAAIKELSETSDPLLRQEIEAKIGIMAVNL<br>TTATTAIITSSLGIASGFSILLVPLAGISAGIPSLVNNELVLRDKATKVVDYFKHVSL<br>VETEGVFTLLDDKIMMPQDDLVISEIDFNNNSIVLGKCEIWRMEGGSGHTVTDDI<br>DHFFSAPSITYREPHLSIYDVLEVQKEELDLSKDLMVLPNAPNRVFAWETGWTPG<br>LRSLENDGTKLLDRIRDNYEGEFYWRYFAFIADALITTLKPRYEDTNIRINLDSNT<br>RSFIVPIITTEYIREKLSYSFYGSGGTYALSLSQYNMGINIELSESDVWIIDVDNVVR<br>DVTIESDKIKKGDLIEGILSTLSIEENKIILNSHEINFSGEVNGSNGFVSLTFSILEGIN<br>AIIEVDLLSKSYKLLISGELKILMLNSNHIQQKIDYIGFNSELQKNIPYSFVDSEGKE<br>NGFINGSTKEGLFVSELPDVVLISKVYMDDSKPSFGYYSNNLKDVKVITKDNVNI<br>LTGYYLKDDIKISLSLTLQDEKTIKLNSVHLDESGVAEILKFMNRKGNTNTSDSL<br>MSFLESMNIKSIFVNFLQSNIKFILDANFIISGTTSIGQFEFICDENDNIQPYFIKFNTL<br>ETNYTLYVGNRQNMIVEPNYDLDDSGDISSTVINFSQKYLYGIDSCVNKVVISPNI<br>YTDEINITPVYETNNTYPEVIVLDANYINEKINVNINDLSIRYVWSNDGNDFILMST<br>SEENKVSQVKIRFVNVFKDKTLANKLSFNFSDKQDVPVSEIILSFTPSYYEDGLIG<br>YDLGLVSLYNEKFYINNFGMMVSGLIYINDSLYYFKPPVNNLITGFVTVGDDKYY<br>FNPINGGAASIGETIIDDKNYYFNQSGVLQTGVFSTEDGFKYFAPANTLDENLEGE<br>AIDFTGKLIIDENIYYFDDNYRGAVEWKELDGEMHYFSPETGKAFKGLNQIGDYK<br>YYFNSDGVMQKGFVSINDNKHYFDDSGVMKVGYTEIDGKHFYFAENGEMQIGV<br>FNTEDGFKYFAHHNEDLGNEEGEEISYSGILNFNNKIYYFDDSFTAVVGWKDLED<br>GSKYYFDEDTAEAYIGLSLINDGQYYFNDDGIMQVGFVTINDKVFYFSDSGIIESG<br>VQNIDDNYFYIDDNGIVQIGVFDTSDGYKYFAPANTVNDNIYGQAVEYSGLVRV<br>GEDVYYFGETYTIETGWIYDMENESDKYYFNPETKKACKGINLIDDIKYYFDEKG<br>IMRTGLISFENNNYYFNENGEMQFGYINIEDKMFYFGEDGVMQIGVFNTPDGFKY<br>FAHQNTLDENFEGESINYTGWLDLDEKRYYFTDEYIAATGSVIIDGEEYYFDPDT<br>AQLVISE |
| SEQ ID NO: 25 - Toxin B-derived recombinant antigen - His-Thioredoxin-[thrombin site]-<br>TxB 4<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALVPRGSVTSLYKKAGSAAAPFTMSIIKDISSKEYISFNPKENKITV<br>KSKNLPELSTLLQEIRNNSNSSDIELEEKVMLTECEINVISNIDTQIVEERIEEAKNL<br>TSDSINYIKDEFKLIESISDALCDLKQQNELEDSHFISFEDISETDEGFSIRFINKETG<br>ESIFVETEKTIFSEYANHITEEISKIKGTIFDTVNGKLVKKVNLDTTHEVNTLNAAF<br>FIQSLIEYNSSKESLSNLSVAMKVQVYAQLFSTGLNTITDAAKVVELVSTALDETI<br>DLLPTLSEGLPIIATIIDGVSLGAAIKELSETSDPLLRQEIEAKIGIMAVNLTTATTAII<br>TSSLGIASGFSILLVPLAGISAGIPSLVNNELVLRDKATKVVDYFKHVSLVETEGVF<br>TLLDDKIMMPQDDLVISEIDFNNNSIVLGKCEIWRMEGGSGHTVTDDIDHFFSAPS<br>ITYREPHLSIYDVLEVQKEELDLSKDLMVLPNAPNRVFAWETGWTPGLRSLEND<br>GTKLLDRIRDNYEGEFYWRYFAFIADALITTLKPRYEDTNIRINLDSNTRSFIVPIIT<br>TEYIREKLSYSFYGSGGTYALSLSQYNMGINIELSESDVWIIDVDNVVRDVTIESD<br>KIKKGDLIEGILSTLSIEENKIILNSHEINFSGEVNGSNGFVSLTFSILEGINAIIEVDL<br>LSKSYKLLISGELKILMLNSNHIQQKIDYIGFNSELQKNIPYSFVDSEGKENGFING<br>STKEGLFVSELPDVVLISKVYMDDSKPSFGYYSNNLKDVKVITKDNVNILTGYYL<br>KDDIKISLSLTLQDEKTIKLNSVHLDESGVAEILKFMNRKGNTNTSDSLMSFLESM<br>NIKSIFVNFLQSNIKFILDANFIISGTTSIGQFEFICDENDNIQPYFIKFNTLETNYTLY<br>VGNRQNMIVEPNYDLDDSGDISSTVINFSQKYLYGIDSCVNKVVISPNIYTDEINIT |

-continued

| SEQ ID NOs |
|---|
| PVYETNNTYPEVIVLDANYINEKINVNINDLSIRYVWSNDGNDFILMSTSEENKVS<br>QVKIRFVNVFKDKTLANKLSFNFSDKQDVPVSEIILSFTPSYYEDGLIGYDLGLVS<br>LYNEKFYINNFGMMVSGLIYINDSLYYFKPPVNNLITGFVTVGDDKYYFNPINGG<br>AASIGETIIDDKNYYFNQSGVLQTGVFSTEDGFKYFAPANTLDENLEGEAIDFTGK<br>LIIDENIYYFDDNYRGAVEWKELDGEMHYFSPETGKAFKGLNQIGDYKYYFNSD<br>GVMQKGFVSINDNKHYFDDSGVMKVGYTEIDGKHFYFAENGEMQIGVFNTEDG<br>FKYFAHHNEDLGNEEGEEISYSGILNFNNKIYYFDDSFTAVVGWKDLEDGSKYYF<br>DEDTAEAYIGLSLINDGQYYFNDDGIMQVGFVTINDKVFYFSDSGIIESGVQNIDD<br>NYFYIDDNGIVQIGVFDTSDGYKYFAPANTVNDNIYGQAVEYSGLVRVGEDVYY<br>FGETYTIETGWIYDMENESDKYYFNPETKKACKGINLIDDIKYYFDEKGIMRTGLI<br>SFENNNYYFNENGEMQFGYINIEDKMFYFGEDGVMQIGVFNTPDGFKYFAHQNT<br>LDENFEGESINYTGWLDLDEKRYYFTDEYIAATGSVIIDGEEYYFDPDTAQLVISE |
| SEQ ID NO: 26 - Toxin B-derived recombinant antigen - His-NusA-[thrombin site]-TxB3<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALVPRGSVTSLYKKAGSAAGGSMPQDDLVISEIDFNN<br>NSIVLGKCEIWRMEGGSGHTVTDDIDHFFSAPSITYREPHLSIYDVLEVQKEELDL<br>SKDLMVLPNAPNRVFAWETGWTPGLRSLENDGTKLLDRIRDNYEGEFYWRYFA<br>FIADALITTLKPRYEDTNIRINLDSNTRSFIVPIITTEYIREKLSYSFYGSGGTYALSL<br>SQYNMGINIELSESDVWIIDVDNVVRDVTIESDKIKKGDLIEGILSTLSIEENKIILNS<br>HEINFSGEVNGSNGFVSLTFSILEGINAIIEVDLLSKSYKLLISGELKILMLNSNHIQ<br>QKIDYIGFNSELQKNIPYSFVDSEGKENGFINGSTKEGLFVSELPDVVLISKVYMD<br>DSKPSFGYYSNNLKDVKVITKDNVNILTGYYLKDDIKISLSLTLQDEKTIKLNSVH<br>LDESGVAEILKFMNRKGNTNTSDSLMSFLESMNIKSIFVNFLQSNIKFILDANFIISG<br>TTSIGQFEFICDENDNIQPYFIKFNTLETNYTLYVGNRQNMIVEPNYDLDDSGDISS<br>TVINFSQKYLYGIDSCVNKVVISPNIYTDEINITPVYETNNTYPEVIVLDANYINEKI<br>NVNINDLSIRYVWSNDGNDFILMSTSEENKVSQVKIRFVNVFKDKTLANKLSFNF<br>SDKQDVPVSEIILSFTPSYYEDGLIGYDLGLVSLYNEKFYINNFGMMVSGLIYINDS<br>LYYFKPPVNNLITGFVTVGDDKYYFNPINGGAASIGETIIDDKNYYFNQSGVLQT<br>GVFSTEDGFKYFAPANTLDENLEGEAIDFTGKLIIDENIYYFDDNYRGAVEWKEL<br>DGEMHYFSPETGKAFKGLNQIGDYKYYFNSDGVMQKGFVSINDNKHYFDDSGV<br>MKVGYTEIDGKHFYFAENGEMQIGVFNTEDGFKYFAHHNEDLGNEEGEEISYSGI<br>LNFNNKIYYFDDSFTAVVGWKDLEDGSKYYFDEDTAEAYIGLSLINDGQYYFND<br>DGIMQVGFVTINDKVFYFSDSGRESGVQNIDDNYFYIDDNGIVQIGVFDTSDGYK<br>YFAPANTVNDNIYGQAVEYSGLVRVGEDVYYFGETYTIETGWIYDMENESDKY<br>YFNPETKKACKGINLIDDIKYYFDEKGIMRTGLISFENNNYYFNENGEMQFGYINI<br>EDKMFYFGEDGVMQIGVFNTPDGFKYFAHQNTLDENFEGESINYTGWLDLDEKR<br>YYFTDEYIAATGSVIIDGEEYYFDPDTAQLVISE |
| SEQ ID NO: 27 - Toxin B -derived recombinant antigen - His-Thioredoxin-[thrombin site]-TxB 3 (-hyd)<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALVPRGSVTSLYKKAGSAAGGSMPQDDLVISEIDFNNNSIVLGKC<br>EIWRMEGGSGHTVTDDIDHFFSAPSITYREPHLSIYDVLEVQKEELDLSKDLMVLP<br>NAPNRVFAWETGWTPGLRSLENDGTKLLDRIRDNYEGEFYWRYFAFIADALITT<br>LKPRYEDTNIRINLDSNTRSFIVPIITTEYIREKLSYSFYGSGGTYALSLSQYNMGIN<br>IELSESDVWIIDVDNVVRDVTIESDKIKKGDLIEGILSTLSIEENKIILNSHEINFSGE<br>VNGSNGFVSLTFSILEGINAIIEVDLLSKSYKLLISGELKILMLNSNHIQQKIDYIGF<br>NSELQKNIPYSFVDSEGKENGFINGSTKEGLFVSELPDVVLISKVYMDDSKPSFGY<br>YSNNLKDVKVITKDNVNILTGYYLKDDIKISLSLTLQDEKTIKLNSVHLDESGVAE<br>ILKFMNRKGNTNTSDSLMSFLESMNIKSIFVNFLQSNIKFILDANFIISGTTSIGQFEF<br>ICDENDNIQPYFIKFNTLETNYTLYVGNRQNMIVEPNYDLDDSGDISSTVINFSQK<br>YLYGIDSCVNKVVISPNIYTDEINITPVYETNNTYPEVIVLDANYINEKINVNINDL<br>SIRYVWSNDGNDFILMSTSEENKVSQVKIRFVNVFKDKTLANKLSFNFSDKQDVP<br>VSEIILSFTPSYYEDGLIGYDLGLVSLYNEKFYINNFGMMVSGLIYINDSLYYFKPP<br>VNNLITGFVTVGDDKYYFNPINGGAASIGETIIDDKNYYFNQSGVLQTGVFSTED<br>GFKYFAPANTLDENLEGEAIDFTGKLIIDENIYYFDDNYRGAVEWKELDGEMHYF<br>SPETGKAFKGLNQIGDYKYYFNSDGVMQKGFVSINDNKHYFDDSGVMKVGYTE<br>IDGKHFYFAENGEMQIGVFNTEDGFKYFAHHNEDLGNEEGEEISYSGILNFNNKI<br>YYFDDSFTAVVGWKDLEDGSKYYFDEDTAEAYIGLSLINDGQYYFNDDGIMQV<br>GFVTINDKVFYFSDSGIIESGVQNIDDNYFYIDDNGIVQIGVFDTSDGYKYFAPAN<br>TVNDNIYGQAVEYSGLVRVGEDVYYFGETYTIETGWIYDMENESDKYYFNPETK<br>KACKGINLIDDIKYYFDEKGIMRTGLISFENNNYYFNENGEMQFGYINIEDKMFYF<br>GEDGVMQIGVFNTPDGFKYFAHQNTLDENFEGESINYTGWLDLDEKRYYFTDEY<br>IAATGSVIIDGEEYYFDPDTAQLVISE |

-continued

| SEQ ID NOs |
|---|
| SEQ ID NO: 28 - Toxin A-derived recombinant antigen - His-[linear spacer]-NusA-[thrombin site]-TxA4<br>HHHHHHHHHHGGSGGSGGSGGSGGSGGSGGSGGSGGSGGSGGSHMASNKEILAVVEA<br>VSNEKALPREKIFEALESALATATKKKYEQEIDVRVQIDRKSGDFDTPRRWLVVD<br>EVTQPTKEITLEAARYEDESLNLGDYVEDQIESVTFDRITTQTAKQVIVQKVREAE<br>RAMVVDQFREHEGEIITGVVKKVNRDNISLDLGNNAEAVILREDMLPRENFRPG<br>DRVRGVLYSVRPEARGAQLFVTRSKPEMLIELFRIEVPEIGEEVIEIKAAARDPGSR<br>AKIAVKTNDKRIDPVGACVGMRGARVQAVSTELGGERIDIVLWDDNPAQFVINA<br>MAPADVASIVVDEDKHTMDIAVEAGNLAQAIGRNGQNVRLASQLSGWELNVMT<br>VDDLQAKHQAEAHAAIDTFTKYLDIDEDFATVLVEEGFSTLEELAYVPMKELLEI<br>EGLDEPTVEALRERAKNALATIAQAQEESLGDNKPADDLLNLEGVDRDLAFKLA<br>ARGVCTLEDLAEQGIDDLADIEGLTDEKAGALIMAARNICWFGDEASGALVPRG<br>SVTSLYKKAGSAAAPFTMIMSDLSSKEYIFFDSIDNKLKAKSKNIPGLASISEDIKT<br>LLLDASVSPDTKFILNNLKLNIESSIGDYIYYEKLEPVKNIIHNSIDDLIDEFNLLEN<br>VSDELYELKKLNNLDEKYLISFEDISKNNSTYSVRFINKSNGESVYVETEKEIFSKY<br>SEHITKEISTIKNSIITDVNGNLLDNIQLDHTSQVNTLNAAFFIQSLIDYSSNKDVLN<br>DLSTSVKVQLYAQLFSTGLNTIYDSIQLVNLISNAVNDTINVLPTITEGIPIVSTILD<br>GINLGAAIKELLDEHDPLLKKELEAKVGVLAINMSLSIAATVASIVGIGAEVTIFLL<br>PIAGISAGIPSLVNNELILHDKATSVVNYFNHLSESKKYGPLKTEDDKILVPIDDLV<br>ISEIDFNNNSIKLGTCNILAMEGGSGHTVTGNIDHFFSSPSISSHIPSLSIYSAIGIETE<br>NLDFSKKIMMLPNAPSRVFWWETGAVPGLRSLENDGTRLLDSIRDLYPGKFYWR<br>FYAFFDYAITTLKPVYEDTNIKIKLDKDTRNFIMPTITTNEIRNKLSYSFDGAGGTY<br>SLLLSSYPISTNINLSKDDLWIFNIDNEVREISIENGTIKKGKLIKDVLSKIDINKNKL<br>IIGNQTIDFSGDIDNKDRYIFLTCELDDKISLIIEINLVAKSYSLLLSGDKNYLISNLS<br>NIIEKINTLGLDSKNIAYNYTDESNNKYFGAISKTSQKSIIHYKKDSKNILEFYNDS<br>TLEFNSKDFIAEDINVFMKDDINTITGKYYVDNNTDKSIDFSISLVSKNQVKVNGL<br>YLNESVYSSYLDFVKNSDGHHNTSNFMNLFLDNISFWKLFGFENINFVIDKYFTL<br>VGKTNLGYVEFICDNNKNIDIYFGEWKTSSSKSTIFSGNGRNVVVEPIYNPDTGED<br>ISTSLDFSYEPLYGIDRYINKVLIAPDLYTSLININTNYYSNEYYPEIIVLNPNTFHK<br>KVNINLDSSSFEYKWSTEGSDFILVRYLEESNKKILQKIRIKGILSNTQSFNKMSIDF<br>KDIKKLSLGYIMSNFKSFNSENELDRDHLGFKIIDNKTYYYDEDSKLVKGLININN<br>SLFYFDPIEFNLVTGWQTINGKKYYFDINTGAALISYKIINGKHFYFNNDGVMQL<br>GVFKGPDGFEYFAPANTQNNNIEGQAIVYQSKFLTLNGKKYYFDNDSKAVTGW<br>RIINNEKYYFNPNNAIAAVGLQVIDNNKYYFNPDTAIISKGWQTVNGSRYYFDTD<br>TAIAFNGYKTIDGKHFYFDSDCVVKIGVFSTSNGFEYFAPANTYNNNIEGQAIVY<br>QSKFLTLNGKKYYFDNNSKAVTGWQTIDSKKYYFNTNTAEAATGWQTIDGKKY<br>YFNTNTAEAATGWQTIDGKKYYFNTNTAIASTGYTIINGKHFYFNTDGIMQIGVF<br>KGPNGFEYFAPANTDANNIEGQAILYQNEFLTLNGKKYYFGSDSKAVTGWRIINN<br>KKYYFNPNNAIAAIHLCTINNDKYYFSYDGILQNGYITIERNNFYFDANNESKMV<br>TGVFKGPNGFEYFAPANTHNNNIEGQAIVYQNKFLTLNGKKYYFDNDSKAVTG<br>WQTIDGKKYYFNLNTAEAATGWQTIDGKKYYFNLNTAEAATGWQTIDGKKYYF<br>NTNTFIASTGYTSINGKHFYFNTDGIMQIGVFKGPNGFEYFAPANTHNNNIEGQAI<br>LYQNKFLTLNGKKYYFGSDSKAVTGLRTIDGKKYYFNTNTAVAVTGWQTINGK<br>KYYFNTNTSIASTGYTIISGKHFYFNTDGIMQIGVFKGPDGFEYFAPANTDANNIE<br>GQAIRYQNRFLYLHDNIYYFGNNSKAATGWVTIDGNRYYFEPNTAMGANGYKTI<br>DNKNFYFRNGLPQIGVFKGSNGFEYFAPANTDANNIEGQAIRYQNRFLHLLGKIY<br>YFGNNSKAVTGWQTINGKVYYFMPDTAMAAAGGLFEIDGVIYFFGVDGVKAPG<br>IYG. |
| SEQ ID NO: 29 - Toxin A-derived recombinant antigen - His-[helical spacer]-NusA-[thrombin site]-TxA4<br>HHHHHHHHHHGGSLAEAAAKEAAAKEAAAKEAAAKEAAAKAAAGGSHMASN<br>KEILAVVEAVSNEKALPREKIFEALESALATATKKKYEQEIDVRVQIDRKSGDFDT<br>FRRWLVVDEVTQPTKEITLEAARYEDESLNLGDYVEDQIESVTFDRITTQTAKQVI<br>VQKVREAERAMVVDQFREHEGEIITGVVKKVNRDNISLDLGNNAEAVILREDML<br>PRENFRPGDRVRGVLYSVRPEARGAQLFVTRSKPEMLIELFRIEVPEIGEEVIEIKA<br>AARDPGSRAKIAVKTNDKRIDPVGACVGMRGARVQAVSTELGGERIDIVLWDD<br>NPAQFVINAMAPADVASIVVDEDKHTMDIAVEAGNLAQAIGRNGQNVRLASQLS<br>GWELNVMTVDDLQAKHQAEAHAAIDTFTKYLDIDEDFATVLVEEGFSTLEELAY<br>VPMKELLEIEGLDEPTVEALRERAKNALATIAQAQEESLGDNKPADDLLNLEGV<br>DRDLAFKLAARGVCTLEDLAEQGIDDLADIEGLTDEKAGALIMAARNICWFGDE<br>ASGALVPRGSVTSLYKKAGSAAAPFTMIMSDLSSKEYIFFDSIDNKLKAKSKNIPG<br>LASISEDIKTLLLDASVSPDTKFILNNLKLNIESSIGDYIYYEKLEPVKNIIHNSIDDL<br>IDEFNLLENVSDELYELKKLNNLDEKYLISFEDISKNNSTYSVRFINKSNGESVYV<br>ETEKEIFSKYSEHITKEISTIKNSIITDVNGNLLDNIQLDHTSQVNTLNAAFFIQSLID<br>YSSNKDVLNDLSTSVKVQLYAQLFSTGLNTIYDSIQLVNLISNAVNDTINVLPTITE<br>GIPIVSTILDGINLGAAIKELLDEHDPLLKKELEAKVGVLAINMSLSIAATVASIVGI<br>GAEVTIFLLPIAGISAGIPSLVNNELILHDKATSVVNYFNHLSESKKYGPLKTEDDK<br>ILVPIDDLVISEIDFNNNSIKLGTCNILAMEGGSGHTVTGNIDHFFSSPSISSHIPSLSI<br>YSAIGIETENLDFSKKIMMLPNAPSRVFWWETGAVPGLRSLENDGTRLLDSIRDL<br>YPGKFYWRFYAFFDYAITTLKPVYEDTNIKIKLDKDTRNFIMPTITTNEIRNKLSYS<br>FDGAGGTYSLLLSSYPISTNINLSKDDLWIFNIDNEVREISIENGTIKKGKLIKDVLS<br>KIDINKNKLIIGNQTIDFSGDIDNKDRYIFLTCELDDKISLIIEINLVAKSYSLLLSGD<br>KNYLISNLSNIIEKINTLGLDSKNIAYNYTDESNNKYFGAISKTSQKSIIHYKKDSK<br>NILEFYNDSTLEFNSKDFIAEDINVFMKDDINTITGKYYVDNNTDKSIDFSISLVSK<br>NQVKVNGLYLNESVYSSYLDFVKNSDGHHNTSNFMNLFLDNISFWKLFGFENIN<br>FVIDKYFTLVGKTNLGYVEFICDNNKNIDIYFGEWKTSSSKSTIFSGNGRNVVVEP |

-continued

| SEQ ID NOs |
|---|
| IYNPDTGEDISTSLDFSYEPLYGIDRYINKVLIAPDLYTSLININTNYYSNEYYPEIIV<br>LNPNTFHKKVNINLDSSSFEYKWSTEGSDFILVRYLEESNKKILQKIRIKGILSNTQ<br>SFNKMSIDFKDIKKLSLGYIMSNFKSFNSENELDRDHLGFKIIDNKTYYYDEDSKL<br>VKGLININNSLFYFDPIEFNLVTGWQTINGKKYYFDINTGAALISYKIINGKHFYFN<br>NDGVMQLGVFKGPDGFENFAPANTQNNNIEGQAIVYQSKFLTLNGKKYYFDND<br>SKAVTGWRIINNEKYYFNPNNAIAAVGLQVIDNNKYYFNPDTAIISKGWQTVNGS<br>RYYIDTDTAIAFNGYKTIDGKHFYFDSDCVVKIGVFSTSNGFEYFAPANTYNNNI<br>EGQAIVYQSKFLTLNGKKYYFDNNSKAVTGWQTIDSKKYYFNTNTAEAATGWQ<br>TIDGKKYYFNTNTAEAATGWQTIDGKKYYFNTNTAIASTGYTIINGKHFYFNTDG<br>IMQIGVFKGPNGFEYFAPANTDANNIEGQAILYQNEFLTLNGKKYYFGSDSKAVT<br>GWRIINNKKYYFNPNNAIAAIHLCTINNDKYYFSYDGILQNGYITIERNNFYFDAN<br>NESKMVTGVFKGPNGFEYFAPANTHNNNIEGQAIVYQNKFLTLNGKKYYFDNDS<br>KAVTGWQTIDGKKYYFNLNTAEAATGWQTIDGKKYYFNLNTAEAATGWQTID<br>GKKYYFNTNTFIASTGYTSINGKHFYFNTDGIMQIGVFKGPNGFEYFAPANTHNN<br>NIEGQAILYQNKFLTLNGKKYYFGSDSKAVTGLRTIDGKKYYFNTNTAVAVTGW<br>QTINGKKYYFNTNTSIASTGYTIISGKHFYFNTDGIMQIGVFKGPDGFEYFAPANT<br>DANNIEGQAIRYQNRFLYLHDNIYYFGNNSKAATGWVTIDGNRYYFEPNTAMGA<br>NGYKTIDNKNFYFRNGLPQIGVFKGSNGFEYFAPANTDANNIEGQAIRYQNRFLH<br>LLGKIYYFGNNSKAVTGWQTINGKVYYFMPDTAMAAAGGLFEIDGVIYFFGVDG<br>VKAPGIYG |
| SEQ ID NO: 30 - Toxin A-derived recombinant antigen - His-NusA-[linear spacer]-[thrombin site]-TxA4<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALGGSGGSGGSGGSGGSGGSGGSGGSGGSLVPRGSGS<br>AAAPFTMIMSDLSSKEYIFFDSIDNKLKAKSKNIPGLASISEDIKTLLLDASVSPDT<br>KFILNNLKLNIESSIGDYIYYEKLEPVKNIIHNSIDDLIDEFNLLENVSDELYELKKL<br>NNLDEKYLISFEDISKNNSTYSVRFINKSNGESVYVETEKEIFSKYSEHITKEISTIK<br>NSIITDVNGNLLDNIQLDHTSQVNTLNAAFFIQSLIDYSSNKDVLNDLSTSVKVQL<br>YAQLFSTGLNTIYDSIQLVNLISNAVNDTINVLPTITEGIPIVSTILDGINLGAAIKEL<br>LDEHDPLLKKELEAKVGVLAINMSLSIAATVASIVGIGAEVTIFLLPIAGISAGIPSL<br>VNNELILHDKATSVVNYFNHLSESKKYGPLKTEDDKILVPIDDLVISEIDFNNNSIK<br>LGTCNILAMEGGSGHTVTGNIDHFFSSPSISSHIPSLSIYSAIGIETENLDFSKKIMM<br>LPNAPSRVFWWETGAVPGLRSLENDGTRLLDSIRDLYPGKFYWRFYAFFDYAITT<br>LKPVYEDTNIKIKLDKDTRNFIMPTITTNEIRNKLSYSFDGAGGTYSLLLSSYPIST<br>NINLSKDDLWIFNIDNEVREISIENGTIKKGKLIKDVLSKIDINKNKLIIGNQTIDFSG<br>DIDNKDRYIFLTCELDDKISLIIEINLVAKSYSLLLSGDKNYLISNLSNIIEKINTLGL<br>DSKNIAYNYTDESNNKYFGAISKTSQKSIIHYKKDSKNILEFYNDSTLEFNSKDFIA<br>EDINVFMKDDINTITGKYYVDNNTDKSIDFSISLVSKNQVKVNGLYLNESVYSSY<br>LDFVKNSDGHHNTSNFMNLFLDNISFWKLFGFENINFVIDKYFTLVGKTNLGYVE<br>FICDNNKNIDIYFGEWKTSSSKSTIFSGNGRNVVVEPIYNPDTGEDISTSLDFSYEPL<br>YGIDRYINKVLIAPDLYTSLININTNYYSNEYYPEIIVLNPNTFHKKVNINLDSSSFE<br>YKWSTEGSDFILVRYLEESNKKILQKIRIKGILSNTQSFNKMSIDFKDIKKLSLGYI<br>MSNFKSFNSENELDRDHLGFKIIDNKTYYYDEDSKLVKGLININNSLFYFDPIEFN<br>LVTGWQTINGKKYYFDINTGAALISYKIINGKHFYFNNDGVMQLGVFKGPDGFE<br>YFAPANTQNNNIEGQAIVYQSKFLTLNGKKYYFDNDSKAVTGWRIINNEKYYFN<br>PNNAIAAVGLQVIDNNKYYFNPDTAIISKGWQTVNGSRYYFDTDTAIAFNGYKTI<br>DGKHFYFDSDCVVKIGVFSTSNGFEYFAPANTYNNNIEGQAIVYQSKFLTLNGKK<br>YYFDNNSKAVTGWQTIDSKKYYFNTNTAEAATGWQTIDGKKYYFNTNTAEAAT<br>GWQTIDGKKYYFNTNTAIASTGYTIINGKHFYFNTDGIMQIGVFKGPNGFEYFAP<br>ANTDANNIEGQAILYQNEFLTLNGKKYYFGSDSKAVTGWRIINNKKYYFNPNNAI<br>AAIHLCTINNDKYYFSYDGILQNGYITIERNNFYFDANNESKMVTGVFKGPNGFE<br>YFAPANTHNNNIEGQAIVYQNKFLTLNGKKYYFDNDSKAVTGWQTIDGKKYYF<br>NLNTAEAATGWQTIDGKKYYFNLNTAEAATGWQTIDGKKYYFNTNTFIASTGYT<br>SINGKHFYFNTDGIMQIGVFKGPNGFEYFAPANTHNNNIEGQAILYQNKFLTLNG<br>KKYYFGSDSKAVTGLRTIDGKKYYFNTNTAVAVTGWQTINGKKYYFNTNTSIAS<br>TGYTIISGKHFYFNTDGIMQIGVFKGPDGFEYFAPANTDANNIEGQAIRYQNRFLY<br>LHDNIYYFGNNSKAATGWVTIDGNRYYFEPNTAMGANGYKTIDNKNFYFRNGL<br>PQIGVFKGSNGFEYFAPANTDANNIEGQAIRYQNRFLHLLGKIYYFGNNSKAVTG<br>WQTINGKVYYFMPDTAMAAAGGLFEIDGVIYFFGVDGVKAPGIYG |
| SEQ ID NO: 31 - Toxin A-derived recombinant antigen - His-NusA-[helical spacer]-[thrombin site]-TxA4<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI |

-continued

| SEQ ID NOs |
| --- |
| GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALLAEAAAKEAAAKEAAAKEAAAKEAAAKAAAGGS<br>LVPRGSGSAAAPFTMIMSDLSSKEYIFFDSIDNKLKAKSKNIPGLASISEDIKTLLL<br>DASVSPDTKFILNNLKLNIESSIGDYIYYEKLEPVKNIIHNSIDDLIDEFNLLENVSD<br>ELYELKKLNNLDEKYLISFEDISKNNSTYSVRFINKSNGESVYVETEKEIFSKYSEH<br>ITKEISTIKNSIITDVNGNLLDNIQLDHTSQVNTLNAAFFIQSLIDYSSNKDVLNDLS<br>TSVKVQLYAQLFSTGLNTIYDSIQLVNLISNAVNDTINVLPTITEGIPIVSTILDGINL<br>GAAIKELLDEHDPLLKKELEAKVGVLAINMSLSIAATVASIVGIGAEVTIFLLPIAG<br>ISAGIPSLVNNELILHDKATSVVNYFNHLSESKKYGPLKTEDDKILVPIDDLVISEID<br>FNNNSIKLGTCNILAMEGGSGHTVTGNIDHFFSSPSISSHIPSLSIYSAIGIETENLDF<br>SKKIMMLPNAPSRVFWWETGAVPGLRSLENDGTRLLDSIRDLYPGKFYWRFYAF<br>FDYAITTLKPVYEDTNIKIKLDKDTRNFIMPTITTNEIRNKLSYSFDGAGGTYSLLL<br>SSYPISTNINLSKDDLWIFNIDNEVREISIENGTIKKGKLIKDVLSKIDINKNKLIIGN<br>QTIDFSGDIDNKDRYIFLTCELDDKISLIIEINLVAKSYSLLLSGDKNYLISNLSNIIE<br>KINTLGLDSKNIAYNYTDESNNKYFGAISKTSQKSIIHYKKDSKNILEFYNDSTLEF<br>NSKDFIAEDINVFMKDDINTITGKYYVDNNTDKSIDFSISLVSKNQVKVNGLYLNE<br>SVYSSYLDFVKNSDGHHNTSNFMNLFLDNISFWKLFGFENINFVIDKYFTLVGKT<br>NLGYVEFICDNNKNIDIYFGEWKTSSSKSTIFSGNGRNVVVEPIYNPDTGEDISTSL<br>DFSYEPLYGIDRYINKVLIAPDLYTSLININTNYYSNEYYPEIIVLNPNTFHKKVNIN<br>LDSSSPENKWSTEGSDFILVRYLEESNKKILQKIRIKGILSNTQSFNKMSIDFKDIKK<br>LSLGYIMSNFKSFNSENELDRDHLGFKIIDNKTYYYDEDSKLVKGLININNSLFYF<br>DPIEFNLVTGWQTINGKKYYFDINTGAALISYKIINGKHFYFNNDGVMQLGVFKG<br>PDGFEYFAPANTQNNNIEGQAIVYQSKFLTLNGKKYYFDNDSKAVTGWRIINNE<br>KYYFNPNNAIAAVGLQVIDNNKYYFNPDTAIISKGWQTVNGSRYYFDTDTAIAFN<br>GYKTIDGKHFYFDSDCVVKIGVFSTSNGFEYFAPANTYNNNIEGQAIVYQSKFLT<br>LNGKKYYPDNNSKAVTGWQTIDSKKYYFNTNTAEAATGWQTIDGKKYYFNTNT<br>AEAATGWQTIDGKKYYFNTNTAIASTGYTIINGKHFYFNTDGIMQIGVFKGPNGF<br>EYFAPANTDANNIEGQAILYQNEFLTLNGKKYYFGSDSKAVTGWRIINNKKYYF<br>NPNNAIAAIHLCTINNDKYYFSYDGILQNGYITIERNNFYFDANNESKMVTGVFK<br>GPNGFEYFAPANTHNNNIEGQAIVYQNKFLTLNGKKYYFDNDSKAVTGWQTIDG<br>KKYYFNLNTAEAATGWQTIDGKKYYFNLNTAEAATGWQTIDGKKYYFNTNTFI<br>ASTGYTSINGKHFYFNTDGIMQIGVFKGPNGFEYFAPANTHNNNIEGQAILYQNK<br>FLTLNGKKYYFGSDSKAVTGLRTIDGKKYYFNTNTAVAVTGWQTINGKKYYFN<br>TNTSIASTGYTIISGKHFYFNTDGIMQIGVFKGPDGFEYFAPANTDANNIEGQAIRY<br>QNRFLYLHDNIYYFGNNSKAATGWVTIDGNRYYFEPNTAMGANGYKTIDNKNF<br>YFRNGLPQIGVFKGSNGFEYFAPANTDANNIEGQAIRYQNRFLHLLGKIYYFGNN<br>SKAVTGWQTINGKVYYFMPDTAMAAAGGLFEIDGVIYFFGVDGVKAPGIYG |
| SEQ ID NO: 32 - Toxin A-derived recombinant antigen - His-[linear spacer]-NusA-[thrombin site]-TxA3<br>HHHHHHHHHHGGSGGSGGSGGSGGSGGSGGSGGSGGSGGSHMASNKEILAVVEA<br>VSNEKALPREKIFEALESALATATKKKYEQEIDVRVQIDRKSGDFDTPRRWLVVD<br>EVTQPTKEITLEAARYEDESLNLGDYVEDQIESVTFDRITTQTAKQVIVQKVREAE<br>RAMVVDQFREHEGEIITGVVKKVNRDNISLDLGNNAEAVILREDMLPRENFRPG<br>DRVRGVLYSVRPEARGAQLFVTRSKPEMLIELFRIEVPEIGEEVIEIKAAARDPGSR<br>AKIAVKTNDKRIDPVGACVGMRGARVQAVSTELGGERIDIVLWDDNPAQFVINA<br>MAPADVASIVVDEDKHTMDIAVEAGNLAQAIGRNGQNVRLASQLSGWELNVMT<br>VDDLQAKHQAEAHAAIDTFTKYLDIDEDFATVLVEEGFSTLEELAYVPMKELLEI<br>EGLDEPTVEALRERAKNALATIAQAQEESLGDNKPADDLLNLEGVDRDLAFKLA<br>ARGVCTLEDLAEQGIDDLADIEGLTDEKAGALIMAARNICWFGDEASGALVPRG<br>SVTSLYKKAGSAAAPFTMESKKYGPLKTEDDKILVPIDDLVISEIDFNNNSIKLGT<br>CNILAMEGGSGHTVTGNIDHFFSSPSISSHIPSLSIYSAIGIETENLDFSKKIMMLPN<br>APSRVFWWETGAVPGLRSLENDGTRLLDSIRDLYPGKFYWRFYAFFDYAITTLKP<br>VYEDTNIKIKLDKDTRNFIMPTITTNEIRNKLSYSFDGAGGTYSLLLSSYPISTNINL<br>SKDDLWIFNIDNEVREISIENGTIKKGKLIKDVLSKIDINKNKLIIGNQTIDFSGDID<br>NKDRYIFLTCELDDKISLIIEINLVAKSYSLLLSGDKNYLISNLSNIIEKINTLGLDSK<br>NIAYNYTDESNNKYFGAISKTSQKSIIHYKKDSKNILEFYNDSTLEFNSKDFIAEDI<br>NVFMKDDINTITGKYYVDNNTDKSIDFSISLVSKNQVKVNGLYLNESVYSSYLDF<br>VKNSDGHHNTSNFMNLFLDNISFWKLFGFENINFVIDKYFTLVGKTNLGYVEFIC<br>DNNKNIDIYFGEWKTSSSKSTIFSGNGRNVVVEPIYNPDTGEDISTSLDFSYEPLYG<br>IDRYINKVLIAPDLYTSLININTNYYSNEYYPEIIVLNPNTFHKKVNINLDSSSFEYK<br>WSTEGSDFILVRYLEESNKKILQKIRIKGILSNTQSFNKMSIDFKDIKKLSLGYIMS<br>NFKSFNSENELDRDHLGFKIIDNKTYYYDEDSKLVKGLININNSLFYFDPIEFNLVT<br>GWQTINGKKYYFDINTGAALISYKIINGKHFYFNNDGVMQLGVFKGPDGFEYFA<br>PANTQNNNIEGQAIVYQSKFLTLNGKKYYFDNDSKAVTGWRIINNEKYYFNPNN<br>AIAAVGLQVIDNNKYYFNPDTAIISKGWQTVNGSRYYFDTDTAIAFNGYKTIDGK<br>HFYFDSDCVVKIGVFSTSNGFEYFAPANTYNNNIEGQAIVYQSKFLTLNGKKYYF<br>DNNSKAVTGWQTIDSKKYYFNTNTAEAATGWQTIDGKKYYFNTNTAEAATGW<br>QTIDGKKYYFNTNTAIASTGYTIINGKHFYFNTDGIMQIGVFKGPNGFENFAPANT<br>DANNIEGQAILYQNEFLTLNGKKYYFGSDSKAVTGWRIINNKKYYFNPNNAIAAI<br>HLCTINNDKYYFSYDGILQNGYITIERNNFYFDANNESKMVTGVFKGPNGFEYFA<br>PANTHNNNIEGQAIVYQNKFLTLNGKKYYFDNDSKAVTGWQTIDGKKYYFNLN<br>TAEAATGWQTIDGKKYYFNLNTAEAATGWQTIDGKKYYFNTNTFIASTGYTSIN<br>GKHFYFNTDGIMQIGVFKGPNGFENFAPANTHNNNIEGQAILYQNKFLTLNGKK<br>YYFGSDSKAVTGLRTIDGKKYYFNTNTAVAVTGWQTINGKKYYFNTNTSIASTG |

-continued

| SEQ ID NOs |
|---|
| YTIISGKHFYFNTDGIMQIGVFKGPDGFEYFAPANTDANNIEGQAIRYQNRFLYLH<br>DNIYYFGNNSKAATGWVTIDGNRYYFEPNTAMGANGYKTIDNKNFYFRNGLPQI<br>GVFKGSNGFEYFAPANTDANNIEGQAIRYQNRFLHLLGKIYYFGNNSKAVTGWQ<br>TINGKVYYFMPDTAMAAAGGLFEIDGVIYFFGVDGVKAPGIYG |
| SEQ ID NO: 33 - Toxin A-derived recombinant antigen - His-[helical spacer]-NusA-[thrombin site]-TxA3<br>HHHHHHHHHHGGSLAEAAAKEAAAKEAAAKEAAAKEAAAKAAAGGSHMASN<br>KEILAVVEAVSNEKALPREKIFEALESALATATKKKYEQEIDVRVQIDRKSGDFDT<br>FRRWLVVDEVTQPTKEITLEAARYEDESLNLGDYVEDQIESVTFDRITTQTAKQVI<br>VQKVREAERAMVVDQFREHEGEIITGVVKKVNRDNISLDLGNNAEAVILREDML<br>PRENFRPGDRVRGVLYSVRPEARGAQLFVTRSKPEMLIELFRIEVPEIGEEVIEIKA<br>AARDPGSRAKIAVKTNDKRIDPVGACVGMRGARVQAVSTELGGERIDIVLWDD<br>NPAQFVINAMAPADVASIVVDEDKHTMDIAVEAGNLAQAIGRNGQNVRLASQLS<br>GWELNVMTVDDLQAKHQAEAHAAIDTFTKYLDIDEDFATVLVEEGFSTLEELAY<br>VPMKELLEIEGLDEPTVEALRERAKNALATIAQAQEESLGDNKPADDLLNLEGV<br>DRDLAFKLAARGVCTLEDLAEQGIDDLADIEGLTDEKAGALIMAARNICWFGDE<br>ASGALVPRGSVTSLYKKAGSAAAPFTMESKKYGPLKTEDDKILVPIDDLVISEIDF<br>NNNSIKLGTCNILAMEGGSGHTVTGNIDHFFSSPSISSHIPSLSIYSAIGIETENLDFS<br>KKIMMLPNAPSRVFWWETGAVPGLRSLENDGTRLLDSIRDLYPGKFYWRFYAFF<br>DYAITTLKPVYEDTNIKIKLDKDTRNFIMPTITTNEIRNKLSYSFDGAGGTYSLLLS<br>SYPISTNINLSKDDLWIFNIDNEVREISIENGTIKKGKLIKDVLSKIDINKNKLIIGNQ<br>TIDFSGDIDNKDRYIFLTCELDDKISLIIEINLVAKSYSLLLSGDKNYLISNLSNIIEKI<br>NTLGLDSKNIAYNYTDESNNKYFGAISKTSQKSIIHYKKDSKNILEFYNDSTLEFN<br>SKDFIAEDINVFMKDDINTITGKYYVDNNTDKSIDFSISLVSKNQVKVNGLYLNES<br>VYSSYLDFVKNSDGHHNTSNFMNLFLDNISFWKLFGFENINFVIDKYFTLVGKTN<br>LGYVEFICDNNKNIDIYFGEWKTSSSKSTIFSGNGRNVVVEPIYNPDTGEDISTSLD<br>FSYEPLYGIDRYINKVLIAPDLYTSLININTNYYSNEYYPEIIVLNPNTFHKKVNINL<br>DSSSFEYKWSTEGSDFILVRYLEESNKKILQKIRIKGILSNTQSFNKMSIDFKDIKKL<br>SLGYIMSNFKSFNSENELDRDHLGFKIIDNKTYYYDEDSKLVKGLININNSLFYI-D<br>PIEFNLVTGWQTINGKKYYFDINTGAALISYKIINGKHFYFNNDGVMQLGVFKGP<br>DGFEYFAPANTQNNNIEGQAIVYQSKFLTLNGKKYYFDNDSKAVTGWRIINNEK<br>YYFNPNNAIAAVGLQVIDNNKYYFNPDTAIISKGWQTVNGSRYYFDTDTAIAFNG<br>YKTIDGKHFYFDSDCVVKIGVFSTSNGFEYFAPANTYNNNIEGQAIVYQSKFLTL<br>NGKKYYFDNNSKAVTGWQTIDSKKYYFNTNTAEAATGWQTIDGKKYYFNTNT<br>AEAATGWQTIDGKKYYFNTNTAIASTGYTIINGKHFYFNTDGIMQIGVFKGPNGF<br>EYFAPANTDANNIEGQAILYQNEFLTLNGKKYYFGSDSKAVTGWRIINNKKYYF<br>NPNNAIAAIHLCTINNDKYYFSYDGILQNGYITIERNNFYFDANNESKMVTGVFK<br>GPNGFEYFAPANTHNNNIEGQAIVYQNKFLTLNGKKYYFDNDSKAVTGWQTIDG<br>KKYYFNLNTAEAATGWQTIDGKKYYFNLNTAEAATGWQTIDGKKYYFNTNTFI<br>ASTGYTSINGKHFYFNTDGIMQIGVFKGPNGFEYFAPANTHNNNIEGQAILYQNK<br>FLTLNGKKYYFGSDSKAVTGLRTIDGKKYYFNTNTAVAVTGWQTINGKKYYFN<br>TNTSIASTGYTIISGKHFYFNTDGIMQIGVFKGPDGFEYFAPANTDANNIEGQAIRY<br>QNRFLYLHDNIYYFGNNSKAATGWVTIDGNRYYFEPNTAMGANGYKTIDNKNF<br>YFRNGLPQIGVFKGSNGFEYFAPANTDANNIEGQAIRYQNRFLHLLGKIYYFGNN<br>SKAVTGWQTINGKVYYFMPDTAMAAAGGLFEIDGVIYFFGVDGVKAPGIYG |
| SEQ ID NO: 34 - Toxin A-derived recombinant antigen - His-NusA-[linear spacer]-[thrombin site]-TxA3<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALGGSGGSGGSGGSGGSGGSGGSGGSGGSLVPRGSGS<br>AAAPFTMESKKYGPLKTEDDKILVPIDDLVISEIDFNNNSIKLGTCNILAMEGGSG<br>HTVTGNIDHFFSSPSISSHIPSLSIYSAIGIETENLDFSKKIMMLPNAPSRVFWWETG<br>AVPGLRSLENDGTRLLDSIRDLYPGKFYWRFYAFFDYAITTLKPVYEDTNIKIKLD<br>KDTRNFIMPTITTNEIRNKLSYSFDGAGGTYSLLLSSYPISTNINLSKDDLWIFNIDN<br>EVREISIENGTIKKGKLIKDVLSKIDINKNKLIIGNQTIDFSGDIDNKDRYIFLTCELD<br>DKISLIIEINLVAKSYSLLLSGDKNYLISNLSNIIEKINTLGLDSKNIAYNYTDESNN<br>KYFGAISKTSQKSIIHYKKDSKNILEFYNDSTLEFNSKDFIAEDINVFMKDDINTIT<br>GKYYVDNNTDKSIDFSISLVSKNQVKVNGLYLNESVYSSYLDFVKNSDGHHNTS<br>NFMNLFLDNISFWKLFGFENINFVIDKYFTLVGKTNLGYVEFICDNNKNIDIYFGE<br>WKTSSSKSTIFSGNGRNVVVEPIYNPDTGEDISTSLDFSYEPLYGIDRYINKVLIAP<br>DLYTSLININTNYYSNEYYPEIIVLNPNTFHKKVNINLDSSSFEYKWSTEGSDFILV<br>RYLEESNKKILQKIRIKGILSNTQSFNKMSIDFKDIKKLSLGYIMSNFKSFNSENEL<br>DRDHLGFKIIDNKTYYYDEDSKLVKGLININNSLFYFDPIEFNLVTGWQTINGKKY<br>YFDINTGAALISYKIINGKHFYFNNDGVMQLGVFKGPDGFEYFAPANTQNNNIEG<br>QAIVYQSKFLTLNGKKYYFDNDSKAVTGWRIINNEKYYFNPNNAIAAVGLQVID<br>NNKYYFNPDTAIISKGWQTVNGSRYYFDTDTAIAFNGYKTIDGKHFYFDSDCVV<br>KIGVFSTSNGFEYFAPANTYNNNIEGQAIVYQSKFLTLNGKKYYFDNNSKAVTG<br>WQTIDSKKYYFNTNTAEAATGWQTIDGKKYYFNTNTAEAATGWQTIDGKKYYF |

-continued

SEQ ID NOs

NTNTAIASTGYTIINGKHFYFNTDGIMQIGVFKGPNGFEYFAPANTDANNIEGQAI
LYQNEFLTLNGKKYYFGSDSKAVTGWRIINNKKYYFNPNNAIAAIHLCTINNDKY
YFSYDGILQNGYITIERNNFYFDANNESKMVTGVFKGPNGFEYFAPANTHNNNIE
GQAIVYQNKFLTLNGKKYYFDNDSKAVTGWQTIDGKKYYFNLNTAEAATGWQ
TIDGKKYYFNLNTAEAATGWQTIDGKKYYFNTNTFIASTGYTSINGKHFYFNTDG
IMQIGVFKGPNGFEYFAPANTHNNNIEGQAILYQNKFLTLNGKKYYFGSDSKAVT
GLRTIDGKKYYFNTNTAVAVTGWQTINGKKYYFNTNTSIASTGYTIISGKHFYFN
TDGIMQIGVFKGPDGFEYFAPANTDANNIEGQAIRYQNRFLYLHDNIYYFGNNSK
AATGWVTIDGNRYYFEPNTAMGANGYKTIDNKNFYFRNGLPQIGVFKGSNGFEY
FAPANTDANNIEGQAIRYQNRFLHLLGKIYYFGNNSKAVTGWQTINGKVYYFMP
DTAMAAAGGLFEIDGVIYFFGVDGVKAPGIYG

SEQ ID NO: 35 - Toxin A-derived recombinant antigen - His-NusA-[helical spacer]-[thrombin site]-TxA3
HHHHHHSHMASNKEILAVVEAVSNEKALPREKIFEALESALATATKKKYEQEID
VRVQIDRKSGDFDTFRRWLVVDEVTQPTKEITLEAARYEDESLNLGDYVEDQIES
VTFDRITTQTAKQVIVQKVREAERAMVVDQFREHEGEIITGVVKKVNRDNISLDL
GNNAEAVILREDMLPRENFRPGDRVRGVLYSVRPEARGAQLFVTRSKPEMLIELF
RIEVPEIGEEVIEIKAAARDPGSRAKIAVKTNDKRIDPVGACVGMRGARVQAVST
ELGGERIDIVLWDDNPAQFVINAMAPADVASIVVDEDKHTMDIAVEAGNLAQAI
GRNGQNVRLASQLSGWELNVMTVDDLQAKHQAEAHAAIDTFTKYLDIDEDFAT
VLVEEGFSTLEELAYVPMKELLEIEGLDEPTVEALRERAKNALATIAQAQEESLG
DNKPADDLLNLEGVDRDLAFKLAARGVCTLEDLAEQGIDDLADIEGLTDEKAGA
LIMAARNICWFGDEASGALLAEAAAKEAAAKEAAAKEAAAKEAAAKAAAGGS
LVPRGSGSAAAPFTMESKKYGPLKTEDDKILVPIDDLVISEIDFNNNSIKLGTCNIL
AMEGGSGHTVTGNIDHFFSSPSISSHIPSLSIYSAIGIETENLDFSKKIMMLPNAPSR
VFWWETGAVPGLRSLENDGTRLLDSIRDLYPGKFYWRFYAFFDYAITTLKPVYE
DTNIKIKLDKDTRNFIMPTITTNEIRNKLSYSI4DGAGGTYSLLLSSYPISTNINLSKD
DLWIFNIDNEVREISIENGTIKKGKLIKDVLSKIDINKNKLIIGNQTIDFSGDIDNKD
RYIFLTCELDDKISLIIEINLVAKSYSLLLSGDKNYLISNLSNIIEKINTLGLDSKNIA
YNYTDESNNKYFGAISKTSQKSIIHYKKDSKNILEFYNDSTLEFNSKDFIAEDINVF
MKDDINTITGKYYVDNNTDKSIDFSISLVSKNQVKVNGLYLNESVYSSYLDFVKN
SDGHHNTSNFMNLFLDNISFWKLFGFENINFVIDKYFTLVGKTNLGYVEFICDNN
KNIDIYFGEWKTSSSKSTIFSGNGRNVVVEPIYNPDTGEDISTSLDFSYEPLYGIDR
YINKVLIAPDLYTSLININTNYYSNEYYPEIIVLNPNTFHKKVNINLDSSSFEYKWS
TEGSDFILVRYLEESNKKILQKIRIKGILSNTQSFNKMSIDFKDIKKLSLGYIMSNFK
SFNSENELDRDHLGFKIIDNKTYYYDEDSKLVKGLININNSLFYFDPIEFNLVTGW
QTINGKKYYFDINTGAALISYKIINGKHFYFNNDGVMQLGVFKGPDGFEYFAPAN
TQNNNIEGQAIVYQSKFLTLNGKKYYFDNDSKAVTGWRIINNEKYYFNPNNAIA
AVGLQVIDNNKYYFNPDTAIISKGWQTVNGSRYYFDTDTAIAFNGYKTIDGKHF
YFDSDCVVKIGVFSTSNGFEYFAPANTYNNNIEGQAIVYQSKFLTLNGKKYYFDN
NSKAVTGWQTIDSKKYYFNTNTAEAATGWQTIDGKKYYFNTNTAEAATGWQTI
DGKKYYFNTNTAIASTGYTIINGKHFYFNTDGIMQIGVFKGPNGFEYFAPANTDA
NNIEGQAILYQNEFLTLNGKKYYFGSDSKAVTGWRIINNKKYYFNPNNAIAAIHL
CTINNDKYYFSYDGILQNGYITIERNNFYFDANNESKMVTGVFKGPNGFEYFAPA
NTHNNNIEGQAIVYQNKFLTLNGKKYYFDNDSKAVTGWQTIDGKKYYFNLNTA
EAATGWQTIDGKKYYFNLNTAEAATGWQTIDGKKYYFNTNTFIASTGYTSINGK
HFYFNTDGIMQIGVFKGPNGFEYFAPANTHNNNIEGQAILYQNKFLTLNGKKYYF
GSDSKAVTGLRTIDGKKYYFNTNTAVAVTGWQTINGKKYYFNTNTSIASTGYTII
SGKHFYFNTDGIMQIGVFKGPDGFEYFAPANTDANNIEGQAIRYQNRFLYLHDNI
YYFGNNSKAATGWVTIDGNRYYFEPNTAMGANGYKTIDNKNFYFRNGLPQIGV
FKGSNGFEYFAPANTDANNIEGQAIRYQNRFLHLLGKIYYFGNNSKAVTGWQTIN
GKVYYFMPDTAMAAAGGLFEIDGVIYFFGVDGVKAPGIYG SEQ ID NO: 36 - Toxin A-derived recombinant antigen - His-[linear spacer]-Thioredoxin-[thrombin site]-TxA4
HHHHHHHHGGSGGSGGSGGSGGSGGSGGSGGSGGSHMASDKIIHLTDDSF
DTDVLKADGAILVDFWAEWCGPCKMIAPILDEIADEYQGKLTVAKLNIDQNPGT
APKYGIRGIPTLLLFKNGEVAATKVGALSKGQLKEFLDANLARALVPRGSVTSLY
KKAGSAAAPFTMIMSDLSSKEYIFFDSIDNKLKAKSKNIPGLASISEDIKTLLLDAS
VSPDTKFILNNLKLNIESSIGDYIYYEKLEPVKNIIHNSIDDLIDEFNLLENVSDELY
ELKKLNNLDEKYLISFEDISKNNSTYSVRFINKSNGESVYVETEKEIFSKYSEHITK
EISTIKNSIITDVNGNLLDNIQLDHTSQVNTLNAAFFIQSLIDYSSNKDVLNDLSTSV
KVQLYAQLFSTGLNTIYDSIQLVNLISNAVNDTINVLPTITEGIPIVSTILDGINLGA
AIKELLDEHDPLLKKELEAKVGVLAINMSLSIAATVASIVGIGAEVTIFLLPIAGISA
GIPSLVNNELILHDKATSVVNYFNHLSESKKYGPLKTEDDKILVPIDDLVISEIDFN
NNSIKLGTCNILAMEGGSGHTVTGNIDHFFSSPSISSHIPSLSIYSAIGIETENLDFSK
KIMMLPNAPSRVFWWETGAVPGLRSLENDGTRLLDSIRDLYPGKFYWRFYAFFD
YAITTLKPVYEDTNIKIKLDKDTRNFIMPTITTNEIRNKLSYSFDGAGGTYSLLLSS
YPISTNINLSKDDLWIFNIDNEVREISIENGTIKKGKLIKDVLSKIDINKNKLIIGNQT
IDFSGDIDNKDRYIFLTCELDDKISLIIEINLVAKSYSLLLSGDKNYLISNLSNIIEKIN
TLGLDSKNIAYNYTDESNNKYFGAISKTSQKSIIHYKKDSKNILEFYNDSTLEFNS
KDFIAEDINVFMKDDINTITGKYYVDNNTDKSIDFSISLVSKNQVKVNGLYLNESV
YSSYLDFVKNSDGHHNTSNFMNLFLDNISFWKLFGFENINFVIDKYFTLVGKTNL
GYVEFICDNNKNIDIYFGEWKTSSSKSTIFSGNGRNVVVEPIYNPDTGEDISTSLDF
SYEPLYGIDRYINKVLIAPDLYTSLININTNYYSNEYYPEIIVLNPNTFHKKVNINLD
SSSFEYKWSTEGSDFILVRYLEESNKKILQKIRIKGILSNTQSFNKMSIDFKDIKKLS -continued

| SEQ ID NOs |
|---|
| LGYIMSNFKSFNSENELDRDHLGFKIIDNKTYYYDEDSKLVKGLININNSLFYFDPI<br>EFNLVTGWQTINGKKYYFDINTGAALISYKIINGKHFYFNNDGVMQLGVFKGPD<br>GFEYFAPANTQNNNIEGQAIVYQSKFLTLNGKKYYFDNDSKAVTGWRIINNEKY<br>YFNPNNAIAAVGLQVIDNNKYYFNPDTAIISKGWQTVNGSRYYFDTDTAIAFNGY<br>KTIDGKHFYFDSDCVVKIGVFSTSNGFEYFAPANTYNNNIEGQAIVYQSKFLTLN<br>GKKYYFDNNSKAVTGWQTIDSKKYYFNTNTAEAATGWQTIDGKKYYFNTNTAE<br>AATGWQTIDGKKYYFNTNTAIASTGYTIINGKHFYFNTDGIMQIGVFKGPNGFEY<br>FAPANTDANNIEGQAILYQNEFLTLNGKKYYFGSDSKAVTGWRIINNKKYYFNP<br>NNAIAAIHLCTINNDKYYFSYDGILQNGYITIERNNFYFDANNESKMVTGVFKGP<br>NGFEYFAPANTHNNNIEGQAIVYQNKFLTLNGKKYYFDNDSKAVTGWQTIDGK<br>KYYFNLNTAEAATGWQTIDGKKYYFNLNTAEAATGWQTIDGKKYYFNTNTFIA<br>STGYTSINGKHFYFNTDGIMQIGVFKGPNGFEYFAPANTHNNNIEGQAILYQNKF<br>LTLNGKKYYFGSDSKAVTGLRTIDGKKYYFNTNTAVAVTGWQTINGKKYYFNT<br>NTSIASTGYTIISGKHFYFNTDGIMQIGVFKGPDGFENFAPANTDANNIEGQAIRY<br>QNRFLYLHDNIYYFGNNSKAATGWVTIDGNRYYFEPNTAMGANGYKTIDNKNF<br>YFRNGLPQIGVFKGSNGFEYFAPANTDANNIEGQAIRYQNRFLHLLGKIYYFGNN<br>SKAVTGWQTINGKVYYFMPDTAMAAAGGLFEIDGVIYFFGVDGVKAPGIYG |
| SEQ ID NO: 37 - Toxin A-derived recombinant antigen - His-[helical spacer]-Thioredoxin-[thrombin site]-TxA4<br>HHHHHHHHHHGGSLAEAAAKEAAAKEAAAKEAAAKEAAAKAAAGGSHMASD<br>KIIHLTDDSFDTDVLKADGAILVDFWAEWCGPCKMIAPILDEIADEYQGKLTVAK<br>LNIDQNPGTAPKYGIRGIPTLLLFKNGEVAATKVGALSKGQLKEFLDANLARALV<br>PRGSVTSLYKKAGSAAAPFTMIMSDLSSKEYIFFDSIDNKLKAKSKNIPGLASISED<br>IKTLLLDASVSPDTKFILNNLKLNIESSIGDYIYYEKLEPVKNIIHNSIDDLIDEFNLL<br>ENVSDELYELKKLNNLDEKYLISFEDISKNNSTYSVRFINKSNGESVYVETEKEIFS<br>KYSEHITKEISTIKNSIITDVNGNLLDNIQLDHTSQVNTLNAAFFIQSLIDYSSNKDV<br>LNDLSTSVKVQLYAQLFSTGLNTIYDSIQLVNLISNAVNDTINVLPTITEGIPIVSTI<br>LDGINLGAAIKELLDEHDPLLKKELEAKVGVLAINMSLSIAATVASIVGIGAEVTIF<br>LLPIAGISAGIPSLVNNELILHDKATSVVNYFNHLSESKKYGPLKTEDDKILVPIDD<br>LVISEIDFNNNSIKLGTCNILAMEGGSGHTVTGNIDHFFSSPSISSHIPSLSIYSAIGIE<br>TENLDFSKKIMMLPNAPSRVFWWETGAVPGLRSLENDGTRLLDSIRDLYPGKFY<br>WRFYAFFDYAITTLKPVYEDTNIKIKLDKDTRNFIMPTITTNEIRNKLSYSFDGAG<br>GTYSLLLSSYPISTNINLSKDDLWIFNIDNEVREISIENGTIKKGKLIKDVLSKIDINK<br>NKLIIGNQTIDFSGDIDNKDRYIFLTCELDDKISLIIEINLVAKSYSLLLSGDKNYLIS<br>NLSNIIEKINTLGLDSKNIAYNYTDESNNKYFGAISKTSQKSIIHYKKDSKNILEFY<br>NDSTLEFNSKDFIAEDINVFMKDDINTITGKYYVDNNTDKSIDFSISLVSKNQVKV<br>NGLYLNESVYSSYLDFVKNSDGHHNTSNFMNLFLDNISFWKLFGFENINFVIDKY<br>FTLVGKTNLGYVEFICDNNKNIDIYFGEWKTSSSKSTIFSGNGRNVVVEPIYNPDT<br>GEDISTSLDFSYEPLYGIDRYINKVLIAPDLYTSLININTNYYSNEYYPEIIVLNPNTF<br>HKKVNINLDSSSFEYKWSTEGSDFILVRYLEESNKKILQKIRIKGILSNTQSFNKMS<br>IDFKDIKKLSLGYIMSNFKSFNSENELDRDHLGFKIIDNKTYYYDEDSKLVKGLINI<br>NNSLFYFDPIEFNLVTGWQTINGKKYYFDINTGAALISYKIINGKHFYFNNDGVM<br>QLGVFKGPDGFEYFAPANTQNNNIEGQAIVYQSKFLTLNGKKYYFDNDSKAVTG<br>WRIINNEKYYFNPNNAIAAVGLQVIDNNKYYFNPDTAIISKGWQTVNGSRYYFDT<br>DTAIAFNGYKTIDGKHFYFDSDCVVKIGVFSTSNGFEYFAPANTYNNNIEGQAIV<br>YQSKFLTLNGKKYYFDNNSKAVTGWQTIDSKKYYFNTNTAEAATGWQTIDGKK<br>YYFNTNTAEAATGWQTIDGKKYYFNTNTAIASTGYTIINGKHFYFNTDGIMQIGV<br>FKGPNGFEYFAPANTDANNIEGQAILYQNEFLTLNGKKYYFGSDSKAVTGWRIIN<br>NKKYYFNPNNAIAAIHLCTINNDKYYFSYDGILQNGYITIERNNFYFDANNESKM<br>VTGVFKGPNGFEYFAPANTHNNNIEGQAIVYQNKFLTLNGKKYYFDNDSKAVTG<br>WQTIDGKKYYFNLNTAEAATGWQTIDGKKYYFNLNTAEAATGWQTIDGKKYYF<br>NTNTFIASTGYTSINGKHFYFNTDGIMQIGVFKGPNGFEYFAPANTHNNNIEGQAI<br>LYQNKFLTLNGKKYYFGSDSKAVTGLRTIDGKKYYFNTNTAVAVTGWQTINGK<br>KYYFNTNTSIASTGYTIISGKHFYFNTDGIMQIGVFKGPDGFEYFAPANTDANNIE<br>GQAIRYQNRFLYLHDNIYYFGNNSKAATGWVTIDGNRYYFEPNTAMGANGYKTI<br>DNKNFYFRNGLPQIGVFKGSNGFEYFAPANTDANNIEGQAIRYQNRFLHLLGKIY<br>YFGNNSKAVTGWQTINGKVYYFMPDTAMAAAGGLFEIDGVIYFFGVDGVKAPG<br>IYG |
| SEQ ID NO: 38 - Toxin A-derived recombinant antigen - His-Thioredoxin-[linear spacer]-[thrombin site]-TxA4<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALGGSGGSGGSGGSGGSGGSGGSGGSGGSGGSLVPRGSGSAAAPFTM<br>IMSDLSSKEYIFFDSIDNKLKAKSKNIPGLASISEDIKTLLLDASVSPDTKFILNNLK<br>LNIESSIGDYIYYEKLEPVKNIIHNSIDDLIDEFNLLENVSDELYELKKLNNLDEKY<br>LISFEDISKNNSTYSVRFINKSNGESVYVETEKEIFSKYSEHITKEISTIKNSIITDVN<br>GNLLDNIQLDHTSQVNTLNAAFFIQSLIDYSSNKDVLNDLSTSVKVQLYAQLFST<br>GLNTIYDSIQLVNLISNAVNDTINVLPTITEGIPIVSTILDGINLGAAIKELLDEHDPL<br>LKKELEAKVGVLAINMSLSIAATVASIVGIGAEVTIFLLPIAGISAGIPSLVNNELIL<br>HDKATSVVNYFNHLSESKKYGPLKTEDDKILVPIDDLVISEIDFNNNSIKLGTCNIL<br>AMEGGSGHTVTGNIDHFFSSPSISSHIPSLSIYSAIGIETENLDFSKKIMMLPNAPSR<br>VFWWETGAVPGLRSLENDGTRLLDSIRDLYPGKFYWRFYAFFDYAITTLKPVYE<br>DTNIKIKLDKDTRNFIMPTITTNEIRNKLSYS14DGAGGTYSLLLSSYPISTNINLSKD<br>DLWIFNIDNEVREISIENGTIKKGKLIKDVLSKIDINKNKLIIGNQTIDFSGDIDNKD<br>RYIFLTCELDDKISLIIEINLVAKSYSLLLSGDKNYLISNLSNIIEKINTLGLDSKNIA |

-continued

| SEQ ID NOs |
|---|
| YNYTDESNNKYFGAISKTSQKSIIHYKKDSKNILEFYNDSTLEFNSKDFIAEDINVF MKDDINTITGKYYVDNNTDKSIDFSISLVSKNQVKVNGLYLNESVYSSYLDFVKN SDGHHNTSNFMNLFLDNISFWKLFGFENINFVIDKYFTLVGKTNLGYVEFICDNN KNIDIYFGEWKTSSSKSTIFSGNGRNVVVEPIYNPDTGEDISTSLDFSYEPLYGIDR YINKVLIAPDLYTSLININTNYYSNEYYPEIIVLNPNTFHKKVNINLDSSSFENKWS TEGSDFILVRYLEESNKKILQKIRIKGILSNTQSFNKMSIDFKDIKKLSLGYIMSNFK SFNSENELDRDHLGFKIIDNKTYYYDEDSKLVKGLININNSLFYFDPIEFNLVTGW QTINGKKYYFDINTGAALISYKIINGKHFYFNNDGVMQLGVFKGPDGFEYFAPAN TQNNNIEGQAIVYQSKFLTLNGKKYYFDNDSKAVTGWRIINNEKYYFNPNNAIA AVGLQVIDNNKYYFNPDTAIISKGWQTVNGSRYYFDTDTAIAFNGYKTIDGKHF YFDSDCVVKIGVFSTSNGFEYFAPANTYNNNIEGQAIVYQSKFLTLNGKKYYPDN NSKAVTGWQTIDSKKYYFNTNTAEAATGWQTIDGKKYYFNTNTAEAATGWQTI DGKKYYFNTNTAIASTGYTIINGKHFYFNTDGIMQIGVFKGPNGFEYFAPANTDA NNIEGQAILYQNEFLTLNGKKYYFGSDSKAVTGWRIINNKKYYFNPNNAIAAIHL CTINNDKYYFSYDGILQNGYITIERNNFYFDANNESKMVTGVFKGPNGFEYFAPA NTHNNNIEGQAIVYQNKFLTLNGKKYYFDNDSKAVTGWQTIDGKKYYFNLNTA EAATGWQTIDGKKYYFNLNTAEAATGWQTIDGKKYYFNTNTFIASTGYTSINGK HFYFNTDGIMQIGVFKGPNGFEYFAPANTHNNNIEGQAILYQNKFLTLNGKKYYF GSDSKAVTGLRTIDGKKYYFNTNTAVAVTGWQTINGKKYYFNTNTSIASTGYTII SGKHFYFNTDGIMQIGVFKGPDGFEYFAPANTDANNIEGQAIRYQNRFLYLHDNI YYFGNNSKAATGWVTIDGNRYYFEPNTAMGANGYKTIDNKNFYFRNGLPQIGV FKGSNGFEYFAPANTDANNIEGQAIRYQNRFLHLLGKIYYFGNNSKAVTGWQTIN GKVYYFMPDTAMAAAGGLFEIDGVIYFFGVDGVKAPGIYG |
| SEQ ID NO: 39 - Toxin A-derived recombinant antigen - His-Thioredoxin-[helical spacer]-[thrombin site]-TxA4<br>HHHHHHSHMASDKIIHLTDDSFDTDVLKADGAILVDFWAEWCGPCKMIAPILDEI ADEYQGKLTVAKLNIDQNPGTAPKYGIRGIPTLLLFKNGEVAATKVGALSKGQL KEFLDANLARALLAEAAAKEAAAKEAAAKEAAAKEAAAKAAAGGSLVPRGSG SAAAPFTMIMSDLSSKEYIFFDSIDNKLKAKSKNIPGLASISEDIKTLLLDASVSPDT KFILNNLKLNIESSIGDYIYYEKLEPVKNIIHNSIDDLIDEFNLLENVSDELYELKKL NNLDEKYLISFEDISKNNSTYSVRFINKSNGESVYVETEKEIFSKYSEHITKEISTIK NSIITDVNGNLLDNIQLDHTSQVNTLNAAFFIQSLIDYSSNKDVLNDLSTSVKVQL YAQLFSTGLNTIYDSIQLVNLISNAVNDTINVLPTITEGIPIVSTILDGINLGAAIKEL LDEHDPLLKKELEAKVGVLAINMSLSIAATVASIVGIGAEVTIFLLPIAGISAGIPSL VNNELILHDKATSVVNYFNHLSESKKYGPLKTEDDKILVPIDDLVISEIDFNNNSIK LGTCNILAMEGGSGHTVTGNIDHFFSSPSISSHIPSLSIYSAIGIETENLDFSKKIMM LPNAPSRVFWWETGAVPGLRSLENDGTRLLDSIRDLYPGKFYWRFYAFFDYAITT LKPVYEDTNIKIKLDKDTRNFIMPTITTNEIRNKLSYSFDGAGGTYSLLLSSYPIST NINLSKDDLWIFNIDNEVREISIENGTIKKGKLIKDVLSKIDINKNKLIIGNQTIDFSG DIDNKDRYIFLTCELDDKISLIIEINLVAKSYSLLLSGDKNYLISNLSNIIEKINTLGL DSKNIAYNYTDESNNKYFGAISKTSQKSIIHYKKDSKNILEFYNDSTLEFNSKDFIA EDINVFMKDDINTITGKYYVDNNTDKSIDFSISLVSKNQVKVNGLYLNESVYSSY LDFVKNSDGHHNTSNFMNLFLDNISFWKLFGFENINFVIDKYFTLVGKTNLGYVE FICDNNKNIDIYFGEWKTSSSKSTIFSGNGRNVVVEPIYNPDTGEDISTSLDFSYEPL YGIDRYINKVLIAPDLYTSLININTNYYSNEYYPEIIVLNPNTFHKKVNINLDSSSFE YKWSTEGSDFILVRYLEESNKKILQKIRIKGILSNTQSFNKMSIDFKDIKKLSLGYI MSNFKSFNSENELDRDHLGFKIIDNKTYYYDEDSKLVKGLININNSLFYFDPIEFN LVTGWQTINGKKYYFDINTGAALISYKIINGKHFYFNNDGVMQLGVFKGPDGFE YFAPANTQNNNIEGQAIVYQSKFLTLNGKKYYFDNDSKAVTGWRIINNEKYYFN PNNAIAAVGLQVIDNNKYYFNPDTAIISKGWQTVNGSRYYFDTDTAIAFNGYKTI DGKHFYFDSDCVVKIGVFSTSNGFEYFAPANTYNNNIEGQAIVYQSKFLTLNGKK YYFDNNSKAVTGWQTIDSKKYYFNTNTAEAATGWQTIDGKKYYFNTNTAEAAT GWQTIDGKKYYFNTNTAIASTGYTIINGKHFYFNTDGIMQIGVFKGPNGFEYFAP ANTDANNIEGQAILYQNEFLTLNGKKYYFGSDSKAVTGWRIINNKKYYFNPNNAI AAIHLCTINNDKYYFSYDGILQNGYITIERNNFYFDANNESKMVTGVFKGPNGFE YFAPANTHNNNIEGQAIVYQNKFLTLNGKKYYFDNDSKAVTGWQTIDGKKYYF NLNTAEAATGWQTIDGKKYYFNLNTAEAATGWQTIDGKKYYFNTNTFIASTGYT SINGKHFYFNTDGIMQIGVFKGPNGFEYFAPANTHNNNIEGQAILYQNKFLTLNG KKYYFGSDSKAVTGLRTIDGKKYYFNTNTAVAVTGWQTINGKKYYFNTNTSIAS TGYTIISGKHFYFNTDGIMQIGVFKGPDGFEYFAPANTDANNIEGQAIRYQNRFLY LHDNIYYFGNNSKAATGWVTIDGNRYYFEPNTAMGANGYKTIDNKNFYFRNGL PQIGVFKGSNGFEYFAPANTDANNIEGQAIRYQNRFLHLLGKIYYFGNNSKAVTG WQTINGKVYYFMPDTAMAAAGGLFEIDGVIYFFGVDGVKAPGIYG |
| SEQ ID NO: 40 - Toxin A-derived recombinant antigen - His-[linear spacer]-Thioredoxin-[thrombin site]-TxA3<br>HHHHHHHHHGGSGGSGGSGGSGGSGGSGGSGGSGGSGGSHMASDKIIHLTDDSF DTDVLKADGAILVDFWAEWCGPCKMIAPILDEIADEYQGKLTVAKLNIDQNPGT APKYGIRGIPTLLLFKNGEVAATKVGALSKGQLKEFLDANLARALVPRGSVTSLY KKAGSAAAPFTMESKKYGPLKTEDDKILVPIDDLVISEIDFNNNSIKLGTCNILAM EGGSGHTVTGNIDHFFSSPSISSHIPSLSIYSAIGIETENLDFSKKIMMLPNAPSRVF WWETGAVPGLRSLENDGTRLLDSIRDLYPGKFYWRFYAFFDYAITTLKPVYEDT NIKIKLDKDTRNFIMPTITTNEIRNKLSYSFDGAGGTYSLLLSSYPISTNINLSKDDL WIFNIDNEVREISIENGTIKKGKLIKDVLSKIDINKNKLIIGNQTIDFSGDIDNKDRYI FLTCELDDKISLIIEINLVAKSYSLLLSGDKNYLISNLSNIIEKINTLGLDSKNIAYNY TDESNNKYFGAISKTSQKSIIHYKKDSKNILEFYNDSTLEFNSKDFIAEDINVFMKD |

-continued

| SEQ ID NOs |
|---|
| DINTITGKYYVDNNTDKSIDFSISLVSKNQVKVNGLYLNESVYSSYLDFVKNSDG<br>HHNTSNFMNLFLDNISFWKLFGFENINFVIDKYFTLVGKTNLGYVEFICDNNKNID<br>IYFGEWKTSSSKSTIFSGNGRNVVVEPIYNPDTGEDISTSLDFSYEPLYGIDRYINK<br>VLIAPDLYTSLININTNYYSNEYYPEIIVLNPNTFHKKVNINLDSSSFEYKWSTEGS<br>DFILVRYLEESNKKILQKIRIKGILSNTQSFNKMSIDFKDIKKLSLGYIMSNFKSFNS<br>ENELDRDHLGFKIIDNKTYYYDEDSKLVKGLININNSLFYFDPIEFNLVTGWQTIN<br>GKKYYFDINTGAALISYKIINGKHFYFNNDGVMQLGVFKGPDGFEYFAPANTQN<br>NNIEGQAIVYQSKFLTLNGKKYYFDNDSKAVTGWRIINNEKYYFNPNNAIAAVG<br>LQVIDNNKYYFNPDTAIISKGWQTVNGSRYYFDTDTAIAFNGYKTIDGKHFYFDS<br>DCVVKIGVFSTSNGFEYFAPANTYNNNIEGQAIVYQSKFLTLNGKKYYFDNNSKA<br>VTGWQTIDSKKYYFNTNTAEAATGWQTIDGKKYYFNTNTAEAATGWQTIDGKK<br>YYFNTNTAIASTGYTIINGKHFYFNTDGIMQIGVFKGPNGFEYFAPANTDANNIEG<br>QAILYQNEFLTLNGKKYYFGSDSKAVTGWRIINNKKYYFNPNNAIAAIHLCTINN<br>DKYYFSYDGILQNGYITIERNNFYFDANNESKMVTGVFKGPNGFEYFAPANTHN<br>NNIEGQAIVYQNKFLTLNGKKYYFDNDSKAVTGWQTIDGKKYYFNLNTAEAAT<br>GWQTIDGKKYYFNLNTAEAATGWQTIDGKKYYFNTNTFIASTGYTSINGKHFYF<br>NTDGIMQIGVFKGPNGFEYFAPANTHNNNIEGQAILYQNKFLTLNGKKYYFGSDS<br>KAVTGLRTIDGKKYYFNTNTAVAVTGWQTINGKKYYFNTNTSIASTGYTIISGKH<br>FYFNTDGIMQIGVFKGPDGFEYFAPANTDANNIEGQAIRYQNRFLYLHDNIYYFG<br>NNSKAATGWVTIDGNRYYFEPNTAMGANGYKTIDNKNFYFRNGLPQIGVFKGS<br>NGFEYFAPANTDANNIEGQAIRYQNRFLHLLGKIYYFGNNSKAVTGWQTINGKV<br>YYFMPDTAMAAAGGLFEIDGVIYFFGVDGVKAPGIYG |
| SEQ ID NO: 41 - Toxin A-derived recombinant antigen - His-[helical spacer]-<br>Thioredoxin-[thrombin site]-TxA3<br>HHHHHHHHHHGGSLAEAAAKEAAAKEAAAKEAAAKEAAAKAAAGGSHMASD<br>KIIHLTDDSFDTDVLKADGAILVDFWAEWCGPCKMIAPILDEIADEYQGKLTVAK<br>LNIDQNPGTAPKYGIRGIPTLLLFKNGEVAATKVGALSKGQLKEFLDANLARALV<br>PRGSVTSLYKKAGSAAAPFTMESKKYGPLKTEDDKILVPIDDLVISEIDFNNNSIK<br>LGTCNILAMEGGSGHTVTGNIDHFFSSPSISSHIPSLSIYSAIGIETENLDFSKKIMM<br>LPNAPSRVFWWETGAVPGLRSLENDGTRLLDSIRDLYPGKFYWRFYAFFDYAITT<br>LKPVYEDTNIKIKLDKDTRNFIMPTITTNEIRNKLSYSFDGAGGTYSLLLSSYPIST<br>NINLSKDDLWIFNIDNEVREISIENGTIKKGKLIKDVLSKIDINKNKLIIGNQTIDFSG<br>DIDNKDRYIFLTCELDDKISLIIEINLVAKSYSLLLSGDKNYLISNLSNIIEKINTLGL<br>DSKNIAYNYTDESNNKYFGAISKTSQKSIIHYKKDSKNILEFYNDSTLEFNSKDFIA<br>EDINVFMKDDINTITGKYYVDNNTDKSIDFSISLVSKNQVKVNGLYLNESVYSSY<br>LDFVKNSDGHHNTSNFMNLFLDNISFWKLFGFENINFVIDKYFTLVGKTNLGYVE<br>FICDNNKNIDIYFGEWKTSSSKSTIFSGNGRNVVVEPIYNPDTGEDISTSLDFSYEPL<br>YGIDRYINKVLIAPDLYTSLININTNYYSNEYYPEIIVLNPNTFHKKVNINLDSSSFE<br>YKWSTEGSDFILVRYLEESNKKILQKIRIKGILSNTQSFNKMSIDFKDIKKLSLGYI<br>MSNFKSFNSENELDRDHLGFKIIDNKTYYYDEDSKLVKGLININNSLFYFDPIEFN<br>LVTGWQTINGKKYYFDINTGAALISYKIINGKHFYFNNDGVMQLGVFKGPDGFE<br>YFAPANTQNNNIEGQAIVYQSKFLTLNGKKYYFDNDSKAVTGWRIINNEKYYFN<br>PNNAIAAVGLQVIDNNKYYFNPDTAIISKGWQTVNGSRYYFDTDTAIAFNGYKTI<br>DGKHFYFDSDCVVKIGVFSTSNGFEYFAPANTYNNNIEGQAIVYQSKFLTLNGKK<br>YYFDNNSKAVTGWQTIDSKKYYFNTNTAEAATGWQTIDGKKYYFNTNTAEAAT<br>GWQTIDGKKYYFNTNTAIASTGYTIINGKHFYFNTDGIMQIGVFKGPNGFEYFAP<br>ANTDANNIEGQAILYQNEFLTLNGKKYYFGSDSKAVTGWRIINNKKYYFNPNNAI<br>AAIHLCTINNDKYYFSYDGILQNGYITIERNNFYFDANNESKMVTGVFKGPNGFE<br>YFAPANTHNNNIEGQAIVYQNKFLTLNGKKYYFDNDSKAVTGWQTIDGKKYYF<br>NLNTAEAATGWQTIDGKKYYFNLNTAEAATGWQTIDGKKYYFNTNTFIASTGYT<br>SINGKHFYFNTDGIMQIGVFKGPNGFEYFAPANTHNNNIEGQAILYQNKFLTLNG<br>KKYYFGSDSKAVTGLRTIDGKKYYFNTNTAVAVTGWQTINGKKYYFNTNTSIAS<br>TGYTIISGKHFYFNTDGIMQIGVFKGPDGFEYFAPANTDANNIEGQAIRYQNRFLY<br>LHDNIYYFGNNSKAATGWVTIDGNRYYFEPNTAMGANGYKTIDNKNFYFRNGL<br>PQIGVFKGSNGFEYFAPANTDANNIEGQAIRYQNRFLHLLGKIYYFGNNSKAVTG<br>WQTINGKVYYFMPDTAMAAAGGLFEIDGVIYFFGVDGVKAPGIYG |
| SEQ ID NO: 42 - Toxin A-derived recombinant antigen - His-Thioredoxin-[linear spacer]-<br>[thrombin site]-TxA3<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALGGSGGSGGSGGSGGSGGSGGSGGSGGSLVPRGSGSAAAPFTM<br>ESKKYGPLKTEDDKILVPIDDLVISEIDFNNNSIKLGTCNILAMEGGSGHTVTGNID<br>HFFSSPSISSHIPSLSIYSAIGIETENLDFSKKIMMLPNAPSRVFWWETGAVPGLRSL<br>ENDGTRLLDSIRDLYPGKFYWRFYAFFDYAITTLKPVYEDTNIKIKLDKDTRNFIM<br>PTITTNEIRNKLSYSFDGAGGTYSLLLSSYPISTNINLSKDDLWIFNIDNEVREISIEN<br>GTIKKGKLIKDVLSKIDINKNKLIIGNQTIDFSGDIDNKDRYIFLTCELDDKISLIIEI<br>NLVAKSYSLLLSGDKNYLISNLSNIIEKINTLGLDSKNIAYNYTDESNNKYFGAISK<br>TSQKSIIHYKKDSKNILEFYNDSTLEFNSKDFIAEDINVFMKDDINTITGKYYVDN<br>NTDKSIDFSISLVSKNQVKVNGLYLNESVYSSYLDFVKNSDGHHNTSNFMNLFLD<br>NISFWKLFGFENINFVIDKYFTLVGKTNLGYVEFICDNNKNIDIYFGEWKTSSSKS<br>TIFSGNGRNVVVEPIYNPDTGEDISTSLDFSYEPLYGIDRYINKVLIAPDLYTSLINI<br>NTNYYSNEYYPEIIVLNPNTFHKKVNINLDSSSFEYKWSTEGSDFILVRYLEESNK<br>KILQKIRIKGILSNTQSFNKMSIDFKDIKKLSLGYIMSNFKSFNSENELDRDHLGFKI<br>IDNKTYYYDEDSKLVKGLININNSLFYFDPIEFNLVTGWQTINGKKYYFDINTGAA<br>LISYKIINGKHFYFNNDGVMQLGVFKGPDGFEYFAPANTQNNNIEGQAIVYQSKF |

-continued

| SEQ ID NOs |
|---|

LTLNGKKYYFDNDSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNG
FEYFAPANTYNNNIEGQAIVYQSKFLTLNGKKYYFDNNSKAVTGWQTIDSKKYY
FNTNTAEAATGWQTIDGKKYYFNTNTAEAATGWQTIDGKKYYFNTNTAIASTG
YTIINGKHFYFNTDGIMQIGVFKGPNGFEYFAPANTDANNIEGQAILYQNEFLTLN
GKKYYFGSDSKAVTGWRIINNKKYYFNPNNAIAAIHLCTINNDKYYFSYDGILQN
GYITIERNNFYFDANNESKMVTGVFKGPNGFEYFAPANTHNNNIEGQAIVYQNKF
LTLNGKKYYFDNDSKAVTGWQTIDGKKYYFNLNTAEAATGWQTIDGKKYYFNL
NTAEAATGWQTIDGKKYYFNTNTFIASTGYTSINGKHFYFNTDGIMQIGVFKGPN
GFEYFAPANTHNNNIEGQAILYQNKFLTLNGKKYYFGSDSKAVTGLRTIDGKKY
YFNTNTAVAVTGWQTINGKKYYFNTNTSIASTGYTIISGKHFYFNTDGIMQIGVF
KGPDGFEYFAPANTDANNIEGQAIRYQNRFLYLHDNIYYFGNNSKAATGWVTID
GNRYYFEPNTAMGANGYKTIDNKNFYFRNGLPQIGVFKGSNGFEYFAPANTDAN
NIEGQAIRYQNRFLHLLGKIYYFGNNSKAVTGWQTINGKVYYFMPDTAMAAAG
GLFEIDGVIYFFGVDGVKAPGIYG

SEQ ID NO: 43 - Toxin A-derived recombinant antigen - His-Thioredoxin-[helical spacer]-[thrombin site]-TxA3
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALLAEAAAKEAAAKEAAAKEAAAKEAAAKAAAGGSLVPRGSG
SAAAPFTMESKKYGPLKTEDDKILVPIDDLVISEIDFNNNSIKLGTCNILAMEGGS
GHTVTGNIDHFFSSPSISSHIPSLSIYSAIGIETENLDFSKKIMMLPNAPSRVFWWET
GAVPGLRSLENDGTRLLDSIRDLYPGKFYWRFYAFFDYAITTLKPVYEDTNIKIKL
DKDTRNFIMPTITTNEIRNKLSYSFDGAGGTYSLLLSSYPISTNINLSKDDLWIFNID
NEVREISIENGTIKKGKLIKDVLSKIDINKNKLIIGNQTIDFSGDIDNKDRYIFLTCEL
DDKISLIIEINLVAKSYSLLLSGDKNYLISNLSNIIEKINTLGLDSKNIAYNYTDESN
NKYFGAISKTSQKSIIHYKKDSKNILEFYNDSTLEFNSKDFIAEDINVFMKDDINTI
TGKYYVDNNTDKSIDFSISLVSKNQVKVNGLYLNESVYSSYLDFVKNSDGHHNT
SNFMNLFLDNISFWKLFGFENINFVIDKYFTLVGKTNLGYVEFICDNNKNIDIYFG
EWKTSSSKSTIFSGNGRNVVVEPIYNPDTGEDISTSLDFSYEPLYGIDRYINKVLIA
PDLYTSLININTNYYSNEYYPEIIVLNPNTFHKKVNINLDSSSFEYKWSTEGSDFIL
VRYLEESNKKILQKIRIKGILSNTQSFNKMSIDFKDIKKLSLGYIMSNFKSFNSENE
LDRDHLGFKIIDNKTYYYDEDSKLVKGLININNSLFYFDPIEFNLVTGWQTINGKK
YYFDINTGAALISYKIINGKHFYFNNDGVMQLGVFKGPDGFEYFAPANTQNNNIE
GQAIVYQSKFLTLNGKKYYFDNDSKAVTGWRIINNEKYYFNPNNAIAAVGLQVI
DNNKYYFNPDTAIISKGWQTVNGSRYYFDTDTAIAFNGYKTIDGKHFYFDSDCV
VKIGVFSTSNGFEYFAPANTYNNNIEGQAIVYQSKFLTLNGKKYYFDNNSKAVTG
WQTIDSKKYYFNTNTAEAATGWQTIDGKKYYFNTNTAEAATGWQTIDGKKYYF
NTNTAIASTGYTIINGKHFYFNTDGIMQIGVFKGPNGFEYFAPANTDANNIEGQAI
LYQNEFLTLNGKKYYFGSDSKAVTGWRIINNKKYYFNPNNAIAAIHLCTINNDKY
YFSYDGILQNGYITIERNNFYFDANNESKMVTGVFKGPNGFEYFAPANTHNNNIE
GQAIVYQNKFLTLNGKKYYFDNDSKAVTGWQTIDGKKYYFNLNTAEAATGWQ
TIDGKKYYFNLNTAEAATGWQTIDGKKYYFNTNTFIASTGYTSINGKHFYFNTDG
IMQIGVFKGPNGFEYFAPANTHNNNIEGQAILYQNKFLTLNGKKYYFGSDSKAVT
GLRTIDGKKYYFNTNTAVAVTGWQTINGKKYYFNTNTSIASTGYTIISGKHFYFN
TDGIMQIGVFKGPDGFEYFAPANTDANNIEGQAIRYQNRFLYLHDNIYYFGNNSK
AATGWVTIDGNRYYFEPNTAMGANGYKTIDNKNFYFRNGLPQIGVFKGSNGFEY
FAPANTDANNIEGQAIRYQNRFLHLLGKIYYFGNNSKAVTGWQTINGKVYYFMP
DTAMAAAGGLFEIDGVIYFFGVDGVKAPGIYG SEQ ID NO: 44 - Toxin B-derived recombinant antigen - His-[linear spacer]-NusA-[thrombin site]-TxB4
HHHHHHHHHGGSGGSGGSGGSGGSGGSGGSGGSGGSGGSGGSHMASNKEILAVVEA
VSNEKALPREKIFEALESALATATKKKYEQEIDVRVQIDRKSGDFDTPRRWLVVD
EVTQPTKEITLEAARYEDESLNLGDYVEDQIESVTFDRITTQTAKQVIVQKVREAE
RAMVVDQFREHEGEIITGVVKKVNRDNISLDLGNNAEAVILREDMLPRENFRPG
DRVRGVLYSVRPEARGAQLFVTRSKPEMLIELFRIEVPEIGEEVIEIKAAARDPGSR
AKIAVKTNDKRIDPVGACVGMRGARVQAVSTELGGERIDIVLWDDNPAQFVINA
MAPADVASIVVDEDKHTMDIAVEAGNLAQAIGRNGQNVRLASQLSGWELNVMT
VDDLQAKHQAEAHAAIDTFTKYLDIDEDFATVLVEEGFSTLEELAYVPMKELLEI
EGLDEPTVEALRERAKNALATIAQAQEESLGDNKPADDLLNLEGVDRDLAFKLA
ARGVCTLEDLAEQGIDDLADIEGLTDEKAGALIMAARNICWFGDEASGALVPRG
SVTSLYKKAGSAAAPFTMSIIKDISSKEYISFNPKENKITVKSKNLPELSTLLQEIRN
NSNSSDIELEEKVMLTECEINVISNIDTQIVEERIEEAKNLTSDSINYIKDEFKLIESIS
DALCDLKQQNELEDSHFISFEDISETDEGFSIRFINKETGESIFVETEKTIFSEYANHI
TEEISKIKGTIFDTVNGKLVKKVNLDTTHEVNTLNAAFFIQSLIEYNSSKESLSNLS
VAMKVQVYAQLFSTGLNTITDAAKVVELVSTALDETIDLLPTLSEGLPIIATIIDGV
SLGAAIKELSETSDPLLRQEIEAKIGIMAVNLTTATTAIITSSLGIASGFSILLVPLAG
ISAGIPSLVNNELVLRDKATKVVDYFKHVSLVETEGVFTLLDDKIMMPQDDLVIS
EIDENNNSIVLGKCEIWRMEGGSGHTVTDDIDHFFSAPSITYREPHLSIYDVLEVQ
KEELDLSKDLMVLPNAPNRVFAWETGWTPGLRSLENDGTKLLDRIRDNYEGEFY
WRYFAFIADALITTLKPRYEDTNIRINLDSNTRSFIVPIITTEYIREKLSYSFYGSGGT
YALSLSQYNMGINIELSESDVWIIDVDNVVRDVTIESDKIKKGDLIEGILSTLSIEEN
KIILNSHEINFSGEVNGSNGFVSLTFSILEGINAIIEVDLLSKSYKLLISGELKILMLN
SNHIQQKIDYIGFNSELQKNIPYSFVDSEGKENGFINGSTKEGLFVSELPDVVLISK
VYMDDSKPSFGYYSNNLKDVKVITKDNVNILTGYYLKDDIKISLSLTLQDEKTIK -continued

| SEQ ID NOs |
|---|
| LNSVHLDESGVAEILKFMNRKGNTNTSDSLMSFLESMNIKSIFVNFLQSNIKFILD<br>ANFIISGTTSIGQFEFICDENDNIQPYFIKFNTLETNYTLYVGNRQNMIVEPNYDLD<br>DSGDISSTVINFSQKYLYGIDSCVNKVVISPNIYTDEINITPVYETNNTYPEVIVLDA<br>NYINEKINVNINDLSIRYVWSNDGNDFILMSTSEENKVSQVKIRFVNVFKDKTLA<br>NKLSFNFSDKQDVPVSEIILSFTPSYYEDGLIGYDLGLVSLYNEKFYINNFGMMVS<br>GLIYINDSLYYFKPPVNNLITGFVTVGDDKYYFNPINGGAASIGETIIDDKNYYFN<br>QSGVLQTGVFSTEDGFKYFAPANTLDENLEGEAIDFTGKLIIDENIYYFDDNYRGA<br>VEWKELDGEMHYFSPETGKAFKGLNQIGDYKYYFNSDGVMQKGFVSINDNKHY<br>FDDSGVMKVGYTEIDGKHFYFAENGEMQIGVFNTEDGFKYFAHHNEDLGNEEG<br>EEISYSGILNFNNKIYYFDDSFTAVVGWKDLEDGSKYYFDEDTAEAYIGLSLINDG<br>QYYFNDDGIMQVGFVTINDKVFYFSDSGIIESGVQNIDDNYFYIDDNGIVQIGVFD<br>TSDGYKYFAPANTVNDNIYGQAVEYSGLVRVGEDVYYFGETYTIETGWIYDME<br>NESDKYYFNPETKKACKGINLIDDIKYYFDEKGIMRTGLISFENNNYYFNENGEM<br>QFGYINIEDKMFYFGEDGVMQIGVFNTPDGFKYFAHQNTLDENFEGESINYTGW<br>LDLDEKRYYFTDEYIAATGSVIIDGEEYYFDPDTAQLVISE. |
| SEQ ID NO: 45 - Toxin B-derived recombinant antigen - His-NusA-[linear spacer]-[thrombin site]-TxB4<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALGGSGGSGGSGGSGGSGGSGGSGGSGGSLVPRGSGS<br>AAAPFTMSIIKDISSKEYISFNPKENKITVKSKNLPELSTLLQEIRNNSNSSDIELEEK<br>VMLTECEINVISNIDTQIVEERIEEAKNLTSDSINYIKDEFKLIESISDALCDLKQQN<br>ELEDSHFISFEDISETDEGFSIRFINKETGESIFVETEKTIFSEYANHITEEISKIKGTIF<br>DTVNGKLVKKVNLDTTHEVNTLNAAFFIQSLIEYNSSKESLSNLSVAMKVQVYA<br>QLFSTGLNTITDAAKVVELVSTALDETIDLLPTLSEGLPIIATIIDGVSLGAAIKELS<br>ETSDPLLRQEIEAKIGIMAVNLTTATTAIITSSLGIASGFSILLVPLAGISAGIPSLVN<br>NELVLRDKATKVVDYFKHVSLVETEGVFTLLDDKIMMPQDDLVISEIDFNNNSIV<br>LGKCEIWRMEGGSGHTVTDDIDHFFSAPSITYREPHLSIYDVLEVQKEELDLSKDL<br>MVLPNAPNRVFAWETGWTPGLRSLENDGTKLLDRIRDNYEGEFYWRYFAFIAD<br>ALITTLKPRYEDTNIRINLDSNTRSFIVPIITTEYIREKLSYSFYGSGGTYALSLSQYN<br>MGINIELSESDVWIIDVDNVVRDVTIESDKIKKGDLIEGILSTLSIEENKIILNSHEIN<br>FSGEVNGSNGFVSLTFSILEGINAIIEVDLLSKSYKLLISGELKILMLNSNHIQQKID<br>YIGFNSELQKNIPYSFVDSEGKENGFINGSTKEGLFVSELPDVVLISKVYMDDSKP<br>SFGYYSNNLKDVKVITKDNVNILTGYYLKDDIKISLSLTLQDEKTIKLNSVHLDES<br>GVAEILKFMNRKGNTNTSDSLMSFLESMNIKSIFVNFLQSNIKFILDANFIISGTTSI<br>GQFEFICDENDNIQPYFIKFNTLETNYTLYVGNRQNMIVEPNYDLDDSGDISSTVI<br>NFSQKYLYGIDSCVNKVVISPNIYTDEINITPVYETNNTYPEVIVLDANYINEKINV<br>NINDLSIRYVWSNDGNDFILMSTSEENKVSQVKIRFVNVFKDKTLANKLSFNFSD<br>KQDVPVSEIILSFTPSYYEDGLIGYDLGLVSLYNEKFYINNFGMMVSGLIYINDSL<br>YYFKPPVNNLITGFVTVGDDKYYFNPINGGAASIGETIIDDKNYYFNQSGVLQTG<br>VFSTEDGFKYFAPANTLDENLEGEAIDFTGKLIIDENIYYFDDNYRGAVEWKELD<br>GEMHYFSPETGKAFKGLNQIGDYKYYFNSDGVMQKGFVSINDNKHYFDDSGVM<br>KVGYTEIDGKHFYFAENGEMQIGVFNTEDGFKYFAHHNEDLGNEEGEEISYSGIL<br>NFNNKIYYFDDSFTAVVGWKDLEDGSKYYFDEDTAEAYIGLSLINDGQYYFNDD<br>GIMQVGFVTINDKVFYFSDSGIIESGVQNIDDNYFYIDDNGIVQIGVFDTSDGYKY<br>FAPANTVNDNIYGQAVEYSGLVRVGEDVYYFGETYTIETGWIYDMENESDKYYF<br>NPETKKACKGINLIDDIKYYFDEKGIMRTGLISFENNNYYFNENGEMQFGYINIED<br>KMFYFGEDGVMQIGVFNTPDGFKYFAHQNTLDENFEGESINYTGWLDLDEKRY<br>YFTDEYIAATGSVIIDGEEYYFDPDTAQLVISE. |
| SEQ ID NO: 46 - Toxin B-derived recombinant antigen - His-[helical spacer]-[thrombin site]-NusA-B4<br>HHHHHHHHHHGGSLAEAAAKEAAAKEAAAKEAAAKEAAAKAAAGGSHMASN<br>KEILAVVEAVSNEKALPREKIFEALESALATATKKKYEQEIDVRVQIDRKSGDFDT<br>FRRWLVVDEVTQPTKEITLEAARYEDESLNLGDYVEDQIESVTFDRITTQTAKQVI<br>VQKVREAERAMVVDQFREHEGEIITGVVKKVNRDNISLDLGNNAEAVILREDML<br>PRENFRPGDRVRGVLYSVRPEARGAQLFVTRSKPEMLIELFRIEVPEIGEEVIEIKA<br>AARDPGSRAKIAVKTNDKRIDPVGACVGMRGARVQAVSTELGGERIDIVLWDD<br>NPAQFVINAMAPADVASIVVDEDKHTMDIAVEAGNLAQAIGRNGQNVRLASQLS<br>GWELNVMTVDDLQAKHQAEAHAAIDTFTKYLDIDEDFATVLVEEGFSTLEELAY<br>VPMKELLEIEGLDEPTVEALRERAKNALATIAQAQEESLGDNKPADDLLNLEGV<br>DRDLAFKLAARGVCTLEDLAEQGIDDLADIEGLTDEKAGALIMAARNICWFGDE<br>ASGALVPRGSVTSLYKKAGSAAAPFTMSIIKDISSKEYISFNPKENKITVKSKNLPE<br>LSTLLQEIRNNSNSSDIELEEKVMLTECEINVISNIDTQIVEERIEEAKNLTSDSINYI<br>KDEFKLIESISDALCDLKQQNELEDSHFISFEDISETDEGFSIRFINKETGESIFVETE<br>KTIFSEYANHITEEISKIKGTIFDTVNGKLVKKVNLDTTHEVNTLNAAFFIQSLIEY<br>NSSKESLSNLSVAMKVQVYAQLFSTGLNTITDAAKVVELVSTALDETIDLLPTLSE<br>GLPIIATIIDGVSLGAAIKELSETSDPLLRQEIEAKIGIMAVNLTTATTAIITSSLGIAS<br>GFSILLVPLAGISAGIPSLVNNELVLRDKATKVVDYFKHVSLVETEGVFTLLDDKI |

-continued

| SEQ ID NOs |
|---|
| MMPQDDLVISEIDFNNNSIVLGKCEIWRMEGGSGHTVTDDIDHFFSAPSITYREPH<br>LSIYDVLEVQKEELDLSKDLMVLPNAPNRVFAWETGWTPGLRSLENDGTKLLDR<br>IRDNYEGEFYWRYFAFIADALITTLKPRYEDTNIRINLDSNTRSFIVPIITTEYIREKL<br>SYSFYGSGGTYALSLSQYNMGINIELSESDVWIIDVDNVVRDVTIESDKIKKGDLI<br>EGILSTLSIEENKIILNSHEINFSGEVNGSNGFVSLTFSILEGINAIIEVDLLSKSYKLL<br>ISGELKILMLNSNHIQQKIDYIGFNSELQKNIPYSFVDSEGKENGFINGSTKEGLFV<br>SELPDVVLISKVYMDDSKPSFGYYSNNLKDVKVITKDNVNILTGYYLKDDIKISLS<br>LTLQDEKTIKLNSVHLDESGVAEILKFMNRKGNTNTSDSLMSFLESMNIKSIFVNF<br>LQSNIKFILDANFIISGTTSIGQFEFICDENDNIQPYFIKFNTLETNYTLYVGNRQNM<br>IVEPNYDLDDSGDISSTVINFSQKYLYGIDSCVNKVVISPNIYTDEINITPVYETNNT<br>YPEVIVLDANYINEKINVNINDLSIRYVWSNDGNDFILMSTSEENKVSQVKIRFVN<br>VFKDKTLANKLSFNFSDKQDVPVSEIILSFTPSYYEDGLIGYDLGLVSLYNEKFYI<br>NNFGMMVSGLIYINDSLYYFKPPVNNLITGFVTVGDDKYYFNPINGGAASIGETII<br>DDKNYYFNQSGVLQTGVFSTEDGFKYFAPANTLDENLEGEAIDFTGKLIIDENIY<br>YFDDNYRGAVEWKELDGEMHYFSPETGKAFKGLNQIGDYKYYFNSDGVMQKG<br>FVSINDNKHYFDDSGVMKVGYTEIDGKHFYFAENGEMQIGVFNTEDGFKYFAHH<br>NEDLGNEEGEEISYSGILNFNNKIYYFDDSFTAVVGWKDLEDGSKYYFDEDTAEA<br>YIGLSLINDGQYYFNDDGIMQVGFVTINDKVFYFSDSGIIESGVQNIDDNYFYIDD<br>NGIVQIGVPDTSDGYKYFAPANTVNDNIYGQAVEYSGLVRVGEDVYYFGETYTI<br>ETGWIYDMENESDKYYFNPETKKACKGINLIDDIKYYFDEKGIMRTGLISFENNN<br>YYFNENGEMQFGYINIEDKMFYFGEDGVMQIGVFNTPDGFKYFAHQNTLDENFE<br>GESINYTGWLDLDEKRYYFTDEYIAATGSVIIDGEEYYPDPDTAQLVISE |
| SEQ ID NO: 47 - Toxin B-derived recombinant antigen - His-NusA-[helical spacer]-[thrombin site]-TxB4<br>HHHHHHSHMASNKEILAVVEAVSNEKALPREKIFEALESALATATKKKYEQEID<br>VRVQIDRKSGDFDTFRRWLVVDEVTQPTKEITLEAARYEDESLNLGDYVEDQIES<br>VTFDRITTQTAKQVIVQKVREAERAMVVDQFREHEGEIITGVVKKVNRDNISLDL<br>GNNAEAVILREDMLPRENFRPGDRVRGVLYSVRPEARGAQLFVTRSKPEMLIELF<br>RIEVPEIGEEVIEIKAAARDPGSRAKIAVKTNDKRIDPVGACVGMRGARVQAVST<br>ELGGERIDIVLWDDNPAQFVINAMAPADVASIVVDEDKHTMDIAVEAGNLAQAI<br>GRNGQNVRLASQLSGWELNVMTVDDLQAKHQAEAHAAIDTFTKYLDIDEDFAT<br>VLVEEGFSTLEELAYVPMKELLEIEGLDEPTVEALRERAKNALATIAQAQEESLG<br>DNKPADDLLNLEGVDRDLAFKLAARGVCTLEDLAEQGIDDLADIEGLTDEKAGA<br>LIMAARNICWFGDEASGALLAEAAAKEAAAKEAAAKEAAAKEAAAKAAAGGS<br>LVPRGSGSAAAPFTMSIIKDISSKEYISFNPKENKITVKSKNLPELSTLLQEIRNNSN<br>SSDIELEEKVMLTECEINVISNIDTQIVEERIEEAKNLTSDSINYIKDEFKLIESISDAL<br>CDLKQQNELEDSHFISFEDISETDEGFSIRFINKETGESIFVETEKTIFSEYANHITEEI<br>SKIKGTIFDTVNGKLVKKVNLDTTHEVNTLNAAFFIQSLIEYNSSKESLSNLSYAM<br>KVQVYAQLFSTGLNTITDAAKVVELVSTALDETIDLLPTLSEGLPIIATIIDGVSLG<br>AAIKELSETSDPLLRQEIEAKIGIMAVNLTTATTAIITSSLGIASGFSILLVPLAGISA<br>GIPSLVNNELVLRDKATKVVDYFKHVSLVETEGVFTLLDDKIMMPQDDLVISEID<br>FNNNSIVLGKCEIWRMEGGSGHTVTDDIDHFFSAPSITYREPHLSIYDVLEVQKEE<br>LDLSKDLMVLPNAPNRVFAWETGWTPGLRSLENDGTKLLDRIRDNYEGEFYWR<br>YFAFIADALITTLKPRYEDTNIRINLDSNTRSFIVPIITTEYIREKLSYSFYGSGGTYA<br>LSLSQYNMGINIELSESDVWIIDVDNVVRDVTIESDKIKKGDLIEGILSTLSIEENKII<br>LNSHEINFSGEVNGSNGFVSLTFSILEGINAIIEVDLLSKSYKLLISGELKILMLNSN<br>HIQQKIDYIGFNSELQKNIPYSFVDSEGKENGFINGSTKEGLFVSELPDVVLISKVY<br>MDDSKPSFGYYSNNLKDVKVITKDNVNILTGYYLKDDIKISLSLTLQDEKTIKLNS<br>VHLDESGVAEILKFMNRKGNTNTSDSLMSFLESMNIKSIFVNFLQSNIKFILDANFI<br>ISGTTSIGQFEFICDENDNIQPYFIKFNTLETNYTLYVGNRQNMIVEPNYDLDDSGD<br>ISSTVINFSQKYLYGIDSCVNKVVISPNIYTDEINITPVYETNNTYPEVIVLDANYIN<br>EKINVNINDLSIRYVWSNDGNDFILMSTSEENKVSQVKIRFVNVFKDKTLANKLS<br>FNFSDKQDVPVSEIILSFTPSYYEDGLIGYDLGLVSLYNEKFYINNFGMMVSGLIYI<br>NDSLYYFKPPVNNLITGFVTVGDDKYYFNPINGGAASIGETIIDDKNYYFNQSGVL<br>QTGVFSTEDGFKYFAPANTLDENLEGEAIDFTGKLIIDENIYYFDDNYRGAVEWK<br>ELDGEMHYFSPETGKAFKGLNQIGDYKYYFNSDGVMQKGFVSINDNKHYFDDS<br>GVMKVGYTEIDGKHFYFAENGEMQIGVFNTEDGFKYFAHHNEDLGNEEGEEISY<br>SGILNFNNKIYYFDDSFTAVVGWKDLEDGSKYYFDEDTAEAYIGLSLINDGQYYF<br>NDDGIMQVGFVTINDKVFYFSDSGIIESGVQNIDDNYFYIDDNGIVQIGVFDTSDG<br>YKYFAPANTVNDNIYGQAVEYSGLVRVGEDVYYFGETYTIETGWIYDMENESD<br>KYYFNPETKKACKGINLIDDIKYYFDEKGIMRTGLISFENNNYYFNENGEMQFGY<br>INIEDKMFYFGEDGVMQIGVFNTPDGFKYFAHQNTLDENFEGESINYTGWLDLDE<br>KRYYFTDEYIAATGSVIIDGEEYYFDPDTAQLVISE |
| SEQ ID NO: 48 - Toxin B-derived recombinant antigen - His-[linear spacer]-Thioredoxin-[thrombin site]-TxB4<br>HHHHHHHHHHGGSGGSGGSGGSGGSGGSGGSGGSGGSGGSGGSHMASDKIIHLTDD<br>SFDTDVLKADGAILVDFWAEWCGPCKMIAPILDEIADEYQGKLTVAKLNIDQNP<br>GTAPKYGIRGIPTLLLFKNGEVAATKVGALSKGQLKEFLDANLARALVPRGSVTS<br>LYKKAGSAAAPFTMSIIKDISSKEYISFNPKENKITVKSKNLPELSTLLQEIRNNSNS<br>SDIELEEKVMLTECEINVISNIDTQIVEERIEEAKNLTSDSINYIKDEFKLIESISDAL<br>CDLKQQNELEDSHFISFEDISETDEGFSIRFINKETGESIFVETEKTIFSEYANHITEEI<br>SKIKGTIFDTVNGKLVKKVNLDTTHEVNTLNAAFFIQSLIEYNSSKESLSNLSYAM<br>KVQVYAQLFSTGLNTITDAAKVVELVSTALDETIDLLPTLSEGLPIIATIIDGVSLG<br>AAIKELSETSDPLLRQEIEAKIGIMAVNLTTATTAIITSSLGIASGFSILLVPLAGISA<br>GIPSLVNNELVLRDKATKVVDYFKHVSLVETEGVFTLLDDKIMMPQDDLVISEID |

-continued

| SEQ ID NOs |
| --- |

FNNNSIVLGKCEIWRMEGGSGHTVTDDIDHFFSAPSITYREPHLSIYDVLEVQKEE
LDLSKDLMVLPNAPNRVFAWETGWTPGLRSLENDGTKLLDRIRDNYEGEFYWR
YFAFIADALITTLKPRYEDTNIRINLDSNTRSFIVPIITTEYIREKLSYSFYGSGGTYA
LSLSQYNMGINIELSESDVWIIDVDNVVRDVTIESDKIKKGDLIEGILSTLSIEENKII
LNSHEINFSGEVNGSNGFVSLTFSILEGINAIIEVDLLSKSYKLLISGELKILMLNSN
HIQQKIDYIGFNSELQKNIPYSFVDSEGKENGFINGSTKEGLFVSELPDVVLISKVY
MDDSKPSFGYYSNNLKDVKVITKDNVNILTGYYLKDDIKISLSLTLQDEKTIKLNS
VHLDESGVAEILKFMNRKGNTNTSDSLMSFLESMNIKSIFVNFLQSNIKFILDANFI
ISGTTSIGQFEFICDENDNIQPYFIKFNTLETNYTLYVGNRQNMIVEPNYDLDDSGD
ISSTVINFSQKYLYGIDSCVNKVVISPNIYTDEINITPVYETNNTYPEVIVLDANYIN
EKINVNINDLSIRYVWSNDGNDFILMSTSEENKVSQVKIRFVNVFKDKTLANKLS
FNFSDKQDVPVSEIILSFTPSYYEDGLIGYDLGLVSLYNEKFYINNFGMMVSGLIYI
NDSLYYFKPPVNNLITGFVTVGDDKYYFNPINGGAASIGETIIDDKNYYFNQSGVL
QTGVFSTEDGFKYFAPANTLDENLEGEAIDFTGKLIIDENIYYFDDNYRGAVEWK
ELDGEMHYFSPETGKAFKGLNQIGDYKYYFNSDGVMQKGFVSINDNKHYFDDS
GVMKVGYTEIDGKHFYFAENGEMQIGVFNTEDGFKYFAHHNEDLGNEEGEEISY
SGILNFNNKIYYFDDSFTAVVGWKDLEDGSKYYFDEDTAEAYIGLSLINDGQYYF
NDDGIMQVGFVTINDKVFYFSDSGRESGVQNIDDNYFYIDDNGIVQIGVFDTSDG
YKYFAPANTVNDNIYGQAVEYSGLVRVGEDVYYFGETYTIETGWIYDMENESD
KYYFNPETKKACKGINLIDDIKYYFDEKGIMRTGLISFENNNYYFNENGEMQFGY
INIEDKMFYFGEDGVMQIGVFNTPDGFKYFAHQNTLDENFEGESINYTGWLDLDE
KRYYFTDEYIAATGSVIIDGEEYYFDPDTAQLVISE

SEQ ID NO: 49 - Toxin B-derived recombinant antigen - His-Thioredoxin-[linear spacer]-[thrombin site]-TxB4
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALGGSGGSGGSGGSGGSGGSGGSGGSGGSLVPRGSGSAAAPFTM
SIIKDISSKEYISFNPKENKITVKSKNLPELSTLLQEIRNNSNSSDIELEEKVMLTECE
INVISNIDTQIVEERIEEAKNLTSDSINYIKDEFKLIESISDALCDLKQQNELEDSHFI
SFEDISETDEGFSIRFINKETGESIFVETEKTIFSEYANHITEEISKIKGTIIDTVNGKL
VKKVNLDTTHEVNTLNAAFFIQSLIEYNSSKESLSNLSVAMKVQVYAQLFSTGLN
TITDAAKVVELVSTALDETIDLLPTLSEGLPIIATIIDGVSLGAAIKELSETSDPLLRQ
EIEAKIGIMAVNLTTATTAIITSSLGIASGFSILLVPLAGISAGIPSLVNNELVLRDKA
TKVVDYFKHVSLVETEGVFTLLDDKIMMPQDDLVISEIDFNNNSIVLGKCEIWRM
EGGSGHTVTDDIDHFFSAPSITYREPHLSIYDVLEVQKEELDLSKDLMVLPNAPNR
VFAWETGWTPGLRSLENDGTKLLDRIRDNYEGEFYWRYFAFIADALITTLKPRYE
DTNIRINLDSNTRSFIVPIITTEYIREKLSYSFYGSGGTYALSLSQYNMGINIELSESD
VWIIDVDNVVRDVTIESDKIKKGDLIEGILSTLSIEENKIILNSHEINFSGEVNGSNG
FVSLTFSILEGINAIIEVDLLSKSYKLLISGELKILMLNSNHIQQKIDYIGFNSELQKN
IPYSFVDSEGKENGFINGSTKEGLFVSELPDVVLISKVYMDDSKPSFGYYSNNLKD
VKVITKDNVNILTGYYLKDDIKISLSLTLQDEKTIKLNSVHLDESGVAEILKFMNR
KGNTNTSDSLMSFLESMNIKSIFVNFLQSNIKFILDANFIISGTTSIGQFEFICDENDN
IQPYFIKFNTLETNYTLYVGNRQNMIVEPNYDLDDSGDISSTVINFSQKYLYGIDS
CVNKVVISPNIYTDEINITPVYETNNTYPEVIVLDANYINEKINVNINDLSIRYVWS
NDGNDFILMSTSEENKVSQVKIRFVNVFKDKTLANKLSFNFSDKQDVPVSEIILSF
TPSYYEDGLIGYDLGLVSLYNEKFYINNFGMMVSGLIYINDSLYYFKPPVNNLITG
FVTVGDDKYYFNPINGGAASIGETIIDDKNYYFNQSGVLQTGVFSTEDGFKYFAP
ANTLDENLEGEAIDFTGKLIIDENIYYFDDNYRGAVEWKELDGEMHYFSPETGKA
FKGLNQIGDYKYYFNSDGVMQKGFVSINDNKHYFDDSGVMKVGYTEIDGKHFY
FAENGEMQIGVFNTEDGFKYFAHHNEDLGNEEGEEISYSGILNFNNKIYYFDDSFT
AVVGWKDLEDGSKYYFDEDTAEAYIGLSLINDGQYYFNDDGIMQVGFVTINDK
VFYFSDSGIIESGVQNIDDNYFYIDDNGIVQIGVFDTSDGYKYFAPANTVNDNIYG
QAVEYSGLVRVGEDVYYFGETYTIETGWIYDMENESDKYYFNPETKKACKGINL
IDDIKYYFDEKGIMRTGLISFENNNYYFNENGEMQFGYINIEDKMFYFGEDGVMQ
IGVFNTPDGFKYFAHQNTLDENFEGESINYTGWLDLDEKRYYFTDEYIAATGSVII
DGEEYYFDPDTAQLVISE SEQ ID NO: 50 - Toxin B-derived recombinant antigen - His-[helical spacer]-Thioredoxin-[thrombin site]-TxB4
HHHHHHHHHHGGSLAEAAAKEAAAKEAAAKEAAAKEAAAKAAAGGSHMASD
KIIHLTDDSFDTDVLKADGAILVDFWAEWCGPCKMIAPILDEIADEYQGKLTVAK
LNIDQNPGTAPKYGIRGIPTLLLFKNGEVAATKVGALSKGQLKEFLDANLARALV
PRGSVTSLYKKAGSAAAPFTMSIIKDISSKEYISFNPKENKITVKSKNLPELSTLLQ
EIRNNSNSSDIELEEKVMLTECEINVISNIDTQIVEERIEEAKNLTSDSINYIKDEFKL
IESISDALCDLKQQNELEDSHFISFEDISETDEGFSIRFINKETGESIFVETEKTIFSEY
ANHITEEISKIKGTIFDTVNGKLVKKVNLDTTHEVNTLNAAFFIQSLIEYNSSKESL
SNLSVAMKVQVYAQLFSTGLNTITDAAKVVELVSTALDETIDLLPTLSEGLPIIATI
IDGVSLGAAIKELSETSDPLLRQEIEAKIGIMAVNLTTATTAIITSSLGIASGFSILLV
PLAGISAGIPSLVNNELVLRDKATKVVDYFKHVSLVETEGVFTLLDDKIMMPQDD
LVISEIDFNNNSIVLGKCEIWRMEGGSGHTVTDDIDHFFSAPSITYREPHLSIYDVL
EVQKEELDLSKDLMVLPNAPNRVFAWETGWTPGLRSLENDGTKLLDRIRDNYE
GEFYWRYFAFIADALITTLKPRYEDTNIRINLDSNTRSFIVPIITTEYIREKLSYSFYG
SGGTYALSLSQYNMGINIELSESDVWIIDVDNVVRDVTIESDKIKKGDLIEGILSTL
SIEENKIILNSHEINFSGEVNGSNGFVSLTFSILEGINAIIEVDLLSKSYKLLISGELKI
LMLNSNHIQQKIDYIGFNSELQKNIPYSFVDSEGKENGFINGSTKEGLFVSELPDV
VLISKVYMDDSKPSFGYYSNNLKDVKVITKDNVNILTGYYLKDDIKISLSLTLQD -continued

| SEQ ID NOs |
|---|
| EKTIKLNSVHLDESGVAEILKFMNRKGNTNTSDSLMSFLESMNIKSIFVNFLQSNI<br>KFILDANFIISGTTSIGQFEFICDENDNIQPYFIKFNTLETNYTLYVGNRQNMIVEPN<br>YDLDDSGDISSTVINFSQKYLYGIDSCVNKVVISPNIYTDEINITPVYETNNTYPEVI<br>VLDANYINEKINVNINDLSIRYVWSNDGNDFILMSTSEENKVSQVKIRFVNVFKD<br>KTLANKLSFNFSDKQDVPVSEIILSFTPSYYEDGLIGYDLGLVSLYNEKFYINNFG<br>MMVSGLIYINDSLYYFKPPVNNLITGFVTVGDDKYYFNPINGGAASIGETIIDDKN<br>YYFNQSGVLQTGVFSTEDGFKYFAPANTLDENLEGEAIDFTGKLIIDENIYYFDDN<br>YRGAVEWKELDGEMHYFSPETGKAFKGLNQIGDYKYYFNSDGVMQKGFVSIND<br>NKHYFDDSGVMKVGYTEIDGKHFYFAENGEMQIGVFNTEDGFKYFAHHNEDLG<br>NEEGEEISYSGILNFNNKIYYFDDSFTAVVGWKDLEDGSKYYFDEDTAEAYIGLS<br>LINDGQYYFNDDGIMQVGFVTINDKVFYFSDSGIIESGVQNIDDNYFYIDDNGIVQ<br>IGVFDTSDGYKYFAPANTVNDNIYGQAVEYSGLVRVGEDVYYFGETYTIETGWI<br>YDMENESDKYYFNPETKKACKGINLIDDIKYYFDEKGIMRTGLISFENNNYYFNE<br>NGEMQFGYINIEDKMFYFGEDGVMQIGVFNTPDGFKYFAHQNTLDENFEGESIN<br>YTGWLDLDEKRYYFTDEYIAATGSVIIDGEEYYFDPDTAQLVISE |
| SEQ ID NO: 51 - Toxin B-derived recombinant antigen - His-Thioredoxin-[Helical spacer]-[thrombin site]-TxB4<br>HHHHHHSHMASDKIIHLTDDSFDTDVLKADGAILVDFWAEWCGPCKMIAPILDEI<br>ADEYQGKLTVAKLNIDQNPGTAPKYGIRGIPTLLLFKNGEVAATKVGALSKGQL<br>KEFLDANLARALLAEAAAKEAAAKEAAAKEAAAKEAAAKAAAGGSLVPRGSG<br>SAAAPFTMSIIKDISSKEYISFNPKENKITVKSKNLPELSTLLQEIRNNSNSSDIELEE<br>KVMLTECEINVISNIDTQIVEERIEEAKNLTSDSINYIKDEFKLIESISDALCDLKQQ<br>NELEDSHFISFEDISETDEGFSIRFINKETGESIFVETEKTIFSEYANHITEEISKIKGTI<br>FDTVNGKLVKKVNLDTTHEVNTLNAAFFIQSLIEYNSSKESLSNLSVAMKVQVY<br>AQLFSTGLNTITDAAKVVELVSTALDETIDLLPTLSEGLPIIATIIDGVSLGAAIKEL<br>SETSDPLLRQEIEAKIGIMAVNLTTATTAIITSSLGIASGFSILLVPLAGISAGIPSLVN<br>NELVLRDKATKVVDYFKHVSLVETEGVFTLLDDKIMMPQDDLVISEIDFNNNSIV<br>LGKCEIWRMEGGSGHTVTDDIDHFFSAPSITYREPHLSIYDVLEVQKEELDLSKDL<br>MVLPNAPNRVFAWETGWTPGLRSLENDGTKLLDRIRDNYEGEFYWRYFAFIAD<br>ALITTLKPRYEDTNIRINLDSNTRSFIVPIITTEYIREKLSYSFYGSGGTYALSLSQYN<br>MGINIELSESDVWIIDVDNVVRDVTIESDKIKKGDLIEGILSTLSIEENKIILNSHEIN<br>FSGEVNGSNGFVSLTFSILEGINAIIEVDLLSKSYKLLISGELKILMLNSNHIQQKID<br>YIGFNSELQKNIPYSFVDSEGKENGFINGSTKEGLFVSELPDVVLISKVYMDDSKP<br>SFGYYSNNLKDVKVITKDNVNILTGYYLKDDIKISLSLTLQDEKTIKLNSVHLDES<br>GVAEILKFMNRKGNTNTSDSLMSFLESMNIKSIFVNFLQSNIKFILDANFIISGTTSI<br>GQFEFICDENDNIQPYFIKFNTLETNYTLYVGNRQNMIVEPNYDLDDSGDISSTVI<br>NFSQKYLYGIDSCVNKVVISPNIYTDEINITPVYETNNTYPEVIVLDANYINEKINV<br>NINDLSIRYVWSNDGNDFILMSTSEENKVSQVKIRFVNVFKDKTLANKLSFNFSD<br>KQDVPVSEIILSFTPSYYEDGLIGYDLGLVSLYNEKFYINNFGMMVSGLIYINDSL<br>YYFKPPVNNLITGFVTVGDDKYYFNPINGGAASIGETIIDDKNYYFNQSGVLQTG<br>VFSTEDGFKYFAPANTLDENLEGEAIDFTGKLIIDENIYYFDDNYRGAVEWKELD<br>GEMHYFSPETGKAFKGLNQIGDYKYYFNSDGVMQKGFVSINDNKHYFDDSGVM<br>KVGYTEIDGKHFYFAENGEMQIGVFNTEDGFKYFAHHNEDLGNEEGEEISYSGIL<br>NFNNKIYYFDDSFTAVVGWKDLEDGSKYYFDEDTAEAYIGLSLINDGQYYFNDD<br>GIMQVGFVTINDKVFYFSDSGIIESGVQNIDDNYFYIDDNGIVQIGVFDTSDGYKY<br>FAPANTVNDNIYGQAVEYSGLVRVGEDVYYFGETYTIETGWIYDMENESDKYYF<br>NPETKKACKGINLIDDIKYYFDEKGIMRTGLISFENNNYYFNENGEMQFGYINIED<br>KMFYFGEDGVMQIGVFNTPDGFKYFAHQNTLDENFEGESINYTGWLDLDEKRY<br>YFTDEYIAATGSVIIDGEEYYFDPDTAQLVISE |
| SEQ ID NO: 52 - Toxin B-derived recombinant antigen - His-[helical spacer]-Thioredoxin-[thrombin site]-TxB3<br>HHHHHHHHHHGGSLAEAAAKEAAAKEAAAKEAAAKEAAAKAAAGGSHMASD<br>KIIHLTDDSFDTDVLKADGAILVDFWAEWCGPCKMIAPILDEIADEYQGKLTVAK<br>LNIDQNPGTAPKYGIRGIPTLLLFKNGEVAATKVGALSKGQLKEFLDANLARALV<br>PRGSVTSLYKKAGSAAGGSMPQDDLVISEIDFNNNSIVLGKCEIWRMEGGSGHTV<br>TDDIDHFFSAPSITYREPHLSIYDVLEVQKEELDLSKDLMVLPNAPNRVFAWETG<br>WTPGLRSLENDGTKLLDRIRDNYEGEFYWRYFAFIADALITTLKPRYEDTNIRINL<br>DSNTRSFIVPIITTEYIREKLSYSFYGSGGTYALSLSQYNMGINIELSESDVWIIDVD<br>NVVRDVTIESDKIKKGDLIEGILSTLSIEENKIILNSHEINFSGEVNGSNGFVSLTFSI<br>LEGINAIIEVDLLSKSYKLLISGELKILMLNSNHIQQKIDYIGFNSELQKNIPYSFVD<br>SEGKENGFINGSTKEGLFVSELPDVVLISKVYMDDSKPSFGYYSNNLKDVKVITK<br>DNVNILTGYYLKDDIKISLSLTLQDEKTIKLNSVHLDESGVAEILKFMNRKGNTNT<br>SDSLMSFLESMNIKSIFVNFLQSNIKFILDANFIISGTTSIGQFEFICDENDNIQPYFIK<br>FNTLETNYTLYVGNRQNMIVEPNYDLDDSGDISSTVINFSQKYLYGIDSCVNKVV<br>ISPNIYTDEINITPVYETNNTYPEVIVLDANYINEKINVNINDLSIRYVWSNDGNDFI<br>LMSTSEENKVSQVKIRFVNVFKDKTLANKLSFNFSDKQDVPVSEIILSFTPSYYED<br>GLIGYDLGLVSLYNEKFYINNFGMMVSGLIYINDSLYYFKPPVNNLITGFVTVGD<br>DKYYFNPINGGAASIGETIIDDKNYYFNQSGVLQTGVFSTEDGFKYFAPANTLDE<br>NLEGEAIDFTGKLIIDENIYYFDDNYRGAVEWKELDGEMHYFSPETGKAFKGLNQ<br>IGDYKYYFNSDGVMQKGFVSINDNKHYFDDSGVMKVGYTEIDGKHFYFAENGE<br>MQIGVFNTEDGFKYFAHHNEDLGNEEGEEISYSGILNFNNKIYYFDDSFTAVVGW<br>KDLEDGSKYYFDEDTAEAYIGLSLINDGQYYFNDDGIMQVGFVTINDKVFYFSDS<br>GIIESGVQNIDDNYFYIDDNGIVQIGVFDTSDGYKYFAPANTVNDNIYGQAVEYS<br>GLVRVGEDVYYFGETYTIETGWIYDMENESDKYYFNPETKKACKGINLIDDIKYY<br>FDEKGIMRTGLISFENNNYYFNENGEMQFGYINIEDKMFYFGEDGVMQIGVFNTP |

-continued

| SEQ ID NOs |
|---|

DGFKYFAHQNTLDENFEGESINYTGWLDLDEKRYYFTDEYIAATGSVIIDGEEYY
FDPDTAQLVISE

SEQ ID NO: 53 - Toxin B-derived recombinant antigen - His-Thioredoxin-[helical spacer]-[thrombin site]-TxB3
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALLAEAAAKEAAAKEAAAKEAAAKEAAAKAAAGGSLVPRGSG
SAAGGSMPQDDLVISEIDFNNNSIVLGKCEIWRMEGGSGHTVTDDIDHFFSAPSIT
YREPHLSIYDVLEVQKEELDLSKDLMVLPNAPNRVFAWETGWTPGLRSLENDGT
KLLDRIRDNYEGEFYWRYFAFIADALITTLKPRYEDTNIRINLDSNTRSFIVPIITTE
YIREKLSYSFYGSGGTYALSLSQYNMGINIELSESDVWIIDVDNVVRDVTIESDKI
KKGDLIEGILSTLSIEENKIILNSHEINFSGEVNGSNGFVSLTFSILEGINAIIEVDLLS
KSYKLLISGELKILMLNSNHIQQKIDYIGFNSELQKNIPYSFVDSEGKENGFINGST
KEGLFVSELPDVVLISKVYMDDSKPSFGYYSNNLKDVKVITKDNVNILTGYYLK
DDIKISLSLTLQDEKTIKLNSVHLDESGVAEILKFMNRKGNTNTSDSLMSFLESMN
IKSIFVNFLQSNIKFILDANFIISGTTSIGQFEFICDENDNIQPYFIKFNTLETNYTLYV
GNRQNMIVEPNYDLDDSGDISSTVINFSQKYLYGIDSCVNKVVISPNIYTDEINITP
VYETNNTYPEVIVLDANYINEKINVNINDLSIRYVWSNDGNDFILMSTSEENKVSQ
VKIRFVNVFKDKTLANKLSFNFSDKQDVPVSEIILSFTPSYYEDGLIGYDLGLVSL
YNEKFYINNFGMMVSGLIYINDSLYYFKPPVNNLITGFVTVGDDKYYFNPINGGA
ASIGETIIDDKNYYFNQSGVLQTGVFSTEDGFKYFAPANTLDENLEGEAIDFTGKL
IIDENIYYFDDNYRGAVEWKELDGEMHYFSPETGKAFKGLNQIGDYKYYFNSDG
VMQKGFVSINDNKHYFDDSGVMKVGYTEIDGKHFYFAENGEMQIGVFNTEDGF
KYFAHHNEDLGNEEGEEISYSGILNFNNKIYYFDDSFTAVVGWKDLEDGSKYYF
DEDTAEAYIGLSLINDGQYYFNDDGIMQVGFVTINDKVFYFSDSGIIESGVQNIDD
NYFYIDDNGIVQIGVFDTSDGYKYFAPANTVNDNIYGQAVEYSGLVRVGEDVYY
FGETYTIETGWIYDMENESDKYYFNPETKKACKGINLIDDIKYYFDEKGIMRTGLI
SFENNNYYFNENGEMQFGYINIEDKMFYFGEDGVMQIGVFNTPDGFKYFAHQNT
LDENFEGESINYTGWLDLDEKRYYFTDEYIAATGSVIIDGEEYYFDPDTAQLVISE SEQ ID NO: 54 - Toxin B-derived recombinant antigen - His-[linear spacer]-Thioredoxin-[thrombin site]-TxB3
HHHHHHHHHGGSGGSGGSGGSGGSGGSGGSGGSGGSGGSHMASDKIIHLTDDSF
DTDVLKADGAILVDFWAEWCGPCKMIAPILDEIADEYQGKLTVAKLNIDQNPGT
APKYGIRGIPTLLLFKNGEVAATKVGALSKGQLKEFLDANLARALVPRGSVTSLY
KKAGSAAGGSMPQDDLVISEIDFNNNSIVLGKCEIWRMEGGSGHTVTDDIDHFFS
APSITYREPHLSIYDVLEVQKEELDLSKDLMVLPNAPNRVFAWETGWTPGLRSLE
NDGTKLLDRIRDNYEGEFYWRYFAFIADALITTLKPRYEDTNIRINLDSNTRSFIVP
IITTEYIREKLSYSFYGSGGTYALSLSQYNMGINIELSESDVWIIDVDNVVRDVTIE
SDKIKKGDLIEGILSTLSIEENKIILNSHEINFSGEVNGSNGFVSLTFSILEGINAIIEV
DLLSKSYKLLISGELKILMLNSNHIQQKIDYIGFNSELQKNIPYSFVDSEGKENGFI
NGSTKEGLFVSELPDVVLISKVYMDDSKPSFGYYSNNLKDVKVITKDNVNILTGY
YLKDDIKISLSLTLQDEKTIKLNSVHLDESGVAEILKFMNRKGNTNTSDSLMSFLE
SMNIKSIFVNFLQSNIKFILDANFIISGTTSIGQFEFICDENDNIQPYFIKFNTLETNYT
LYVGNRQNMIVEPNYDLDDSGDISSTVINFSQKYLYGIDSCVNKVVISPNIYTDEI
NITPVYETNNTYPEVIVLDANYINEKINVNINDLSIRYVWSNDGNDFILMSTSEEN
KVSQVKIRFVNVFKDKTLANKLSFNFSDKQDVPVSEIILSFTPSYYEDGLIGYDLG
LVSLYNEKFYINNFGMMVSGLIYINDSLYYFKPPVNNLITGFVTVGDDKYYFNPI
NGGAASIGETIIDDKNYYFNQSGVLQTGVFSTEDGFKYFAPANTLDENLEGEAIDF
TGKLIIDENIYYFDDNYRGAVEWKELDGEMHYFSPETGKAFKGLNQIGDYKYYF
NSDGVMQKGFVSINDNKHYFDDSGVMKVGYTEIDGKHFYFAENGEMQIGVFNT
EDGFKYFAHHNEDLGNEEGEEISYSGILNFNNKIYYFDDSFTAVVGWKDLEDGSK
YYFDEDTAEAYIGLSLINDGQYYFNDDGIMQVGFVTINDKVFYFSDSGIIESGVQN
IDDNYFYIDDNGIVQIGVFDTSDGYKYFAPANTVNDNIYGQAVEYSGLVRVGED
VYYFGETYTIETGWIYDMENESDKYYFNPETKKACKGINLIDDIKYYFDEKGIMR
TGLISFENNNYYFNENGEMQFGYINIEDKMFYFGEDGVMQIGVFNTPDGFKYFA
HQNTLDENFEGESINYTGWLDLDEKRYYFTDEYIAATGSVIIDGEEYYFDPDTAQ
LVISE SEQ ID NO: 55 - Toxin B-derived recombinant antigen - His-Thioredoxin-[linear spacer]-[thrombin site]-TxB3
HHHHHHSHMASDKIIHLTDDSFDTDVLKADGAILVDFWAEWCGPCKMIAPILDEI
ADEYQGKLTVAKLNIDQNPGTAPKYGIRGIPTLLLFKNGEVAATKVGALSKGQL
KEFLDANLARALGGSGGSGGSGGSGGSGGSGGSGGSGGSLVPRGSGSAAGGSMP
QDDLVISEIDFNNNSIVLGKCEIWRMEGGSGHTVTDDIDHFFSAPSITYREPHLSIY
DVLEVQKEELDLSKDLMVLPNAPNRVFAWETGWTPGLRSLENDGTKLLDRIRD
NYEGEFYWRYFAFIADALITTLKPRYEDTNIRINLDSNTRSFIVPIITTEYIREKLSY
SFYGSGGTYALSLSQYNMGINIELSESDVWIIDVDNVVRDVTIESDKIKKGDLIEGI
LSTLSIEENKIILNSHEINFSGEVNGSNGFVSLTFSILEGINAIIEVDLLSKSYKLLISG
ELKILMLNSNHIQQKIDYIGFNSELQKNIPYSFVDSEGKENGFINGSTKEGLFVSEL
PDVVLISKVYMDDSKPSFGYYSNNLKDVKVITKDNVNILTGYYLKDDIKISLSLTL
QDEKTIKLNSVHLDESGVAEILKFMNRKGNTNTSDSLMSFLESMNIKSIFVNFLQS
NIKFILDANFIISGTTSIGQFEFICDENDNIQPYFIKFNTLETNYTLYVGNRQNMIVE
PNYDLDDSGDISSTVINFSQKYLYGIDSCVNKVVISPNIYTDEINITPVYETNNTYP
EVIVLDANYINEKINVNINDLSIRYVWSNDGNDFILMSTSEENKVSQVKIRFVNVF
KDKTLANKLSFNFSDKQDVPVSEIILSFTPSYYEDGLIGYDLGLVSLYNEKFYINN -continued SEQ ID NOs FGMMVSGLIYINDSLYYFKPPVNNLITGFVTVGDDKYYFNPINGGAASIGETIIDD
KNYYFNQSGVLQTGVFSTEDGFKYFAPANTLDENLEGEAIDFTGKLIIDENIYYFD
DNYRGAVEWKELDGEMHYFSPETGKAFKGLNQIGDYKYYFNSDGVMQKGFVSI
NDNKHYFDDSGVMKVGYTEIDGKHFYFAENGEMQIGVFNTEDGFKYFAHHNED
LGNEEGEEISYSGILNFNNKIYYFDDSFTAVVGWKDLEDGSKYYFDEDTAEAYIG
LSLINDGQYYFNDDGIMQVGFVTINDKVFYFSDSGIIESGVQNIDDNYFYIDDNGI
VQIGVFDTSDGYKYFAPANTVNDNIYGQAVEYSGLVRVGEDVYYFGETYTIETG
WIYDMENESDKYYFNPETKKACKGINLIDDIKYYFDEKGIMRTGLISFENNNYYF
NENGEMQFGYINIEDKMFYFGEDGVMQIGVFNTPDGFKYFAHQNTLDENFEGESI
NYTGWLDLDEKRYYFTDEYIAATGSVIIDGEEYYFDPDTAQLVISE SEQ ID NO: 56 - Toxin B-derived recombinant antigen - His-NusA-[Intein A sequence]-TxB4-His
MGSSHHHHHHSHMASNKEILAVVEAVSNEKALPREKIFEALESALATATKKKYE
QEIDVRVQIDRKSGDFDTFRRWLVVDEVTQPTKEITLEAARYEDESLNLGDYVED
QIESVTFDRITTQTAKQVIVQKVREAERAMVVDQFREHEGEIITGVVKKVNRDNI
SLDLGNNAEAVILREDMLPRENFRPGDRVRGVLYSVRPEARGAQLFVTRSKPEM
LIELFRIEVPEIGEEVIEIKAAARDPGSRAKIAVKTNDKRIDPVGACVGMRGARVQ
AVSTELGGERIDIVLWDDNPAQFVINAMAPADVASIVVDEDKHTMDIAVEAGNL
AQAIGRNGQNVRLASQLSGWELNVMTVDDLQAKHQAEAHAAIDTFTKYLDIDE
DFATVLVEEGFSTLEELAYVPMKELLEIEGLDEPTVEALRERAKNALATIAQAQE
ESLGDNKPADDLLNLEGVDRDLAFKLAARGVCTLEDLAEQGIDDLADIEGLTDE
KAGALIMAARNICWFGDEASGALRTRVKVVKNKALAEGTRIFDPVTGTTHRIED
VVDGRKPIHVVAAAKDGTLHARPVVSWFDQGTRDVIGLRIAGGAILWATPDHK
VLTEYGWRAAGELRKGDRVAQPRRFDGFGDSAPIPARVQALADALDDKFLHDM
LAEELRYSVIREVLPTRRARTFGLEVEELHTLVAEGVVVHNSSPPFKQAEFGSAA
APFTMSIIKDISSKEYISFNPKENKITVKSKNLPELSTLLQEIRNNSNSSDIELEEKV
MLTECEINVISNIDTQIVEERIEEAKNLTSDSINYIKDEFKLIESISDALCDLKQQNE
LEDSHFISFEDISETDEGFSIRFINKETGESIFVETEKTIFSEYANHITEEISKIKGTIFD
TVNGKLVKKVNLDTTHEVNTLNAAFFIQSLIEYNSSKESLSNLSVAMKVQVYAQ
LFSTGLNTITDAAKVVELVSTALDETIDLLPTLSEGLPIIATIIDGVSLGAAIKELSET
SDPLLRQEIEAKIGIMAVNLTTATTAIITSSLGIASGFSILLVPLAGISAGIPSLVNNE
LVLRDKATKVVDYFKHVSLVETEGVFTLLDDKIMMPQDDLVISEIDFNNNSIVLG
KCEIWRMEGGSGHTVTDDIDHFFSAPSITYREPHLSIYDVLEVQKEELDLSKDLM
VLPNAPNRVFAWETGWTPGLRSLENDGTKLLDRIRDNYEGEFYWRYFAFIADAL
ITTLKPRYEDTNIRINLDSNTRSFIVPIITTEYIREKLSYSFYGSGGTYALSLSQYNM
GINIELSESDVWIIDVDNVVRDVTIESDKIKKGDLIEGILSTLSIEENKIILNSHEINFS
GEVNGSNGFVSLTFSILEGINAIIEVDLLSKSYKLLISGELKILMLNSNHIQQKIDYI
GFNSELQKNIPYSFVDSEGKENGFINGSTKEGLFVSELPDVVLISKVYMDDSKPSF
GYYSNNLKDVKVITKDNVNILTGYYLKDDIKISLSLTLQDEKTIKLNSVHLDESG
VAEILKFMNRKGNTNTSDSLMSFLESMNIKSIFVNFLQSNIKFILDANFIISGTTSIG
QFEFICDENDNIQPYFIKFNTLETNYTLYVGNRQNMIVEPNYDLDDSGDISSTVINF
SQKYLYGIDSCVNKVVISPNIYTDEINITPVYETNNTYPEVIVLDANYINEKINVNI
NDLSIRYVWSNDGNDFILMSTSEENKVSQVKIRFVNVFKDKTLANKLSFNFSDKQ
DVPVSEIILSFTPSYYEDGLIGYDLGLVSLYNEKFYINNFGMMVSGLIYINDSLYYF
KPPVNNLITGFVTVGDDKYYFNPINGGAASIGETIIDDKNYYFNQSGVLQTGVFST
EDGFKYFAPANTLDENLEGEAIDFTGKLIIDENIYYFDDNYRGAVEWKELDGEM
HYFSPETGKAFKGLNQIGDYKYYFNSDGVMQKGFVSINDNKHYFDDSGVMKVG
YTEIDGKHFYFAENGEMQIGVFNTEDGFKYFAHHNEDLGNEEGEEISYSGILNFN
NKIYYFDDSFTAVVGWKDLEDGSKYYFDEDTAEAYIGLSLINDGQYYFNDDGIM
QVGFVTINDKVFYFSDSGIIESGVQNIDDNYFYIDDNGIVQIGVFDTSDGYKYFAP
ANTVNDNIYGQAVEYSGLVRVGEDVYYFGETYTIETGWIYDMENESDKYYFNPE
TKKACKGINLIDDIKYYFDEKGIMRTGLISFENNNYYFNENGEMQFGYINIEDKM
FYFGEDGVMQIGVFNTPDGFKYFAHQNTLDENFEGESINYTGWLDLDEKRYYFT
DEYIAATGSVIIDGEEYYFDPDTAQLVISEGHHHHHH SEQ ID NO: 57 - Toxin B-derived recombinant antigen - His-NusA-[Intein BT sequence]-TxB4-His
MGSSHHHHHHSHMASNKEILAVVEAVSNEKALPREKIFEALESALATATKKKYE
QEIDVRVQIDRKSGDFDTFRRWLVVDEVTQPTKEITLEAARYEDESLNLGDYVED
QIESVTFDRITTQTAKQVIVQKVREAERAMVVDQFREHEGEIITGVVKKVNRDNI
SLDLGNNAEAVILREDMLPRENFRPGDRVRGVLYSVRPEARGAQLFVTRSKPEM
LIELFRIEVPEIGEEVIEIKAAARDPGSRAKIAVKTNDKRIDPVGACVGMRGARVQ
AVSTELGGERIDIVLWDDNPAQFVINAMAPADVASIVVDEDKHTMDIAVEAGNL
AQAIGRNGQNVRLASQLSGWELNVMTVDDLQAKHQAEAHAAIDTFTKYLDIDE
DFATVLVEEGFSTLEELAYVPMKELLEIEGLDEPTVEALRERAKNALATIAQAQE
ESLGDNKPADDLLNLEGVDRDLAFKLAARGVCTLEDLAEQGIDDLADIEGLTDE
KAGALIMAARNICWFGDEASGALEVFGEFGSGKAFARDTEVYYENDTVPHMESI
EEMYSKYASMNGELPFDNGYAVPLDNVFVYTLDIASGEIKKTRASYIYREKVEK
LIEIKLSSGYSLKVTPSHPVLLFRDGLQWVPAAEVKPGDVVVGVREEVLRRRIISK
GELEFHEVSSVRIIDYNNWVYDLVIPETHNFIAPNGLVLHNTQLAHTLAVMGSAA
APFTMSIIKDISSKEYISFNPKENKITVKSKNLPELSTLLQEIRNNSNSSDIELEEKV
MLTECEINVISNIDTQIVEERIEEAKNLTSDSINYIKDEFKLIESISDALCDLKQQNE
LEDSHFISFEDISETDEGFSIRFINKETGESIFVETEKTIFSEYANHITEEISKIKGTIFD
TVNGKLVKKVNLDTTHEVNTLNAAFFIQSLIEYNSSKESLSNLSVAMKVQVYAQ
LFSTGLNTITDAAKVVELVSTALDETIDLLPTLSEGLPIIATIIDGVSLGAAIKELSET
SDPLLRQEIEAKIGIMAVNLTTATTAIITSSLGIASGFSILLVPLAGISAGIPSLVNNE

| SEQ ID NOs |
|---|

LVLRDKATKVVDYFKHVSLVETEGVFTLLDDKIMMPQDDLVISEIDFNNNSIVLG
KCEIWRMEGGSGHTVTDDIDHFFSAPSITYREPHLSIYDVLEVQKEELDLSKDLM
VLPNAPNRVFAWETGWTPGLRSLENDGTKLLDRIRDNYEGEFYWRYFAFIADAL
ITTLKPRYEDTNIRINLDSNTRSFIVPIITTEYIREKLSYSFYGSGGTYALSLSQYNM
GINIELSESDVWIIDVDNVVRDVTIESDKIKKGDLIEGILSTLSIEENKIILNSHEINFS
GEVNGSNGFVSLTFSILEGINAIIEVDLLSKSYKLLISGELKILMLNSNHIQQKIDYI
GFNSELQKNIPYSFVDSEGKENGFINGSTKEGLFVSELPDVVLISKVYMDDSKPSF
GYYSNNLKDVKVITKDNVNILTGYYLKDDIKISLSLTLQDEKTIKLNSVHLDESG
VAEILKFMNRKGNTNTSDSLMSFLESMNIKSIFVNFLQSNIKFILDANFIISGTTSIG
QFEFICDENDNIQPYFIKFNTLETNYTLYVGNRQNMIVEPNYDLDDSGDISSTVINF
SQKYLYGIDSCVNKVVISPNIYTDEINITPVYETNNTYPEVIVLDANYINEKINVNI
NDLSIRYVWSNDGNDFILMSTSEENKVSQVKIRFVNVFKDKTLANKLSFNFSDKQ
DVPVSEIILSFTPSYYEDGLIGYDLGLVSLYNEKFYINNFGMMVSGLIYINDSLYYF
KPPVNNLITGFVTVGDDKYYFNPINGGAASIGETIIDDKNYYFNQSGVLQTGVFST
EDGFKYFAPANTLDENLEGEAIDFTGKLIIDENIYYFDDNYRGAVEWKELDGEM
HYFSPETGKAFKGLNQIGDYKYYFNSDGVMQKGFVSINDNKHYFDDSGVMKVG
YTEIDGKHFYFAENGEMQIGVFNTEDGFKYFAHHNEDLGNEEGEEISYSGILNFN
NKIYYFDDSFTAVVGWKDLEDGSKYYFDEDTAEAYIGLSLINDGQYYFNDDGIM
QVGFVTINDKVFYFSDSGIIESGVQNIDDNYFYIDDNGIVQIGVFDTSDGYKYFAP
ANTVNDNIYGQAVEYSGLVRVGEDVYYFGETYTIETGWIYDMENESDKYYFNPE
TKKACKGINLIDDIKYYFDEKGIMRTGLISFENNNYYFNENGEMQFGYINIEDKM
FYFGEDGVMQIGVFNTPDGFKYFAHQNTLDENFEGESINYTGWLDLDEKRYYFT
DEYIAATGSVIIDGEEYYFDPDTAQLVISEGHHHHHH

SEQ ID NO: 58 - Toxin A-derived recombinant antigen (TxA4; residues 770-2710) expression construct
MGSSHHHHHHSHMASDKIIHLTDDSIDTDVLKADGAILVDFWAEWCGPCKMIA
PILDEIADEYQGKLTVAKLNIDQNPGTAPKYGIRGIPTLLLFKNGEVAATKVGALS
KGQLKEFLDANLARALEVLFQGPGGSADARAKAQFEEYKRNYFEGAGGSIMSDL
SSKEYIFFDSIDNKLKAKSKNIPGLASISEDIKTLLLDASVSPDTKFILNNLKLNIESS
IGDYIYYEKLEPVKNIIHNSIDDLIDEFNLLENVSDELYELKKLNNLDEKYLISFEDI
SKNNSTYSVRFINKSNGESVYVETEKEIFSKYSEHITKEISTIKNSIITDVNGNLLDN
IQLDHTSQVNTLNAAFFIQSLIDYSSNKDVLNDLSTSVKVQLYAQLFSTGLNTIYD
SIQLVNLISNAVNDTINVLPTITEGIPIVSTILDGINLGAAIKELLDEHDPLLKKELEA
KVGVLAINMSLSIAATVASIVGIGAEVTIFLLPIAGISAGIPSLVNNELILHDKATSV
VNYFNHLSESKKYGPLKTEDDKILVPIDDLVISEIDFNNNSIKLGTCNILAMEGGS
GHTVTGNIDHFISSPSISSHIPSLSIYSAIGIETENLDFSKKIMMLPNAPSRVFWWET
GAVPGLRSLENDGTRLLDSIRDLYPGKFYWRFYAFFDYAITTLKPVYEDTNIKIKL
DKDTRNFIMPTITTNEIRNKLSYSFDGAGGTYSLLLSSYPISTNINLSKDDLWIFNID
NEVREISIENGTIKKGKLIKDVLSKIDINKNKLIIGNQTIDFSGDIDNKDRYIFLTCEL
DDKISLIIEINLVAKSYSLLLSGDKNYLISNLSNIIEKINTLGLDSKNIAYNYTDESN
NKYFGAISKTSQKSIIHYKKDSKNILEFYNDSTLEFNSKDFIAEDINVFMKDDINTI
TGKYYVDNNTDKSIDFSISLVSKNQVKVNGLYLNESVYSSYLDFVKNSDGHHNT
SNFMNLFLDNISFWKLFGFENINFVIDKYFTLVGKTNLGYVEFICDNNKNIDIYFG
EWKTSSSKSTIFSGNGRNVVVEPIYNPDTGEDISTSLDFSYEPLYGIDRYINKVLIA
PDLYTSLININTNYYSNEYYPEIIVLNPNTFHKKVNINLDSSSFEYKWSTEGSDFIL
VRYLEESNKKILQKIRIKGILSNTQSFNKMSIDFKDIKKLSLGYIMSNFKSFNSENE
LDRDHLGFKIIDNKTYYYDEDSKLVKGLININNSLFYFDPIEFNLVTGWQTINGKK
YYFDINTGAALISYKIINGKHFYFNNDGVMQLGVFKGPDGFEYFAPANTQNNNIE
GQAIVYQSKFLTLNGKKYYFDNDSKAVTGWRIINNEKYYFNPNNAIAAVGLQVI
DNNKYYFNPDTAIISKGWQTVNGSRYYFDTDTAIAFNGYKTIDGKHFYFDSDCV
VKIGVFSTSNGFEYFAPANTYNNNIEGQAIVYQSKFLTLNGKKYYFDNNSKAVTG
WQTIDSKKYYFNTNTAEAATGWQTIDGKKYYFNTNTAEAATGWQTIDGKKYYF
NTNTAIASTGYTIINGKHFYFNTDGIMQIGVFKGPNGFEYFAPANTDANNIEGQAI
LYQNEFLTLNGKKYYFGSDSKAVTGWRIINNKKYYFNPNNAIAAIHLCTINNDKY
YFSYDGILQNGYITIERNNFYFDANNESKMVTGVFKGPNGFEYFAPANTHNNNIE
GQAIVYQNKFLTLNGKKYYFDNDSKAVTGWQTIDGKKYYFNLNTAEAATGWQ
TIDGKKYYFNLNTAEAATGWQTIDGKKYYFNTNTFIASTGYTSINGKHFYFNTDG
IMQIGVFKGPNGFEYFAPANTHNNNIEGQAILYQNKFLTLNGKKYYFGSDSKAVT
GLRTIDGKKYYFNTNTAVAVTGWQTINGKKYYFNTNTSIASTGYTIISGKHFYFN
TDGIMQIGVFKGPDGFEYFAPANTDANNIEGQAIRYQNRFLYLHDNIYYFGNNSK
AATGWVTIDGNRYYFEPNTAMGANGYKTIDNKNFYFRNGLPQIGVFKGSNGFEY
FAPANTDANNIEGQAIRYQNRFLHLLGKIYYFGNNSKAVTGWQTINGKVYYFMP
DTAMAAAGGLFEIDGVIYFFGVDGVKAPGIYG SEQ ID NO: 59 - Toxin A-derived recombinant antigen (TxA4 truncate; residues 770-2389) expression construct
MGSSHHHHHHSHMASDKIIHLTDDSFDTDVLKADGAILVDFWAEWCGPCKMIA
PILDEIADEYQGKLTVAKLNIDQNPGTAPKYGIRGIPTLLLFKNGEVAATKVGALS
KGQLKEFLDANLARALVPRGSGGSADARAKAQFBEYKRNYFEGAGGSAAAPFT
MIMSDLSSKEYIFFDSIDNKLKAKSKNIPGLASISEDIKTLLLDASVSPDTKFILNNL
KLNIESSIGDYIYYEKLEPVKNIIHNSIDDLIDEFNLLENVSDELYELKKLNNLDEK
YLISFEDISKNNSTYSVRFINKSNGESVYVETEKEIFSKYSEHITKEISTIKNSIITDV
NGNLLDNIQLDHTSQVNTLNAAFFIQSLIDYSSNKDVLNDLSTSVKVQLYAQLFS
TGLNTIYDSIQLVNLISNAVNDTINVLPTITEGIPIVSTILDGINLGAAIKELLDEHDP
LLKKELEAKVGVLAINMSLSIAATVASIVGIGAEVTIFLLPIAGISAGIPSLVNNELI
LHDKATSVVNYFNHLSESKKYGPLKTEDDKILVPIDDLVISEIDFNNNSIKLGTCNI -continued

| SEQ ID NOs |
|---|
| LAMEGGSGHTVTGNIDHFFSSPSISSHIPSLSIYSAIGIETENLDFSKKIMMLPNAPS<br>RVFWWETGAVPGLRSLENDGTRLLDSIRDLYPGKFYWRFYAFFDYAITTLKPVY<br>EDTNIKIKLDKDTRNFIMPTITTNEIRNKLSYSFDGAGGTYSLLLSSYPISTNINLSK<br>DDLWIFNIDNEVREISIENGTIKKGKLIKDVLSKIDINKNKLIIGNQTIDFSGDIDNK<br>DRYIFLTCELDDKISLIIEINLVAKSYSLLLSGDKNYLISNLSNIIEKINTLGLDSKNI<br>AYNYTDESNNKYFGAISKTSQKSIIHYKKDSKNILEFYNDSTLEFNSKDFIAEDINV<br>FMKDDINTITGKYYVDNNTDKSIDFSISLVSKNQVKVNGLYLNESVYSSYLDFVK<br>NSDGHHNTSNFMNLFLDNISFWKLFGFENINFVIDKYFTLVGKTNLGYVEFICDN<br>NKNIDIYFGEWKTSSSKSTIFSGNGRNVVVEPIYNPDTGEDISTSLDFSYEPLYGID<br>RYINKVLIAPDLYTSLININTNYYSNEYYPEIIVLNPNTFHKKVNINLDSSSFENKW<br>STEGSDFILVRYLEESNKKILQKIRIKGILSNTQSFNKMSIDFKDIKKLSLGYIMSNF<br>KSFNSENELDRDHLGFKIIDNKTYYYDEDSKLVKGLININNSLFYFDPIEFNLVTG<br>WQTINGKKYYFDINTGAALISYKIINGKHFYFNNDGVMQLGVFKGPDGFEYFAP<br>ANTQNNNIEGQAIVYQSKFLTLNGKKYYFDNDSKAVTGWRIINNEKYYFNPNNA<br>IAAVGLQVIDNNKYYFNPDTAIISKGWQTVNGSRYYPDTDTAIAFNGYKTIDGKH<br>FYFDSDCVVKIGVFSTSNGFEYFAPANTYNNNIEGQAIVYQSKFLTLNGKKYYFD<br>NNSKAVTGWQTIDSKKYYFNTNTAEAATGWQTIDGKKYYFNTNTAEAATGWQ<br>TIDGKKYYFNTNTAIASTGYTIINGKHFYFNTDGIMQIGVFKGPNGFEYFAPANTD<br>ANNIEGQAILYQNEFLTLNGKKYYFGSDSKAVTGWRIINNKKYYFNPNNAIAAIH<br>LCTINNDKYYFSYDGILQNGYITIERNNFYFDANNESKMVTGVFKGPNGFEYFAP<br>ANTHNNNIEGQAIVYQNKFLTLNGKKYYFDNDSKAVTGWQTIDGKKYYFNLNT<br>AEAATGWQTIDGKKYYFNLNTAEAATGWQTIDGKKYYFNTNTFIAST |

The embodiments of the invention in which an exclusive property or privilege is claimed are defined as follows:

1. A method for preventing or suppressing *C. difficile* infection in a human, said method comprising administering to said human a therapeutically effective amount of a nucleic acid; wherein the nucleic acid encodes a protein, the protein comprising:

a) an amino acid sequence that comprises amino acid residues 767-2366 of a *C. difficile* Toxin B sequence; or b) an amino acid sequence that comprises amino acid residues 1145-2366 of a *C. difficile* Toxin B sequence;

with the proviso that the protein is not a polypeptide comprising an amino acid sequence having at least 97% sequence identity to amino acid residues 544-767 of the *C. difficile* Toxin B sequence of SEQ ID NO:2 or SEQ ID NO:4;

wherein the protein can elicit a toxin-neutralizing immune response; and wherein said *C. difficile* Toxin B sequences are the *C. difficile* Toxin B amino acid residue sequence 767-2366 or 1145-2366 of SEQ ID NO:2 or the *C. difficile* Toxin B amino acid residue sequence 767-2366 or 1145-2366 of SEQ ID NO:4.

* * * * *